US010272055B2

(12) United States Patent
Potter et al.

(10) Patent No.: US 10,272,055 B2
(45) Date of Patent: Apr. 30, 2019

(54) THERAPEUTIC COMPOUNDS AND METHODS

(71) Applicants: Regents of the University of Minnesota, Minneapolis, MN (US); The Regents of the University of California, Oakland, CA (US)

(72) Inventors: David A. Potter, Minneapolis, MN (US); Zhijun Guo, Minneapolis, MN (US); Elizabeth Amin, Minneapolis, MN (US); Gunda Georg, Minneapolis, MN (US); Tom Poulos, Irvine, CA (US); Irina Sevrioukova, Irvine, CA (US)

(73) Assignees: Regents of the University of Minnesota, Minneapolis, MN (US); The Regents of the University of California, Oakland, CA (US)

(*) Notice: Subject to any disclaimer, the term of this patent is extended or adjusted under 35 U.S.C. 154(b) by 0 days.

(21) Appl. No.: 14/641,122

(22) Filed: Mar. 6, 2015

(65) Prior Publication Data
US 2015/0342909 A1 Dec. 3, 2015

Related U.S. Application Data

(60) Provisional application No. 61/949,218, filed on Mar. 6, 2014.

(51) Int. Cl.
*A61K 31/155* (2006.01)
*A61K 31/4409* (2006.01)
*A61K 31/426* (2006.01)
*A61K 31/417* (2006.01)
*A61K 45/06* (2006.01)
*C07C 279/26* (2006.01)
*C07D 213/36* (2006.01)
*C07D 277/28* (2006.01)
*C07D 233/64* (2006.01)
*C12N 9/02* (2006.01)

(52) U.S. Cl.
CPC .......... *A61K 31/155* (2013.01); *A61K 31/417* (2013.01); *A61K 31/426* (2013.01); *A61K 31/4409* (2013.01); *A61K 45/06* (2013.01); *C07C 279/26* (2013.01); *C07D 213/36* (2013.01); *C07D 233/64* (2013.01); *C07D 277/28* (2013.01); *C12N 9/0073* (2013.01); *C07K 2299/00* (2013.01); *C07K 2319/21* (2013.01)

(58) Field of Classification Search
None
See application file for complete search history.

(56) References Cited

U.S. PATENT DOCUMENTS

| 4,559,157 A | 12/1985 | Smith |
| 4,608,392 A | 8/1986 | Jacquet |
| 4,820,508 A | 4/1989 | Wortzman |
| 4,938,949 A | 7/1990 | Borch et al. |
| 4,992,478 A | 2/1991 | Geria |
| 8,501,792 B2* | 8/2013 | Potter ................. A61K 31/164 514/365 |
| 2012/0283299 A1* | 11/2012 | Kim ..................... C07C 279/26 514/357 |

OTHER PUBLICATIONS

Appleyard et al. "Phenformin as Prophylaxis and Therapy in Breast Cancer Xenografts". British Journal of Cancer. 2012; 106:1117-1122. Published Online Feb. 23, 2012.*
Hudis et al. "Triple-Negative Breast Cancer: An Unmet Medical Need". The Oncologist. 2011; 16(Suppl.1):1-11.*
Holliday et al. "Choosing the Right Cell Line for Breast Cancer Research". Breast Cancer Research. 2011; 13:215. (Year: 2011).*
Perez EA. "Paclitaxel in Breast Cancer". Oncologist. 1998; 3(6):373-389. (Year: 1998).*
Wellcome Trust Sanger Institute [Online]. "The Measure of Man". [Retrieved Feb. 5, 2013]. Retrieved from the Internet: <URL: http://www.sanger.ac.uk/about/press/2002/021205.html.> Published Dec. 5, 2002. (Year: 2002).*
Wu et al. "Multiparanneter Metabolic Analysis Reveals a Close Link Between Attenuated Mitochondrial Bioenergetic Function and Enhanced Glycolysis Dependency in Human Tumor Cells". Am J Physiol Cell Physiol. 2007; 292:C125-C136. (Year: 2007).*
Dranka et al. "Assessing Bioenergetic Function in Response to Oxidative Stress by Metabolic Profiling". Free Radical Biology and Medicine. 2011; 51:1621-1635. (Year: 2011).*
Tan et al. "The Profiles of Mitochondrial Respiration and Glycolysis Using Extracellular Flux Analysis in Porcine Enterocyte IPEC-J2 ". Animal Nutrition. 2015; 1:239-243. (Year: 2015).*
Bottini, et al., "Cytotoxic and antiproliferative activity of the single agent epirubicin versus epirubicin plus tamoxifen as primary chemotherapy in human breast cancer: a single-institution phase III trial", Endocrine-Related Cancer 12, 383-392 (2005).
Choi, et al., "Pharmacokinetic and pharmacodynamic interaction between nifedipine and metformin in rats: competitive inhibition for metabolism of nifedipine and metformin by each other via CYP isozymes", Xenobiotca, 42 (5), 183-495 (2012).
Fleming, et al., "The cytochrome P450 pathway in angiogenesis and endothelial cell biology", Cancer Metastasis Reviews, 30 (3-4), 541-555 (2011).
Gianni, et al., "Efficacy and safety of neoadjuvant pertuzumab and trastuzumab in women with locally advanced, inflammatory, or early HER2-positive breast cancer (NeoSphere): a randomised multicentre, open-label, phase 2 trial", Lancet Oncol. 13, 25-32 (2012).
Guo, et al., "Breast cancer inhibition by a novel and potent biguanide, N1-hexyl-N5-benzyl-biguanide", AACR Annual Meeting, San Diego, CA, Apr. 5-9, 2014.

(Continued)

*Primary Examiner* — Leslie A. Royds Draper
(74) *Attorney, Agent, or Firm* — Viksnins Harris Padys Malen LLP

(57) ABSTRACT

Biguanide compounds and salts thereof are disclosed. Also disclosed are pharmaceutical compositions and therapeutic methods for treating certain diseases including cancer such as breast cancer.

3 Claims, 108 Drawing Sheets

(56) References Cited

OTHER PUBLICATIONS

Jiang, et al., "Cytochrome P450 2J2 promotes the neoplastic phenotype of carcinoma cells and is up-regulated in human tumors", Cancer Res 65 (11), 4707-4715 (2005).

Jiang, et al., "Cytochrome p450 epoxygenase promotes human cancer metastasis", Cancer Res 67 (14), 6665-6674 (2007).

Mitra, et al., "CYP3A4 mediates growth of estrogen receptor-positive breast cancer cells in part by inducing nuclear translocation of phospho-Stat3 through biosynthesis of (±)-14,15-epoxyeicosatrienoic acid (EET)", Journal of Biological Chemistry 286 (20), 17543-17559 (2011).

Oguro, et al., "Overexpression of CYP3A4, but not of CYP2D6, promotes hypoxic response and cell growth of Hep3B cells", Drug Metab Pharmacokinet 26 (4), 407-415 (2011).

Panigrahy, et al., "EET signaling in cancer", Cancer Metastasis Reviews 30 (34), 525-540 (2011).

Panigrahy, et al., "Epoxyeicosanoids stimulate multiorgan metastasis and tumor dormancy escape in mice", Journal of Clinical Investigation 122 (1), 178-191 (2012).

Peng, et al., "The effects of type II binding on metabolic stability and binding affinity in cytochrome P450 CYP3A4", Archives of Biochemistry and Biophysics 497 (1-2), 68-81 (2010).

Potter, et al., "Roles of Cell Intrinsic Epdxygenase in Breast Cancer Progression", 15th Annual International Winter Eicosanoid Conference, (WEC), Baltimore, Maryland, Abstract, Mar. 9-12, 2014.

Sevrioukova, et al., "Structure and mechanism of the complex between cytochrome P4503A4 and ritonavir", Proc Natl Acad Sci 107 (43), 18422-18427 (2010).

Silver, et al., "Efficacy of neoadjuvant Cisplatin in triple-negative breast cancer", J Clin Oncol. 28 (7), 1145-1153 (2010).

Wang, et al., "JMJD5 regulates PKM2 nuclear translocation and reprograms HIF-1α-mediated glucose metabolism", PNAS vol. 111 (1), 279-284 (2014).

Zhang, et al. "Stabilized epoxygenated fatty acids regulate inflammation, pain, angiogenesis and cancer", Progress in Lipid Research, 53, 108-123 (2013).

Choi, et al., "Inhibiting stemness and invasive properties of glioblastoma tumorsphere by combined treatment with temozolomide and a newly designed biguanide (HL156A)", Oncotarget, Advance Publications 2016, 17 pages, (Aug. 25, 2016).

Ju, et al., "HL156A: a novel AMP-activated protein kinase activator, is protective against peritoneal fibrosis in an in vivo and in vitro model of peritoneal fibrosis"; Am J Physiol Renal Physiol 310, F342-F350 (2016).

Guo, et al., "Heme Binding Biguanides Target Cytochrome P450-Dependent Cancer Cell Mitochondria", Cell Chemical Biology 24, 1259-1275 (2017).

Chuong, et al., "Role of the CYP3A4-mediated 11,12-epoxyeicosatrienoic acid pathway in the development of tamoxifen-resistant breast cancer", Oncotarget 8(41), 71054-71069 (2017).

\* cited by examiner

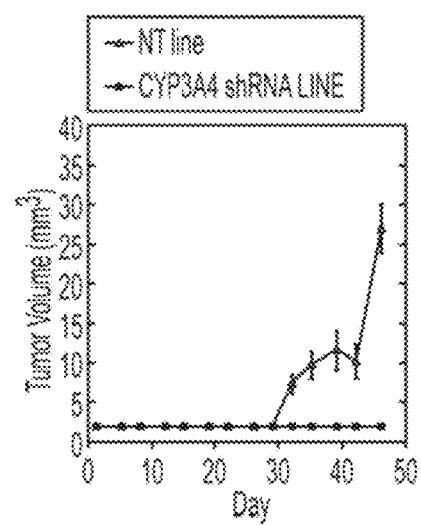 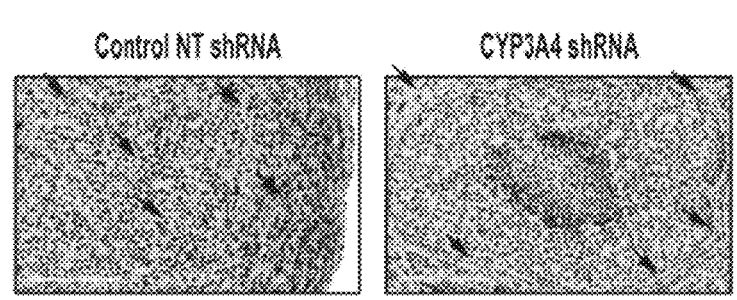
FIG. 1A  FIG. 1B  FIG. 1C

Metformin

N1 Hexyl N5 benzyl biguanide

```
REMARK   3   PROGRAM      : REFMAC 5.6.0117
REMARK   3     REFINEMENT TARGET : MAXIMUM LIKELIHOOD
REMARK   3
REMARK   3   DATA USED IN REFINEMENT.
REMARK   3    RESOLUTION RANGE HIGH (ANGSTROMS) :   2.60
REMARK   3    RESOLUTION RANGE LOW  (ANGSTROMS) :  37.40
REMARK   3    DATA CUTOFF            (SIGMA(F)) :  NONE
REMARK   3    COMPLETENESS FOR RANGE        (%) :  97.71
REMARK   3    NUMBER OF REFLECTIONS             :  14658
REMARK   3
REMARK   3   FIT TO DATA USED IN REFINEMENT.
REMARK   3    CROSS-VALIDATION METHOD           : THROUGHOUT
REMARK   3    FREE R VALUE TEST SET SELECTION   : RANDOM
REMARK   3    R VALUE     (WORKING + TEST SET)  : 0.21531
REMARK   3    R VALUE            (WORKING SET)  : 0.21188
REMARK   3    FREE R VALUE                      : 0.28143
REMARK   3    FREE R VALUE TEST SET SIZE   (%)  : 5.0
REMARK   3    FREE R VALUE TEST SET COUNT       : 770
REMARK   3
REMARK   3   FIT IN THE HIGHEST RESOLUTION BIN.
REMARK   3    TOTAL NUMBER OF BINS USED         :   20
REMARK   3    BIN RESOLUTION RANGE HIGH         :   2.600
REMARK   3    BIN RESOLUTION RANGE LOW          :   2.667
REMARK   3    REFLECTION IN BIN    (WORKING SET):  1009
REMARK   3    BIN COMPLETENESS (WORKING+TEST) (%):  99.26
REMARK   3    BIN R VALUE         (WORKING SET) :   0.277
REMARK   3    BIN FREE R VALUE SET COUNT        :   57
REMARK   3    BIN FREE R VALUE                  :   0.353
REMARK   3
REMARK   3   NUMBER OF NON-HYDROGEN ATOMS USED IN REFINEMENT.
REMARK   3    ALL ATOMS            :   3744
REMARK   3
REMARK   3   B VALUES.
REMARK   3    FROM WILSON PLOT           (A**2) : NULL
REMARK   3    MEAN B VALUE      (OVERALL, A**2) : 42.326
REMARK   3    OVERALL ANISOTROPIC B VALUE.
REMARK   3     B11 (A**2) :  -0.21
REMARK   3     B22 (A**2) :   0.14
REMARK   3     B33 (A**2) :   0.07
REMARK   3     B12 (A**2) :   0.00
REMARK   3     B13 (A**2) :   0.00
REMARK   3     B23 (A**2) :   0.00
REMARK   3
REMARK   3   ESTIMATED OVERALL COORDINATE ERROR.
REMARK   3    ESU BASED ON R VALUE                      (A): NULL
REMARK   3    ESU BASED ON FREE R VALUE                 (A): 0.379
REMARK   3    ESU BASED ON MAXIMUM LIKELIHOOD           (A): 0.315
REMARK   3    ESU FOR B VALUES BASED ON MAXIMUM LIKELIHOOD (A**2): 32.216
REMARK   3
REMARK   3   CORRELATION COEFFICIENTS.
REMARK   3    CORRELATION COEFFICIENT FO-FC      : 0.947
REMARK   3    CORRELATION COEFFICIENT FO-FC FREE : 0.912
REMARK   3
REMARK   3   RMS DEVIATIONS FROM IDEAL VALUES        COUNT    RMS    WEIGHT
REMARK   3    BOND LENGTHS REFINED ATOMS     (A):   3820 ; 0.010 ; 0.020
REMARK   3    BOND ANGLES REFINED ATOMS (DEGREES):  5180 ; 1.924 ; 2.005
REMARK   3    TORSION ANGLES, PERIOD 1  (DEGREES):   452 ; 5.802 ; 5.000
REMARK   3    TORSION ANGLES, PERIOD 2  (DEGREES):   160 ;38.549 ;24.000
REMARK   3    TORSION ANGLES, PERIOD 3  (DEGREES):   686 ;19.008 ;15.000
REMARK   3    TORSION ANGLES, PERIOD 4  (DEGREES):    20 ;20.070 ;15.000
REMARK   3    CHIRAL-CENTER RESTRAINTS    (A**3):    570 ; 0.097 ; 0.200
REMARK   3    GENERAL PLANES REFINED ATOMS   (A):   2850 ; 0.007 ; 0.021
REMARK   3
REMARK   3   ISOTROPIC THERMAL FACTOR RESTRAINTS.    COUNT    RMS    WEIGHT
REMARK   3
REMARK   3   NCS RESTRAINTS STATISTICS
```

FIG. 49

```
REMARK   3   NUMBER OF NCS GROUPS : NULL
REMARK   3
REMARK   3   TWIN DETAILS
REMARK   3    NUMBER OF TWIN DOMAINS  : NULL
REMARK   3
REMARK   3
REMARK   3   TLS DETAILS
REMARK   3    NUMBER OF TLS GROUPS  :    1
REMARK   3    ATOM RECORD CONTAINS RESIDUAL B FACTORS ONLY
REMARK   3
REMARK   3    TLS GROUP :     1
REMARK   3    NUMBER OF COMPONENTS GROUP :    1
REMARK   3    COMPONENTS       C SSSEQI   TO   C SSSEQI
REMARK   3    RESIDUE RANGE :    A   -10        A  9999
REMARK   3    ORIGIN FOR THE GROUP (A):  19.0436 -23.6700  13.2657
REMARK   3    T TENSOR
REMARK   3       T11:   0.0596 T22:   0.1839
REMARK   3       T33:   0.0661 T12:  -0.0315
REMARK   3       T13:   0.0156 T23:   0.0596
REMARK   3    L TENSOR
REMARK   3       L11:   2.3235 L22:   4.8550
REMARK   3       L33:   1.9619 L12:   1.6793
REMARK   3       L13:  -0.2882 L23:  -0.5516
REMARK   3    S TENSOR
REMARK   3       S11:   0.0523 S12:  -0.2211 S13:  -0.1754
REMARK   3       S21:  -0.0611 S22:  -0.1027 S23:   0.0458
REMARK   3       S31:   0.2542 S32:  -0.0458 S33:   0.0503
REMARK   3
REMARK   3
REMARK   3   BULK SOLVENT MODELLING.
REMARK   3    METHOD USED : MASK
REMARK   3    PARAMETERS FOR MASK CALCULATION
REMARK   3    VDW PROBE RADIUS    :   1.20
REMARK   3    ION PROBE RADIUS    :   0.80
REMARK   3    SHRINKAGE RADIUS    :   0.80
REMARK   3
REMARK   3   OTHER REFINEMENT REMARKS:
REMARK   3   HYDROGENS HAVE BEEN USED IF PRESENT IN THE INPUT
REMARK   3   U VALUES      : RESIDUAL ONLY
REMARK   3
LINK              GLU A 258                 GLU A 262              gap
LINK              GLN A 265                 VAL A 269              gap
LINK              GLN A 279                 HIS A 287              gap
CISPEP  1 ILE A  473    PRO A  474          0.00
CRYST1   77.000  101.070  128.370  90.00  90.00  90.00 I 2 2 2
SCALE1     0.012987  0.000000  0.000000       0.00000
SCALE2     0.000000  0.009894  0.000000       0.00000
SCALE3     0.000000  0.000000  0.007790       0.00000
ATOM      1  N   HIS A  28      26.005   4.844  11.515  1.00 88.51           A   N
ATOM      2  CA  HIS A  28      25.251   5.534  12.615  1.00 90.61           A   C
ATOM      3  CB  HIS A  28      23.997   4.746  13.023  1.00 92.74           A   C
ATOM      4  CG  HIS A  28      23.119   4.294  11.855  1.00 96.90           A   C
ATOM      5  ND1 HIS A  28      23.001   2.988  11.499  1.00 97.52           A   N
ATOM      6  CE1 HIS A  28      22.163   2.886  10.453  1.00 95.37           A   C
ATOM      7  NE2 HIS A  28      21.734   4.130  10.137  1.00 95.79           A   N
ATOM      8  CD2 HIS A  28      22.302   5.022  10.983  1.00 96.35           A   C
ATOM      9  C   HIS A  28      26.102   5.802  13.852  1.00 82.14           A   C
ATOM     10  O   HIS A  28      26.568   4.870  14.528  1.00 75.76           A   O
ATOM     11  N   SER A  29      26.234   7.084  14.180  1.00 68.50           A   N
ATOM     12  CA  SER A  29      26.940   7.503  15.397  1.00 62.80           A   C
ATOM     13  CB  SER A  29      26.915   9.034  15.502  1.00 63.44           A   C
ATOM     14  OG  SER A  29      27.990   9.624  14.788  1.00 68.39           A   O
ATOM     15  C   SER A  29      26.383   6.856  16.704  1.00 56.37           A   C
ATOM     16  O   SER A  29      25.304   6.220  16.745  1.00 52.97           A   O
ATOM     17  N   HIS A  30      27.140   7.059  17.772  1.00 48.83           A   N
ATOM     18  CA  HIS A  30      26.873   6.432  19.048  1.00 44.06           A   C
```

| | | | | | | | | | | | | |
|---|---|---|---|---|---|---|---|---|---|---|---|---|
|ATOM|85|CG2|ILE|A|38|17.675|1.553|24.948|1.00|34.40|A|C|
|ATOM|86|C|ILE|A|38|18.973|3.380|26.820|1.00|31.65|A|C|
|ATOM|87|O|ILE|A|38|20.022|3.819|26.327|1.00|29.47|A|O|
|ATOM|88|N|PRO|A|39|18.987|2.566|27.901|1.00|29.41|A|N|
|ATOM|89|CA|PRO|A|39|20.229|2.153|28.506|1.00|28.62|A|C|
|ATOM|90|CB|PRO|A|39|19.801|1.493|29.812|1.00|27.36|A|C|
|ATOM|91|CG|PRO|A|39|18.426|0.989|29.553|1.00|28.26|A|C|
|ATOM|92|CD|PRO|A|39|17.804|1.938|28.562|1.00|29.42|A|C|
|ATOM|93|C|PRO|A|39|20.987|1.146|27.643|1.00|30.70|A|C|
|ATOM|94|O|PRO|A|39|20.385|0.410|26.840|1.00|28.04|A|O|
|ATOM|95|N|GLY|A|40|22.308|1.140|27.831|1.00|33.40|A|N|
|ATOM|96|CA|GLY|A|40|23.224|0.162|27.240|1.00|33.22|A|C|
|ATOM|97|C|GLY|A|40|24.686|0.428|27.620|1.00|33.76|A|C|
|ATOM|98|O|GLY|A|40|25.029|1.512|28.113|1.00|30.32|A|O|
|ATOM|99|N|PRO|A|41|25.560|-0.562|27.370|1.00|33.85|A|N|
|ATOM|100|CA|PRO|A|41|26.982|-0.375|27.588|1.00|31.73|A|C|
|ATOM|101|CB|PRO|A|41|27.584|-1.699|27.124|1.00|32.85|A|C|
|ATOM|102|CG|PRO|A|41|26.608|-2.222|26.122|1.00|33.78|A|C|
|ATOM|103|CD|PRO|A|41|25.262|-1.820|26.653|1.00|32.42|A|C|
|ATOM|104|C|PRO|A|41|27.471|0.750|26.700|1.00|31.09|A|C|
|ATOM|105|O|PRO|A|41|26.991|0.916|25.578|1.00|31.15|A|O|
|ATOM|106|N|THR|A|42|28.411|1.525|27.212|1.00|31.81|A|N|
|ATOM|107|CA|THR|A|42|28.879|2.695|26.511|1.00|33.13|A|C|
|ATOM|108|CB|THR|A|42|29.546|3.639|27.473|1.00|34.49|A|C|
|ATOM|109|OG1|THR|A|42|28.850|3.673|28.729|1.00|37.72|A|O|
|ATOM|110|CG2|THR|A|42|29.531|5.135|26.904|1.00|31.60|A|C|
|ATOM|111|C|THR|A|42|29.845|2.205|25.433|1.00|33.51|A|C|
|ATOM|112|O|THR|A|42|30.803|1.485|25.752|1.00|33.32|A|O|
|ATOM|113|N|PRO|A|43|29.583|2.563|24.154|1.00|31.55|A|N|
|ATOM|114|CA|PRO|A|43|30.332|2.180|22.996|1.00|30.27|A|C|
|ATOM|115|CB|PRO|A|43|29.479|2.625|21.814|1.00|31.30|A|C|
|ATOM|116|CG|PRO|A|43|28.798|3.844|22.345|1.00|31.47|A|C|
|ATOM|117|CD|PRO|A|43|28.473|3.499|23.769|1.00|31.91|A|C|
|ATOM|118|C|PRO|A|43|31.686|2.820|22.943|1.00|29.02|A|C|
|ATOM|119|O|PRO|A|43|31.817|3.980|23.334|1.00|27.36|A|O|
|ATOM|120|N|LEU|A|44|32.679|2.067|22.477|1.00|26.08|A|N|
|ATOM|121|CA|LEU|A|44|33.981|2.603|22.141|1.00|26.48|A|C|
|ATOM|122|CB|LEU|A|44|35.051|1.516|22.309|1.00|24.43|A|C|
|ATOM|123|CG|LEU|A|44|35.481|1.116|23.738|1.00|23.43|A|C|
|ATOM|124|CD1|LEU|A|44|36.485|-0.029|23.700|1.00|22.02|A|C|
|ATOM|125|CD2|LEU|A|44|36.072|2.262|24.543|1.00|21.67|A|C|
|ATOM|126|C|LEU|A|44|33.922|3.111|20.688|1.00|26.73|A|C|
|ATOM|127|O|LEU|A|44|33.142|2.596|19.869|1.00|24.03|A|O|
|ATOM|128|N|PRO|A|45|34.726|4.140|20.370|1.00|26.59|A|N|
|ATOM|129|CA|PRO|A|45|34.856|4.635|18.982|1.00|26.93|A|C|
|ATOM|130|CB|PRO|A|45|35.965|5.741|19.105|1.00|25.80|A|C|
|ATOM|131|CG|PRO|A|45|35.802|6.194|20.519|1.00|26.44|A|C|
|ATOM|132|CD|PRO|A|45|35.477|4.966|21.325|1.00|26.55|A|C|
|ATOM|133|C|PRO|A|45|35.325|3.546|18.020|1.00|26.58|A|C|
|ATOM|134|O|PRO|A|45|36.219|3.750|18.353|1.00|27.72|A|O|
|ATOM|135|N|PHE|A|46|34.704|3.532|16.833|1.00|30.72|A|N|
|ATOM|136|CA|PHE|A|46|34.896|2.524|15.777|1.00|29.23|A|C|
|ATOM|137|CB|PHE|A|46|36.341|2.454|15.280|1.00|32.39|A|C|
|ATOM|138|CG|PHE|A|46|36.925|3.774|14.816|1.00|33.77|A|C|
|ATOM|139|CD1|PHE|A|46|37.726|4.550|15.683|1.00|35.99|A|C|
|ATOM|140|CE1|PHE|A|46|38.327|5.745|15.250|1.00|35.84|A|C|
|ATOM|141|CZ|PHE|A|46|38.134|6.167|13.932|1.00|35.69|A|C|
|ATOM|142|CE2|PHE|A|46|37.354|5.394|13.059|1.00|34.41|A|C|
|ATOM|143|CD2|PHE|A|46|36.769|4.205|13.494|1.00|34.37|A|C|
|ATOM|144|C|PHE|A|46|34.406|1.121|16.135|1.00|29.52|A|C|
|ATOM|145|O|PHE|A|46|33.652|0.519|15.349|1.00|33.01|A|O|
|ATOM|146|N|LEU|A|47|34.832|0.571|17.277|1.00|27.44|A|N|
|ATOM|147|CA|LEU|A|47|34.416|-0.813|17.659|1.00|25.97|A|C|
|ATOM|148|CB|LEU|A|47|35.358|-1.441|18.674|1.00|24.35|A|C|
|ATOM|149|CG|LEU|A|47|36.826|-1.432|18.267|1.00|25.62|A|C|
|ATOM|150|CD1|LEU|A|47|37.676|-2.020|19.380|1.00|24.46|A|C|

```
ATOM    413  CA  GLN A  79      25.402  -0.465  13.846  1.00 32.15           A      C
ATOM    414  CB  GLN A  79      25.378  -1.835  13.152  1.00 31.78           A      C
ATOM    415  CG  GLN A  79      23.994  -2.494  13.128  1.00 33.40           A      C
ATOM    416  CD  GLN A  79      23.014  -1.743  12.241  1.00 33.78           A      C
ATOM    417  OE1 GLN A  79      23.304  -1.503  11.099  1.00 30.55           A      O
ATOM    418  NE2 GLN A  79      21.864  -1.348  12.765  1.00 35.41           A      N
ATOM    419  C   GLN A  79      24.864  -0.510  15.184  1.00 31.12           A      C
ATOM    420  O   GLN A  79      25.016  -1.295  16.083  1.00 33.29           A      O
ATOM    421  N   PRO A  80      23.827   0.318  15.324  1.00 31.95           A      N
ATOM    422  CA  PRO A  80      22.839   0.301  16.551  1.00 29.85           A      C
ATOM    423  CB  PRO A  80      22.041   1.594  16.474  1.00 28.19           A      C
ATOM    424  CG  PRO A  80      21.896   1.850  15.020  1.00 30.20           A      C
ATOM    425  CD  PRO A  80      23.159   1.350  14.383  1.00 33.42           A      C
ATOM    426  C   PRO A  80      21.921  -0.913  16.598  1.00 29.88           A      C
ATOM    427  O   PRO A  80      21.168  -1.168  15.652  1.00 30.85           A      O
ATOM    428  N   VAL A  81      21.959  -1.664  17.685  1.00 26.32           A      N
ATOM    429  CA  VAL A  81      21.157  -2.835  17.827  1.00 28.14           A      C
ATOM    430  CB  VAL A  81      21.995  -4.142  17.930  1.00 27.31           A      C
ATOM    431  CG1 VAL A  81      21.086  -5.345  18.011  1.00 25.15           A      C
ATOM    432  CG2 VAL A  81      22.944  -4.313  16.741  1.00 27.69           A      C
ATOM    433  C   VAL A  81      20.262  -2.657  19.058  1.00 30.99           A      C
ATOM    434  O   VAL A  81      20.780  -2.458  20.186  1.00 30.24           A      O
ATOM    435  N   LEU A  82      18.943  -2.722  18.835  1.00 29.14           A      N
ATOM    436  CA  LEU A  82      18.002  -2.661  19.929  1.00 30.01           A      C
ATOM    437  CB  LEU A  82      16.817  -1.745  19.698  1.00 28.80           A      C
ATOM    438  CG  LEU A  82      15.792  -1.577  20.751  1.00 27.85           A      C
ATOM    439  CD1 LEU A  82      16.344  -0.708  21.858  1.00 27.55           A      C
ATOM    440  CD2 LEU A  82      14.488  -0.987  20.259  1.00 27.94           A      C
ATOM    441  C   LEU A  82      17.501  -4.051  20.322  1.00 31.75           A      C
ATOM    442  O   LEU A  82      16.702  -4.652  19.585  1.00 34.35           A      O
ATOM    443  N   ALA A  83      17.974  -4.543  21.472  1.00 30.04           A      N
ATOM    444  CA  ALA A  83      17.413  -5.723  22.124  1.00 31.88           A      C
ATOM    445  CB  ALA A  83      18.366  -6.270  23.159  1.00 30.52           A      C
ATOM    446  C   ALA A  83      16.086  -5.400  22.783  1.00 33.14           A      C
ATOM    447  O   ALA A  83      15.363  -4.380  23.448  1.00 36.91           A      O
ATOM    448  N   ILE A  84      15.682  -6.262  22.582  1.00 33.69           A      N
ATOM    449  CA  ILE A  84      13.777  -6.111  23.207  1.00 33.03           A      C
ATOM    450  CB  ILE A  84      12.710  -5.631  22.189  1.00 32.92           A      C
ATOM    451  CG1 ILE A  84      12.656  -6.551  20.961  1.00 32.25           A      C
ATOM    452  CD1 ILE A  84      11.250  -6.867  20.511  1.00 30.37           A      C
ATOM    453  CG2 ILE A  84      12.974  -4.199  21.743  1.00 31.29           A      C
ATOM    454  C   ILE A  84      13.328  -7.438  23.825  1.00 33.65           A      C
ATOM    455  O   ILE A  84      13.449  -8.472  23.179  1.00 32.34           A      O
ATOM    456  N   THR A  85      12.800  -7.420  25.057  1.00 37.03           A      N
ATOM    457  CA  THR A  85      12.336  -8.677  25.713  1.00 37.39           A      C
ATOM    458  CB  THR A  85      13.209  -9.072  26.932  1.00 37.30           A      C
ATOM    459  OG1 THR A  85      12.971  -8.137  27.988  1.00 40.25           A      O
ATOM    460  CG2 THR A  85      14.692  -9.119  26.568  1.00 37.02           A      C
ATOM    461  C   THR A  85      10.866  -8.720  26.154  1.00 36.72           A      C
ATOM    462  O   THR A  85      10.474  -9.612  26.912  1.00 38.25           A      O
ATOM    463  N   ASP A  86      10.065  -7.766  25.691  1.00 39.03           A      N
ATOM    464  CA  ASP A  86       8.634  -7.719  26.096  1.00 39.77           A      C
ATOM    465  CB  ASP A  86       8.130  -6.270  25.950  1.00 40.87           A      C
ATOM    466  CG  ASP A  86       6.644  -6.116  26.339  1.00 44.03           A      C
ATOM    467  OD1 ASP A  86       6.049  -6.991  27.028  1.00 42.97           A      O
ATOM    468  OD2 ASP A  86       6.072  -5.067  25.955  1.00 46.15           A      O
ATOM    469  C   ASP A  86       7.869  -8.606  25.020  1.00 41.58           A      C
ATOM    470  O   ASP A  86       7.873  -8.324  23.814  1.00 43.57           A      O
ATOM    471  N   PRO A  87       7.216  -9.684  25.524  1.00 40.87           A      N
ATOM    472  CA  PRO A  87       6.544 -10.656  24.653  1.00 39.11           A      C
ATOM    473  CB  PRO A  87       5.785 -11.543  25.632  1.00 40.39           A      C
ATOM    474  CG  PRO A  87       6.472 -11.407  26.932  1.00 41.09           A      C
ATOM    475  CD  PRO A  87       7.081 -10.033  26.954  1.00 40.81           A      C
ATOM    476  C   PRO A  87       5.581  -9.998  23.666  1.00 39.52           A      C
ATOM    477  O   PRO A  87       5.460 -10.466  22.525  1.00 39.99           A      O
```

FIG. 49 (CONT.)

```
ATOM    542  CB  LYS A  96       1.094  -7.411  13.861  1.00 50.51           A    C
ATOM    543  CG  LYS A  96      -0.014  -8.431  14.159  1.00 56.51           A    C
ATOM    544  CD  LYS A  96      -0.420  -8.533  15.620  1.00 59.12           A    C
ATOM    545  CE  LYS A  96      -1.375  -9.711  15.844  1.00 60.85           A    C
ATOM    546  NZ  LYS A  96      -1.961  -9.812  17.225  1.00 57.25           A    N
ATOM    547  C   LYS A  96       2.764  -6.914  11.951  1.00 48.97           A    C
ATOM    548  O   LYS A  96       2.231  -6.627  10.882  1.00 51.20           A    O
ATOM    549  N   GLU A  97       3.919  -6.378  12.340  1.00 49.53           A    N
ATOM    550  CA  GLU A  97       4.604  -5.370  11.522  1.00 47.62           A    C
ATOM    551  CB  GLU A  97       5.203  -4.255  12.404  1.00 49.98           A    C
ATOM    552  CG  GLU A  97       4.259  -3.536  13.353  1.00 52.20           A    C
ATOM    553  CD  GLU A  97       3.318  -2.529  12.669  1.00 56.29           A    C
ATOM    554  OE1 GLU A  97       3.535  -2.303  12.823  1.00 54.75           A    O
ATOM    555  OE2 GLU A  97       2.346  -2.957  11.996  1.00 55.05           A    O
ATOM    556  C   GLU A  97       5.695  -5.988  10.623  1.00 47.06           A    C
ATOM    557  O   GLU A  97       6.571  -5.280  10.110  1.00 46.73           A    O
ATOM    558  N   CYS A  98       5.639  -7.304  10.435  1.00 43.89           A    N
ATOM    559  CA  CYS A  98       6.653  -8.006   9.650  1.00 42.51           A    C
ATOM    560  CB  CYS A  98       6.403  -7.513   9.652  1.00 42.87           A    C
ATOM    561  SG  CYS A  98       7.582 -10.485   8.684  1.00 45.51           A    S
ATOM    562  C   CYS A  98       6.709  -7.486   8.221  1.00 43.48           A    C
ATOM    563  O   CYS A  98       7.772  -7.077   7.746  1.00 42.93           A    O
ATOM    564  N   TYR A  99       5.562  -7.498   7.545  1.00 44.18           A    N
ATOM    565  CA  TYR A  99       5.458  -7.066   6.145  1.00 41.26           A    C
ATOM    566  CB  TYR A  99       4.107  -7.479   5.551  1.00 40.07           A    C
ATOM    567  CG  TYR A  99       4.011  -8.966   5.319  1.00 40.15           A    C
ATOM    568  CD1 TYR A  99       2.957  -9.686   5.536  1.00 33.69           A    C
ATOM    569  CE1 TYR A  99       2.787 -11.056   5.409  1.00 41.91           A    C
ATOM    570  CZ  TYR A  99       3.895 -11.719   4.881  1.00 42.59           A    C
ATOM    571  OH  TYR A  99       3.910 -13.079   4.644  1.00 41.94           A    O
ATOM    572  CE2 TYR A  99       5.036 -11.019   4.574  1.00 41.65           A    C
ATOM    573  CD2 TYR A  99       5.099  -9.657   4.785  1.00 40.42           A    C
ATOM    574  C   TYR A  99       5.712  -5.583   5.960  1.00 38.91           A    C
ATOM    575  O   TYR A  99       6.468  -5.195   5.080  1.00 38.62           A    O
ATOM    576  N   SER A 100       5.105  -4.757   6.803  1.00 40.15           A    N
ATOM    577  CA  SER A 100       5.254  -3.298   6.680  1.00 42.96           A    C
ATOM    578  CB  SER A 100       4.182  -2.578   7.507  1.00 41.85           A    C
ATOM    579  OG  SER A 100       4.426  -2.730   8.898  1.00 42.94           A    O
ATOM    580  C   SER A 100       6.654  -2.786   7.084  1.00 44.45           A    C
ATOM    581  O   SER A 100       7.206  -2.076   6.305  1.00 45.62           A    O
ATOM    582  N   VAL A 101       7.118  -3.155   8.279  1.00 42.19           A    N
ATOM    583  CA  VAL A 101       8.336  -2.574   8.845  1.00 42.61           A    C
ATOM    584  CB  VAL A 101       8.098  -2.003  10.258  1.00 44.07           A    C
ATOM    585  CG1 VAL A 101       9.382  -1.427  10.835  1.00 43.46           A    C
ATOM    586  CG2 VAL A 101       6.978  -0.952  10.220  1.00 41.07           A    C
ATOM    587  C   VAL A 101       9.521  -3.533   8.903  1.00 40.41           A    C
ATOM    588  O   VAL A 101      10.490  -3.355   8.178  1.00 40.38           A    O
ATOM    589  N   PHE A 102       9.409  -4.543   9.763  1.00 37.84           A    N
ATOM    590  CA  PHE A 102      10.484  -5.484  10.101  1.00 35.87           A    C
ATOM    591  CB  PHE A 102      10.297  -5.932  11.561  1.00 32.86           A    C
ATOM    592  CG  PHE A 102      10.159  -4.796  12.539  1.00 31.72           A    C
ATOM    593  CD1 PHE A 102       8.932  -4.485  13.087  1.00 33.38           A    C
ATOM    594  CE1 PHE A 102       8.802  -3.439  13.979  1.00 32.79           A    C
ATOM    595  CZ  PHE A 102       9.911  -2.694  14.338  1.00 31.13           A    C
ATOM    596  CE2 PHE A 102      11.141  -2.999  13.802  1.00 30.62           A    C
ATOM    597  CD2 PHE A 102      11.260  -4.036  12.906  1.00 31.75           A    C
ATOM    598  C   PHE A 102      10.617  -6.738   9.212  1.00 37.22           A    C
ATOM    599  O   PHE A 102      10.611  -7.854   9.722  1.00 39.22           A    O
ATOM    600  N   THR A 103      10.772  -6.573   7.903  1.00 38.36           A    N
ATOM    601  CA  THR A 103      10.797  -7.740   6.976  1.00 41.55           A    C
ATOM    602  CB  THR A 103      10.437  -7.306   5.540  1.00 40.34           A    C
ATOM    603  OG1 THR A 103       9.437  -6.292   5.592  1.00 40.92           A    O
ATOM    604  CG2 THR A 103       9.947  -8.480   4.713  1.00 39.02           A    C
ATOM    605  C   THR A 103      12.102  -8.544   6.827  1.00 41.37           A    C
```

```
ATOM    736  C   ILE A 120      18.105 -12.663   1.676  1.00 40.49           A  C
ATOM    737  O   ILE A 120      18.279 -11.484   1.943  1.00 42.89           A  O
ATOM    738  N   ALA A 121      17.228 -13.081   0.762  1.00 42.01           A  N
ATOM    739  CA  ALA A 121      16.405 -12.178  -0.073  1.00 37.72           A  C
ATOM    740  CB  ALA A 121      15.463 -12.996  -0.949  1.00 35.75           A  C
ATOM    741  C   ALA A 121      15.600 -11.157   0.727  1.00 37.55           A  C
ATOM    742  O   ALA A 121      15.281 -11.387   1.917  1.00 34.17           A  O
ATOM    743  N   GLU A 122      15.218 -10.074   0.055  1.00 38.55           A  N
ATOM    744  CA  GLU A 122      14.608  -8.957   0.757  1.00 39.85           A  C
ATOM    745  CB  GLU A 122      15.604  -7.807   0.837  1.00 43.51           A  C
ATOM    746  CG  GLU A 122      16.737  -8.100   1.803  1.00 41.01           A  C
ATOM    747  CD  GLU A 122      17.635  -6.922   2.035  1.00 43.61           A  C
ATOM    748  OE1 GLU A 122      17.425  -5.857   1.393  1.00 44.94           A  O
ATOM    749  OE2 GLU A 122      18.563  -7.071   2.863  1.00 46.71           A  O
ATOM    750  C   GLU A 122      13.251  -8.471   0.265  1.00 40.95           A  C
ATOM    751  O   GLU A 122      12.928  -8.555  -0.927  1.00 44.73           A  O
ATOM    752  N   ASP A 123      12.462  -7.967   1.212  1.00 40.53           A  N
ATOM    753  CA  ASP A 123      11.113  -7.415   0.944  1.00 42.95           A  C
ATOM    754  CB  ASP A 123      11.198  -5.958   0.439  1.00 39.49           A  C
ATOM    755  CG  ASP A 123      12.195  -5.122   1.195  1.00 40.24           A  C
ATOM    756  OD1 ASP A 123      12.068  -4.993   2.441  1.00 37.50           A  O
ATOM    757  OD2 ASP A 123      13.098  -4.577   0.520  1.00 42.94           A  O
ATOM    758  C   ASP A 123      10.249  -8.243  -0.025  1.00 42.26           A  C
ATOM    759  O   ASP A 123       9.781  -9.324   0.316  1.00 42.07           A  O
ATOM    760  N   GLU A 124      10.040  -7.712  -1.225  1.00 42.80           A  N
ATOM    761  CA  GLU A 124       9.078  -8.282  -2.164  1.00 47.00           A  C
ATOM    762  CB  GLU A 124       8.704  -7.283  -3.280  1.00 48.74           A  C
ATOM    763  CG  GLU A 124       7.957  -6.042  -2.806  1.00 52.59           A  C
ATOM    764  CD  GLU A 124       6.577  -6.342  -2.224  1.00 55.79           A  C
ATOM    765  OE1 GLU A 124       6.088  -7.493  -2.335  1.00 54.36           A  O
ATOM    766  OE2 GLU A 124       5.963  -5.410  -1.650  1.00 58.78           A  O
ATOM    767  C   GLU A 124       9.636  -9.545  -2.769  1.00 44.58           A  C
ATOM    768  O   GLU A 124       8.916 -10.530  -2.951  1.00 41.56           A  O
ATOM    769  N   GLU A 125      10.927  -9.502  -3.081  1.00 44.79           A  N
ATOM    770  CA  GLU A 125      11.608 -10.652  -3.627  1.00 46.56           A  C
ATOM    771  CB  GLU A 125      13.002 -10.238  -4.139  1.00 54.09           A  C
ATOM    772  CG  GLU A 125      14.168 -11.188  -3.866  1.00 64.98           A  C
ATOM    773  CD  GLU A 125      14.469 -12.170  -4.994  1.00 70.24           A  C
ATOM    774  OE1 GLU A 125      13.529 -12.858  -5.464  1.00 71.19           A  O
ATOM    775  OE2 GLU A 125      15.682 -12.270  -5.385  1.00 70.58           A  O
ATOM    776  C   GLU A 125      11.675 -11.803  -2.591  1.00 45.58           A  C
ATOM    777  O   GLU A 125      11.381 -12.964  -2.967  1.00 48.22           A  O
ATOM    778  N   TRP A 126      11.685 -11.474  -1.296  1.00 39.89           A  N
ATOM    779  CA  TRP A 126      11.528 -12.472  -0.243  1.00 39.84           A  C
ATOM    780  CB  TRP A 126      11.908 -11.944   1.165  1.00 37.29           A  C
ATOM    781  CG  TRP A 126      11.420 -12.931   2.193  1.00 37.25           A  C
ATOM    782  CD1 TRP A 126      11.952 -14.181   2.503  1.00 39.40           A  C
ATOM    783  NE1 TRP A 126      11.213 -14.813   3.474  1.00 40.49           A  N
ATOM    784  CE2 TRP A 126      10.153 -14.059   3.831  1.00 40.48           A  C
ATOM    785  CD2 TRP A 126      10.226 -12.819   3.042  1.00 39.38           A  C
ATOM    786  CE3 TRP A 126       9.243 -11.859   3.225  1.00 39.52           A  C
ATOM    787  CZ3 TRP A 126       8.243 -12.102   4.171  1.00 38.74           A  C
ATOM    788  CH2 TRP A 126       8.205 -13.285   4.928  1.00 39.40           A  C
ATOM    789  CZ2 TRP A 126       9.149 -14.286   4.765  1.00 40.27           A  C
ATOM    790  C   TRP A 126      10.143 -13.038  -0.189  1.00 39.85           A  C
ATOM    791  O   TRP A 126       9.988 -14.256  -0.106  1.00 40.87           A  O
ATOM    792  N   LYS A 127       9.128 -12.172  -0.197  1.00 40.47           A  N
ATOM    793  CA  LYS A 127       7.738 -12.621  -0.066  1.00 42.06           A  C
ATOM    794  CB  LYS A 127       6.777 -11.436   0.053  1.00 46.33           A  C
ATOM    795  CG  LYS A 127       5.445 -11.778   0.726  1.00 48.25           A  C
ATOM    796  CD  LYS A 127       4.659 -10.520   1.076  1.00 51.95           A  C
ATOM    797  CE  LYS A 127       5.571  -9.383   1.544  1.00 54.50           A  C
ATOM    798  NZ  LYS A 127       4.931  -8.038   1.385  1.00 56.35           A  N
ATOM    799  C   LYS A 127       7.325 -13.541  -1.216  1.00 39.98           A  C
ATOM    800  O   LYS A 127       6.593 -14.506  -1.007  1.00 37.63           A  O
```

```
ATOM    930  CG  GLU A 144       4.134 -37.579   0.181  1.00 42.82           A    C
ATOM    931  CD  GLU A 144       3.893 -37.538  -1.309  1.00 45.42           A    C
ATOM    932  OE1 GLU A 144       3.452 -38.574  -1.865  1.00 48.37           A    O
ATOM    933  OE2 GLU A 144       4.160 -36.480  -1.922  1.00 44.73           A    O
ATOM    934  C   GLU A 144       7.388 -38.746   1.851  1.00 37.51           A    C
ATOM    935  O   GLU A 144       7.854 -39.733   1.278  1.00 34.89           A    O
ATOM    936  N   MET A 145       8.125 -37.889   2.552  1.00 37.46           A    N
ATOM    937  CA  MET A 145       9.591 -37.987   2.677  1.00 37.06           A    C
ATOM    938  CB  MET A 145      10.183 -36.801   2.861  1.00 38.64           A    C
ATOM    939  CG  MET A 145       9.998 -35.709   1.649  1.00 38.47           A    C
ATOM    940  SD  MET A 145      10.729 -34.103   1.917  1.00 36.53           A    S
ATOM    941  CE  MET A 145      10.735 -33.504   0.230  1.00 37.25           A    C
ATOM    942  C   MET A 145      10.014 -38.857   3.838  1.00 37.24           A    C
ATOM    943  O   MET A 145      11.164 -39.307   3.904  1.00 37.33           A    O
ATOM    944  N   VAL A 146       9.089 -39.066   4.765  1.00 37.11           A    N
ATOM    945  CA  VAL A 146       9.317 -39.935   5.897  1.00 37.83           A    C
ATOM    946  CB  VAL A 146       8.020 -40.030   6.745  1.00 38.80           A    C
ATOM    947  CG1 VAL A 146       8.092 -41.301   7.587  1.00 38.28           A    C
ATOM    948  CG2 VAL A 146       7.755 -38.806   7.528  1.00 38.68           A    C
ATOM    949  C   VAL A 146       9.839 -41.286   5.458  1.00 37.99           A    C
ATOM    950  O   VAL A 146      10.990 -41.668   5.376  1.00 35.57           A    O
ATOM    951  N   PRO A 147       9.317 -42.004   4.490  1.00 38.27           A    N
ATOM    952  CA  PRO A 147       9.944 -43.282   4.104  1.00 37.70           A    C
ATOM    953  CB  PRO A 147       9.100 -43.736   2.911  1.00 35.14           A    C
ATOM    954  CG  PRO A 147       7.772 -43.097   3.120  1.00 33.89           A    C
ATOM    955  CD  PRO A 147       9.046 -41.777   3.768  1.00 35.64           A    C
ATOM    956  C   PRO A 147      11.431 -43.145   3.697  1.00 40.94           A    C
ATOM    957  O   PRO A 147      12.217 -44.077   3.912  1.00 42.74           A    O
ATOM    958  N   ILE A 148      11.801 -41.989   3.135  1.00 39.05           A    N
ATOM    959  CA  ILE A 148      13.152 -41.750   2.616  1.00 39.02           A    C
ATOM    960  CB  ILE A 148      13.146 -40.689   1.480  1.00 39.52           A    C
ATOM    961  CG1 ILE A 148      12.588 -41.267   0.167  1.00 41.78           A    C
ATOM    962  CD1 ILE A 148      11.105 -41.619   0.161  1.00 42.23           A    C
ATOM    963  CG2 ILE A 148      14.551 -40.191   1.194  1.00 39.62           A    C
ATOM    964  C   ILE A 148      14.126 -41.371   3.748  1.00 39.40           A    C
ATOM    965  O   ILE A 148      15.286 -41.799   3.754  1.00 40.91           A    O
ATOM    966  N   ILE A 149      13.653 -40.575   4.702  1.00 35.96           A    N
ATOM    967  CA  ILE A 149      14.422 -40.225   5.905  1.00 35.46           A    C
ATOM    968  CB  ILE A 149      13.742 -39.186   6.728  1.00 36.02           A    C
ATOM    969  CG1 ILE A 149      13.449 -37.965   5.846  1.00 35.74           A    C
ATOM    970  CD1 ILE A 149      12.512 -36.963   6.483  1.00 34.68           A    C
ATOM    971  CG2 ILE A 149      14.599 -38.804   7.937  1.00 36.35           A    C
ATOM    972  C   ILE A 149      14.581 -41.566   6.762  1.00 37.37           A    C
ATOM    973  O   ILE A 149      15.666 -41.882   7.258  1.00 34.29           A    O
ATOM    974  N   ALA A 150      13.493 -42.303   6.918  1.00 40.54           A    N
ATOM    975  CA  ALA A 150      13.462 -43.506   7.738  1.00 38.00           A    C
ATOM    976  CB  ALA A 150      12.107 -44.165   7.647  1.00 38.71           A    C
ATOM    977  C   ALA A 150      14.567 -44.473   7.303  1.00 40.67           A    C
ATOM    978  O   ALA A 150      15.160 -45.158   8.156  1.00 39.44           A    O
ATOM    979  N   GLN A 151      14.851 -44.489   6.067  1.00 42.34           A    N
ATOM    980  CA  GLN A 151      15.867 -45.348   5.405  1.00 41.19           A    C
ATOM    981  CB  GLN A 151      15.903 -45.104   3.905  1.00 43.45           A    C
ATOM    982  CG  GLN A 151      16.664 -46.137   3.094  1.00 45.46           A    C
ATOM    983  CD  GLN A 151      16.673 -45.813   1.606  1.00 46.63           A    C
ATOM    984  OE1 GLN A 151      17.719 -45.858   0.955  1.00 48.03           A    O
ATOM    985  NE2 GLN A 151      15.503 -45.485   1.060  1.00 46.79           A    N
ATOM    986  C   GLN A 151      17.246 -45.106   6.001  1.00 40.41           A    C
ATOM    987  O   GLN A 151      18.014 -46.039   6.198  1.00 40.59           A    O
ATOM    988  N   TYR A 152      17.554 -43.853   6.301  1.00 40.75           A    N
ATOM    989  CA  TYR A 152      18.850 -43.535   6.902  1.00 41.76           A    C
ATOM    990  CB  TYR A 152      19.413 -42.228   6.361  1.00 39.56           A    C
ATOM    991  CG  TYR A 152      19.527 -42.249   4.864  1.00 39.73           A    C
ATOM    992  CD1 TYR A 152      18.731 -41.432   4.078  1.00 39.25           A    C
ATOM    993  CE1 TYR A 152      18.824 -41.474   2.701  1.00 40.62           A    C
```

```
ATOM   1058  CD2 LEU A 160      23.772 -44.616  16.569  1.00 47.89           A  C
ATOM   1059  C   LEU A 160      26.754 -49.439  15.923  1.00 54.73           A  C
ATOM   1060  O   LEU A 160      27.507 -48.489  16.900  1.00 56.87           A  O
ATOM   1061  N   ARG A 161      26.193 -49.821  15.383  1.00 54.46           A  N
ATOM   1062  CA  ARG A 161      26.450 -50.861  15.890  1.00 56.18           A  C
ATOM   1063  CB  ARG A 161      25.811 -51.916  14.980  1.00 52.84           A  C
ATOM   1064  CG  ARG A 161      25.519 -53.250  15.652  1.00 49.76           A  C
ATOM   1065  CD  ARG A 161      24.022 -53.472  15.804  1.00 47.81           A  C
ATOM   1066  NE  ARG A 161      23.334 -53.405  14.511  1.00 47.12           A  N
ATOM   1067  CZ  ARG A 161      22.010 -53.413  14.347  1.00 47.00           A  C
ATOM   1068  NH1 ARG A 161      21.198 -53.487  15.402  1.00 45.83           A  N
ATOM   1069  NH2 ARG A 161      21.494 -53.344  13.123  1.00 43.79           A  N
ATOM   1070  C   ARG A 161      27.952 -51.083  15.961  1.00 61.21           A  C
ATOM   1071  O   ARG A 161      28.516 -51.190  17.051  1.00 61.98           A  O
ATOM   1072  N   ARG A 162      28.580 -51.121  14.783  1.00 65.73           A  N
ATOM   1073  CA  ARG A 162      30.017 -51.348  14.622  1.00 66.65           A  C
ATOM   1074  CB  ARG A 162      30.455 -50.993  13.193  1.00 69.09           A  C
ATOM   1075  CG  ARG A 162      30.607 -52.192  12.270  1.00 73.31           A  C
ATOM   1076  CD  ARG A 162      30.637 -51.783  10.801  1.00 73.73           A  C
ATOM   1077  NE  ARG A 162      29.321 -51.904  10.165  1.00 75.02           A  N
ATOM   1078  CZ  ARG A 162      28.835 -53.025   9.627  1.00 73.55           A  C
ATOM   1079  NH1 ARG A 162      27.626 -53.027   9.077  1.00 72.91           A  N
ATOM   1080  NH2 ARG A 162      29.547 -54.147   9.634  1.00 72.43           A  N
ATOM   1081  C   ARG A 162      30.848 -50.560  15.618  1.00 65.47           A  C
ATOM   1082  O   ARG A 162      31.484 -51.138  16.495  1.00 65.08           A  O
ATOM   1083  N   GLU A 163      30.803 -49.237  15.492  1.00 66.59           A  N
ATOM   1084  CA  GLU A 163      31.698 -48.349  16.226  1.00 65.82           A  C
ATOM   1085  CB  GLU A 163      31.627 -46.937  15.636  1.00 66.24           A  C
ATOM   1086  CG  GLU A 163      32.381 -46.397  15.204  1.00 66.83           A  C
ATOM   1087  CD  GLU A 163      33.154 -44.918  15.500  1.00 68.10           A  C
ATOM   1088  OE1 GLU A 163      32.172 -44.159  15.362  1.00 66.20           A  O
ATOM   1089  OE2 GLU A 163      34.280 -44.515  15.873  1.00 68.02           A  O
ATOM   1090  C   GLU A 163      31.436 -48.330  17.743  1.00 62.70           A  C
ATOM   1091  O   GLU A 163      32.157 -47.871  18.498  1.00 62.42           A  O
ATOM   1092  N   ALA A 164      30.403 -49.056  18.171  1.00 58.58           A  N
ATOM   1093  CA  ALA A 164      30.056 -49.194  19.584  1.00 56.42           A  C
ATOM   1094  CB  ALA A 164      28.586 -48.839  19.813  1.00 53.84           A  C
ATOM   1095  C   ALA A 164      30.325 -50.620  20.021  1.00 52.75           A  C
ATOM   1096  O   ALA A 164      30.763 -50.863  21.147  1.00 51.32           A  O
ATOM   1097  N   GLU A 165      30.054 -51.507  19.112  1.00 51.66           A  N
ATOM   1098  CA  GLU A 165      30.395 -52.973  19.285  1.00 51.06           A  C
ATOM   1099  CB  GLU A 165      29.793 -53.822  18.148  1.00 51.92           A  C
ATOM   1100  CG  GLU A 165      30.114 -55.316  18.187  1.00 50.01           A  C
ATOM   1101  CD  GLU A 165      29.022 -56.206  17.597  1.00 48.78           A  C
ATOM   1102  OE1 GLU A 165      28.661 -57.339  18.106  1.00 48.92           A  O
ATOM   1103  OE2 GLU A 165      28.327 -55.796  16.638  1.00 49.82           A  O
ATOM   1104  C   GLU A 165      31.915 -53.168  19.416  1.00 52.57           A  C
ATOM   1105  O   GLU A 165      32.370 -54.137  20.030  1.00 54.06           A  O
ATOM   1106  N   THR A 166      32.689 -52.237  18.854  1.00 51.23           A  N
ATOM   1107  CA  THR A 166      34.137 -52.202  19.056  1.00 53.82           A  C
ATOM   1108  CB  THR A 166      34.820 -51.091  18.224  1.00 53.50           A  C
ATOM   1109  OG1 THR A 166      34.001 -50.728  17.110  1.00 54.20           A  O
ATOM   1110  CG2 THR A 166      36.179 -51.554  17.716  1.00 53.00           A  C
ATOM   1111  C   THR A 166      34.463 -51.941  20.528  1.00 55.35           A  C
ATOM   1112  O   THR A 166      35.496 -52.406  21.033  1.00 56.09           A  O
ATOM   1113  N   GLY A 167      33.571 -51.231  21.215  1.00 54.18           A  N
ATOM   1114  CA  GLY A 167      33.884 -50.573  22.481  1.00 54.43           A  C
ATOM   1115  C   GLY A 167      34.343 -49.200  22.053  1.00 56.62           A  C
ATOM   1116  O   GLY A 167      34.135 -48.828  20.891  1.00 60.97           A  O
ATOM   1117  N   LYS A 168      34.965 -48.442  22.956  1.00 56.84           A  N
ATOM   1118  CA  LYS A 168      35.525 -47.107  22.614  1.00 57.29           A  C
ATOM   1119  CB  LYS A 168      36.487 -47.195  21.415  1.00 57.99           A  C
ATOM   1120  CG  LYS A 168      37.748 -48.016  21.659  1.00 59.65           A  C
ATOM   1121  CD  LYS A 168      38.413 -48.432  20.351  1.00 60.54           A  C
```

| | | | | | | | | | |
|---|---|---|---|---|---|---|---|---|---|
| ATOM | 1186 | CE2 | PHE | A | 176 | 23.637 | -38.242 | 17.956 | 1.00 33.29 | A | C |
| ATOM | 1187 | CD2 | PHE | A | 176 | 24.189 | -37.431 | 16.973 | 1.00 34.99 | A | C |
| ATOM | 1188 | C | PHE | A | 176 | 25.122 | -36.438 | 12.213 | 1.00 36.39 | A | C |
| ATOM | 1189 | O | PHE | A | 176 | 24.242 | -36.293 | 11.357 | 1.00 35.82 | A | O |
| ATOM | 1190 | N | GLY | A | 177 | 26.315 | -35.863 | 12.104 | 1.00 36.82 | A | N |
| ATOM | 1191 | CA | GLY | A | 177 | 26.671 | -35.113 | 10.885 | 1.00 39.17 | A | C |
| ATOM | 1192 | C | GLY | A | 177 | 26.409 | -35.980 | 9.665 | 1.00 42.06 | A | C |
| ATOM | 1193 | O | GLY | A | 177 | 25.609 | -35.628 | 8.792 | 1.00 42.24 | A | O |
| ATOM | 1194 | N | ALA | A | 178 | 27.060 | -37.143 | 9.632 | 1.00 42.40 | A | N |
| ATOM | 1195 | CA | ALA | A | 178 | 26.922 | -38.081 | 8.524 | 1.00 43.04 | A | C |
| ATOM | 1196 | CB | ALA | A | 178 | 27.760 | -39.321 | 8.751 | 1.00 41.77 | A | C |
| ATOM | 1197 | C | ALA | A | 178 | 25.467 | -38.460 | 8.328 | 1.00 43.58 | A | C |
| ATOM | 1198 | O | ALA | A | 178 | 25.024 | -38.698 | 7.201 | 1.00 42.44 | A | O |
| ATOM | 1199 | N | TYR | A | 179 | 24.727 | -38.516 | 9.432 | 1.00 41.35 | A | N |
| ATOM | 1200 | CA | TYR | A | 179 | 23.298 | -38.754 | 9.356 | 1.00 39.55 | A | C |
| ATOM | 1201 | CB | TYR | A | 179 | 22.716 | -39.086 | 10.734 | 1.00 36.45 | A | C |
| ATOM | 1202 | CG | TYR | A | 179 | 21.214 | -39.047 | 10.736 | 1.00 33.03 | A | C |
| ATOM | 1203 | CD1 | TYR | A | 179 | 20.489 | -40.057 | 10.134 | 1.00 32.37 | A | C |
| ATOM | 1204 | CE1 | TYR | A | 179 | 19.111 | -40.038 | 10.110 | 1.00 31.04 | A | C |
| ATOM | 1205 | CZ | TYR | A | 179 | 18.446 | -39.004 | 10.685 | 1.00 31.48 | A | C |
| ATOM | 1206 | OH | TYR | A | 179 | 17.087 | -39.021 | 10.649 | 1.00 32.86 | A | O |
| ATOM | 1207 | CE2 | TYR | A | 179 | 19.135 | -37.957 | 11.281 | 1.00 32.72 | A | C |
| ATOM | 1208 | CD2 | TYR | A | 179 | 20.522 | -37.986 | 11.306 | 1.00 31.83 | A | C |
| ATOM | 1209 | C | TYR | A | 179 | 22.575 | -37.550 | 8.731 | 1.00 39.47 | A | C |
| ATOM | 1210 | O | TYR | A | 179 | 21.794 | -37.701 | 7.786 | 1.00 37.67 | A | O |
| ATOM | 1211 | N | SER | A | 180 | 22.844 | -36.358 | 9.259 | 1.00 40.08 | A | N |
| ATOM | 1212 | CA | SER | A | 180 | 22.204 | -35.155 | 8.732 | 1.00 40.80 | A | C |
| ATOM | 1213 | CB | SER | A | 180 | 22.776 | -33.917 | 9.368 | 1.00 38.74 | A | C |
| ATOM | 1214 | OG | SER | A | 180 | 22.004 | -32.819 | 8.959 | 1.00 40.71 | A | O |
| ATOM | 1215 | C | SER | A | 180 | 22.313 | -35.030 | 7.220 | 1.00 41.49 | A | C |
| ATOM | 1216 | O | SER | A | 180 | 21.314 | -34.798 | 6.541 | 1.00 42.97 | A | O |
| ATOM | 1217 | N | MET | A | 181 | 23.523 | -35.195 | 6.700 | 1.00 42.82 | A | N |
| ATOM | 1218 | CA | MET | A | 181 | 23.761 | -35.118 | 5.266 | 1.00 43.09 | A | C |
| ATOM | 1219 | CB | MET | A | 181 | 25.237 | -35.095 | 5.005 | 1.00 48.31 | A | C |
| ATOM | 1220 | CG | MET | A | 181 | 25.561 | -34.684 | 3.584 | 1.00 54.16 | A | C |
| ATOM | 1221 | SD | MET | A | 181 | 27.305 | -34.989 | 3.368 | 1.00 61.62 | A | S |
| ATOM | 1222 | CE | MET | A | 181 | 27.989 | -33.696 | 4.432 | 1.00 53.31 | A | C |
| ATOM | 1223 | C | MET | A | 181 | 23.168 | -36.273 | 4.465 | 1.00 43.30 | A | C |
| ATOM | 1224 | O | MET | A | 181 | 22.646 | -36.074 | 3.372 | 1.00 45.12 | A | O |
| ATOM | 1225 | N | ASP | A | 182 | 23.278 | -37.488 | 4.989 | 1.00 40.97 | A | N |
| ATOM | 1226 | CA | ASP | A | 182 | 22.541 | -38.605 | 4.422 | 1.00 38.63 | A | C |
| ATOM | 1227 | CB | ASP | A | 182 | 22.599 | -39.820 | 5.362 | 1.00 41.60 | A | C |
| ATOM | 1228 | CG | ASP | A | 182 | 23.903 | -40.586 | 5.258 | 1.00 41.23 | A | C |
| ATOM | 1229 | OD1 | ASP | A | 182 | 23.927 | -41.774 | 5.629 | 1.00 39.97 | A | O |
| ATOM | 1230 | OD2 | ASP | A | 182 | 24.903 | -40.002 | 4.804 | 1.00 43.99 | A | O |
| ATOM | 1231 | C | ASP | A | 182 | 21.082 | -38.241 | 4.169 | 1.00 37.69 | A | C |
| ATOM | 1232 | O | ASP | A | 182 | 20.549 | -38.583 | 3.112 | 1.00 37.85 | A | O |
| ATOM | 1233 | N | VAL | A | 183 | 20.440 | -37.571 | 5.137 | 1.00 36.07 | A | N |
| ATOM | 1234 | CA | VAL | A | 183 | 19.044 | -37.138 | 4.997 | 1.00 34.96 | A | C |
| ATOM | 1235 | CB | VAL | A | 183 | 18.365 | -36.913 | 6.362 | 1.00 32.58 | A | C |
| ATOM | 1236 | CG1 | VAL | A | 183 | 17.076 | -36.127 | 6.211 | 1.00 31.96 | A | C |
| ATOM | 1237 | CG2 | VAL | A | 183 | 18.071 | -38.242 | 7.040 | 1.00 33.67 | A | C |
| ATOM | 1238 | C | VAL | A | 183 | 18.903 | -35.911 | 4.079 | 1.00 37.18 | A | C |
| ATOM | 1239 | O | VAL | A | 183 | 17.895 | -35.767 | 3.391 | 1.00 36.42 | A | O |
| ATOM | 1240 | N | ILE | A | 184 | 19.908 | -35.038 | 4.080 | 1.00 37.64 | A | N |
| ATOM | 1241 | CA | ILE | A | 184 | 19.947 | -33.884 | 3.185 | 1.00 40.38 | A | C |
| ATOM | 1242 | CB | ILE | A | 184 | 21.109 | -32.909 | 3.543 | 1.00 42.63 | A | C |
| ATOM | 1243 | CG1 | ILE | A | 184 | 20.729 | -31.972 | 4.706 | 1.00 41.05 | A | C |
| ATOM | 1244 | CD1 | ILE | A | 184 | 19.351 | -31.342 | 4.607 | 1.00 40.83 | A | C |
| ATOM | 1245 | CG2 | ILE | A | 184 | 21.580 | -32.122 | 2.321 | 1.00 40.95 | A | C |
| ATOM | 1246 | C | ILE | A | 184 | 20.047 | -34.304 | 1.711 | 1.00 40.29 | A | C |
| ATOM | 1247 | O | ILE | A | 184 | 19.166 | -33.978 | 0.914 | 1.00 37.67 | A | O |
| ATOM | 1248 | N | THR | A | 185 | 21.103 | -35.037 | 1.355 | 1.00 41.49 | A | N |
| ATOM | 1249 | CA | THR | A | 185 | 21.359 | -35.361 | -0.053 | 1.00 43.38 | A | C |
| ATOM | 1250 | CB | THR | A | 185 | 22.628 | -36.229 | -0.261 | 1.00 45.50 | A | C |

| ATOM | 1316 | OD1 | ASP A 194 | 26.683 | -45.179 | 5.436 | 1.00 | 49.20 | A | O |
| ATOM | 1317 | OD2 | ASP A 194 | 27.080 | -47.035 | 4.336 | 1.00 | 43.99 | A | O |
| ATOM | 1318 | C | ASP A 194 | 27.461 | -42.639 | 3.266 | 1.00 | 49.66 | A | C |
| ATOM | 1319 | O | ASP A 194 | 28.572 | -42.881 | 2.870 | 1.00 | 52.99 | A | O |
| ATOM | 1320 | N | SER A 195 | 27.136 | -41.489 | 3.857 | 1.00 | 50.97 | A | N |
| ATOM | 1321 | CA | SER A 195 | 28.145 | -40.436 | 4.055 | 1.00 | 51.34 | A | C |
| ATOM | 1322 | CB | SER A 195 | 27.536 | -39.229 | 4.761 | 1.00 | 53.29 | A | C |
| ATOM | 1323 | OG | SER A 195 | 26.490 | -38.684 | 3.981 | 1.00 | 61.03 | A | O |
| ATOM | 1324 | C | SER A 195 | 29.367 | -40.883 | 4.845 | 1.00 | 49.74 | A | C |
| ATOM | 1325 | O | SER A 195 | 30.495 | -40.463 | 4.569 | 1.00 | 48.96 | A | O |
| ATOM | 1326 | N | LEU A 196 | 29.141 | -41.709 | 5.852 | 1.00 | 48.26 | A | N |
| ATOM | 1327 | CA | LEU A 196 | 30.253 | -42.206 | 6.625 | 1.00 | 49.31 | A | C |
| ATOM | 1328 | CB | LEU A 196 | 29.763 | -42.873 | 7.899 | 1.00 | 48.08 | A | C |
| ATOM | 1329 | CG | LEU A 196 | 30.875 | -43.249 | 8.867 | 1.00 | 48.15 | A | C |
| ATOM | 1330 | CD1 | LEU A 196 | 31.753 | -42.047 | 9.188 | 1.00 | 46.72 | A | C |
| ATOM | 1331 | CD2 | LEU A 196 | 30.256 | -43.836 | 10.124 | 1.00 | 48.31 | A | C |
| ATOM | 1332 | C | LEU A 196 | 31.140 | -43.147 | 5.794 | 1.00 | 50.90 | A | C |
| ATOM | 1333 | O | LEU A 196 | 32.363 | -42.986 | 5.766 | 1.00 | 52.38 | A | O |
| ATOM | 1334 | N | ASN A 197 | 30.521 | -44.094 | 5.093 | 1.00 | 48.40 | A | N |
| ATOM | 1335 | CA | ASN A 197 | 31.267 | -45.096 | 4.313 | 1.00 | 46.74 | A | C |
| ATOM | 1336 | CB | ASN A 197 | 30.568 | -46.483 | 4.402 | 1.00 | 45.14 | A | C |
| ATOM | 1337 | CG | ASN A 197 | 30.334 | -46.897 | 5.839 | 1.00 | 44.12 | A | C |
| ATOM | 1338 | OD1 | ASN A 197 | 31.261 | -46.919 | 6.647 | 1.00 | 43.99 | A | O |
| ATOM | 1339 | ND2 | ASN A 197 | 29.092 | -47.223 | 6.169 | 1.00 | 43.44 | A | N |
| ATOM | 1340 | C | ASN A 197 | 31.541 | -44.683 | 2.859 | 1.00 | 45.00 | A | C |
| ATOM | 1341 | O | ASN A 197 | 31.771 | -45.555 | 2.009 | 1.00 | 44.07 | A | O |
| ATOM | 1342 | N | ASN A 198 | 31.516 | -43.392 | 2.584 | 1.00 | 47.35 | A | N |
| ATOM | 1343 | CA | ASN A 198 | 31.823 | -42.836 | 1.265 | 1.00 | 47.06 | A | C |
| ATOM | 1344 | CB | ASN A 198 | 30.593 | -42.302 | 0.347 | 1.00 | 46.49 | A | C |
| ATOM | 1345 | CG | ASN A 198 | 30.691 | -43.093 | -0.700 | 1.00 | 44.83 | A | C |
| ATOM | 1346 | OD1 | ASN A 198 | 29.885 | -44.030 | -0.693 | 1.00 | 43.95 | A | O |
| ATOM | 1347 | ND2 | ASN A 198 | 31.651 | -43.876 | -1.610 | 1.00 | 42.77 | A | N |
| ATOM | 1348 | C | ASN A 198 | 32.363 | -41.440 | 1.300 | 1.00 | 46.64 | A | C |
| ATOM | 1349 | O | ASN A 198 | 31.877 | -40.589 | 0.543 | 1.00 | 46.49 | A | O |
| ATOM | 1350 | N | PRO A 199 | 33.380 | -41.176 | 2.156 | 1.00 | 47.72 | A | N |
| ATOM | 1351 | CA | PRO A 199 | 33.896 | -39.788 | 2.239 | 1.00 | 48.20 | A | C |
| ATOM | 1352 | CB | PRO A 199 | 34.921 | -39.844 | 3.372 | 1.00 | 46.95 | A | C |
| ATOM | 1353 | CG | PRO A 199 | 35.276 | -41.291 | 3.535 | 1.00 | 46.17 | A | C |
| ATOM | 1354 | CD | PRO A 199 | 34.144 | -42.120 | 2.997 | 1.00 | 45.01 | A | C |
| ATOM | 1355 | C | PRO A 199 | 34.529 | -39.318 | 0.920 | 1.00 | 47.22 | A | C |
| ATOM | 1356 | O | PRO A 199 | 34.756 | -38.117 | 0.742 | 1.00 | 44.85 | A | O |
| ATOM | 1357 | N | GLN A 200 | 34.766 | -40.279 | 0.021 | 1.00 | 49.99 | A | N |
| ATOM | 1358 | CA | GLN A 200 | 35.339 | -40.078 | -1.313 | 1.00 | 50.12 | A | C |
| ATOM | 1359 | CB | GLN A 200 | 35.645 | -41.427 | -1.983 | 1.00 | 54.21 | A | C |
| ATOM | 1360 | CG | GLN A 200 | 35.333 | -42.676 | -1.162 | 1.00 | 60.60 | A | C |
| ATOM | 1361 | CD | GLN A 200 | 36.415 | -42.997 | -0.133 | 1.00 | 66.07 | A | C |
| ATOM | 1362 | OE1 | GLN A 200 | 36.835 | -42.119 | 0.646 | 1.00 | 68.52 | A | O |
| ATOM | 1363 | NE2 | GLN A 200 | 36.872 | -44.262 | -0.121 | 1.00 | 65.00 | A | N |
| ATOM | 1364 | C | GLN A 200 | 34.383 | -39.353 | -2.233 | 1.00 | 47.46 | A | C |
| ATOM | 1365 | O | GLN A 200 | 34.804 | -38.540 | -3.057 | 1.00 | 45.31 | A | O |
| ATOM | 1366 | N | ASP A 201 | 33.098 | -39.672 | -2.096 | 1.00 | 46.04 | A | N |
| ATOM | 1367 | CA | ASP A 201 | 32.071 | -39.202 | -3.006 | 1.00 | 46.35 | A | C |
| ATOM | 1368 | CB | ASP A 201 | 30.695 | -39.720 | -2.584 | 1.00 | 46.19 | A | C |
| ATOM | 1369 | CG | ASP A 201 | 29.659 | -39.594 | -3.688 | 1.00 | 46.75 | A | C |
| ATOM | 1370 | OD1 | ASP A 201 | 29.096 | -38.494 | -3.823 | 1.00 | 49.55 | A | O |
| ATOM | 1371 | OD2 | ASP A 201 | 29.392 | -40.582 | -4.412 | 1.00 | 44.57 | A | O |
| ATOM | 1372 | C | ASP A 201 | 32.092 | -37.687 | -3.063 | 1.00 | 51.08 | A | C |
| ATOM | 1373 | O | ASP A 201 | 32.023 | -37.021 | -2.019 | 1.00 | 54.01 | A | O |
| ATOM | 1374 | N | PRO A 202 | 32.214 | -37.133 | -4.285 | 1.00 | 50.77 | A | N |
| ATOM | 1375 | CA | PRO A 202 | 32.333 | -35.691 | -4.437 | 1.00 | 50.62 | A | C |
| ATOM | 1376 | CB | PRO A 202 | 32.306 | -35.492 | -5.959 | 1.00 | 50.93 | A | C |
| ATOM | 1377 | CG | PRO A 202 | 32.736 | -36.799 | -6.526 | 1.00 | 49.98 | A | C |
| ATOM | 1378 | CD | PRO A 202 | 32.197 | -37.831 | -5.583 | 1.00 | 50.15 | A | C |
| ATOM | 1379 | C | PRO A 202 | 31.174 | -34.946 | -3.760 | 1.00 | 52.35 | A | C |

FIG. 49 (CONT.)

| ATOM | 1380 | O | PRO | A | 202 | 31.398 | -33.943 | -3.061 | 1.00 | 52.34 | A | O |
|---|---|---|---|---|---|---|---|---|---|---|---|---|
| ATOM | 1381 | N | PHE | A | 203 | 29.955 | -35.447 | -3.940 | 1.00 | 51.98 | A | N |
| ATOM | 1382 | CA | PHE | A | 203 | 28.756 | -34.825 | -3.371 | 1.00 | 53.01 | A | C |
| ATOM | 1383 | CB | PHE | A | 203 | 27.523 | -35.588 | -3.838 | 1.00 | 54.97 | A | C |
| ATOM | 1384 | CG | PHE | A | 203 | 26.358 | -34.730 | -4.182 | 1.00 | 55.58 | A | C |
| ATOM | 1385 | CD1 | PHE | A | 203 | 26.134 | -34.257 | -5.481 | 1.00 | 57.92 | A | C |
| ATOM | 1386 | CE1 | PHE | A | 203 | 25.116 | -33.453 | -5.810 | 1.00 | 59.35 | A | C |
| ATOM | 1387 | CZ | PHE | A | 203 | 24.182 | -33.117 | -4.837 | 1.00 | 61.81 | A | C |
| ATOM | 1388 | CE2 | PHE | A | 203 | 24.331 | -33.530 | -3.539 | 1.00 | 57.65 | A | C |
| ATOM | 1389 | CD2 | PHE | A | 203 | 25.415 | -34.395 | -3.220 | 1.00 | 55.29 | A | C |
| ATOM | 1390 | C | PHE | A | 203 | 28.780 | -34.759 | -1.839 | 1.00 | 54.18 | A | C |
| ATOM | 1391 | O | PHE | A | 203 | 27.984 | -34.041 | -1.228 | 1.00 | 55.67 | A | O |
| ATOM | 1392 | N | VAL | A | 204 | 29.682 | -35.523 | -1.225 | 1.00 | 56.77 | A | N |
| ATOM | 1393 | CA | VAL | A | 204 | 29.842 | -35.536 | 0.234 | 1.00 | 60.44 | A | C |
| ATOM | 1394 | CB | VAL | A | 204 | 30.158 | -36.968 | 0.759 | 1.00 | 60.14 | A | C |
| ATOM | 1395 | CG1 | VAL | A | 204 | 30.761 | -36.952 | 2.160 | 1.00 | 60.76 | A | C |
| ATOM | 1396 | CG2 | VAL | A | 204 | 28.903 | -37.829 | 0.745 | 1.00 | 58.68 | A | C |
| ATOM | 1397 | C | VAL | A | 204 | 30.904 | -34.506 | 0.645 | 1.00 | 62.96 | A | C |
| ATOM | 1398 | O | VAL | A | 204 | 30.703 | -33.709 | 1.577 | 1.00 | 61.58 | A | O |
| ATOM | 1399 | N | GLU | A | 205 | 32.014 | -34.520 | -0.087 | 1.00 | 63.04 | A | N |
| ATOM | 1400 | CA | GLU | A | 205 | 33.139 | -33.621 | 0.144 | 1.00 | 65.32 | A | C |
| ATOM | 1401 | CB | GLU | A | 205 | 34.280 | -33.944 | -0.851 | 1.00 | 69.10 | A | C |
| ATOM | 1402 | CG | GLU | A | 205 | 35.455 | -32.968 | -0.898 | 1.00 | 77.85 | A | C |
| ATOM | 1403 | CD | GLU | A | 205 | 36.129 | -32.711 | 0.449 | 1.00 | 84.71 | A | C |
| ATOM | 1404 | OE1 | GLU | A | 205 | 35.592 | -33.107 | 1.515 | 1.00 | 86.89 | A | O |
| ATOM | 1405 | OE2 | GLU | A | 205 | 37.209 | -32.082 | 0.441 | 1.00 | 85.88 | A | O |
| ATOM | 1406 | C | GLU | A | 205 | 32.744 | -32.153 | 0.152 | 1.00 | 56.22 | A | C |
| ATOM | 1407 | O | GLU | A | 205 | 33.201 | -31.366 | 0.984 | 1.00 | 57.39 | A | O |
| ATOM | 1408 | N | ASN | A | 206 | 31.887 | -31.737 | -0.808 | 1.00 | 50.33 | A | N |
| ATOM | 1409 | CA | ASN | A | 206 | 31.441 | -30.337 | -0.894 | 1.00 | 47.69 | A | C |
| ATOM | 1410 | CB | ASN | A | 206 | 30.839 | -29.986 | -2.287 | 1.00 | 43.39 | A | C |
| ATOM | 1411 | CG | ASN | A | 206 | 31.960 | -30.082 | -3.361 | 1.00 | 43.39 | A | C |
| ATOM | 1412 | OD1 | ASN | A | 206 | 32.759 | -29.167 | -3.569 | 1.00 | 44.32 | A | O |
| ATOM | 1413 | ND2 | ASN | A | 206 | 31.978 | -31.198 | -4.048 | 1.00 | 45.09 | A | N |
| ATOM | 1414 | C | ASN | A | 206 | 30.437 | -29.972 | 0.195 | 1.00 | 44.64 | A | C |
| ATOM | 1415 | O | ASN | A | 206 | 30.676 | -29.057 | 0.988 | 1.00 | 41.90 | A | O |
| ATOM | 1416 | N | THR | A | 207 | 29.333 | -30.702 | 0.252 | 1.00 | 44.51 | A | N |
| ATOM | 1417 | CA | THR | A | 207 | 28.287 | -30.409 | 1.231 | 1.00 | 48.62 | A | C |
| ATOM | 1418 | CB | THR | A | 207 | 27.018 | -31.258 | 0.986 | 1.00 | 50.18 | A | C |
| ATOM | 1419 | OG1 | THR | A | 207 | 27.132 | -32.496 | -1.676 | 1.00 | 51.82 | A | O |
| ATOM | 1420 | CG2 | THR | A | 207 | 26.836 | -31.554 | -0.499 | 1.00 | 49.04 | A | C |
| ATOM | 1421 | C | THR | A | 207 | 28.769 | -30.464 | 2.712 | 1.00 | 49.67 | A | C |
| ATOM | 1422 | O | THR | A | 207 | 28.159 | -29.857 | 3.598 | 1.00 | 50.33 | A | O |
| ATOM | 1423 | N | LYS | A | 208 | 29.872 | -31.164 | 2.975 | 1.00 | 51.25 | A | N |
| ATOM | 1424 | CA | LYS | A | 208 | 30.505 | -31.120 | 4.302 | 1.00 | 51.33 | A | C |
| ATOM | 1425 | CB | LYS | A | 208 | 31.704 | -32.063 | 4.361 | 1.00 | 51.81 | A | C |
| ATOM | 1426 | CG | LYS | A | 208 | 31.425 | -33.401 | 5.017 | 1.00 | 53.71 | A | C |
| ATOM | 1427 | CD | LYS | A | 208 | 32.597 | -34.360 | 4.850 | 1.00 | 56.70 | A | C |
| ATOM | 1428 | CE | LYS | A | 208 | 32.589 | -35.494 | 5.869 | 1.00 | 58.36 | A | C |
| ATOM | 1429 | NZ | LYS | A | 208 | 32.949 | -35.012 | 7.230 | 1.00 | 58.95 | A | N |
| ATOM | 1430 | C | LYS | A | 208 | 30.954 | -29.708 | 4.685 | 1.00 | 51.69 | A | C |
| ATOM | 1431 | O | LYS | A | 208 | 30.914 | -29.341 | 5.851 | 1.00 | 52.10 | A | O |
| ATOM | 1432 | N | LYS | A | 209 | 31.387 | -28.931 | 3.698 | 1.00 | 52.59 | A | N |
| ATOM | 1433 | CA | LYS | A | 209 | 31.932 | -27.577 | 3.893 | 1.00 | 47.09 | A | C |
| ATOM | 1434 | CB | LYS | A | 209 | 32.843 | -27.196 | 2.729 | 1.00 | 47.22 | A | C |
| ATOM | 1435 | CG | LYS | A | 209 | 34.043 | -28.115 | 2.599 | 1.00 | 48.32 | A | C |
| ATOM | 1436 | CD | LYS | A | 209 | 34.867 | -27.752 | 1.395 | 1.00 | 49.12 | A | C |
| ATOM | 1437 | CE | LYS | A | 209 | 36.059 | -28.677 | 1.298 | 1.00 | 58.57 | A | C |
| ATOM | 1438 | NZ | LYS | A | 209 | 37.088 | -28.085 | 0.388 | 1.00 | 58.57 | A | N |
| ATOM | 1439 | C | LYS | A | 209 | 30.842 | -26.523 | 4.077 | 1.00 | 45.29 | A | C |
| ATOM | 1440 | O | LYS | A | 209 | 31.108 | -25.410 | 4.515 | 1.00 | 41.07 | A | O |
| ATOM | 1441 | N | LEU | A | 210 | 29.612 | -26.884 | 3.738 | 1.00 | 42.95 | A | N |
| ATOM | 1442 | CA | LEU | A | 210 | 28.477 | -26.025 | 3.994 | 1.00 | 42.70 | A | C |
| ATOM | 1443 | CB | LEU | A | 210 | 27.276 | -26.499 | 3.170 | 1.00 | 42.58 | A | C |

| ATOM | 1701 | CA  | PHE | A | 241 | 29.469 | -19.377 | 0.458  | 1.00 | 38.57 | A | C |
| ---- | ---- | --- | --- | - | --- | ------ | ------- | ------ | ---- | ----- | - | - |
| ATOM | 1702 | CB  | PHE | A | 241 | 28.094 | -19.530 | -0.193 | 1.00 | 35.83 | A | C |
| ATOM | 1703 | CG  | PHE | A | 241 | 26.962 | -19.283 | 0.757  | 1.00 | 35.39 | A | C |
| ATOM | 1704 | CD1 | PHE | A | 241 | 26.303 | -18.059 | 0.779  | 1.00 | 34.67 | A | C |
| ATOM | 1705 | CE1 | PHE | A | 241 | 25.265 | -17.825 | 1.659  | 1.00 | 32.59 | A | C |
| ATOM | 1706 | CZ  | PHE | A | 241 | 24.882 | -18.805 | 2.534  | 1.00 | 32.85 | A | C |
| ATOM | 1707 | CE2 | PHE | A | 241 | 25.508 | -20.018 | 2.533  | 1.00 | 35.41 | A | C |
| ATOM | 1708 | CD2 | PHE | A | 241 | 26.575 | -20.253 | 1.649  | 1.00 | 33.79 | A | C |
| ATOM | 1709 | C   | PHE | A | 241 | 30.593 | -19.735 | -0.496 | 1.00 | 37.92 | A | C |
| ATOM | 1710 | O   | PHE | A | 241 | 30.550 | -19.256 | -1.626 | 1.00 | 42.20 | A | O |
| ATOM | 1711 | N   | PRO | A | 242 | 31.535 | -20.567 | -0.032 | 1.00 | 41.21 | A | N |
| ATOM | 1712 | CA  | PRO | A | 242 | 32.753 | -20.896 | -0.797 | 1.00 | 42.09 | A | C |
| ATOM | 1713 | CB  | PRO | A | 242 | 33.323 | -22.115 | -0.071 | 1.00 | 41.19 | A | C |
| ATOM | 1714 | CG  | PRO | A | 242 | 32.247 | -22.599 | 0.858  | 1.00 | 40.44 | A | C |
| ATOM | 1715 | CD  | PRO | A | 242 | 31.412 | -21.401 | 1.183  | 1.00 | 39.71 | A | C |
| ATOM | 1716 | C   | PRO | A | 242 | 32.427 | -21.241 | -2.242 | 1.00 | 44.23 | A | C |
| ATOM | 1717 | O   | PRO | A | 242 | 31.498 | -22.010 | -2.461 | 1.00 | 46.74 | A | O |
| ATOM | 1718 | N   | ARG | A | 243 | 33.192 | -20.687 | -3.179 | 1.00 | 47.35 | A | N |
| ATOM | 1719 | CA  | ARG | A | 243 | 32.939 | -20.822 | -4.618 | 1.00 | 51.54 | A | C |
| ATOM | 1720 | CB  | ARG | A | 243 | 33.876 | -19.909 | -5.420 | 1.00 | 55.14 | A | C |
| ATOM | 1721 | CG  | ARG | A | 243 | 33.172 | -19.216 | -6.574 | 1.00 | 57.05 | A | C |
| ATOM | 1722 | CD  | ARG | A | 243 | 34.140 | -18.451 | -7.449 | 1.00 | 66.14 | A | C |
| ATOM | 1723 | NE  | ARG | A | 243 | 34.797 | -17.358 | -6.730 | 1.00 | 69.51 | A | N |
| ATOM | 1724 | CZ  | ARG | A | 243 | 35.982 | -16.867 | -7.048 | 1.00 | 70.70 | A | C |
| ATOM | 1725 | NH1 | ARG | A | 243 | 36.662 | -17.389 | -8.064 | 1.00 | 66.47 | A | N |
| ATOM | 1726 | NH2 | ARG | A | 243 | 36.503 | -15.864 | -6.343 | 1.00 | 72.86 | A | N |
| ATOM | 1727 | C   | ARG | A | 243 | 32.977 | -22.239 | -5.206 | 1.00 | 50.36 | A | C |
| ATOM | 1728 | O   | ARG | A | 243 | 32.153 | -22.570 | -6.054 | 1.00 | 50.25 | A | O |
| ATOM | 1729 | N   | GLU | A | 244 | 33.827 | -23.061 | -4.773 | 1.00 | 50.21 | A | N |
| ATOM | 1730 | CA  | GLU | A | 244 | 34.059 | -24.418 | -5.314 | 1.00 | 52.54 | A | C |
| ATOM | 1731 | CB  | GLU | A | 244 | 35.331 | -25.078 | -4.798 | 1.00 | 55.18 | A | C |
| ATOM | 1732 | CG  | GLU | A | 244 | 36.600 | -24.382 | -5.277 | 1.00 | 62.80 | A | C |
| ATOM | 1733 | CD  | GLU | A | 244 | 37.855 | -25.184 | -4.969 | 1.00 | 69.00 | A | C |
| ATOM | 1734 | OE1 | GLU | A | 244 | 39.025 | -25.583 | -3.789 | 1.00 | 76.40 | A | O |
| ATOM | 1735 | OE2 | GLU | A | 244 | 38.663 | -25.421 | -5.906 | 1.00 | 65.43 | A | O |
| ATOM | 1736 | C   | GLU | A | 244 | 32.837 | -25.285 | -5.000 | 1.00 | 52.51 | A | C |
| ATOM | 1737 | O   | GLU | A | 244 | 32.388 | -26.065 | -5.851 | 1.00 | 49.51 | A | O |
| ATOM | 1738 | N   | VAL | A | 245 | 32.305 | -25.118 | -3.784 | 1.00 | 47.75 | A | N |
| ATOM | 1739 | CA  | VAL | A | 245 | 31.107 | -25.820 | -3.324 | 1.00 | 46.05 | A | C |
| ATOM | 1740 | CB  | VAL | A | 245 | 30.858 | -25.618 | -1.814 | 1.00 | 47.78 | A | C |
| ATOM | 1741 | CG1 | VAL | A | 245 | 29.686 | -26.466 | -1.342 | 1.00 | 42.13 | A | C |
| ATOM | 1742 | CG2 | VAL | A | 245 | 32.107 | -25.937 | -1.012 | 1.00 | 52.16 | A | C |
| ATOM | 1743 | C   | VAL | A | 245 | 29.875 | -25.339 | -4.068 | 1.00 | 43.93 | A | C |
| ATOM | 1744 | O   | VAL | A | 245 | 29.107 | -26.146 | -4.582 | 1.00 | 43.23 | A | O |
| ATOM | 1745 | N   | THR | A | 246 | 29.670 | -24.026 | -4.126 | 1.00 | 40.87 | A | N |
| ATOM | 1746 | CA  | THR | A | 246 | 28.552 | -23.503 | -4.884 | 1.00 | 40.35 | A | C |
| ATOM | 1747 | CB  | THR | A | 246 | 28.353 | -21.984 | -4.888 | 1.00 | 37.99 | A | C |
| ATOM | 1748 | OG1 | THR | A | 246 | 29.596 | -21.314 | -4.855 | 1.00 | 38.21 | A | O |
| ATOM | 1749 | CG2 | THR | A | 246 | 27.856 | -21.694 | -3.307 | 1.00 | 35.93 | A | C |
| ATOM | 1750 | C   | THR | A | 246 | 28.683 | -23.900 | -6.375 | 1.00 | 43.29 | A | C |
| ATOM | 1751 | O   | THR | A | 246 | 27.870 | -24.283 | -6.993 | 1.00 | 46.34 | A | O |
| ATOM | 1752 | N   | ASN | A | 247 | 29.863 | -23.851 | -6.948 | 1.00 | 41.03 | A | N |
| ATOM | 1753 | CA  | ASN | A | 247 | 30.045 | -24.299 | -8.329 | 1.00 | 43.55 | A | C |
| ATOM | 1754 | CB  | ASN | A | 247 | 31.475 | -24.070 | -8.814 | 1.00 | 41.92 | A | C |
| ATOM | 1755 | CG  | ASN | A | 247 | 31.755 | -22.624 | -9.141 | 1.00 | 40.71 | A | C |
| ATOM | 1756 | OD1 | ASN | A | 247 | 32.806 | -22.203 | -9.181 | 1.00 | 40.89 | A | O |
| ATOM | 1757 | ND2 | ASN | A | 247 | 30.701 | -21.851 | -9.374 | 1.00 | 42.04 | A | N |
| ATOM | 1758 | C   | ASN | A | 247 | 29.643 | -25.753 | -8.571 | 1.00 | 44.05 | A | C |
| ATOM | 1759 | O   | ASN | A | 247 | 28.927 | -26.055 | -9.540 | 1.00 | 43.54 | A | O |
| ATOM | 1760 | N   | PHE | A | 248 | 30.099 | -26.645 | -7.690 | 1.00 | 44.01 | A | N |
| ATOM | 1761 | CA  | PHE | A | 248 | 29.805 | -28.073 | -7.821 | 1.00 | 41.88 | A | C |
| ATOM | 1762 | CB  | PHE | A | 248 | 30.357 | -28.899 | -6.769 | 1.00 | 41.52 | A | C |
| ATOM | 1763 | CG  | PHE | A | 248 | 30.339 | -30.393 | -6.880 | 1.00 | 44.43 | A | C |
| ATOM | 1764 | CD1 | PHE | A | 248 | 31.076 | -31.171 | -7.275 | 1.00 | 44.16 | A | C |
| ATOM | 1765 | CE1 | PHE | A | 248 | 30.868 | -32.543 | -7.872 | 1.00 | 43.90 | A | C |

| | | | | | | | | | | |
|---|---|---|---|---|---|---|---|---|---|---|
| ATOM | 1896 | C | VAL | A | 269 | 11.353 | -36.640 | -3.428 | 1.00 | 51.07 | A | C |
| ATOM | 1897 | O | VAL | A | 269 | 11.935 | -37.237 | -2.506 | 1.00 | 50.99 | A | O |
| ATOM | 1898 | N | ASP | A | 270 | 11.680 | -35.362 | -3.719 | 1.00 | 49.37 | A | N |
| ATOM | 1899 | CA | ASP | A | 270 | 12.603 | -34.577 | -3.042 | 1.00 | 45.98 | A | C |
| ATOM | 1900 | CB | ASP | A | 270 | 13.985 | -35.037 | -3.511 | 1.00 | 44.59 | A | C |
| ATOM | 1901 | CG | ASP | A | 270 | 14.101 | -35.072 | -5.023 | 1.00 | 47.21 | A | C |
| ATOM | 1902 | OD1 | ASP | A | 270 | 13.371 | -34.320 | -5.708 | 1.00 | 46.02 | A | O |
| ATOM | 1903 | OD2 | ASP | A | 270 | 14.927 | -35.853 | -5.534 | 1.00 | 49.09 | A | O |
| ATOM | 1904 | C | ASP | A | 270 | 12.401 | -33.079 | -3.317 | 1.00 | 43.13 | A | C |
| ATOM | 1905 | O | ASP | A | 270 | 11.559 | -32.688 | -4.142 | 1.00 | 42.07 | A | O |
| ATOM | 1906 | N | PHE | A | 271 | 13.181 | -32.246 | -2.641 | 1.00 | 39.40 | A | N |
| ATOM | 1907 | CA | PHE | A | 271 | 13.031 | -30.806 | -2.778 | 1.00 | 39.35 | A | C |
| ATOM | 1908 | CB | PHE | A | 271 | 13.895 | -30.074 | -1.756 | 1.00 | 39.87 | A | C |
| ATOM | 1909 | CG | PHE | A | 271 | 13.356 | -30.150 | -0.371 | 1.00 | 37.97 | A | C |
| ATOM | 1910 | CD1 | PHE | A | 271 | 12.161 | -29.515 | -0.045 | 1.00 | 36.74 | A | C |
| ATOM | 1911 | CE1 | PHE | A | 271 | 11.656 | -29.594 | 1.244 | 1.00 | 35.33 | A | C |
| ATOM | 1912 | CZ | PHE | A | 271 | 12.340 | -30.302 | 2.224 | 1.00 | 34.42 | A | C |
| ATOM | 1913 | CE2 | PHE | A | 271 | 13.533 | -30.923 | 1.915 | 1.00 | 36.74 | A | C |
| ATOM | 1914 | CD2 | PHE | A | 271 | 14.036 | -30.848 | 0.618 | 1.00 | 39.56 | A | C |
| ATOM | 1915 | C | PHE | A | 271 | 13.302 | -30.287 | -4.186 | 1.00 | 38.63 | A | C |
| ATOM | 1916 | O | PHE | A | 271 | 12.676 | -29.327 | -4.624 | 1.00 | 35.58 | A | O |
| ATOM | 1917 | N | LEU | A | 272 | 14.227 | -30.917 | -4.892 | 1.00 | 35.96 | A | N |
| ATOM | 1918 | CA | LEU | A | 272 | 14.514 | -30.499 | -6.251 | 1.00 | 37.82 | A | C |
| ATOM | 1919 | CB | LEU | A | 272 | 15.649 | -31.328 | -6.876 | 1.00 | 37.80 | A | C |
| ATOM | 1920 | CG | LEU | A | 272 | 16.000 | -31.065 | -8.349 | 1.00 | 38.12 | A | C |
| ATOM | 1921 | CD1 | LEU | A | 272 | 15.998 | -29.577 | -8.685 | 1.00 | 39.82 | A | C |
| ATOM | 1922 | CD2 | LEU | A | 272 | 17.353 | -31.651 | -8.704 | 1.00 | 38.42 | A | C |
| ATOM | 1923 | C | LEU | A | 272 | 13.239 | -30.620 | -7.061 | 1.00 | 39.65 | A | C |
| ATOM | 1924 | O | LEU | A | 272 | 12.812 | -29.657 | -7.702 | 1.00 | 39.63 | A | O |
| ATOM | 1925 | N | GLN | A | 273 | 12.622 | -31.798 | -7.002 | 1.00 | 41.11 | A | N |
| ATOM | 1926 | CA | GLN | A | 273 | 11.437 | -32.091 | -7.799 | 1.00 | 43.06 | A | C |
| ATOM | 1927 | CB | GLN | A | 273 | 10.975 | -33.531 | -7.553 | 1.00 | 45.51 | A | C |
| ATOM | 1928 | CG | GLN | A | 273 | 10.273 | -34.171 | -8.739 | 1.00 | 46.77 | A | C |
| ATOM | 1929 | CD | GLN | A | 273 | 10.986 | -33.878 | -10.046 | 1.00 | 47.99 | A | C |
| ATOM | 1930 | OE1 | GLN | A | 273 | 12.207 | -34.049 | -10.158 | 1.00 | 52.02 | A | O |
| ATOM | 1931 | NE2 | GLN | A | 273 | 10.236 | -33.408 | -11.032 | 1.00 | 44.64 | A | N |
| ATOM | 1932 | C | GLN | A | 273 | 10.785 | -31.105 | -7.529 | 1.00 | 44.03 | A | C |
| ATOM | 1933 | O | GLN | A | 273 | 9.782 | -30.459 | -8.459 | 1.00 | 42.72 | A | O |
| ATOM | 1934 | N | LEU | A | 274 | 9.935 | -30.981 | -6.249 | 1.00 | 42.04 | A | N |
| ATOM | 1935 | CA | LEU | A | 274 | 8.853 | -30.118 | -5.801 | 1.00 | 40.04 | A | C |
| ATOM | 1936 | CB | LEU | A | 274 | 8.770 | -30.150 | -4.274 | 1.00 | 40.04 | A | C |
| ATOM | 1937 | CG | LEU | A | 274 | 9.371 | -31.471 | -3.595 | 1.00 | 40.62 | A | C |
| ATOM | 1938 | CD1 | LEU | A | 274 | 8.724 | -31.467 | -2.115 | 1.00 | 38.00 | A | C |
| ATOM | 1939 | CD2 | LEU | A | 274 | 8.893 | -31.791 | -4.786 | 1.00 | 39.49 | A | C |
| ATOM | 1940 | C | LEU | A | 274 | 9.054 | -28.684 | -6.296 | 1.00 | 39.94 | A | C |
| ATOM | 1941 | O | LEU | A | 274 | 8.090 | -27.955 | -6.544 | 1.00 | 39.30 | A | O |
| ATOM | 1942 | N | MET | A | 275 | 10.315 | -28.292 | -6.442 | 1.00 | 40.04 | A | N |
| ATOM | 1943 | CA | MET | A | 275 | 10.649 | -26.953 | -6.946 | 1.00 | 41.90 | A | C |
| ATOM | 1944 | CB | MET | A | 275 | 12.020 | -26.489 | -6.440 | 1.00 | 41.78 | A | C |
| ATOM | 1945 | CG | MET | A | 275 | 12.043 | -26.114 | -4.952 | 1.00 | 41.85 | A | C |
| ATOM | 1946 | SD | MET | A | 275 | 13.614 | -25.422 | -4.381 | 1.00 | 40.19 | A | S |
| ATOM | 1947 | CE | MET | A | 275 | 13.723 | -24.061 | -5.534 | 1.00 | 44.65 | A | C |
| ATOM | 1948 | C | MET | A | 275 | 10.578 | -26.968 | -8.457 | 1.00 | 41.55 | A | C |
| ATOM | 1949 | O | MET | A | 275 | 10.012 | -26.052 | -9.043 | 1.00 | 41.94 | A | O |
| ATOM | 1950 | N | ILE | A | 276 | 11.117 | -28.013 | -9.083 | 1.00 | 43.14 | A | N |
| ATOM | 1951 | CA | ILE | A | 276 | 11.038 | -28.141 | -10.540 | 1.00 | 45.47 | A | C |
| ATOM | 1952 | CB | ILE | A | 276 | 11.630 | -29.470 | -11.063 | 1.00 | 43.23 | A | C |
| ATOM | 1953 | CG1 | ILE | A | 276 | 13.161 | -29.385 | -11.104 | 1.00 | 42.03 | A | C |
| ATOM | 1954 | CD1 | ILE | A | 276 | 13.869 | -30.645 | -11.570 | 1.00 | 40.02 | A | C |
| ATOM | 1955 | CG2 | ILE | A | 276 | 11.079 | -29.786 | -12.453 | 1.00 | 41.47 | A | C |
| ATOM | 1956 | C | ILE | A | 276 | 9.588 | -28.011 | -10.986 | 1.00 | 47.73 | A | C |
| ATOM | 1957 | O | ILE | A | 276 | 9.298 | -27.446 | -12.040 | 1.00 | 46.69 | A | O |
| ATOM | 1958 | N | ASP | A | 277 | 8.689 | -28.509 | -10.145 | 1.00 | 51.09 | A | N |
| ATOM | 1959 | CA | ASP | A | 277 | 7.276 | -28.570 | -10.472 | 1.00 | 54.27 | A | C |
| ATOM | 1960 | CB | ASP | A | 277 | 6.562 | -29.566 | -9.558 | 1.00 | 54.32 | A | C |

FIG. 49 (CONT.)

| ATOM | 1961 | CG | ASP A 277 | 6.813 | -30.994 | -10.005 | 1.00 | 57.13 | A | C |
| ATOM | 1962 | OD1 | ASP A 277 | 7.679 | -31.199 | -10.895 | 1.00 | 55.52 | A | O |
| ATOM | 1963 | OD2 | ASP A 277 | 6.131 | -31.906 | -9.488 | 1.00 | 57.82 | A | O |
| ATOM | 1964 | C | ASP A 277 | 6.549 | -27.225 | -10.512 | 1.00 | 56.33 | A | C |
| ATOM | 1965 | O | ASP A 277 | 5.630 | -27.036 | -11.323 | 1.00 | 55.26 | A | O |
| ATOM | 1966 | N | SER A 278 | 6.268 | -26.291 | -9.662 | 1.00 | 54.57 | A | N |
| ATOM | 1967 | CA | SER A 278 | 6.417 | -24.944 | -9.717 | 1.00 | 54.10 | A | C |
| ATOM | 1968 | CB | SER A 278 | 6.427 | -24.292 | -8.334 | 1.00 | 53.72 | A | C |
| ATOM | 1969 | OG | SER A 278 | 7.656 | -24.525 | -7.669 | 1.00 | 51.82 | A | O |
| ATOM | 1970 | C | SER A 278 | 7.140 | -24.086 | -10.761 | 1.00 | 54.46 | A | C |
| ATOM | 1971 | O | SER A 278 | 7.318 | -22.884 | -10.573 | 1.00 | 54.91 | A | O |
| ATOM | 1972 | N | GLN A 279 | 7.591 | -24.716 | -11.860 | 1.00 | 53.12 | A | N |
| ATOM | 1973 | CA | GLN A 279 | 8.086 | -23.997 | -13.022 | 1.00 | 52.53 | A | C |
| ATOM | 1974 | CB | GLN A 279 | 9.587 | -24.272 | -13.200 | 1.00 | 51.63 | A | C |
| ATOM | 1975 | CG | GLN A 279 | 10.485 | -23.688 | -12.113 | 1.00 | 47.83 | A | C |
| ATOM | 1976 | CD | GLN A 279 | 11.972 | -23.808 | -12.430 | 1.00 | 46.21 | A | C |
| ATOM | 1977 | OE1 | GLN A 279 | 12.684 | -22.807 | -12.499 | 1.00 | 45.87 | A | O |
| ATOM | 1978 | NE2 | GLN A 279 | 12.445 | -25.033 | -12.619 | 1.00 | 45.08 | A | N |
| ATOM | 1979 | C | GLN A 279 | 7.324 | -24.360 | -14.307 | 1.00 | 51.33 | A | C |
| ATOM | 1980 | O | GLN A 279 | 6.440 | -25.231 | -14.309 | 1.00 | 49.37 | A | O |
| ATOM | 1981 | N | HIS A 287 | 3.298 | -11.432 | -8.951 | 1.00 | 83.29 | A | N |
| ATOM | 1982 | CA | HIS A 287 | 4.472 | -12.293 | -8.873 | 1.00 | 81.75 | A | C |
| ATOM | 1983 | CB | HIS A 287 | 5.256 | -12.034 | -7.580 | 1.00 | 79.22 | A | C |
| ATOM | 1984 | CG | HIS A 287 | 4.716 | -12.776 | -6.364 | 1.00 | 77.32 | A | C |
| ATOM | 1985 | ND1 | HIS A 287 | 4.641 | -14.127 | -6.396 | 1.00 | 74.20 | A | N |
| ATOM | 1986 | CE1 | HIS A 287 | 4.124 | -14.497 | -5.121 | 1.00 | 71.75 | A | C |
| ATOM | 1987 | NE2 | HIS A 287 | 3.887 | -13.383 | -4.404 | 1.00 | 74.08 | A | N |
| ATOM | 1988 | CD2 | HIS A 287 | 4.242 | -12.306 | -5.140 | 1.00 | 75.05 | A | C |
| ATOM | 1989 | C | HIS A 287 | 4.119 | -13.766 | -8.963 | 1.00 | 82.26 | A | C |
| ATOM | 1990 | O | HIS A 287 | 3.108 | -14.205 | -8.397 | 1.00 | 79.42 | A | O |
| ATOM | 1991 | N | LYS A 288 | 4.945 | -14.521 | -9.693 | 1.00 | 80.69 | A | N |
| ATOM | 1992 | CA | LYS A 288 | 5.021 | -15.994 | -9.392 | 1.00 | 76.62 | A | C |
| ATOM | 1993 | CB | LYS A 288 | 3.682 | -16.710 | -9.843 | 1.00 | 76.02 | A | C |
| ATOM | 1994 | CG | LYS A 288 | 2.892 | -16.360 | -11.115 | 1.00 | 77.75 | A | C |
| ATOM | 1995 | CD | LYS A 288 | 1.708 | -15.398 | -10.897 | 1.00 | 75.16 | A | C |
| ATOM | 1996 | CE | LYS A 288 | 0.805 | -15.772 | -9.724 | 1.00 | 71.24 | A | C |
| ATOM | 1997 | NZ | LYS A 288 | 0.322 | -17.177 | -9.774 | 1.00 | 68.86 | A | N |
| ATOM | 1998 | C | LYS A 288 | 6.152 | -16.613 | -10.410 | 1.00 | 73.29 | A | C |
| ATOM | 1999 | O | LYS A 288 | 6.858 | -15.913 | -11.183 | 1.00 | 71.39 | A | O |
| ATOM | 2000 | N | ALA A 289 | 6.409 | -17.915 | -10.185 | 1.00 | 67.84 | A | N |
| ATOM | 2001 | CA | ALA A 289 | 7.409 | -18.770 | -10.877 | 1.00 | 61.66 | A | C |
| ATOM | 2002 | CB | ALA A 289 | 7.177 | -18.798 | -12.387 | 1.00 | 65.38 | A | C |
| ATOM | 2003 | C | ALA A 289 | 8.898 | -18.535 | -10.550 | 1.00 | 57.77 | A | C |
| ATOM | 2004 | O | ALA A 289 | 9.509 | -17.549 | -10.986 | 1.00 | 54.56 | A | O |
| ATOM | 2005 | N | LEU A 290 | 9.466 | -19.480 | -9.786 | 1.00 | 52.93 | A | N |
| ATOM | 2006 | CA | LEU A 290 | 10.903 | -19.551 | -9.483 | 1.00 | 49.84 | A | C |
| ATOM | 2007 | CB | LEU A 290 | 11.186 | -20.766 | -8.591 | 1.00 | 46.89 | A | C |
| ATOM | 2008 | CG | LEU A 290 | 11.228 | -20.664 | -7.062 | 1.00 | 44.91 | A | C |
| ATOM | 2009 | CD1 | LEU A 290 | 10.687 | -21.931 | -6.406 | 1.00 | 40.39 | A | C |
| ATOM | 2010 | CD2 | LEU A 290 | 12.647 | -20.374 | -6.600 | 1.00 | 43.45 | A | C |
| ATOM | 2011 | C | LEU A 290 | 11.721 | -19.696 | -10.760 | 1.00 | 47.33 | A | C |
| ATOM | 2012 | O | LEU A 290 | 11.392 | -20.519 | -11.617 | 1.00 | 44.79 | A | O |
| ATOM | 2013 | N | SER A 291 | 12.784 | -18.902 | -10.879 | 1.00 | 47.04 | A | N |
| ATOM | 2014 | CA | SER A 291 | 13.708 | -18.995 | -12.014 | 1.00 | 46.89 | A | C |
| ATOM | 2015 | CB | SER A 291 | 14.411 | -17.663 | -12.237 | 1.00 | 46.40 | A | C |
| ATOM | 2016 | OG | SER A 291 | 15.159 | -17.310 | -11.093 | 1.00 | 47.42 | A | O |
| ATOM | 2017 | C | SER A 291 | 14.752 | -20.079 | -11.771 | 1.00 | 49.27 | A | C |
| ATOM | 2018 | O | SER A 291 | 14.749 | -20.716 | -10.713 | 1.00 | 52.13 | A | O |
| ATOM | 2019 | N | ASP A 292 | 15.642 | -20.286 | -12.745 | 1.00 | 48.13 | A | N |
| ATOM | 2020 | CA | ASP A 292 | 16.724 | -21.259 | -12.604 | 1.00 | 46.61 | A | C |
| ATOM | 2021 | CB | ASP A 292 | 17.527 | -21.405 | -13.898 | 1.00 | 47.51 | A | C |
| ATOM | 2022 | CG | ASP A 292 | 17.121 | -22.635 | -14.713 | 1.00 | 49.81 | A | C |
| ATOM | 2023 | OD1 | ASP A 292 | 17.839 | -22.957 | -15.669 | 1.00 | 48.40 | A | O |
| ATOM | 2024 | OD2 | ASP A 292 | 16.099 | -23.288 | -14.382 | 1.00 | 48.77 | A | O |
| ATOM | 2025 | C | ASP A 292 | 17.652 | -20.911 | -11.453 | 1.00 | 46.80 | A | C |

```
ATOM   2091  CD1 ILE A 301      21.229 -19.760   2.557  1.00 25.97           A    C
ATOM   2092  CG2 ILE A 301      18.061 -21.554   1.282  1.00 29.32           A    C
ATOM   2093  C   ILE A 301      19.675 -23.725   2.348  1.00 32.77           A    C
ATOM   2094  O   ILE A 301      19.822 -23.650   3.568  1.00 30.61           A    O
ATOM   2095  N   PHE A 302      18.938 -24.695   1.750  1.00 33.53           A    N
ATOM   2096  CA  PHE A 302      18.337 -25.789   2.531  1.00 33.26           A    C
ATOM   2097  CB  PHE A 302      17.355 -26.653   1.733  1.00 34.06           A    C
ATOM   2098  CG  PHE A 302      16.174 -25.913   1.176  1.00 34.57           A    C
ATOM   2099  CD1 PHE A 302      15.644 -24.808   1.825  1.00 33.55           A    C
ATOM   2100  CE1 PHE A 302      14.568 -24.116   1.298  1.00 34.23           A    C
ATOM   2101  CZ  PHE A 302      13.980 -24.553   0.118  1.00 36.85           A    C
ATOM   2102  CE2 PHE A 302      14.490 -25.666  -0.539  1.00 36.57           A    C
ATOM   2103  CD2 PHE A 302      15.585 -26.339  -0.007  1.00 35.24           A    C
ATOM   2104  C   PHE A 302      19.409 -26.690   3.127  1.00 34.14           A    C
ATOM   2105  O   PHE A 302      19.263 -27.167   4.276  1.00 39.79           A    O
ATOM   2106  N   ILE A 303      20.475 -26.931   2.367  1.00 29.97           A    N
ATOM   2107  CA  ILE A 303      21.604 -27.674   2.904  1.00 31.04           A    C
ATOM   2108  CB  ILE A 303      22.621 -28.040   1.831  1.00 30.82           A    C
ATOM   2109  CG1 ILE A 303      21.950 -28.892   0.740  1.00 31.19           A    C
ATOM   2110  CD1 ILE A 303      22.884 -29.302  -0.374  1.00 31.99           A    C
ATOM   2111  CG2 ILE A 303      23.793 -28.761   2.474  1.00 30.95           A    C
ATOM   2112  C   ILE A 303      22.293 -26.931   4.048  1.00 32.65           A    C
ATOM   2113  O   ILE A 303      22.441 -27.457   5.155  1.00 34.32           A    O
ATOM   2114  N   PHE A 304      22.675 -25.696   3.782  1.00 33.14           A    N
ATOM   2115  CA  PHE A 304      23.282 -24.824   4.775  1.00 36.23           A    C
ATOM   2116  CB  PHE A 304      23.524 -23.465   4.127  1.00 37.83           A    C
ATOM   2117  CG  PHE A 304      23.919 -22.389   5.086  1.00 38.49           A    C
ATOM   2118  CD1 PHE A 304      25.216 -22.330   5.588  1.00 37.38           A    C
ATOM   2119  CE1 PHE A 304      25.587 -21.317   6.461  1.00 35.64           A    C
ATOM   2120  CZ  PHE A 304      24.669 -20.338   6.821  1.00 36.75           A    C
ATOM   2121  CE2 PHE A 304      23.370 -20.380   6.322  1.00 38.47           A    C
ATOM   2122  CD2 PHE A 304      23.004 -21.393   5.445  1.00 37.29           A    C
ATOM   2123  C   PHE A 304      22.461 -24.664   6.065  1.00 36.18           A    C
ATOM   2124  O   PHE A 304      23.003 -24.690   7.158  1.00 40.79           A    O
ATOM   2125  N   ALA A 305      21.156 -24.503   5.938  1.00 34.53           A    N
ATOM   2126  CA  ALA A 305      20.316 -24.214   7.089  1.00 35.22           A    C
ATOM   2127  CB  ALA A 305      19.043 -23.530   6.617  1.00 34.09           A    C
ATOM   2128  C   ALA A 305      19.985 -25.480   7.916  1.00 38.24           A    C
ATOM   2129  O   ALA A 305      19.577 -25.397   9.095  1.00 36.79           A    O
ATOM   2130  N   GLY A 306      20.169 -26.647   7.303  1.00 37.07           A    N
ATOM   2131  CA  GLY A 306      19.677 -27.868   7.898  1.00 36.81           A    C
ATOM   2132  C   GLY A 306      20.721 -28.899   8.284  1.00 36.96           A    C
ATOM   2133  O   GLY A 306      20.428 -29.826   9.037  1.00 37.04           A    O
ATOM   2134  N   TYR A 307      21.930 -28.724   7.762  1.00 36.02           A    N
ATOM   2135  CA  TYR A 307      22.976 -29.716   7.965  1.00 37.07           A    C
ATOM   2136  CB  TYR A 307      24.028 -29.610   6.863  1.00 36.64           A    C
ATOM   2137  CG  TYR A 307      25.306 -30.393   7.070  1.00 36.96           A    C
ATOM   2138  CD1 TYR A 307      26.551 -29.774   6.913  1.00 37.07           A    C
ATOM   2139  CE1 TYR A 307      27.729 -30.490   7.076  1.00 37.67           A    C
ATOM   2140  CZ  TYR A 307      27.673 -31.830   7.405  1.00 40.22           A    C
ATOM   2141  OH  TYR A 307      28.829 -32.536   7.558  1.00 39.61           A    O
ATOM   2142  CE2 TYR A 307      26.455 -32.476   7.567  1.00 39.87           A    C
ATOM   2143  CD2 TYR A 307      25.280 -31.751   7.396  1.00 39.63           A    C
ATOM   2144  C   TYR A 307      23.610 -29.678   9.357  1.00 39.01           A    C
ATOM   2145  O   TYR A 307      23.539 -30.671  10.087  1.00 39.89           A    O
ATOM   2146  N   GLU A 308      24.236 -28.561   9.721  1.00 38.33           A    N
ATOM   2147  CA  GLU A 308      24.989 -28.522  10.974  1.00 40.62           A    C
ATOM   2148  CB  GLU A 308      26.175 -27.541  10.902  1.00 43.85           A    C
ATOM   2149  CG  GLU A 308      26.615 -26.917  12.224  1.00 46.89           A    C
ATOM   2150  CD  GLU A 308      28.103 -26.569  12.261  1.00 52.33           A    C
ATOM   2151  OE1 GLU A 308      28.488 -25.559  11.638  1.00 55.69           A    O
ATOM   2152  OE2 GLU A 308      28.897 -27.291  12.928  1.00 51.31           A    O
ATOM   2153  C   GLU A 308      24.037 -28.190  12.102  1.00 41.51           A    C
ATOM   2154  O   GLU A 308      24.356 -28.403  13.265  1.00 42.61           A    O
ATOM   2155  N   THR A 309      22.860 -27.687  11.763  1.00 40.04           A    N
```

```
ATOM   2221  N    MET A 318      21.362 -36.107  22.841  1.00 41.02           A          N
ATOM   2222  CA   MET A 318      21.945 -37.338  23.362  1.00 40.80           A          C
ATOM   2223  CB   MET A 318      22.760 -38.060  22.298  1.00 43.90           A          C
ATOM   2224  CG   MET A 318      21.935 -38.735  21.223  1.00 48.42           A          C
ATOM   2225  SD   MET A 318      20.509 -39.656  21.840  1.00 56.99           A          S
ATOM   2226  CE   MET A 318      21.230 -40.869  22.922  1.00 46.51           A          C
ATOM   2227  C    MET A 318      22.814 -37.099  24.587  1.00 39.39           A          C
ATOM   2228  O    MET A 318      22.928 -37.975  25.438  1.00 39.94           A          O
ATOM   2229  N    TYR A 319      23.446 -35.929  24.653  1.00 37.77           A          N
ATOM   2230  CA   TYR A 319      24.193 -35.520  25.837  1.00 35.77           A          C
ATOM   2231  CB   TYR A 319      24.833 -34.133  25.661  1.00 34.53           A          C
ATOM   2232  CG   TYR A 319      25.383 -33.542  26.953  1.00 33.29           A          C
ATOM   2233  CD1  TYR A 319      26.654 -33.906  27.428  1.00 32.99           A          C
ATOM   2234  CE1  TYR A 319      27.165 -33.363  28.604  1.00 31.85           A          C
ATOM   2235  CZ   TYR A 319      26.391 -32.475  29.333  1.00 32.63           A          C
ATOM   2236  OH   TYR A 319      26.885 -31.951  30.505  1.00 34.97           A          O
ATOM   2237  CD2  TYR A 319      25.123 -32.115  28.901  1.00 32.54           A          C
ATOM   2238  CE2  TYR A 319      24.626 -32.646  27.715  1.00 32.95           A          C
ATOM   2239  C    TYR A 319      23.255 -35.498  27.022  1.00 35.81           A          C
ATOM   2240  O    TYR A 319      23.540 -36.092  28.051  1.00 36.28           A          O
ATOM   2241  N    GLU A 320      22.131 -34.805  26.870  1.00 38.88           A          N
ATOM   2242  CA   GLU A 320      21.122 -34.750  27.926  1.00 38.32           A          C
ATOM   2243  CB   GLU A 320      19.994 -33.707  27.560  1.00 37.41           A          C
ATOM   2244  CG   GLU A 320      20.450 -32.344  27.378  1.00 39.56           A          C
ATOM   2245  CD   GLU A 320      21.244 -31.806  28.551  1.00 40.10           A          C
ATOM   2246  OE1  GLU A 320      21.937 -30.785  28.307  1.00 42.63           A          O
ATOM   2247  OE2  GLU A 320      21.189 -32.400  29.636  1.00 41.09           A          O
ATOM   2248  C    GLU A 320      20.568 -36.120  28.280  1.00 38.22           A          C
ATOM   2249  O    GLU A 320      20.406 -36.423  29.457  1.00 40.25           A          O
ATOM   2250  N    LEU A 321      20.296 -36.957  27.283  1.00 35.67           A          N
ATOM   2251  CA   LEU A 321      19.835 -38.313  27.567  1.00 37.24           A          C
ATOM   2252  CB   LEU A 321      19.401 -39.042  26.277  1.00 35.50           A          C
ATOM   2253  CG   LEU A 321      18.247 -38.491  25.429  1.00 32.30           A          C
ATOM   2254  CD1  LEU A 321      17.913 -39.431  24.298  1.00 31.18           A          C
ATOM   2255  CD2  LEU A 321      17.016 -38.220  26.270  1.00 32.70           A          C
ATOM   2256  C    LEU A 321      20.870 -39.152  28.255  1.00 39.29           A          C
ATOM   2257  O    LEU A 321      20.506 -39.947  29.230  1.00 37.31           A          O
ATOM   2258  N    ALA A 322      22.152 -38.967  28.040  1.00 39.13           A          N
ATOM   2259  CA   ALA A 322      23.231 -39.736  28.670  1.00 38.49           A          C
ATOM   2260  CB   ALA A 322      24.484 -39.695  27.814  1.00 39.79           A          C
ATOM   2261  C    ALA A 322      23.590 -39.239  30.063  1.00 38.84           A          C
ATOM   2262  O    ALA A 322      23.930 -40.026  30.925  1.00 39.58           A          O
ATOM   2263  N    THR A 323      23.424 -37.929  30.277  1.00 38.76           A          N
ATOM   2264  CA   THR A 323      23.633 -37.352  31.608  1.00 39.25           A          C
ATOM   2265  CB   THR A 323      24.260 -35.938  31.560  1.00 36.41           A          C
ATOM   2266  OG1  THR A 323      23.374 -35.011  30.924  1.00 37.39           A          O
ATOM   2267  CG2  THR A 323      25.572 -35.966  30.807  1.00 35.82           A          C
ATOM   2268  C    THR A 323      22.359 -37.335  32.468  1.00 39.87           A          C
ATOM   2269  O    THR A 323      22.387 -37.627  33.649  1.00 40.97           A          O
ATOM   2270  N    HIS A 324      21.259 -37.066  31.873  1.00 39.73           A          N
ATOM   2271  CA   HIS A 324      20.008 -38.098  32.396  1.00 40.67           A          C
ATOM   2272  CB   HIS A 324      19.026 -36.959  32.316  1.00 39.91           A          C
ATOM   2273  CG   HIS A 324      19.522 -35.594  32.752  1.00 41.21           A          C
ATOM   2274  ND1  HIS A 324      20.349 -34.840  31.929  1.00 42.33           A          N
ATOM   2275  CE1  HIS A 324      20.610 -33.671  32.622  1.00 40.14           A          C
ATOM   2276  NE2  HIS A 324      19.942 -33.675  33.790  1.00 41.36           A          N
ATOM   2277  CD2  HIS A 324      19.264 -34.848  33.905  1.00 39.73           A          C
ATOM   2278  C    HIS A 324      19.391 -34.462  32.282  1.00 41.05           A          C
ATOM   2279  O    HIS A 324      19.326 -39.541  31.655  1.00 44.12           A          O
ATOM   2280  N    PRO A 325      20.030 -40.564  32.740  1.00 39.43           A          N
ATOM   2281  CA   PRO A 325      19.621 -41.929  32.347  1.00 37.94           A          C
ATOM   2282  CB   PRO A 325      20.536 -42.831  33.191  1.00 38.51           A          C
ATOM   2283  CG   PRO A 325      20.898 -41.993  34.357  1.00 39.83           A          C
ATOM   2284  CD   PRO A 325      21.051 -40.600  33.801  1.00 40.09           A          C
ATOM   2285  C    PRO A 325      19.166 -42.273  32.640  1.00 35.59           A          C
```

FIG. 49 (CONT.)

```
ATOM   2286  O   PRO A 325      17.642 -43.203  32.035  1.00 34.68           A    O
ATOM   2287  N   ASP A 326      17.536 -41.541  33.563  1.00 35.09           A    N
ATOM   2288  CA  ASP A 326      16.102 -41.703  33.859  1.00 34.53           A    C
ATOM   2289  CB  ASP A 326      15.685 -40.852  35.151  1.00 37.82           A    C
ATOM   2290  CG  ASP A 326      16.241 -39.520  35.236  1.00 41.12           A    C
ATOM   2291  OD1 ASP A 326      17.476 -39.342  35.163  1.00 40.93           A    O
ATOM   2292  OD2 ASP A 326      15.441 -38.570  35.405  1.00 43.62           A    O
ATOM   2293  C   ASP A 326      15.249 -41.293  32.657  1.00 30.75           A    C
ATOM   2294  O   ASP A 326      14.457 -42.060  32.122  1.00 28.19           A    O
ATOM   2295  N   VAL A 327      15.453 -40.050  32.224  1.00 30.18           A    N
ATOM   2296  CA  VAL A 327      14.822 -39.521  31.026  1.00 29.07           A    C
ATOM   2297  CB  VAL A 327      15.324 -38.090  30.745  1.00 28.42           A    C
ATOM   2298  CG1 VAL A 327      14.694 -37.531  29.473  1.00 30.38           A    C
ATOM   2299  CG2 VAL A 327      15.048 -37.182  31.944  1.00 26.46           A    C
ATOM   2300  C   VAL A 327      15.080 -40.468  29.851  1.00 28.35           A    C
ATOM   2301  O   VAL A 327      14.159 -40.765  29.072  1.00 26.80           A    O
ATOM   2302  N   GLN A 328      16.314 -40.976  29.760  1.00 28.49           A    N
ATOM   2303  CA  GLN A 328      16.680 -41.909  28.699  1.00 29.15           A    C
ATOM   2304  CB  GLN A 328      16.148 -42.345  28.783  1.00 29.82           A    C
ATOM   2305  CG  GLN A 328      18.592 -43.151  27.551  1.00 31.80           A    C
ATOM   2306  CD  GLN A 328      20.104 -43.245  27.349  1.00 32.89           A    C
ATOM   2307  OE1 GLN A 328      20.569 -44.078  26.570  1.00 33.43           A    O
ATOM   2308  NE2 GLN A 328      20.873 -42.378  28.018  1.00 32.57           A    N
ATOM   2309  C   GLN A 328      15.781 -43.116  28.727  1.00 28.95           A    C
ATOM   2310  O   GLN A 328      15.209 -43.497  27.712  1.00 29.29           A    O
ATOM   2311  N   GLN A 329      15.698 -43.701  29.914  1.00 29.63           A    N
ATOM   2312  CA  GLN A 329      14.823 -44.868  30.126  1.00 29.28           A    C
ATOM   2313  CB  GLN A 329      15.005 -45.424  31.552  1.00 29.09           A    C
ATOM   2314  CG  GLN A 329      13.979 -46.483  31.949  1.00 27.09           A    C
ATOM   2315  CD  GLN A 329      14.386 -47.322  33.149  1.00 26.85           A    C
ATOM   2316  OE1 GLN A 329      15.266 -46.950  33.927  1.00 27.39           A    O
ATOM   2317  NE2 GLN A 329      13.708 -48.465  33.304  1.00 26.05           A    N
ATOM   2318  C   GLN A 329      13.352 -44.578  29.800  1.00 30.14           A    C
ATOM   2319  O   GLN A 329      12.730 -45.307  29.016  1.00 30.47           A    O
ATOM   2320  N   LYS A 330      12.805 -43.512  30.386  1.00 31.31           A    N
ATOM   2321  CA  LYS A 330      11.389 -43.172  30.191  1.00 34.29           A    C
ATOM   2322  CB  LYS A 330      11.035 -41.874  30.933  1.00 37.48           A    C
ATOM   2323  CG  LYS A 330       9.536 -41.563  30.975  1.00 40.44           A    C
ATOM   2324  CD  LYS A 330       9.228 -40.317  31.805  1.00 43.02           A    C
ATOM   2325  CE  LYS A 330       7.722 -40.226  32.107  1.00 46.09           A    C
ATOM   2326  NZ  LYS A 330       7.419 -39.391  33.304  1.00 48.03           A    N
ATOM   2327  C   LYS A 330      11.034 -43.070  28.703  1.00 34.00           A    C
ATOM   2328  O   LYS A 330       9.975 -43.549  28.293  1.00 31.99           A    O
ATOM   2329  N   LEU A 331      11.916 -42.450  27.916  1.00 34.81           A    N
ATOM   2330  CA  LEU A 331      11.735 -42.316  26.470  1.00 35.65           A    C
ATOM   2331  CB  LEU A 331      12.746 -41.317  25.890  1.00 35.09           A    C
ATOM   2332  CG  LEU A 331      12.865 -41.013  24.405  1.00 35.08           A    C
ATOM   2333  CD1 LEU A 331      11.524 -40.641  23.769  1.00 36.27           A    C
ATOM   2334  CD2 LEU A 331      13.874 -39.898  24.146  1.00 32.58           A    C
ATOM   2335  C   LEU A 331      11.841 -43.690  25.786  1.00 37.36           A    C
ATOM   2336  O   LEU A 331      10.953 -44.063  24.999  1.00 38.35           A    O
ATOM   2337  N   GLN A 332      12.903 -44.420  26.117  1.00 36.02           A    N
ATOM   2338  CA  GLN A 332      13.113 -45.758  25.578  1.00 35.84           A    C
ATOM   2339  CB  GLN A 332      14.350 -46.339  26.185  1.00 36.47           A    C
ATOM   2340  CG  GLN A 332      15.663 -45.895  25.600  1.00 38.21           A    C
ATOM   2341  CD  GLN A 332      16.869 -46.499  26.299  1.00 38.62           A    C
ATOM   2342  OE1 GLN A 332      16.823 -46.806  27.493  1.00 38.44           A    O
ATOM   2343  NE2 GLN A 332      17.956 -46.674  25.559  1.00 39.19           A    N
ATOM   2344  C   GLN A 332      11.906 -46.649  25.830  1.00 36.13           A    C
ATOM   2345  O   GLN A 332      11.601 -47.541  25.029  1.00 37.77           A    O
ATOM   2346  N   GLU A 333      11.223 -46.393  26.944  1.00 34.04           A    N
ATOM   2347  CA  GLU A 333      10.017 -47.124  27.300  1.00 32.66           A    C
ATOM   2348  CB  GLU A 333       9.778 -47.076  28.808  1.00 31.88           A    C
ATOM   2349  CG  GLU A 333      10.585 -48.119  29.564  1.00 31.88           A    C
ATOM   2350  CD  GLU A 333      10.593 -47.901  31.068  1.00 32.01           A    C
```

FIG. 49 (CONT.)

```
ATOM   2351  OE1 GLU A 333      10.424 -46.738  31.498  1.00 31.26           A    O
ATOM   2352  OE2 GLU A 333      10.702 -46.898  31.816  1.00 31.95           A    O
ATOM   2353  C   GLU A 333       8.794 -46.634  26.546  1.00 32.39           A    C
ATOM   2354  O   GLU A 333       7.933 -47.448  26.187  1.00 31.92           A    O
ATOM   2355  N   GLU A 334       8.722 -45.321  26.293  1.00 32.01           A    N
ATOM   2356  CA  GLU A 334       7.628 -44.760  25.485  1.00 32.15           A    C
ATOM   2357  CB  GLU A 334       7.605 -43.230  25.503  1.00 32.62           A    C
ATOM   2358  CG  GLU A 334       6.542 -42.633  24.581  1.00 36.26           A    C
ATOM   2359  CD  GLU A 334       6.481 -41.108  24.591  1.00 39.34           A    C
ATOM   2360  OE1 GLU A 334       5.528 -40.563  25.211  1.00 42.25           A    O
ATOM   2361  OE2 GLU A 334       7.360 -40.452  23.977  1.00 38.70           A    O
ATOM   2362  C   GLU A 334       7.699 -45.285  24.049  1.00 32.51           A    C
ATOM   2363  O   GLU A 334       6.679 -45.697  23.478  1.00 29.88           A    O
ATOM   2364  N   ILE A 335       8.915 -45.284  23.492  1.00 33.65           A    N
ATOM   2365  CA  ILE A 335       9.180 -45.801  22.144  1.00 32.82           A    C
ATOM   2366  CB  ILE A 335      10.675 -45.642  21.755  1.00 33.62           A    C
ATOM   2367  CG1 ILE A 335      11.061 -44.151  21.719  1.00 35.38           A    C
ATOM   2368  CD1 ILE A 335      12.516 -43.883  21.379  1.00 34.30           A    C
ATOM   2369  CG2 ILE A 335      10.974 -46.314  20.414  1.00 31.78           A    C
ATOM   2370  C   ILE A 335       8.720 -47.265  22.004  1.00 33.34           A    C
ATOM   2371  O   ILE A 335       8.125 -47.636  20.982  1.00 32.40           A    O
ATOM   2372  N   ASP A 336       8.980 -48.081  23.031  1.00 32.20           A    N
ATOM   2373  CA  ASP A 336       8.585 -49.485  23.065  1.00 31.49           A    C
ATOM   2374  CB  ASP A 336       9.296 -50.293  24.097  1.00 30.75           A    C
ATOM   2375  CG  ASP A 336      10.815 -50.265  23.964  1.00 31.03           A    C
ATOM   2376  OD1 ASP A 336      11.344 -49.392  22.662  1.00 29.68           A    O
ATOM   2377  OD2 ASP A 336      11.490 -50.508  24.989  1.00 31.30           A    O
ATOM   2378  C   ASP A 336       7.062 -49.654  23.087  1.00 32.16           A    C
ATOM   2379  O   ASP A 336       6.498 -50.519  22.408  1.00 32.95           A    O
ATOM   2380  N   ALA A 337       6.399 -48.823  23.891  1.00 32.64           A    N
ATOM   2381  CA  ALA A 337       4.934 -48.860  24.008  1.00 33.04           A    C
ATOM   2382  CB  ALA A 337       4.673 -47.957  25.141  1.00 32.49           A    C
ATOM   2383  C   ALA A 337       4.197 -48.515  22.696  1.00 34.29           A    C
ATOM   2384  O   ALA A 337       3.077 -48.979  22.461  1.00 35.57           A    O
ATOM   2385  N   VAL A 338       4.837 -47.711  21.849  1.00 35.76           A    N
ATOM   2386  CA  VAL A 338       4.280 -47.282  20.560  1.00 37.19           A    C
ATOM   2387  CB  VAL A 338       4.619 -45.804  20.283  1.00 35.38           A    C
ATOM   2388  CG1 VAL A 338       4.013 -45.342  18.968  1.00 35.14           A    C
ATOM   2389  CG2 VAL A 338       4.131 -44.929  21.428  1.00 35.65           A    C
ATOM   2390  C   VAL A 338       4.770 -48.154  19.391  1.00 39.43           A    C
ATOM   2391  O   VAL A 338       3.985 -48.531  18.515  1.00 41.69           A    O
ATOM   2392  N   LEU A 339       6.065 -48.472  19.397  1.00 39.40           A    N
ATOM   2393  CA  LEU A 339       6.702 -49.291  18.372  1.00 39.40           A    C
ATOM   2394  CB  LEU A 339       7.819 -48.493  17.689  1.00 38.58           A    C
ATOM   2395  CG  LEU A 339       7.513 -47.089  17.156  1.00 37.39           A    C
ATOM   2396  CD1 LEU A 339       8.792 -46.464  16.557  1.00 38.64           A    C
ATOM   2397  CD2 LEU A 339       6.405 -47.123  16.115  1.00 38.77           A    C
ATOM   2398  C   LEU A 339       7.284 -50.554  19.008  1.00 41.88           A    C
ATOM   2399  O   LEU A 339       8.483 -50.600  19.287  1.00 41.45           A    O
ATOM   2400  N   PRO A 340       6.428 -51.578  19.246  1.00 44.09           A    N
ATOM   2401  CA  PRO A 340       6.793 -52.791  19.991  1.00 46.58           A    C
ATOM   2402  CB  PRO A 340       5.467 -53.522  20.181  1.00 46.06           A    C
ATOM   2403  CG  PRO A 340       4.391 -52.519  19.847  1.00 45.54           A    C
ATOM   2404  CD  PRO A 340       5.020 -51.631  18.815  1.00 45.08           A    C
ATOM   2405  C   PRO A 340       7.785 -53.698  19.264  1.00 48.86           A    C
ATOM   2406  O   PRO A 340       7.951 -54.094  18.110  1.00 51.12           A    O
ATOM   2407  N   ASN A 341       8.875 -54.021  19.955  1.00 50.22           A    N
ATOM   2408  CA  ASN A 341       9.958 -54.877  19.455  1.00 49.85           A    C
ATOM   2409  CB  ASN A 341       9.512 -56.355  19.323  1.00 50.25           A    C
ATOM   2410  CG  ASN A 341      10.602 -57.340  19.736  1.00 50.24           A    C
ATOM   2411  OD1 ASN A 341      11.796 -57.108  19.510  1.00 51.10           A    O
ATOM   2412  ND2 ASN A 341      10.194 -58.442  20.349  1.00 47.44           A    N
ATOM   2413  C   ASN A 341      10.601 -54.322  18.175  1.00 46.55           A    C
ATOM   2414  O   ASN A 341      10.528 -54.930  17.094  1.00 42.64           A    O
ATOM   2415  N   LYS A 342      11.218 -53.148  18.330  1.00 44.55           A    N
```

FIG. 49 (CONT.)

| ATOM | 2416 | CA | LYS | A | 342 | 11.966 | -52.461 | 17.271 | 1.00 | 43.50 | A | C |
| ATOM | 2417 | CB | LYS | A | 342 | 13.249 | -53.226 | 16.910 | 1.00 | 43.85 | A | C |
| ATOM | 2418 | CG | LYS | A | 342 | 14.375 | -53.001 | 17.891 | 1.00 | 45.80 | A | C |
| ATOM | 2419 | CD | LYS | A | 342 | 15.590 | -53.851 | 17.551 | 1.00 | 47.31 | A | C |
| ATOM | 2420 | CE | LYS | A | 342 | 16.519 | -53.930 | 18.753 | 1.00 | 48.31 | A | C |
| ATOM | 2421 | NZ | LYS | A | 342 | 17.709 | -54.761 | 18.473 | 1.00 | 50.49 | A | N |
| ATOM | 2422 | C | LYS | A | 342 | 11.167 | -52.117 | 16.008 | 1.00 | 42.85 | A | C |
| ATOM | 2423 | O | LYS | A | 342 | 11.746 | -52.002 | 14.923 | 1.00 | 43.82 | A | O |
| ATOM | 2424 | N | ALA | A | 343 | 9.853 | -51.939 | 16.147 | 1.00 | 40.43 | A | N |
| ATOM | 2425 | CA | ALA | A | 343 | 8.998 | -51.601 | 15.004 | 1.00 | 39.75 | A | C |
| ATOM | 2426 | CB | ALA | A | 343 | 7.534 | -51.557 | 15.425 | 1.00 | 38.46 | A | C |
| ATOM | 2427 | C | ALA | A | 343 | 9.427 | -50.272 | 14.350 | 1.00 | 40.17 | A | C |
| ATOM | 2428 | O | ALA | A | 343 | 9.832 | -49.337 | 15.056 | 1.00 | 38.30 | A | O |
| ATOM | 2429 | N | PRO | A | 344 | 9.359 | -50.195 | 13.002 | 1.00 | 39.69 | A | N |
| ATOM | 2430 | CA | PRO | A | 344 | 9.826 | -48.994 | 12.311 | 1.00 | 41.48 | A | C |
| ATOM | 2431 | CB | PRO | A | 344 | 9.792 | -49.397 | 10.821 | 1.00 | 40.06 | A | C |
| ATOM | 2432 | CG | PRO | A | 344 | 9.687 | -50.882 | 10.809 | 1.00 | 38.78 | A | C |
| ATOM | 2433 | CD | PRO | A | 344 | 8.911 | -51.222 | 12.048 | 1.00 | 39.50 | A | C |
| ATOM | 2434 | C | PRO | A | 344 | 8.899 | -47.811 | 12.561 | 1.00 | 42.04 | A | C |
| ATOM | 2435 | O | PRO | A | 344 | 7.683 | -47.972 | 12.465 | 1.00 | 42.95 | A | O |
| ATOM | 2436 | N | PRO | A | 345 | 9.474 | -46.636 | 12.883 | 1.00 | 41.49 | A | N |
| ATOM | 2437 | CA | PRO | A | 345 | 8.746 | -45.383 | 13.087 | 1.00 | 40.50 | A | C |
| ATOM | 2438 | CB | PRO | A | 345 | 9.849 | -44.401 | 13.479 | 1.00 | 40.49 | A | C |
| ATOM | 2439 | CG | PRO | A | 345 | 11.093 | -44.974 | 12.872 | 1.00 | 41.05 | A | C |
| ATOM | 2440 | CD | PRO | A | 345 | 10.927 | -46.452 | 13.051 | 1.00 | 42.51 | A | C |
| ATOM | 2441 | C | PRO | A | 345 | 8.079 | -44.898 | 11.810 | 1.00 | 41.43 | A | C |
| ATOM | 2442 | O | PRO | A | 345 | 8.582 | -45.157 | 10.707 | 1.00 | 41.37 | A | O |
| ATOM | 2443 | N | THR | A | 346 | 6.949 | -44.215 | 11.982 | 1.00 | 40.06 | A | N |
| ATOM | 2444 | CA | THR | A | 346 | 6.237 | -43.620 | 10.829 | 1.00 | 39.51 | A | C |
| ATOM | 2445 | CB | THR | A | 346 | 5.016 | -44.468 | 10.340 | 1.00 | 38.69 | A | C |
| ATOM | 2446 | OG1 | THR | A | 346 | 3.890 | -44.260 | 11.198 | 1.00 | 38.29 | A | O |
| ATOM | 2447 | CG2 | THR | A | 346 | 5.326 | -45.963 | 10.294 | 1.00 | 38.74 | A | C |
| ATOM | 2448 | C | THR | A | 346 | 5.794 | -42.212 | 11.233 | 1.00 | 39.67 | A | C |
| ATOM | 2449 | O | THR | A | 346 | 5.853 | -41.850 | 12.405 | 1.00 | 38.28 | A | O |
| ATOM | 2450 | N | TYR | A | 347 | 5.376 | -41.417 | 10.255 | 1.00 | 41.31 | A | N |
| ATOM | 2451 | CA | TYR | A | 347 | 4.889 | -40.057 | 10.503 | 1.00 | 41.79 | A | C |
| ATOM | 2452 | CB | TYR | A | 347 | 4.140 | -39.558 | 9.268 | 1.00 | 42.62 | A | C |
| ATOM | 2453 | CG | TYR | A | 347 | 3.623 | -38.143 | 9.385 | 1.00 | 44.36 | A | C |
| ATOM | 2454 | CD1 | TYR | A | 347 | 4.352 | -37.074 | 8.862 | 1.00 | 47.39 | A | C |
| ATOM | 2455 | CE1 | TYR | A | 347 | 3.892 | -35.768 | 8.969 | 1.00 | 46.79 | A | C |
| ATOM | 2456 | CZ | TYR | A | 347 | 2.680 | -35.524 | 9.597 | 1.00 | 47.32 | A | C |
| ATOM | 2457 | OH | TYR | A | 347 | 2.202 | -34.237 | 9.713 | 1.00 | 45.73 | A | O |
| ATOM | 2458 | CE2 | TYR | A | 347 | 1.938 | -36.573 | 10.113 | 1.00 | 45.92 | A | C |
| ATOM | 2459 | CD2 | TYR | A | 347 | 2.410 | -37.869 | 10.006 | 1.00 | 43.93 | A | C |
| ATOM | 2460 | C | TYR | A | 347 | 3.995 | -40.028 | 11.749 | 1.00 | 40.59 | A | C |
| ATOM | 2461 | O | TYR | A | 347 | 4.239 | -39.245 | 12.680 | 1.00 | 38.99 | A | O |
| ATOM | 2462 | N | ASP | A | 348 | 2.982 | -40.894 | 11.760 | 1.00 | 40.04 | A | N |
| ATOM | 2463 | CA | ASP | A | 348 | 1.901 | -40.836 | 12.735 | 1.00 | 43.31 | A | C |
| ATOM | 2464 | CB | ASP | A | 348 | 0.710 | -41.676 | 12.264 | 1.00 | 42.59 | A | C |
| ATOM | 2465 | CG | ASP | A | 348 | 0.136 | -41.230 | 10.913 | 1.00 | 45.15 | A | C |
| ATOM | 2466 | OD1 | ASP | A | 348 | -0.121 | -42.079 | 9.996 | 1.00 | 46.59 | A | O |
| ATOM | 2467 | OD2 | ASP | A | 348 | -0.127 | -40.027 | 10.760 | 1.00 | 43.23 | A | O |
| ATOM | 2468 | C | ASP | A | 348 | 2.358 | -41.289 | 14.103 | 1.00 | 39.01 | A | C |
| ATOM | 2469 | O | ASP | A | 348 | 1.988 | -40.685 | 15.112 | 1.00 | 40.10 | A | O |
| ATOM | 2470 | N | THR | A | 349 | 3.186 | -42.345 | 14.128 | 1.00 | 34.59 | A | N |
| ATOM | 2471 | CA | THR | A | 349 | 3.743 | -42.866 | 15.372 | 1.00 | 34.22 | A | C |
| ATOM | 2472 | CB | THR | A | 349 | 4.401 | -44.237 | 15.144 | 1.00 | 33.78 | A | C |
| ATOM | 2473 | OG1 | THR | A | 349 | 5.061 | -44.234 | 13.869 | 1.00 | 32.49 | A | O |
| ATOM | 2474 | CG2 | THR | A | 349 | 3.347 | -45.341 | 15.181 | 1.00 | 32.26 | A | C |
| ATOM | 2475 | C | THR | A | 349 | 4.771 | -41.919 | 16.010 | 1.00 | 33.85 | A | C |
| ATOM | 2476 | O | THR | A | 349 | 4.965 | -41.919 | 17.241 | 1.00 | 30.85 | A | O |
| ATOM | 2477 | N | VAL | A | 350 | 5.426 | -41.131 | 15.161 | 1.00 | 32.83 | A | N |
| ATOM | 2478 | CA | VAL | A | 350 | 6.353 | -40.126 | 15.617 | 1.00 | 34.61 | A | C |
| ATOM | 2479 | CB | VAL | A | 350 | 7.222 | -39.564 | 14.473 | 1.00 | 32.16 | A | C |
| ATOM | 2480 | CG1 | VAL | A | 350 | 7.929 | -38.297 | 14.919 | 1.00 | 32.04 | A | C |

FIG. 49 (CONT.)

```
ATOM   2481  CG2 VAL A 350       8.251 -40.580  14.051  1.00 30.33           A        C
ATOM   2482  C   VAL A 350       5.581 -39.008  16.298  1.00 37.65           A        C
ATOM   2483  O   VAL A 350       6.007 -38.523  17.346  1.00 40.49           A        O
ATOM   2484  N   LEU A 351       4.449 -38.613  15.717  1.00 39.69           A        N
ATOM   2485  CA  LEU A 351       3.680 -37.484  16.237  1.00 42.83           A        C
ATOM   2486  CB  LEU A 351       2.732 -36.905  15.182  1.00 43.00           A        C
ATOM   2487  CG  LEU A 351       3.266 -35.944  14.128  1.00 45.53           A        C
ATOM   2488  CD1 LEU A 351       2.071 -35.256  13.474  1.00 46.64           A        C
ATOM   2489  CD2 LEU A 351       4.231 -34.900  14.686  1.00 42.35           A        C
ATOM   2490  C   LEU A 351       2.879 -37.870  17.463  1.00 45.56           A        C
ATOM   2491  O   LEU A 351       2.231 -37.023  18.079  1.00 50.95           A        O
ATOM   2492  N   GLN A 352       2.913 -39.149  17.809  1.00 45.48           A        N
ATOM   2493  CA  GLN A 352       2.178 -39.631  18.957  1.00 45.63           A        C
ATOM   2494  CB  GLN A 352       1.815 -41.098  18.777  1.00 48.38           A        C
ATOM   2495  CG  GLN A 352       0.489 -41.333  18.077  1.00 49.89           A        C
ATOM   2496  CD  GLN A 352       0.205 -42.807  17.872  1.00 51.09           A        C
ATOM   2497  OE1 GLN A 352      -0.400 -43.195  16.870  1.00 54.09           A        O
ATOM   2498  NE2 GLN A 352       0.655 -43.640  18.810  1.00 48.17           A        N
ATOM   2499  C   GLN A 352       2.971 -39.475  20.235  1.00 45.59           A        C
ATOM   2500  O   GLN A 352       2.389 -39.420  21.319  1.00 48.51           A        O
ATOM   2501  N   MET A 353       4.291 -39.394  20.112  1.00 40.22           A        N
ATOM   2502  CA  MET A 353       5.156 -39.558  21.274  1.00 38.53           A        C
ATOM   2503  CB  MET A 353       6.473 -40.173  20.833  1.00 35.95           A        C
ATOM   2504  CG  MET A 353       6.305 -41.579  20.306  1.00 34.49           A        C
ATOM   2505  SD  MET A 353       7.888 -42.168  19.717  1.00 34.81           A        S
ATOM   2506  CE  MET A 353       7.375 -43.634  18.829  1.00 32.59           A        C
ATOM   2507  C   MET A 353       5.384 -38.305  22.128  1.00 38.66           A        C
ATOM   2508  O   MET A 353       6.341 -37.554  21.904  1.00 38.92           A        O
ATOM   2509  N   GLU A 354       4.513 -38.094  23.116  1.00 38.67           A        N
ATOM   2510  CA  GLU A 354       4.574 -36.897  23.970  1.00 39.69           A        C
ATOM   2511  CB  GLU A 354       3.505 -36.902  25.073  1.00 46.51           A        C
ATOM   2512  CG  GLU A 354       2.189 -36.219  24.728  1.00 52.71           A        C
ATOM   2513  CD  GLU A 354       1.059 -37.201  24.443  1.00 56.76           A        C
ATOM   2514  OE1 GLU A 354       1.170 -37.982  23.470  1.00 60.28           A        O
ATOM   2515  OE2 GLU A 354       0.059 -37.185  25.189  1.00 56.69           A        O
ATOM   2516  C   GLU A 354       5.913 -36.720  24.607  1.00 38.82           A        C
ATOM   2517  O   GLU A 354       5.565 -35.624  24.531  1.00 34.71           A        O
ATOM   2518  N   TYR A 355       6.464 -37.785  25.227  1.00 35.15           A        N
ATOM   2519  CA  TYR A 355       7.760 -37.659  25.931  1.00 34.27           A        C
ATOM   2520  CB  TYR A 355       8.141 -38.877  26.770  1.00 31.40           A        C
ATOM   2521  CG  TYR A 355       9.136 -38.482  27.847  1.00 29.84           A        C
ATOM   2522  CD1 TYR A 355       8.795 -37.514  28.799  1.00 29.27           A        C
ATOM   2523  CE1 TYR A 355       9.679 -37.128  29.793  1.00 30.06           A        C
ATOM   2524  CZ  TYR A 355      10.941 -37.699  29.842  1.00 30.09           A        C
ATOM   2525  OH  TYR A 355      11.792 -37.299  30.854  1.00 28.70           A        O
ATOM   2526  CE2 TYR A 355      11.316 -38.663  28.899  1.00 29.69           A        C
ATOM   2527  CD2 TYR A 355      10.416 -39.042  27.901  1.00 28.52           A        C
ATOM   2528  C   TYR A 355       8.937 -37.239  25.045  1.00 35.33           A        C
ATOM   2529  O   TYR A 355       9.739 -36.371  25.436  1.00 32.53           A        O
ATOM   2530  N   LEU A 356       9.027 -37.865  23.874  1.00 32.64           A        N
ATOM   2531  CA  LEU A 356       9.944 -37.465  22.812  1.00 32.95           A        C
ATOM   2532  CB  LEU A 356       9.589 -38.204  21.520  1.00 32.42           A        C
ATOM   2533  CG  LEU A 356      10.596 -38.183  20.390  1.00 29.35           A        C
ATOM   2534  CD1 LEU A 356      11.996 -38.346  20.937  1.00 29.17           A        C
ATOM   2535  CD2 LEU A 356      10.266 -39.319  19.453  1.00 30.99           A        C
ATOM   2536  C   LEU A 356       9.883 -35.974  22.557  1.00 32.98           A        C
ATOM   2537  O   LEU A 356      10.888 -35.280  22.683  1.00 33.47           A        O
ATOM   2538  N   ASP A 357       8.669 -35.497  22.206  1.00 33.82           A        N
ATOM   2539  CA  ASP A 357       8.429 -34.083  21.976  1.00 33.52           A        C
ATOM   2540  CB  ASP A 357       6.936 -33.844  21.797  1.00 33.35           A        C
ATOM   2541  CG  ASP A 357       6.640 -32.522  21.137  1.00 36.74           A        C
ATOM   2542  OD1 ASP A 357       7.024 -32.360  19.946  1.00 36.28           A        O
ATOM   2543  OD2 ASP A 357       6.028 -31.650  21.805  1.00 34.24           A        O
ATOM   2544  C   ASP A 357       8.935 -33.261  23.146  1.00 33.27           A        C
ATOM   2545  O   ASP A 357       9.762 -32.314  22.952  1.00 36.55           A        O
```

```
ATOM   2676  O   LEU A 373      16.609  -11.094  16.794  1.00 34.50           O
ATOM   2677  N   GLU A 374      16.711  -11.527  14.596  1.00 31.80           N
ATOM   2678  CA  GLU A 374      16.868  -10.119  14.298  1.00 31.90           C
ATOM   2679  CB  GLU A 374      18.335   -9.783  13.991  1.00 33.16           C
ATOM   2680  CG  GLU A 374      19.334  -10.258  15.029  1.00 36.49           C
ATOM   2681  CD  GLU A 374      20.796   -9.904  14.715  1.00 45.20           C
ATOM   2682  OE1 GLU A 374      21.116   -9.477  13.556  1.00 43.55           O
ATOM   2683  OE2 GLU A 374      21.647  -10.065  15.651  1.00 46.40           O
ATOM   2684  C   GLU A 374      15.983   -9.674  13.143  1.00 32.75           C
ATOM   2685  O   GLU A 374      15.695  -10.455  12.240  1.00 34.32           O
ATOM   2686  N   ARG A 375      15.587   -8.406  13.159  1.00 30.77           N
ATOM   2687  CA  ARG A 375      14.564   -7.777  12.001  1.00 29.88           C
ATOM   2688  CB  ARG A 375      13.439   -7.676  12.206  1.00 31.19           C
ATOM   2689  CG  ARG A 375      12.694   -8.995  12.371  1.00 30.06           C
ATOM   2690  CD  ARG A 375      12.635   -9.784  11.061  1.00 29.86           C
ATOM   2691  NE  ARG A 375      11.907  -11.025  11.225  1.00 28.69           N
ATOM   2692  CZ  ARG A 375      12.469  -12.151  11.664  1.00 31.62           C
ATOM   2693  NH1 ARG A 375      13.785  -12.182  11.962  1.00 28.76           N
ATOM   2694  NH2 ARG A 375      11.730  -13.266  11.822  1.00 30.13           N
ATOM   2695  C   ARG A 375      15.533   -6.369  11.833  1.00 31.48           C
ATOM   2696  O   ARG A 375      15.834   -5.698  12.813  1.00 35.35           O
ATOM   2697  N   VAL A 376      15.679   -5.917  10.598  1.00 33.36           N
ATOM   2698  CA  VAL A 376      16.069   -4.539  10.329  1.00 34.35           C
ATOM   2699  CB  VAL A 376      16.843   -4.412   9.006  1.00 33.27           C
ATOM   2700  CG1 VAL A 376      16.908   -2.962   8.574  1.00 30.61           C
ATOM   2701  CG2 VAL A 376      18.234   -4.980   9.167  1.00 30.38           C
ATOM   2702  C   VAL A 376      14.807   -3.730  10.203  1.00 37.35           C
ATOM   2703  O   VAL A 376      13.813   -4.226   9.665  1.00 40.45           O
ATOM   2704  N   CYS A 377      14.853   -2.490  10.698  1.00 39.38           N
ATOM   2705  CA  CYS A 377      13.706   -1.584  10.720  1.00 38.12           C
ATOM   2706  CB  CYS A 377      13.765   -0.736  11.988  1.00 38.05           C
ATOM   2707  SG  CYS A 377      12.419   -0.466  12.175  1.00 46.10           S
ATOM   2708  C   CYS A 377      13.670   -0.708   9.457  1.00 39.80           C
ATOM   2709  O   CYS A 377      14.531    0.163   9.274  1.00 40.88           O
ATOM   2710  N   LYS A 378      12.682   -0.961   8.591  1.00 38.33           N
ATOM   2711  CA  LYS A 378      12.567   -0.326   7.259  1.00 40.18           C
ATOM   2712  CB  LYS A 378      11.487   -1.028   6.405  1.00 40.15           C
ATOM   2713  CG  LYS A 378      12.020   -2.049   5.397  1.00 40.64           C
ATOM   2714  CD  LYS A 378      11.103   -3.254   5.193  1.00 37.32           C
ATOM   2715  CE  LYS A 378      10.041   -3.021   4.138  1.00 40.18           C
ATOM   2716  NZ  LYS A 378      10.300   -4.267   3.765  1.00 40.88           N
ATOM   2717  C   LYS A 378      12.293    1.193   7.291  1.00 43.69           C
ATOM   2718  O   LYS A 378      12.675    1.902   6.367  1.00 44.09           O
ATOM   2719  N   LYS A 379      11.636    1.661   8.350  1.00 45.40           N
ATOM   2720  CA  LYS A 379      11.214    3.065   8.452  1.00 45.37           C
ATOM   2721  CB  LYS A 379       9.917    3.201   7.667  1.00 47.34           C
ATOM   2722  CG  LYS A 379       8.873    2.189   7.850  1.00 47.65           C
ATOM   2723  CD  LYS A 379       7.956    2.063   6.640  1.00 49.69           C
ATOM   2724  CE  LYS A 379       6.639    2.816   6.821  1.00 52.31           C
ATOM   2725  NZ  LYS A 379       5.736    2.198   7.888  1.00 52.29           N
ATOM   2726  C   LYS A 379      11.017    3.438   9.912  1.00 45.65           C
ATOM   2727  O   LYS A 379      10.876    2.554  10.740  1.00 50.00           O
ATOM   2728  N   ASP A 380      11.013    4.728  10.240  1.00 44.60           N
ATOM   2729  CA  ASP A 380      10.681    5.151  11.609  1.00 47.21           C
ATOM   2730  CB  ASP A 380      10.725    6.672  11.723  1.00 48.15           C
ATOM   2731  CG  ASP A 380      12.114    7.228  11.507  1.00 52.40           C
ATOM   2732  OD1 ASP A 380      13.034    6.893  12.286  1.00 53.81           O
ATOM   2733  OD2 ASP A 380      12.292    8.011  10.554  1.00 58.23           O
ATOM   2734  C   ASP A 380       9.303    4.625  12.055  1.00 47.95           C
ATOM   2735  O   ASP A 380       8.331    4.706  11.301  1.00 47.73           O
ATOM   2736  N   VAL A 381       9.233    4.076  13.269  1.00 46.95           N
ATOM   2737  CA  VAL A 381       7.976    3.547  13.819  1.00 46.67           C
ATOM   2738  CB  VAL A 381       7.700    2.079  13.422  1.00 49.62           C
ATOM   2739  CG1 VAL A 381       6.842    2.006  12.166  1.00 50.93           C
ATOM   2740  CG2 VAL A 381       8.991    1.275  13.325  1.00 45.98           C
```

```
ATOM   2936  NZ   LYS A 406       8.531  -8.762  35.183  1.00 53.99           A           N
ATOM   2937  C    LYS A 406       9.731 -15.452  34.419  1.00 52.37           A           C
ATOM   2938  O    LYS A 406       8.539 -15.420  34.737  1.00 53.10           A           O
ATOM   2939  N    TYR A 407      10.228 -16.328  33.549  1.00 52.56           A           N
ATOM   2940  CA   TYR A 407       9.377 -17.310  32.880  1.00 51.43           A           C
ATOM   2941  CB   TYR A 407       9.375 -17.101  31.360  1.00 52.02           A           C
ATOM   2942  CG   TYR A 407       9.112 -15.672  30.923  1.00 58.66           A           C
ATOM   2943  CD1  TYR A 407      10.184 -14.812  30.611  1.00 60.37           A           C
ATOM   2944  CE1  TYR A 407       9.965 -13.498  30.203  1.00 59.01           A           C
ATOM   2945  CZ   TYR A 407       8.656 -13.017  30.106  1.00 61.82           A           C
ATOM   2946  OH   TYR A 407       8.466 -11.706  29.697  1.00 60.48           A           O
ATOM   2947  CE2  TYR A 407       7.587 -13.851  30.411  1.00 59.42           A           C
ATOM   2948  CD2  TYR A 407       7.799 -15.169  30.814  1.00 56.76           A           C
ATOM   2949  C    TYR A 407       9.727 -18.762  33.198  1.00 48.62           A           C
ATOM   2950  O    TYR A 407       8.914 -19.653  32.946  1.00 45.79           A           O
ATOM   2951  N    TRP A 408      10.920 -19.011  33.743  1.00 48.64           A           N
ATOM   2952  CA   TRP A 408      11.401 -20.339  33.901  1.00 50.13           A           C
ATOM   2953  CB   TRP A 408      12.489 -20.730  32.869  1.00 48.55           A           C
ATOM   2954  CG   TRP A 408      12.105 -20.372  31.449  1.00 48.24           A           C
ATOM   2955  CD1  TRP A 408      12.410 -19.203  30.757  1.00 48.29           A           C
ATOM   2956  NE1  TRP A 408      11.883 -19.229  29.492  1.00 47.77           A           N
ATOM   2957  CE2  TRP A 408      11.210 -20.378  29.274  1.00 48.83           A           C
ATOM   2958  CD2  TRP A 408      11.306 -21.172  30.503  1.00 49.46           A           C
ATOM   2959  CE3  TRP A 408      10.694 -22.424  30.547  1.00 49.95           A           C
ATOM   2960  CZ3  TRP A 408      10.005 -22.870  29.411  1.00 47.49           A           C
ATOM   2961  CH2  TRP A 408       9.930 -22.095  28.247  1.00 49.86           A           C
ATOM   2962  CZ2  TRP A 408      10.534 -20.837  28.155  1.00 49.07           A           C
ATOM   2963  C    TRP A 408      11.856 -20.779  35.289  1.00 52.73           A           C
ATOM   2964  O    TRP A 408      12.701 -20.101  35.889  1.00 55.91           A           O
ATOM   2965  N    THR A 409      11.297 -21.878  35.801  1.00 52.19           A           N
ATOM   2966  CA   THR A 409      11.717 -22.456  37.072  1.00 53.20           A           C
ATOM   2967  CB   THR A 409      10.631 -23.396  37.650  1.00 52.89           A           C
ATOM   2968  OG1  THR A 409       9.394 -22.684  37.779  1.00 52.34           A           O
ATOM   2969  CG2  THR A 409      11.041 -23.933  39.022  1.00 49.37           A           C
ATOM   2970  C    THR A 409      13.021 -23.232  36.886  1.00 52.45           A           C
ATOM   2971  O    THR A 409      13.089 -24.116  36.050  1.00 51.86           A           O
ATOM   2972  N    GLU A 410      14.037 -22.899  37.683  1.00 56.75           A           N
ATOM   2973  CA   GLU A 410      15.344 -23.572  37.661  1.00 56.63           A           C
ATOM   2974  CB   GLU A 410      15.271 -24.971  38.286  1.00 59.47           A           C
ATOM   2975  CG   GLU A 410      14.602 -25.063  39.650  1.00 59.94           A           C
ATOM   2976  CD   GLU A 410      14.124 -26.475  39.957  1.00 61.76           A           C
ATOM   2977  OE1  GLU A 410      14.869 -27.375  40.158  1.00 61.29           A           O
ATOM   2978  OE2  GLU A 410      12.894 -26.686  39.997  1.00 64.08           A           O
ATOM   2979  C    GLU A 410      15.838 -23.676  36.230  1.00 58.94           A           C
ATOM   2980  O    GLU A 410      15.968 -24.784  35.692  1.00 62.63           A           O
ATOM   2981  N    PRO A 411      16.130 -22.520  35.607  1.00 59.55           A           N
ATOM   2982  CA   PRO A 411      16.328 -22.427  34.157  1.00 52.64           A           C
ATOM   2983  CB   PRO A 411      16.665 -20.947  33.935  1.00 55.46           A           C
ATOM   2984  CG   PRO A 411      16.322 -20.240  35.207  1.00 57.62           A           C
ATOM   2985  CD   PRO A 411      15.492 -21.282  36.289  1.00 60.08           A           C
ATOM   2986  C    PRO A 411      17.457 -23.304  33.626  1.00 50.07           A           C
ATOM   2987  O    PRO A 411      17.390 -23.759  32.485  1.00 52.87           A           O
ATOM   2988  N    GLU A 412      18.479 -23.534  34.446  1.00 47.93           A           N
ATOM   2989  CA   GLU A 412      19.664 -24.307  34.057  1.00 46.18           A           C
ATOM   2990  CB   GLU A 412      20.860 -23.954  34.972  1.00 49.77           A           C
ATOM   2991  CG   GLU A 412      21.374 -22.508  34.878  1.00 52.74           A           C
ATOM   2992  CD   GLU A 412      22.051 -22.163  33.542  1.00 57.25           A           C
ATOM   2993  OE1  GLU A 412      22.875 -22.977  33.056  1.00 58.69           A           O
ATOM   2994  OE2  GLU A 412      21.762 -21.072  32.972  1.00 58.17           A           O
ATOM   2995  C    GLU A 412      19.432 -25.829  34.039  1.00 43.19           A           C
ATOM   2996  O    GLU A 412      20.255 -26.586  33.522  1.00 40.33           A           O
ATOM   2997  N    LYS A 413      18.314 -26.278  34.611  1.00 43.03           A           N
ATOM   2998  CA   LYS A 413      18.014 -27.898  34.730  1.00 40.36           A           C
ATOM   2999  CB   LYS A 413      17.081 -27.953  35.919  1.00 41.80           A           C
ATOM   3000  CG   LYS A 413      17.024 -27.594  37.305  1.00 42.03           A           C
```

| | | | | | | | | | | |
|---|---|---|---|---|---|---|---|---|---|---|
| ATOM | 3131 | CG | ASP | A | 428 | 4.393 | -15.437 | 25.816 | 1.00 | 53.34 | A | C |
| ATOM | 3132 | OD1 | ASP | A | 428 | 4.238 | -15.494 | 24.571 | 1.00 | 57.99 | A | O |
| ATOM | 3133 | OD2 | ASP | A | 428 | 3.993 | -14.459 | 26.492 | 1.00 | 52.98 | A | O |
| ATOM | 3134 | C | ASP | A | 428 | 5.643 | -18.198 | 24.655 | 1.00 | 44.58 | A | C |
| ATOM | 3135 | O | ASP | A | 428 | 6.078 | -18.167 | 24.673 | 1.00 | 41.63 | A | O |
| ATOM | 3136 | N | PRO | A | 429 | 4.339 | -18.394 | 23.523 | 1.00 | 43.86 | A | N |
| ATOM | 3137 | CA | PRO | A | 429 | 5.549 | -18.618 | 22.203 | 1.00 | 41.54 | A | C |
| ATOM | 3138 | CB | PRO | A | 429 | 4.135 | -18.752 | 21.267 | 1.00 | 42.39 | A | C |
| ATOM | 3139 | CG | PRO | A | 429 | 3.208 | -18.080 | 21.993 | 1.00 | 45.49 | A | C |
| ATOM | 3140 | CD | PRO | A | 429 | 3.464 | -18.357 | 23.449 | 1.00 | 44.30 | A | C |
| ATOM | 3141 | C | PRO | A | 429 | 6.419 | -17.453 | 21.739 | 1.00 | 41.84 | A | C |
| ATOM | 3142 | O | PRO | A | 429 | 7.044 | -17.539 | 20.680 | 1.00 | 38.95 | A | O |
| ATOM | 3143 | N | TYR | A | 430 | 6.450 | -16.371 | 22.508 | 1.00 | 41.93 | A | N |
| ATOM | 3144 | CA | TYR | A | 430 | 7.315 | -15.248 | 22.165 | 1.00 | 41.76 | A | C |
| ATOM | 3145 | CB | TYR | A | 430 | 6.518 | -13.964 | 22.060 | 1.00 | 42.17 | A | C |
| ATOM | 3146 | CG | TYR | A | 430 | 5.411 | -14.112 | 21.057 | 1.00 | 44.30 | A | C |
| ATOM | 3147 | CD1 | TYR | A | 430 | 4.123 | -14.527 | 21.443 | 1.00 | 45.41 | A | C |
| ATOM | 3148 | CE1 | TYR | A | 430 | 3.108 | -14.681 | 20.501 | 1.00 | 46.48 | A | C |
| ATOM | 3149 | CZ | TYR | A | 430 | 3.394 | -14.427 | 19.148 | 1.00 | 47.49 | A | C |
| ATOM | 3150 | OH | TYR | A | 430 | 2.446 | -14.564 | 18.155 | 1.00 | 43.95 | A | O |
| ATOM | 3151 | CE2 | TYR | A | 430 | 4.663 | -14.032 | 18.765 | 1.00 | 46.19 | A | C |
| ATOM | 3152 | CD2 | TYR | A | 430 | 5.655 | -13.880 | 19.714 | 1.00 | 43.65 | A | C |
| ATOM | 3153 | C | TYR | A | 430 | 8.493 | -15.136 | 23.116 | 1.00 | 41.99 | A | C |
| ATOM | 3154 | O | TYR | A | 430 | 9.413 | -14.357 | 22.866 | 1.00 | 42.24 | A | O |
| ATOM | 3155 | N | ILE | A | 431 | 8.467 | -15.937 | 24.185 | 1.00 | 41.42 | A | N |
| ATOM | 3156 | CA | ILE | A | 431 | 9.664 | -16.203 | 25.065 | 1.00 | 41.99 | A | C |
| ATOM | 3157 | CB | ILE | A | 431 | 9.337 | -16.338 | 26.502 | 1.00 | 42.25 | A | C |
| ATOM | 3158 | CG1 | ILE | A | 431 | 8.613 | -15.092 | 27.032 | 1.00 | 40.46 | A | C |
| ATOM | 3159 | CD1 | ILE | A | 431 | 9.178 | -13.755 | 26.568 | 1.00 | 39.64 | A | C |
| ATOM | 3160 | CG2 | ILE | A | 431 | 10.592 | -16.679 | 27.306 | 1.00 | 41.59 | A | C |
| ATOM | 3161 | C | ILE | A | 431 | 10.423 | -17.449 | 24.497 | 1.00 | 45.27 | A | C |
| ATOM | 3162 | O | ILE | A | 431 | 11.665 | -17.431 | 24.420 | 1.00 | 45.14 | A | O |
| ATOM | 3163 | N | TYR | A | 432 | 9.676 | -18.505 | 24.129 | 1.00 | 43.93 | A | N |
| ATOM | 3164 | CA | TYR | A | 432 | 10.255 | -19.744 | 23.567 | 1.00 | 39.75 | A | C |
| ATOM | 3165 | CB | TYR | A | 432 | 9.526 | -20.963 | 24.101 | 1.00 | 38.29 | A | C |
| ATOM | 3166 | CG | TYR | A | 432 | 10.089 | -22.300 | 23.657 | 1.00 | 36.31 | A | C |
| ATOM | 3167 | CD1 | TYR | A | 432 | 9.394 | -23.099 | 22.755 | 1.00 | 34.67 | A | C |
| ATOM | 3168 | CE1 | TYR | A | 432 | 9.895 | -24.323 | 22.359 | 1.00 | 34.38 | A | C |
| ATOM | 3169 | CZ | TYR | A | 432 | 11.108 | -24.774 | 22.870 | 1.00 | 34.14 | A | C |
| ATOM | 3170 | OH | TYR | A | 432 | 11.586 | -26.001 | 22.469 | 1.00 | 37.35 | A | O |
| ATOM | 3171 | CE2 | TYR | A | 432 | 11.810 | -24.013 | 23.773 | 1.00 | 32.54 | A | C |
| ATOM | 3172 | CD2 | TYR | A | 432 | 11.303 | -22.787 | 24.170 | 1.00 | 35.43 | A | C |
| ATOM | 3173 | C | TYR | A | 432 | 10.214 | -19.758 | 22.055 | 1.00 | 40.72 | A | C |
| ATOM | 3174 | O | TYR | A | 432 | 9.190 | -20.040 | 21.459 | 1.00 | 46.29 | A | O |
| ATOM | 3175 | N | THR | A | 433 | 11.345 | -19.470 | 21.432 | 1.00 | 43.13 | A | N |
| ATOM | 3176 | CA | THR | A | 433 | 11.391 | -19.315 | 19.956 | 1.00 | 40.39 | A | C |
| ATOM | 3177 | CB | THR | A | 433 | 11.448 | -17.828 | 19.637 | 1.00 | 39.61 | A | C |
| ATOM | 3178 | OG1 | THR | A | 433 | 12.568 | -17.233 | 20.316 | 1.00 | 39.04 | A | O |
| ATOM | 3179 | CG2 | THR | A | 433 | 10.155 | -17.157 | 20.053 | 1.00 | 37.61 | A | C |
| ATOM | 3180 | C | THR | A | 433 | 12.562 | -20.090 | 19.265 | 1.00 | 37.67 | A | C |
| ATOM | 3181 | O | THR | A | 433 | 13.296 | -19.366 | 18.451 | 1.00 | 41.60 | A | O |
| ATOM | 3182 | N | PRO | A | 434 | 12.809 | -21.298 | 19.516 | 1.00 | 37.42 | A | N |
| ATOM | 3183 | CA | PRO | A | 434 | 13.938 | -21.966 | 18.849 | 1.00 | 35.64 | A | C |
| ATOM | 3184 | CB | PRO | A | 434 | 13.858 | -23.403 | 19.379 | 1.00 | 36.69 | A | C |
| ATOM | 3185 | CG | PRO | A | 434 | 12.444 | -23.581 | 19.879 | 1.00 | 37.46 | A | C |
| ATOM | 3186 | CD | PRO | A | 434 | 12.010 | -22.231 | 20.349 | 1.00 | 39.24 | A | C |
| ATOM | 3187 | C | PRO | A | 434 | 13.982 | -21.930 | 17.292 | 1.00 | 35.92 | A | C |
| ATOM | 3188 | O | PRO | A | 434 | 14.932 | -22.080 | 16.626 | 1.00 | 37.74 | A | O |
| ATOM | 3189 | N | PHE | A | 435 | 12.721 | -21.707 | 16.736 | 1.00 | 34.63 | A | N |
| ATOM | 3190 | CA | PHE | A | 435 | 12.518 | -21.581 | 15.306 | 1.00 | 32.39 | A | C |
| ATOM | 3191 | CB | PHE | A | 435 | 11.550 | -22.677 | 14.820 | 1.00 | 30.28 | A | C |
| ATOM | 3192 | CG | PHE | A | 435 | 12.068 | -24.086 | 15.020 | 1.00 | 29.23 | A | C |
| ATOM | 3193 | CD1 | PHE | A | 435 | 13.007 | -24.642 | 14.141 | 1.00 | 28.14 | A | C |
| ATOM | 3194 | CE1 | PHE | A | 435 | 13.497 | -25.942 | 14.323 | 1.00 | 28.77 | A | C |
| ATOM | 3195 | CZ | PHE | A | 435 | 13.040 | -26.708 | 15.399 | 1.00 | 27.65 | A | C |

```
ATOM   3326  CA  LYS A 453      12.736 -37.616  15.980  1.00 33.49           A  C
ATOM   3327  CB  LYS A 453      11.277 -37.197  16.083  1.00 31.20           A  C
ATOM   3328  CG  LYS A 453      11.038 -35.955  16.854  1.00 31.73           A  C
ATOM   3329  CD  LYS A 453       9.565 -35.749  17.167  1.00 29.40           A  C
ATOM   3330  CE  LYS A 453       9.339 -34.394  17.799  1.00 29.44           A  C
ATOM   3331  NZ  LYS A 453       7.896 -34.027  17.775  1.00 28.30           A  N
ATOM   3332  C   LYS A 453      12.932 -39.010  15.369  1.00 34.68           A  C
ATOM   3333  O   LYS A 453      13.076 -40.052  16.087  1.00 37.48           A  O
ATOM   3334  N   LEU A 454      12.990 -39.083  14.049  1.00 34.81           A  N
ATOM   3335  CA  LEU A 454      13.290 -40.369  13.417  1.00 34.25           A  C
ATOM   3336  CB  LEU A 454      12.979 -40.336  11.916  1.00 33.19           A  C
ATOM   3337  CG  LEU A 454      11.880 -40.153  11.607  1.00 33.71           A  C
ATOM   3338  CD1 LEU A 454      11.217 -39.473  10.262  1.00 31.25           A  C
ATOM   3339  CD2 LEU A 454      10.738 -41.464  11.694  1.00 32.45           A  C
ATOM   3340  C   LEU A 454      14.715 -40.861  13.732  1.00 33.94           A  C
ATOM   3341  O   LEU A 454      14.920 -42.061  13.938  1.00 32.44           A  O
ATOM   3342  N   ALA A 455      15.690 -39.954  13.811  1.00 33.75           A  N
ATOM   3343  CA  ALA A 455      17.024 -40.383  14.266  1.00 34.89           A  C
ATOM   3344  CB  ALA A 455      18.028 -39.239  14.292  1.00 31.89           A  C
ATOM   3345  C   ALA A 455      16.904 -41.001  15.650  1.00 34.64           A  C
ATOM   3346  O   ALA A 455      17.333 -42.138  15.871  1.00 35.64           A  O
ATOM   3347  N   LEU A 456      16.286 -40.258  16.563  1.00 32.47           A  N
ATOM   3348  CA  LEU A 456      16.257 -40.659  17.955  1.00 32.01           A  C
ATOM   3349  CB  LEU A 456      15.694 -39.531  18.809  1.00 30.89           A  C
ATOM   3350  CG  LEU A 456      16.586 -38.306  18.812  1.00 29.81           A  C
ATOM   3351  CD1 LEU A 456      15.829 -37.047  19.244  1.00 26.94           A  C
ATOM   3352  CD2 LEU A 456      17.818 -38.587  19.665  1.00 28.90           A  C
ATOM   3353  C   LEU A 456      15.493 -41.959  18.183  1.00 30.85           A  C
ATOM   3354  O   LEU A 456      15.938 -42.809  18.986  1.00 30.85           A  O
ATOM   3355  N   ILE A 457      14.357 -42.117  17.914  1.00 30.09           A  N
ATOM   3356  CA  ILE A 457      13.540 -43.319  17.670  1.00 30.49           A  C
ATOM   3357  CB  ILE A 457      12.209 -43.234  16.851  1.00 30.83           A  C
ATOM   3358  CG1 ILE A 457      11.273 -42.219  17.489  1.00 29.13           A  C
ATOM   3359  CD1 ILE A 457      10.023 -41.975  16.691  1.00 27.59           A  C
ATOM   3360  CG2 ILE A 457      11.597 -44.603  16.725  1.00 31.25           A  C
ATOM   3361  C   ILE A 457      14.347 -44.581  17.345  1.00 31.82           A  C
ATOM   3362  O   ILE A 457      14.441 -45.485  18.169  1.00 30.84           A  O
ATOM   3363  N   ARG A 458      14.977 -44.607  16.175  1.00 34.22           A  N
ATOM   3364  CA  ARG A 458      15.846 -45.718  15.775  1.00 36.05           A  C
ATOM   3365  CB  ARG A 458      16.232 -45.587  14.288  1.00 38.52           A  C
ATOM   3366  CG  ARG A 458      15.153 -46.066  13.322  1.00 40.80           A  C
ATOM   3367  CD  ARG A 458      15.474 -47.443  12.759  1.00 41.00           A  C
ATOM   3368  NE  ARG A 458      14.287 -48.184  12.336  1.00 43.96           A  N
ATOM   3369  CZ  ARG A 458      13.816 -49.270  12.957  1.00 45.23           A  C
ATOM   3370  NH1 ARG A 458      12.731 -49.876  12.506  1.00 42.76           A  N
ATOM   3371  NH2 ARG A 458      14.424 -49.757  14.031  1.00 43.44           A  N
ATOM   3372  C   ARG A 458      17.095 -45.890  16.669  1.00 35.73           A  C
ATOM   3373  O   ARG A 458      17.430 -47.008  17.032  1.00 37.55           A  O
ATOM   3374  N   VAL A 459      17.771 -44.802  17.027  1.00 34.28           A  N
ATOM   3375  CA  VAL A 459      18.983 -44.832  17.858  1.00 34.69           A  C
ATOM   3376  CB  VAL A 459      19.670 -43.502  18.006  1.00 34.67           A  C
ATOM   3377  CG1 VAL A 459      20.687 -43.532  19.130  1.00 35.01           A  C
ATOM   3378  CG2 VAL A 459      20.349 -43.084  16.704  1.00 34.46           A  C
ATOM   3379  C   VAL A 459      18.727 -45.469  19.256  1.00 36.51           A  C
ATOM   3380  O   VAL A 459      19.510 -46.232  19.762  1.00 36.84           A  O
ATOM   3381  N   LEU A 460      17.629 -45.040  19.870  1.00 36.52           A  N
ATOM   3382  CA  LEU A 460      17.274 -45.436  21.230  1.00 34.37           A  C
ATOM   3383  CB  LEU A 460      16.395 -44.361  21.858  1.00 33.66           A  C
ATOM   3384  CG  LEU A 460      17.185 -43.092  22.155  1.00 33.75           A  C
ATOM   3385  CD1 LEU A 460      16.260 -41.898  22.261  1.00 33.67           A  C
ATOM   3386  CD2 LEU A 460      18.007 -43.283  23.422  1.00 34.67           A  C
ATOM   3387  C   LEU A 460      16.576 -46.788  21.277  1.00 33.65           A  C
ATOM   3388  O   LEU A 460      16.532 -47.436  22.325  1.00 32.14           A  O
ATOM   3389  N   GLN A 461      16.026 -47.198  20.130  1.00 33.62           A  N
ATOM   3390  CA  GLN A 461      15.417 -48.492  19.950  1.00 33.47           A  C
```

```
ATOM   3521  O   LYS A 476      31.176 -25.877  26.443  1.00 47.16           A  O
ATOM   3522  N   LEU A 477      29.514 -24.444  27.059  1.00 45.77           A  N
ATOM   3523  CA  LEU A 477      29.317 -23.614  25.744  1.00 47.89           A  C
ATOM   3524  CB  LEU A 477      28.007 -22.899  25.745  1.00 47.64           A  C
ATOM   3525  CG  LEU A 477      26.724 -23.459  26.164  1.00 48.22           A  C
ATOM   3526  CD1 LEU A 477      26.723 -22.339  26.421  1.00 46.39           A  C
ATOM   3527  CD2 LEU A 477      26.197 -24.471  25.157  1.00 45.55           A  C
ATOM   3528  C   LEU A 477      30.529 -23.011  25.291  1.00 45.23           A  C
ATOM   3529  O   LEU A 477      31.281 -22.444  26.109  1.00 43.25           A  O
ATOM   3530  N   SER A 478      30.709 -22.970  23.975  1.00 48.90           A  N
ATOM   3531  CA  SER A 478      31.830 -22.298  23.325  1.00 48.60           A  C
ATOM   3532  CB  SER A 478      31.350 -22.663  21.834  1.00 49.82           A  C
ATOM   3533  OG  SER A 478      32.709 -21.617  21.101  1.00 49.41           A  O
ATOM   3534  C   SER A 478      31.782 -20.783  23.496  1.00 50.69           A  C
ATOM   3535  O   SER A 478      30.726 -20.197  23.763  1.00 50.73           A  O
ATOM   3536  N   LEU A 479      32.953 -20.177  23.310  1.00 55.89           A  N
ATOM   3537  CA  LEU A 479      33.209 -18.747  23.478  1.00 55.61           A  C
ATOM   3538  CB  LEU A 479      34.649 -18.564  23.961  1.00 59.64           A  C
ATOM   3539  CG  LEU A 479      35.257 -19.634  24.897  1.00 59.55           A  C
ATOM   3540  CD1 LEU A 479      36.777 -19.496  25.085  1.00 61.55           A  C
ATOM   3541  CD2 LEU A 479      34.614 -19.605  26.280  1.00 58.40           A  C
ATOM   3542  C   LEU A 479      33.001 -17.961  22.172  1.00 58.50           A  C
ATOM   3543  O   LEU A 479      32.920 -18.728  22.188  1.00 60.67           A  O
ATOM   3544  N   GLY A 480      32.914 -18.677  21.048  1.00 53.73           A  N
ATOM   3545  CA  GLY A 480      32.714 -18.064  19.740  1.00 46.20           A  C
ATOM   3546  C   GLY A 480      31.271 -17.678  19.482  1.00 45.32           A  C
ATOM   3547  O   GLY A 480      30.485 -17.402  20.413  1.00 41.39           A  O
ATOM   3548  N   GLY A 481      30.913 -17.679  18.200  1.00 45.31           A  N
ATOM   3549  CA  GLY A 481      29.646 -17.116  17.723  1.00 44.99           A  C
ATOM   3550  C   GLY A 481      28.595 -18.121  17.309  1.00 44.83           A  C
ATOM   3551  O   GLY A 481      27.526 -17.741  16.838  1.00 46.96           A  O
ATOM   3552  N   LEU A 482      28.909 -19.398  17.499  1.00 45.40           A  N
ATOM   3553  CA  LEU A 482      27.981 -20.502  17.257  1.00 46.77           A  C
ATOM   3554  CB  LEU A 482      28.665 -21.543  16.371  1.00 49.09           A  C
ATOM   3555  CG  LEU A 482      28.961 -21.127  14.934  1.00 47.29           A  C
ATOM   3556  CD1 LEU A 482      29.772 -22.186  14.211  1.00 44.40           A  C
ATOM   3557  CD2 LEU A 482      27.646 -20.865  14.224  1.00 49.13           A  C
ATOM   3558  C   LEU A 482      27.658 -21.138  18.592  1.00 44.13           A  C
ATOM   3559  O   LEU A 482      28.493 -21.143  19.468  1.00 43.16           A  O
ATOM   3560  N   LEU A 483      26.443 -21.663  18.761  1.00 45.07           A  N
ATOM   3561  CA  LEU A 483      26.104 -22.301  20.018  1.00 43.94           A  C
ATOM   3562  CB  LEU A 483      24.673 -22.030  20.454  1.00 41.93           A  C
ATOM   3563  CG  LEU A 483      24.202 -22.517  21.819  1.00 44.29           A  C
ATOM   3564  CD1 LEU A 483      24.989 -21.874  22.961  1.00 46.67           A  C
ATOM   3565  CD2 LEU A 483      22.727 -22.201  21.982  1.00 46.78           A  C
ATOM   3566  C   LEU A 483      26.356 -23.763  19.833  1.00 48.76           A  C
ATOM   3567  O   LEU A 483      25.521 -24.517  19.327  1.00 52.97           A  O
ATOM   3568  N   GLN A 484      27.582 -24.133  20.216  1.00 48.65           A  N
ATOM   3569  CA  GLN A 484      28.076 -25.470  20.115  1.00 45.67           A  C
ATOM   3570  CB  GLN A 484      28.983 -25.597  18.905  1.00 49.34           A  C
ATOM   3571  CG  GLN A 484      30.320 -24.878  19.014  1.00 50.93           A  C
ATOM   3572  CD  GLN A 484      31.136 -25.048  17.758  1.00 51.48           A  C
ATOM   3573  OE1 GLN A 484      32.240 -25.574  17.792  1.00 57.52           A  O
ATOM   3574  NE2 GLN A 484      30.576 -24.636  16.633  1.00 57.11           A  N
ATOM   3575  C   GLN A 484      28.864 -25.698  21.374  1.00 49.41           A  C
ATOM   3576  O   GLN A 484      29.158 -24.739  22.091  1.00 54.03           A  O
ATOM   3577  N   PRO A 485      29.207 -26.957  21.665  1.00 50.20           A  N
ATOM   3578  CA  PRO A 485      29.988 -27.232  22.873  1.00 50.31           A  C
ATOM   3579  CB  PRO A 485      29.737 -28.733  23.111  1.00 48.93           A  C
ATOM   3580  CG  PRO A 485      28.757 -29.192  22.058  1.00 52.34           A  C
ATOM   3581  CD  PRO A 485      28.869 -28.194  20.942  1.00 49.02           A  C
ATOM   3582  C   PRO A 485      31.443 -26.961  22.636  1.00 50.16           A  C
ATOM   3583  O   PRO A 485      31.926 -27.149  21.512  1.00 48.54           A  O
ATOM   3584  N   GLU A 486      32.134 -26.531  23.693  1.00 53.89           A  N
ATOM   3585  CA  GLU A 486      33.577 -26.219  23.872  1.00 57.12           A  C
```

FIG. 49 (CONT.)

| ATOM | 3586 | CB  | GLU | A | 486 | 34.034 | -25.809 | 25.082 | 1.00 | 63.01 | A | C |
| ATOM | 3587 | CG  | GLU | A | 486 | 35.514 | -25.483 | 25.244 | 1.00 | 70.40 | A | C |
| ATOM | 3588 | CD  | GLU | A | 486 | 36.128 | -26.203 | 26.438 | 1.00 | 71.51 | A | C |
| ATOM | 3589 | OE1 | GLU | A | 486 | 36.076 | -25.568 | 27.513 | 1.00 | 72.63 | A | O |
| ATOM | 3590 | OE2 | GLU | A | 486 | 35.854 | -27.413 | 26.606 | 1.00 | 72.49 | A | O |
| ATOM | 3591 | C   | GLU | A | 486 | 34.422 | -27.379 | 23.110 | 1.00 | 55.59 | A | C |
| ATOM | 3592 | O   | GLU | A | 486 | 35.124 | -27.207 | 22.115 | 1.00 | 54.15 | A | O |
| ATOM | 3593 | N   | LYS | A | 487 | 34.351 | -28.545 | 23.753 | 1.00 | 56.14 | A | N |
| ATOM | 3594 | CA  | LYS | A | 487 | 34.897 | -29.784 | 23.201 | 1.00 | 57.08 | A | C |
| ATOM | 3595 | CB  | LYS | A | 487 | 35.682 | -30.564 | 24.270 | 1.00 | 58.05 | A | C |
| ATOM | 3596 | CG  | LYS | A | 487 | 36.971 | -29.883 | 24.749 | 1.00 | 61.50 | A | C |
| ATOM | 3597 | CD  | LYS | A | 487 | 38.274 | -30.443 | 24.155 | 1.00 | 61.31 | A | C |
| ATOM | 3598 | CE  | LYS | A | 487 | 38.414 | -30.305 | 22.635 | 1.00 | 61.69 | A | C |
| ATOM | 3599 | NZ  | LYS | A | 487 | 38.048 | -28.967 | 22.076 | 1.00 | 58.95 | A | N |
| ATOM | 3600 | C   | LYS | A | 487 | 33.730 | -30.624 | 22.659 | 1.00 | 60.30 | A | C |
| ATOM | 3601 | O   | LYS | A | 487 | 32.656 | -30.661 | 23.286 | 1.00 | 59.94 | A | O |
| ATOM | 3602 | N   | PRO | A | 488 | 33.929 | -31.234 | 21.494 | 1.00 | 59.26 | A | N |
| ATOM | 3603 | CA  | PRO | A | 488 | 32.803 | -32.029 | 20.889 | 1.00 | 53.67 | A | C |
| ATOM | 3604 | CB  | PRO | A | 488 | 33.363 | -32.482 | 19.532 | 1.00 | 56.35 | A | C |
| ATOM | 3605 | CG  | PRO | A | 488 | 34.616 | -31.678 | 19.323 | 1.00 | 57.01 | A | C |
| ATOM | 3606 | CD  | PRO | A | 488 | 35.153 | -31.450 | 20.702 | 1.00 | 56.42 | A | C |
| ATOM | 3607 | C   | PRO | A | 488 | 32.446 | -33.227 | 21.735 | 1.00 | 52.01 | A | C |
| ATOM | 3608 | O   | PRO | A | 488 | 33.330 | -33.993 | 22.092 | 1.00 | 52.69 | A | O |
| ATOM | 3609 | N   | VAL | A | 489 | 31.156 | -33.372 | 22.044 | 1.00 | 52.41 | A | N |
| ATOM | 3610 | CA  | VAL | A | 489 | 30.640 | -34.390 | 22.978 | 1.00 | 48.03 | A | C |
| ATOM | 3611 | CB  | VAL | A | 489 | 29.098 | -34.257 | 23.172 | 1.00 | 48.20 | A | C |
| ATOM | 3612 | CG1 | VAL | A | 489 | 28.550 | -35.314 | 24.117 | 1.00 | 47.26 | A | C |
| ATOM | 3613 | CG2 | VAL | A | 489 | 28.736 | -32.886 | 23.717 | 1.00 | 50.78 | A | C |
| ATOM | 3614 | C   | VAL | A | 489 | 31.007 | -35.827 | 22.580 | 1.00 | 47.30 | A | C |
| ATOM | 3615 | O   | VAL | A | 489 | 30.728 | -36.256 | 21.459 | 1.00 | 44.99 | A | O |
| ATOM | 3616 | N   | VAL | A | 490 | 31.643 | -36.550 | 23.507 | 1.00 | 45.57 | A | N |
| ATOM | 3617 | CA  | VAL | A | 490 | 31.894 | -37.992 | 23.350 | 1.00 | 45.09 | A | C |
| ATOM | 3618 | CB  | VAL | A | 490 | 33.411 | -38.356 | 23.433 | 1.00 | 46.66 | A | C |
| ATOM | 3619 | CG1 | VAL | A | 490 | 34.197 | -37.695 | 22.305 | 1.00 | 45.66 | A | C |
| ATOM | 3620 | CG2 | VAL | A | 490 | 34.015 | -37.999 | 24.784 | 1.00 | 46.17 | A | C |
| ATOM | 3621 | C   | VAL | A | 490 | 31.084 | -38.805 | 24.374 | 1.00 | 42.80 | A | C |
| ATOM | 3622 | O   | VAL | A | 490 | 31.018 | -38.438 | 25.548 | 1.00 | 41.55 | A | O |
| ATOM | 3623 | N   | LEU | A | 491 | 30.451 | -39.822 | 23.930 | 1.00 | 41.85 | A | N |
| ATOM | 3624 | CA  | LEU | A | 491 | 29.684 | -40.768 | 24.833 | 1.00 | 41.21 | A | C |
| ATOM | 3625 | CB  | LEU | A | 491 | 28.179 | -40.406 | 24.851 | 1.00 | 39.22 | A | C |
| ATOM | 3626 | CG  | LEU | A | 491 | 27.445 | -39.011 | 25.237 | 1.00 | 37.56 | A | C |
| ATOM | 3627 | CD1 | LEU | A | 491 | 26.182 | -38.872 | 24.862 | 1.00 | 36.71 | A | C |
| ATOM | 3628 | CD2 | LEU | A | 491 | 27.842 | -38.663 | 26.703 | 1.00 | 37.19 | A | C |
| ATOM | 3629 | C   | LEU | A | 491 | 29.864 | -42.244 | 24.465 | 1.00 | 43.14 | A | C |
| ATOM | 3630 | O   | LEU | A | 491 | 30.125 | -42.580 | 23.304 | 1.00 | 42.69 | A | O |
| ATOM | 3631 | N   | LYS | A | 492 | 29.728 | -43.121 | 25.459 | 1.00 | 44.91 | A | N |
| ATOM | 3632 | CA  | LYS | A | 492 | 29.787 | -44.556 | 25.217 | 1.00 | 45.94 | A | C |
| ATOM | 3633 | CB  | LYS | A | 492 | 30.227 | -45.304 | 26.486 | 1.00 | 47.77 | A | C |
| ATOM | 3634 | CG  | LYS | A | 492 | 31.064 | -46.566 | 26.245 | 1.00 | 48.66 | A | C |
| ATOM | 3635 | CD  | LYS | A | 492 | 32.486 | -46.275 | 25.745 | 1.00 | 49.20 | A | C |
| ATOM | 3636 | CE  | LYS | A | 492 | 33.540 | -46.369 | 26.850 | 1.00 | 49.71 | A | C |
| ATOM | 3637 | NZ  | LYS | A | 492 | 34.934 | -46.553 | 26.338 | 1.00 | 49.91 | A | N |
| ATOM | 3638 | C   | LYS | A | 492 | 28.420 | -45.030 | 24.722 | 1.00 | 46.56 | A | C |
| ATOM | 3639 | O   | LYS | A | 492 | 27.397 | -44.489 | 25.122 | 1.00 | 46.79 | A | O |
| ATOM | 3640 | N   | VAL | A | 493 | 28.423 | -46.027 | 23.839 | 1.00 | 46.44 | A | N |
| ATOM | 3641 | CA  | VAL | A | 493 | 27.200 | -46.549 | 23.213 | 1.00 | 45.34 | A | C |
| ATOM | 3642 | CB  | VAL | A | 493 | 27.142 | -46.175 | 21.709 | 1.00 | 45.81 | A | C |
| ATOM | 3643 | CG1 | VAL | A | 493 | 25.784 | -46.524 | 21.103 | 1.00 | 46.77 | A | C |
| ATOM | 3644 | CG2 | VAL | A | 493 | 27.465 | -44.709 | 21.500 | 1.00 | 44.42 | A | C |
| ATOM | 3645 | C   | VAL | A | 493 | 27.147 | -48.078 | 23.349 | 1.00 | 44.69 | A | C |
| ATOM | 3646 | O   | VAL | A | 493 | 28.143 | -48.751 | 23.080 | 1.00 | 43.38 | A | O |
| ATOM | 3647 | N   | GLU | A | 494 | 25.992 | -48.619 | 23.754 | 1.00 | 44.16 | A | N |
| ATOM | 3648 | CA  | GLU | A | 494 | 25.825 | -50.074 | 23.941 | 1.00 | 43.73 | A | C |
| ATOM | 3649 | CB  | GLU | A | 494 | 25.669 | -50.445 | 25.427 | 1.00 | 44.87 | A | C |
| ATOM | 3650 | CG  | GLU | A | 494 | 26.084 | -49.390 | 26.443 | 1.00 | 46.11 | A | C |

FIG. 49 (CONT.)

| | | | | | | | | | | | |
|---|---|---|---|---|---|---|---|---|---|---|---|
| ATOM | 3651 | CD | GLU | A | 494 | 25.577 | -49.718 | 27.840 | 1.00 | 47.59 | A | C |
| ATOM | 3652 | OE1 | GLU | A | 494 | 24.808 | -49.062 | 28.292 | 1.00 | 48.91 | A | O |
| ATOM | 3653 | OE2 | GLU | A | 494 | 26.134 | -50.636 | 28.479 | 1.00 | 45.28 | A | O |
| ATOM | 3654 | C | GLU | A | 494 | 24.626 | -50.644 | 23.176 | 1.00 | 42.56 | A | C |
| ATOM | 3655 | O | GLU | A | 494 | 23.670 | -49.920 | 22.897 | 1.00 | 42.06 | A | O |
| ATOM | 3656 | N | SER | A | 495 | 24.681 | -51.946 | 22.872 | 1.00 | 41.99 | A | N |
| ATOM | 3657 | CA | SER | A | 495 | 23.882 | -52.676 | 22.221 | 1.00 | 41.32 | A | C |
| ATOM | 3658 | CB | SER | A | 495 | 24.097 | -53.901 | 21.454 | 1.00 | 40.74 | A | C |
| ATOM | 3659 | OG | SER | A | 495 | 24.858 | -53.549 | 20.323 | 1.00 | 40.95 | A | O |
| ATOM | 3660 | C | SER | A | 495 | 22.887 | -53.158 | 23.255 | 1.00 | 42.54 | A | C |
| ATOM | 3661 | O | SER | A | 495 | 22.980 | -53.843 | 24.215 | 1.00 | 43.65 | A | O |
| ATOM | 3662 | N | ARG | A | 496 | 21.915 | -52.831 | 23.046 | 1.00 | 42.31 | A | N |
| ATOM | 3663 | CA | ARG | A | 496 | 20.254 | -53.283 | 23.956 | 1.00 | 41.92 | A | C |
| ATOM | 3664 | CB | ARG | A | 496 | 18.969 | -52.461 | 23.737 | 1.00 | 39.73 | A | C |
| ATOM | 3665 | CG | ARG | A | 496 | 19.024 | -51.066 | 24.349 | 1.00 | 38.13 | A | C |
| ATOM | 3666 | CD | ARG | A | 496 | 17.718 | -50.271 | 24.145 | 1.00 | 37.50 | A | C |
| ATOM | 3667 | NE | ARG | A | 496 | 16.853 | -50.736 | 25.068 | 1.00 | 37.20 | A | N |
| ATOM | 3668 | CZ | ARG | A | 496 | 15.423 | -50.228 | 25.019 | 1.00 | 37.98 | A | C |
| ATOM | 3669 | NH1 | ARG | A | 496 | 15.101 | -49.214 | 24.217 | 1.00 | 37.50 | A | N |
| ATOM | 3670 | NH2 | ARG | A | 496 | 14.506 | -50.739 | 25.836 | 1.00 | 35.81 | A | N |
| ATOM | 3671 | C | ARG | A | 496 | 19.989 | -54.805 | 23.905 | 1.00 | 41.95 | A | C |
| ATOM | 3672 | O | ARG | A | 496 | 19.082 | -55.320 | 24.975 | 1.00 | 42.14 | A | O |
| ATOM | 3673 | OXT | ARG | A | 496 | 20.866 | -55.585 | 23.223 | 1.00 | 42.61 | A | O |
| ATOM | 3674 | O2D | HEM | A | 500 | 13.933 | -16.112 | 5.804 | 1.00 | 36.54 | A | O |
| ATOM | 3675 | CGD | HEM | A | 500 | 13.117 | -17.070 | 5.836 | 1.00 | 35.67 | A | C |
| ATOM | 3676 | O1D | HEM | A | 500 | 11.988 | -16.960 | 5.297 | 1.00 | 32.74 | A | O |
| ATOM | 3677 | CBD | HEM | A | 500 | 13.483 | -18.377 | 6.546 | 1.00 | 31.77 | A | C |
| ATOM | 3678 | CAD | HEM | A | 500 | 14.990 | -18.685 | 6.546 | 1.00 | 31.15 | A | C |
| ATOM | 3679 | C3D | HEM | A | 500 | 15.145 | -20.099 | 6.968 | 1.00 | 30.75 | A | C |
| ATOM | 3680 | C2D | HEM | A | 500 | 15.191 | -21.297 | 6.136 | 1.00 | 32.04 | A | C |
| ATOM | 3681 | C4D | HEM | A | 500 | 15.121 | -21.421 | 8.624 | 1.00 | 28.34 | A | C |
| ATOM | 3682 | C4D | HEM | A | 500 | 15.247 | -20.671 | 8.328 | 1.00 | 30.86 | A | C |
| ATOM | 3683 | CHA | HEM | A | 500 | 15.313 | -19.775 | 9.457 | 1.00 | 32.58 | A | C |
| ATOM | 3684 | ND | HEM | A | 500 | 15.383 | -22.002 | 8.460 | 1.00 | 30.38 | A | N |
| ATOM | 3685 | C1D | HEM | A | 500 | 15.324 | -22.368 | 7.166 | 1.00 | 29.13 | A | C |
| ATOM | 3686 | CHD | HEM | A | 500 | 15.414 | -23.749 | 6.727 | 1.00 | 28.37 | A | C |
| ATOM | 3687 | FE+3 | HEM | A | 500 | 15.503 | -23.305 | 10.153 | 1.00 | 28.03 | A | FE |
| ATOM | 3688 | NB | HEM | A | 500 | 16.251 | -24.363 | 11.839 | 1.00 | 30.42 | A | N |
| ATOM | 3689 | C4B | HEM | A | 500 | 16.601 | -25.680 | 11.921 | 1.00 | 31.61 | A | C |
| ATOM | 3690 | C3B | HEM | A | 500 | 16.987 | -26.122 | 13.297 | 1.00 | 31.09 | A | C |
| ATOM | 3691 | CAB | HEM | A | 500 | 17.459 | -27.433 | 13.733 | 1.00 | 31.86 | A | C |
| ATOM | 3692 | CBB | HEM | A | 500 | 16.831 | -28.299 | 14.221 | 1.00 | 33.37 | A | C |
| ATOM | 3693 | C2B | HEM | A | 500 | 16.819 | -24.945 | 14.131 | 1.00 | 33.78 | A | C |
| ATOM | 3694 | CMB | HEM | A | 500 | 17.052 | -24.765 | 15.604 | 1.00 | 31.95 | A | C |
| ATOM | 3695 | C1B | HEM | A | 500 | 16.353 | -23.958 | 13.123 | 1.00 | 32.49 | A | C |
| ATOM | 3696 | CHB | HEM | A | 500 | 16.093 | -22.580 | 13.224 | 1.00 | 32.60 | A | C |
| ATOM | 3697 | NC | HEM | A | 500 | 16.171 | -24.720 | 8.978 | 1.00 | 28.95 | A | N |
| ATOM | 3698 | C4C | HEM | A | 500 | 15.685 | -24.871 | 7.608 | 1.00 | 29.46 | A | C |
| ATOM | 3699 | C3C | HEM | A | 500 | 15.633 | -26.286 | 7.139 | 1.00 | 27.55 | A | C |
| ATOM | 3700 | CAC | HEM | A | 500 | 15.259 | -26.931 | 5.842 | 1.00 | 25.63 | A | C |
| ATOM | 3701 | CBC | HEM | A | 500 | 15.286 | -26.350 | 4.672 | 1.00 | 25.76 | A | C |
| ATOM | 3702 | C2C | HEM | A | 500 | 15.972 | -27.109 | 8.281 | 1.00 | 27.40 | A | C |
| ATOM | 3703 | CMC | HEM | A | 500 | 15.895 | -28.609 | 8.212 | 1.00 | 27.39 | A | C |
| ATOM | 3704 | C1C | HEM | A | 500 | 16.201 | -26.140 | 9.394 | 1.00 | 28.65 | A | C |
| ATOM | 3705 | CHC | HEM | A | 500 | 16.434 | -26.586 | 10.746 | 1.00 | 30.08 | A | C |
| ATOM | 3706 | NA | HEM | A | 500 | 15.940 | -21.637 | 11.116 | 1.00 | 31.15 | A | N |
| ATOM | 3707 | C1A | HEM | A | 500 | 15.511 | -20.271 | 10.796 | 1.00 | 32.81 | A | C |
| ATOM | 3708 | C4A | HEM | A | 500 | 15.841 | -21.505 | 12.570 | 1.00 | 32.82 | A | C |
| ATOM | 3709 | C3A | HEM | A | 500 | 15.582 | -20.136 | 13.100 | 1.00 | 33.82 | A | C |
| ATOM | 3710 | CMA | HEM | A | 500 | 15.586 | -19.699 | 14.537 | 1.00 | 35.33 | A | C |
| ATOM | 3711 | C2A | HEM | A | 500 | 15.373 | -19.310 | 11.928 | 1.00 | 33.13 | A | C |
| ATOM | 3712 | CAA | HEM | A | 500 | 15.052 | -17.833 | 11.901 | 1.00 | 35.03 | A | C |
| ATOM | 3713 | CBA | HEM | A | 500 | 13.566 | -17.537 | 12.099 | 1.00 | 38.13 | A | C |
| ATOM | 3714 | CGA | HEM | A | 500 | 13.376 | -16.053 | 12.351 | 1.00 | 41.95 | A | C |

FIG. 49 (CONT.)

```
ATOM   3715  O1A HEM A 500      12.428 -15.719  13.098  1.00 43.16           A    O
ATOM   3716  O2A HEM A 500      14.163 -15.208  11.822  1.00 43.15           A    O
ATOM   3717  N08 MF8 A 600      19.340 -17.685  12.301  1.00 74.14                N
ATOM   3718  C07 MF8 A 600      19.426 -18.674  11.506  1.00 81.36                C
ATOM   3719  N09 MF8 A 600      19.005 -19.883  11.909  1.00 75.14                N
ATOM   3720  N06 MF8 A 600      19.971 -18.506  10.286  1.00 81.65                N
ATOM   3721  C04 MF8 A 600      19.310 -18.558   9.112  1.00 83.43                C
ATOM   3722  N05 MF8 A 600      18.729 -17.500   8.703  1.00 67.82                N
ATOM   3723  N02 MF8 A 600      19.304 -19.700   8.365  1.00 85.64                N
ATOM   3724  C03 MF8 A 600      18.680 -20.952   8.803  1.00 75.58                C
ATOM   3725  C01 MF8 A 600      19.929 -19.809   7.041  1.00 69.89                C
ATOM   3726  O   HOH W   1       6.439 -19.061  18.595  1.00 58.65                O
ATOM   3727  O   HOH W   2      16.665 -13.969  12.676  1.00 42.64                O
ATOM   3728  O   HOH W   3       7.126 -23.868   9.991  1.00 51.31                O
ATOM   3729  O   HOH W   4      30.944 -38.170   8.701  1.00 61.99                O
ATOM   3730  O   HOH W   5      15.790  -8.394  33.629  1.00 71.12                O
ATOM   3731  O   HOH W   6       3.625 -29.010 -12.431  1.00 56.95                O
ATOM   3732  O   HOH W   7      36.521 -39.636   0.548  0.50 65.09                O
ATOM   3733  O   HOH W   8      29.623  -9.979  14.291  1.00 50.21                O
ATOM   3734  O   HOH W   9       2.263 -42.753  -2.013  1.00 70.78                O
ATOM   3735  O   HOH W  10       1.047 -43.344   5.019  1.00 71.93                O
ATOM   3736  O   HOH W  11      -0.877 -18.351  30.086  1.00 62.73                O
ATOM   3737  O   HOH W  12      18.103 -37.490 -15.441  1.00 63.82                O
ATOM   3738  O   HOH W  13       0.285 -16.029  22.045  1.00 75.24                O
ATOM   3739  O   HOH W  14      20.370  -0.672   8.387  1.00 52.70                O
ATOM   3740  O   HOH W  15       2.248   2.251  18.778  1.00 69.56                O
ATOM   3741  O   HOH W  16      12.537   5.829  21.368  1.00 69.50                O
ATOM   3742  O   HOH W  17       6.020  -6.956  25.530  1.00 90.17                O
ATOM   3743  O   HOH W  18       2.020  -9.941  26.617  1.00 59.29                O
ATOM   3744  O   HOH W  19       3.185  -7.490  15.410  1.00 80.00                O
```

FIG. 49 (CONT.)

THERAPEUTIC COMPOUNDS AND METHODS

CROSS-REFERENCE TO RELATED APPLICATIONS

This patent application claims the benefit of priority of U.S. application Ser. No. 61/949,218, filed Mar. 2, 2014, which application is herein incorporated by reference.

GOVERNMENT FUNDING

This invention was made with government support under R01-CA113570 awarded by the National Cancer Institute. The government has certain rights in the invention.

BACKGROUND

Metformin is a widely used biguanide diabetes drug that is associated with decreased breast cancer risk and is currently being studied for treatment and prevention of breast cancer. While metformin and biguanides buformin and phenformin exhibit inhibitory activity against breast cancer they lack potency and their mechanisms of action are unclear. Accordingly, there is a need for more potent agents, including biguanides that treat breast cancer including estrogen positive breast cancer including estrogen positive HER2 negative breast cancer (ER+ HER2−).

SUMMARY OF THE INVENTION

Applicant has discovered that compounds disclosed herein (e.g., compounds of formula I) have as one activity the ability to inhibit CYP3A4 epoxygenase. Accordingly, the compounds disclosed herein (e.g., compounds of formula I) may be useful for treating various diseases such as cancer including breast cancer (e.g., estrogen positive breast cancer (ER+ breast cancer) and estrogen positive HER2 negative breast cancer (ER+ HER2−)). Applicant has also discovered that compounds disclosed herein (e.g., compounds of formula I) enhance the effect of other chemotherapeutic agents (e.g., chemotherapeutic agents for treating breast cancer). Accordingly, compounds and methods are provided for combination therapy for the treatment of various diseases including the treatment of breast cancer (e.g., estrogen positive breast cancer (ER+ breast cancer) and estrogen positive HER2 negative breast cancer (ER+ HER2−)).

One embodiment provides a method for treating or preventing breast cancer (e.g., estrogen positive breast cancer (ER+ breast cancer), estrogen positive HER2 negative breast cancer (ER+ HER2−)) occurrence or recurrence in a patient (e.g., mammal such as a human) in need thereof, comprising administering to the patient in need thereof an effective amount of a compound of formula I:

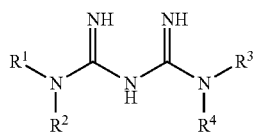

wherein:
$R^1$ is H, $(C_1\text{-}C_{12})$alkyl, $(C_2\text{-}C_{12})$alkenyl, $(C_2\text{-}C_{12})$alkynyl, $-O(C_1\text{-}C_{12})$alkyl, $-O(C_2\text{-}C_{12})$alkenyl, $-O(C_2\text{-}C_{12})$alkynyl, $-OH$, $(C_3\text{-}C_8)$carbocycle, 5-10 membered heteroaryl or aryl, wherein any $(C_1\text{-}C_{12})$alkyl, $(C_2\text{-}C_{12})$alkenyl, $(C_2\text{-}C_{12})$alkynyl, $-O(C_1\text{-}C_{12})$alkyl, $-O(C_2\text{-}C_{12})$alkenyl, or $-O(C_2\text{-}C_{12})$alkynyl of $R^1$ is optionally substituted with one or more (e.g., 1, 2, 3, 4, 5 or more) $Z^{1a}$ groups and wherein any $(C_3\text{-}C_8)$carbocycle, 5-10 membered heteroaryl or aryl of $R^1$ is optionally substituted with one or more (e.g., 1, 2, 3, 4, 5 or more) $Z^{1b}$ groups;

$R^2$ is H, $(C_1\text{-}C_{12})$alkyl, $(C_2\text{-}C_{12})$alkenyl, $(C_2\text{-}C_{12})$alkynyl, $-O(C_2\text{-}C_{12})$alkyl, $-O(C_2\text{-}C_{12})$alkenyl, $-O(C_2\text{-}C_{12})$alkynyl, $-OH$, $(C_3\text{-}C_8)$carbocycle, 5-10 membered heteroaryl or aryl, wherein any $(C_1\text{-}C_{12})$alkyl, $(C_2\text{-}C_{12})$alkenyl, $(C_2\text{-}C_{12})$alkynyl, $-O(C_1\text{-}C_{12})$alkyl, $-O(C_2\text{-}C_{12})$alkenyl, or $-O(C_2\text{-}C_{12})$alkynyl of $R^2$ is optionally substituted with one or more (e.g., 1, 2, 3, 4, 5 or more) $Z^{2a}$ groups and wherein any $(C_3\text{-}C_8)$carbocycle, 5-10 membered heteroaryl or aryl of $R^1$ is optionally substituted with one or more (e.g., 1, 2, 3, 4, 5 or more) $Z^{2b}$ groups;

$R^3$ is H, $(C_1\text{-}C_{12})$alkyl, $(C_2\text{-}C_{12})$alkenyl, $(C_2\text{-}C_{12})$alkynyl, $-O(C_1\text{-}C_{12})$alkyl, $-O(C_2\text{-}C_{12})$alkenyl, $-O(C_2\text{-}C_{12})$alkynyl, $-OH$, $(C_3\text{-}C_8)$carbocycle, 5-10 membered heteroaryl or aryl, wherein any $(C_1\text{-}C_{12})$alkyl, $(C_2\text{-}C_{12})$alkenyl, $(C_2\text{-}C_{12})$alkynyl, $-O(C_1\text{-}C_{12})$alkyl, $-O(C_2\text{-}C_{12})$alkenyl or $-O(C_2\text{-}C_{12})$alkynyl of $R^3$ is optionally substituted with one or more (e.g., 1, 2, 3, 4, 5 or more) $Z^{3a}$ groups and wherein any $(C_3\text{-}C_8)$carbocycle, 5-10 membered heteroaryl or aryl of $R^3$ is optionally substituted with one or more (e.g., 1, 2, 3, 4, 5 or more) $Z^{3b}$ groups;

$R^4$ is H, $(C_1\text{-}C_{12})$alkyl, $(C_2\text{-}C_{12})$alkenyl, $(C_2\text{-}C_{12})$alkynyl, $-O(C_1\text{-}C_{12})$alkyl, $-O(C_2\text{-}C_{12})$alkenyl, $-O(C_2\text{-}C_{12})$alkynyl, $-OH$, $(C_3\text{-}C_8)$carbocycle, 5-10 membered heteroaryl or aryl, wherein any $(C_1\text{-}C_{12})$alkyl, $(C_2\text{-}C_{12})$alkenyl, $(C_2\text{-}C_{12})$alkynyl, $-O(C_1\text{-}C_{12})$alkyl, $-O(C_2\text{-}C_{12})$alkenyl or $-O(C_2\text{-}C_{12})$alkynyl of $R^4$ is optionally substituted with one or more (e.g., 1, 2, 3, 4, 5 or more) $Z^{4a}$ groups and wherein any $(C_3\text{-}C_8)$carbocycle, 5-10 membered heteroaryl or aryl of $R^4$ is optionally substituted with one or more (e.g., 1, 2, 3, 4, 5 or more) $Z^{4b}$ groups;

$Z^{1a}$ is $-OH$, halogen, $-O(C_1\text{-}C_6)$alkyl, $-C(=O)O(C_1\text{-}C_6)$alkyl, $(C_3\text{-}C_8)$carbocycle, 5-10 membered heteroaryl or aryl, wherein any $(C_3\text{-}C_8)$carbocycle, 5-10 membered heteroaryl or aryl of $Z^{1a}$ is optionally substituted with one or more (e.g., 1, 2, 3, 4, 5 or more) groups selected from $(C_1\text{-}C_6)$alkyl, $-OH$, halogen and $-O(C_1\text{-}C_6)$alkyl;

$Z^{1b}$ is $(C_1\text{-}C_6)$alkyl, halogen or $-O(C_1\text{-}C_6)$alkyl;

$Z^{2a}$ is $-OH$, halogen, $-O(C_1\text{-}C_6)$alkyl, $-C(=O)O(C_1\text{-}C_6)$alkyl, $(C_3\text{-}C_8)$carbocycle, 5-10 membered heteroaryl or aryl, wherein any $(C_3\text{-}C_8)$carbocycle, 5-10 membered heteroaryl or aryl of $Z^{2a}$ is optionally substituted with one or more (e.g., 1, 2, 3, 4, 5 or more) groups selected from $(C_1\text{-}C_6)$alkyl, $-OH$, halogen and $-O(C_1\text{-}C_6)$alkyl;

$Z^{2b}$ is $(C_1\text{-}C_6)$alkyl, $-OH$, halogen or $-O(C_1\text{-}C_6)$alkyl;

$Z^{3a}$ is $-OH$, halogen, $-O(C_1\text{-}C_6)$alkyl, $-C(=O)O(C_1\text{-}C_6)$alkyl, $(C_3\text{-}C_8)$carbocycle, 5-10 membered heteroaryl or aryl, wherein any $(C_3\text{-}C_8)$carbocycle, 5-10 membered heteroaryl or aryl of $Z^{3a}$ is optionally substituted with one or more (e.g., 1, 2, 3, 4, 5 or more) groups selected from $(C_1\text{-}C_6)$alkyl, $-OH$, halogen and $-O(C_1\text{-}C_6)$alkyl;

$Z^{3b}$ is $(C_1\text{-}C_6)$alkyl, $-OH$, halogen or $-O(C_1\text{-}C_6)$alkyl;

$Z^{4a}$ is $-OH$, halogen, $-O(C_1\text{-}C_6)$alkyl, $-C(=O)O(C_1\text{-}C_6)$alkyl, $(C_3\text{-}C_8)$carbocycle, 5-10 membered heteroaryl or aryl, wherein any $(C_3\text{-}C_8)$carbocycle, 5-10 membered heteroaryl or aryl of $Z^{4a}$ is optionally substituted with one or more (e.g., 1, 2, 3, 4, 5 or more) groups selected from $(C_1\text{-}C_6)$alkyl, $-OH$, halogen and $-O(C_1\text{-}C_6)$alkyl; and $Z^{4b}$ is $(C_1\text{-}C_6)$alkyl, $-OH$, halogen or $-O(C_1\text{-}C_6)$alkyl; or a pharmaceutically acceptable salt thereof.

One embodiment provides a method for treating or preventing breast cancer occurrence or recurrence in a patient in need thereof, comprising administering to the patient in need thereof an effective amount of a compound that inhibits CYP3A4 epoxygenase activity.

One embodiment provides a pharmaceutical composition comprising a compound of formula I as described herein or a pharmaceutically acceptable salt thereof, one or more additional chemotherapeutic agents and a pharmaceutically acceptable carrier.

One embodiment provides a compound of formula Ib:

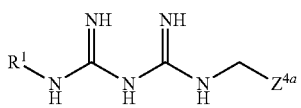

wherein $R^1$ is H, $(C_1-C_{12})$alkyl, $(C_2-C_{12})$alkenyl, $(C_2-C_{12})$alkynyl, —O$(C_1-C_{12})$alkyl, —O$(C_2-C_{12})$alkenyl, —O$(C_2-C_{12})$alkynyl, —OH, $(C_3-C_8)$carbocycle, 5-10 membered heteroaryl or aryl, wherein any $(C_1-C_{12})$alkyl, $(C_2-C_{12})$alkenyl, $(C_2-C_{12})$alkynyl, —O$(C_1-C_{12})$alkyl, —O$(C_2-C_{12})$alkenyl or —O$(C_2-C_{12})$alkynyl of $R^1$ is optionally substituted with one or more $Z^{1a}$ groups and wherein any $(C_3-C_8)$carbocycle, 5-10 membered heteroaryl or aryl of $R^1$ is optionally substituted with one or more $Z^{1b}$ groups; and $Z^{1a}$ is —OH, halogen, —O$(C_1-C_6)$alkyl, —C(=O)O$(C_1-C_6)$alkyl, $(C_3-C_8)$carbocycle, 5-10 membered heteroaryl or aryl, wherein any $(C_3-C_8)$carbocycle, 5-10 membered heteroaryl or aryl of $Z^{1a}$ is optionally substituted with one or more groups selected from $(C_1-C_6)$alkyl, —OH, halogen and —O$(C_1-C_6)$alkyl;

$Z^{1b}$ is $(C_1-C_6)$alkyl, —OH, halogen or —O$(C_1-C_6)$alkyl; and $Z^{4a}$ is —OH, halogen, —O$(C_1-C_6)$alkyl, —C(=O)O$(C_1-C_6)$alkyl, $(C_3-C_8)$carbocycle, 5-10 membered heteroaryl or aryl, wherein any $(C_3-C_8)$carbocycle, 5-10 membered heteroaryl or aryl of $Z^{4a}$ is optionally substituted with one or more groups selected from $(C_1-C_6)$alkyl, —OH, halogen and —O$(C_1-C_6)$alkyl;

or a salt thereof.

One embodiment provides a pharmaceutical composition comprising a compound of formula Ib as described herein or a pharmaceutically acceptable salt thereof and a pharmaceutically acceptable carrier.

One embodiment provides a method for treating or preventing breast cancer occurrence or recurrence in a patient in need thereof, comprising administering to the patient in need thereof an effective amount of a compound of formula Ib as described herein or pharmaceutically acceptable salt thereof.

One embodiment provides a compound of formula I or Ib as described herein or a pharmaceutically acceptable salt thereof, for use in medical therapy.

One embodiment provides a compound of formula I or Ib as described herein or a pharmaceutically acceptable salt thereof, for the prophylactic or therapeutic treatment of breast cancer (e.g., estrogen positive breast cancer).

One embodiment provides a compound of formula I or Ib as described herein or a pharmaceutically acceptable salt thereof, in combination with one or more additional chemotherapeutic agents or a pharmaceutically acceptable salt thereof, for the prophylactic or therapeutic treatment of breast cancer (e.g., estrogen positive breast cancer) occurrence or recurrence.

One embodiment provides a compound of formula I or Ib as described in herein or a pharmaceutically acceptable salt thereof, for the manufacture of a medicament for the treatment or prevention of breast cancer (e.g., estrogen positive breast cancer) occurrence or recurrence in a patient (e.g., a mammal such as a human).

One embodiment provides processes and intermediates disclosed herein that are useful for preparing a compound of formula I or Ib or a salt thereof.

BRIEF DESCRIPTION OF THE FIGURES

FIGS. 1A 1B and 1C illustrate the CYP3A4 shRNA knockdown inhibits the MCF-7 xenograft. FIG. 1A. Nude mice were inoculated with 2×106 cells of the NT2 scramble shRNA line (ρ) or the 3-18 CYP3A4 shRNA line (v). CYP3A4 shRNA tumors exhibited decreased growth (Gompertzian P=0.0018). Error bars are SEM. FIG. 1B. CD31 stain of control tumor and FIG. 1C. CD31 stain of shRNA tumor; arrows indicate endothelial cells. vWF stain similar (results not shown). Size bar 200 microns.

FIG. 2A. HBB docked in the active site of CYP3A4. Proposed hydrogen (H) bonds with R212 are shown in red. Surflex Dock score, SYBYL-X v1.3. FIG. 2B. Metformin-CYP3A4 co-crystal at 2.6 Å resolution showing H bonding with R212.

FIG. 3A. MCF-7 xenograft with 3×106 cells in the 2nd mammary fat pad on day 0. HBB (4 mg/kg ip daily) (v) or PBS (ρ) treatment began on day 1. * indicates P<0.05. FIG. 3B. MDAMB-231 xenograft with 1×106 cells in the 2nd mammary fat pad on day 0. HBB (4 mg/kg ip daily) (v) or PBS (ρ) treatment began on day 1. N=20 mice per arm for each study; error bars are SEM.

FIG. 9A. Metformin was titrated on CYP3A4 nanodiscs (no CPR). A weak spin shift is observed in the difference spectrum (C-A). Metformin titration attenuates the Soret band of CYP3A4 nanodiscs (A=vehicle control; B=156 uM; C=1.1 mM metformin), indicating metformin binding to functional CYP3A4. FIG. 9B. NADPH-dependent synthesis of EETs by CYP3A4 nanodiscs. In a 1 ml reaction ~20 ng of the (±)-14,15-EET regioisomer is synthesized in 2 minutes. Initial [AA]=55 uM and [NADPH]=160 uM. NADPH-dependent EET synthesis is observed (P<0.05;*).

FIG. 21A. Nude mice aged 6 weeks were inoculated in the right mammary fat pad with $2 \times 10^6$ cells of the NT2 scramble shRNA line (r) or the 3-18 CYP3A4 shRNA line (n). The CYP3A4 shRNA tumors exhibited decreased growth vs. the NT2 control (p=0.0018; error bars=SEM) FIG. 21B. The CYP3A4 knock down tumors exhibited necrosis (5 of 6 evaluable mice; right) whereas the NT2 control tumors did not (0 of 6 evaluable mice; left). (p=0.0152; 2 tailed Fisher's exact test).

FIG. 44A. Nude mice were inoculated with $3 \times 10^6$ MCF-7 cells and treated with vehicle (Δ) HBB at the MTD (4 mg/kg/day ip) (■). (* indicates P<0.05). Error bars are SEM. Gompertzian fit for days 8 onward shows a significant difference between the HBB and vehicle growth curves (P=0.035). The dose limiting toxicity was weight loss. At the MTD there was a well-tolerated 4% reduction of weight at 42 days (P<0.0001; data not shown). FIG. 44B. Nude mice were inoculated with $1 \times 10^6$ MDA-MB-231 cells and treated with HBB at the MTD (4 mg/kg/day ip). There was no significant difference between the HBB and vehicle growth curves.

DETAILED DESCRIPTION

Figure 2A:
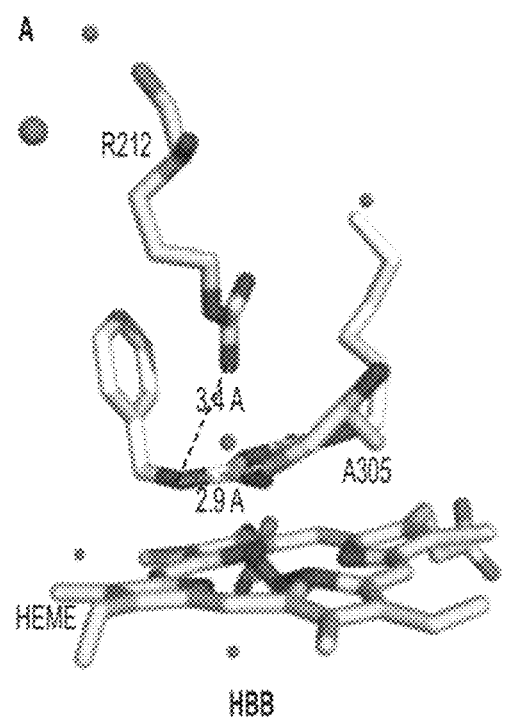
FIGS. 2A and 2B illustrate the docking of HBB compared with the metformin-CYP3A4 co-crystal.

The following definitions are used, unless otherwise described.

The term "alkyl" is a straight or branched saturated hydrocarbon. For example, an alkyl group can have 1 to 8 carbon atoms (i.e., ($C_1$-$C_8$)alkyl) or 1 to 6 carbon atoms (i.e., ($C_1$-$C_6$ alkyl) or 1 to 4 carbon atoms.

The term "alkenyl" is a straight or branched hydrocarbon with at least one carbon-carbon double bond. For example, an alkenyl group can have 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$) and 5-hexenyl (—$CH_2CH_2CH_2CH_2$CH=$CH_2$).

The term "alkynyl" is a straight or branched hydrocarbon with at least one carbon-carbon triple bond. For example, an alkynyl group can have 2 to 8 carbon atoms (i.e., $C_2$-$C_8$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

The term "halo" or "halogen" as used herein refers to fluoro, chloro, bromo and iodo.

The term "haloalkyl" as used herein refers to an alkyl as defined herein, wherein one or more hydrogen atoms are each replaced by a halo substituent. For example, a ($C_1$-$C_6$) haloalkyl is a ($C_1$-$C_6$)alkyl wherein one or more of the hydrogen atoms have been independently replaced by a halo substituent. Such a range includes one halo substituent on the alkyl group to complete halogenation of the alkyl group. The halo substituents may be the same or different.

The term "carbocycle" or "carbocyclyl" refers to a single saturated (i.e., cycloalkyl) or a single partially unsaturated (e.g., cycloalkenyl, cycloalkadienyl, etc.) all carbon ring having for example 3 to 8 carbon atoms (i.e., ($C_3$-$C_8$) carbocycle) or 3 to 7 carbon atoms (i.e., ($C_3$-$C_7$)carbocycle). The term "carbocycle" or "carbocyclyl" also includes multiple condensed, saturated and partially unsaturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, Spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2] octane, etc). The "carbocycle" or "carbocyclyl" can also be optionally substituted with one or more (e.g., 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

The term "aryl" as used herein refers to a single all carbon aromatic ring or a multiple condensed all carbon ring system wherein at least one of the rings is aromatic. For example, an aryl group can have 6 to 20 carbon atoms, 6 to 14 carbon atoms, or 6 to 12 carbon atoms or 6 to 10 carbon atoms. Aryl includes a phenyl radical. Aryl also includes multiple condensed ring systems (e.g., ring systems comprising 2 or 3 rings) having about 9 to 20 carbon atoms in which at least one ring is aromatic and wherein the other rings may be aromatic or not aromatic (i.e., carbocycle). Such multiple condensed ring systems may be optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Typical aryl groups include, but are not limited to phenyl, indenyl, naphthyl, 1,2,3,4-tetrahydronaphthyl, anthracenyl, and the like.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system such as a 5-10 membered heteroaryl) has about 1-9 carbon atoms and about 1-4 heteroatoms within the heteroaryl ring; or a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5-14 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclopenta[1,2-c]pyrazole.

The term "treatment" or "treating," to the extent it relates to a disease or condition includes inhibiting the disease or condition, eliminating the disease or condition, and/or relieving one or more symptoms of the disease or condition.

The term "patient" as used herein refers to any animal including mammals such as humans, higher non-human primates, rodents domestic and farm animals such as cow, horses, dogs and cats. In one embodiment, the patient is a human patient.

The phrase "therapeutically effective amount" means an amount of a compound described herein that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase. It is to be understood that all rotational isomers for compounds of formula I, Ia and Ib are within the scope of the invention.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents. It is to be understood that one or more values may be combined. Specific values listed below are values for compounds of formula I as well as all related formulas (e.g., compounds of formulas Ia, Ib).

A specific value for $R^2$ is H.
A specific value for $R^4$ is H.
A specific group of compounds of formula I are compounds of formula Ia:

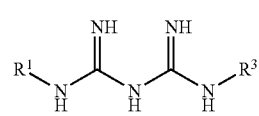

Ia or a salt thereof.

A specific value for $R^1$ is $(C_1\text{-}C_{12})$alkyl, $(C_2\text{-}C_{12})$alkenyl, or $(C_2\text{-}C_{12})$alkynyl, wherein any $(C_1\text{-}C_{12})$alkyl, $(C_2\text{-}C_{12})$alkenyl or $(C_2\text{-}C_{12})$alkynyl of $R^1$ is optionally substituted with one or more $Z^{1a}$ groups.

A specific value for $R^1$ is $(C_1\text{-}C_{12})$alkyl, $(C_2\text{-}C_{12})$alkenyl or $(C_2\text{-}C_{12})$alkynyl.

A specific value for $R^1$ is $(C_4\text{-}C_8)$alkyl, $(C_4\text{-}C_8)$alkenyl or $(C_4\text{-}C_8)$alkynyl.

A specific value for $R^1$ is $(C_1\text{-}C_{12})$alkyl.
A specific value for $R^1$ is $(C_2\text{-}C_{10})$alkyl.
A specific value for $R^1$ is $(C_4\text{-}C_8)$alkyl.

A specific value for $R^1$ is $(C_6)$alkyl.
A specific value for $R^1$ is hexyl.
A specific value for $R^4$ is $(C_1-C_{12})$alkyl, $(C_2-C_{12})$alkenyl, $(C_2-C_{12})$alkynyl, wherein any $(C_1-C_{12})$alkyl, $(C_2-C_{12})$alkenyl or $(C_2-C_{12})$alkynyl of $R^4$ is optionally substituted with one or more $Z^{4a}$ groups.
A specific value for $R^4$ is $(C_1-C_{12})$alkyl, $(C_2-C_{12})$alkenyl, $(C_2-C_{12})$alkynyl, wherein any $(C_1-C_{12})$alkyl, $(C_2-C_{12})$alkenyl or $(C_2-C_{12})$alkynyl of $R^4$ is substituted with one or more $Z^{4a}$ groups.
A specific value for $R^4$ is $(C_1-C_4)$alkyl, $(C_2-C_4)$alkenyl, $(C_2-C_4)$alkynyl, wherein any $(C_1-C_4)$alkyl, $(C_2-C_4)$alkenyl or $(C_2-C_4)$alkynyl of $R^4$ is substituted with one or more $Z^{4a}$ groups.
A specific value for $R^4$ is $(C_1-C_6)$alkyl, wherein any $(C_1-C_6)$alkyl of $R^4$ is substituted with one or more $Z^{4a}$ groups.
A specific value for $R^4$ is $(C_1-C_3)$alkyl, wherein any $(C_1-C_3)$alkyl of $R^4$ is substituted with one or more $Z^{4a}$ groups.
A specific value for $R^4$ is $-CH_2-Z^{4a}$.
A specific group of compounds of formula I are compounds of formula Ib:

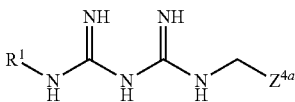

or a salt thereof.
A specific value for $Z^{4a}$ is $(C_3-C_8)$carbocycle, 5-10 membered heteroaryl or aryl, wherein any $(C_3-C_8)$carbocycle, 5-10 membered heteroaryl or aryl of $Z^{4a}$ is optionally substituted with one or more groups selected from $(C_1-C_6)$alkyl, $-OH$, halogen and $-O(C_1-C_6)$alkyl.
A specific value for $Z^{4a}$ is 5-10 membered heteroaryl or aryl, wherein any 5-10 membered heteroaryl or aryl of $Z^{4a}$ is optionally substituted with one or more groups selected from $(C_1-C_6)$alkyl, $-OH$, halogen and $-O(C_1-C_6)$alkyl.
A specific value for $Z^{4a}$ is a 5 membered heteroaryl, 6 membered heteroaryl or phenyl, wherein any 5 membered heteroaryl, 6 membered heteroaryl or phenyl of $Z^{4a}$ is optionally substituted with one or more groups selected from $(C_1-C_6)$alkyl, $-OH$, halogen and $-O(C_1-C_6)$alkyl.
A specific value for $Z^{4a}$ is a 5 membered heteroaryl, 6 membered heteroaryl or phenyl.
A specific compound of formula I is:

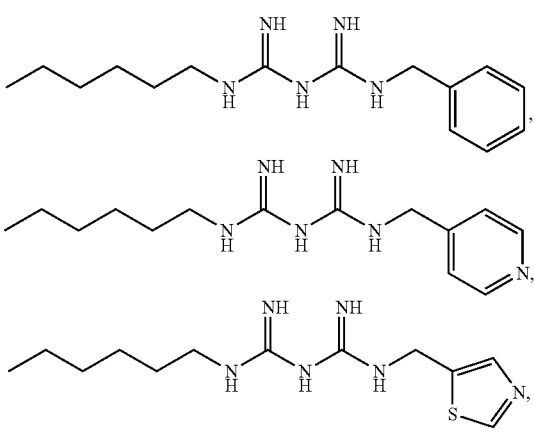

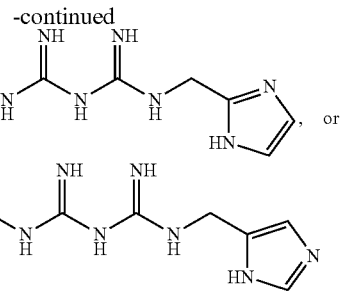

or a salt thereof.
In one embodiment the compound of formula I is metformin or a pharmaceutically acceptable salt thereof.
In one embodiment the compound of formula I does not include metformin.
A specific group of compounds of formula I are compounds of formula Ib:

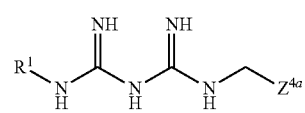

wherein
$R^1$ is H, $(C_1-C_{12})$alkyl, $(C_2-C_{12})$alkenyl, $(C_2-C_{12})$alkynyl, $-O(C_1-C_{12})$alkyl, $-O(C_2-C_{12})$alkenyl, $-O(C_2-C_{12})$alkynyl, $-OH$, $(C_3-C_8)$carbocycle, 5-10 membered heteroaryl or aryl, wherein any $(C_1-C_{12})$alkyl, $(C_2-C_{12})$alkenyl, $(C_2-C_{12})$alkynyl, $-O(C_1-C_{12})$alkyl, $-O(C_2-C_{12})$alkenyl, $-O(C_2-C_{12})$alkynyl of $R^1$ is optionally substituted with one or more $Z^{1a}$ groups and wherein any $(C_3-C_8)$carbocycle, 5-10 membered heteroaryl or aryl of $R^1$ is optionally substituted with one or more $Z^{1b}$ groups; and
$Z^{1a}$ is $-OH$, halogen, $-O(C_1-C_6)$alkyl, $-C(=O)O(C_1-C_6)$alkyl, $(C_3-C_8)$carbocycle, 5-10 membered heteroaryl or aryl, wherein any $(C_3-C_8)$carbocycle, 5-10 membered heteroaryl or aryl of $Z^{1a}$ is optionally substituted with one or more groups selected from $(C_1-C_6)$alkyl, $-OH$, halogen and $-O(C_1-C_6)$alkyl;
$Z^{1b}$ is $(C_1-C_6)$alkyl, $-OH$, halogen or $-O(C_1-C_6)$alkyl; and
$Z^{4a}$ is $-OH$, halogen, $-O(C_1-C_6)$alkyl, $-C(=O)O(C_1-C_6)$alkyl, $(C_3-C_8)$carbocycle, 5-10 membered heteroaryl or aryl, wherein any $(C_3-C_8)$carbocycle, 5-10 membered heteroaryl or aryl of $Z^{4a}$ is optionally substituted with one or more groups selected from $(C_1-C_6)$alkyl, $-OH$, halogen and $-O(C_1-C_6)$alkyl;
or a salt thereof.
A specific value for $R^1$ is $(C_1-C_{12})$alkyl, $(C_2-C_{12})$alkenyl or $(C_2-C_{12})$alkynyl, wherein any $(C_1-C_{12})$alkyl, $(C_2-C_{12})$alkenyl or $(C_2-C_{12})$alkynyl of $R^1$ is optionally substituted with one or more $Z^{1a}$ groups.
A specific value for $R^1$ is $(C_1-C_{12})$alkyl, $(C_2-C_{12})$alkenyl or $(C_2-C_{12})$alkynyl.
A specific value for $R^1$ is $(C_4-C_8)$alkyl, $(C_4-C_8)$alkenyl or $(C_4-C_8)$alkynyl.
A specific value for $R^1$ is $(C_1-C_{12})$alkyl.
A specific value for $R^1$ is $(C_2-C_{10})$alkyl.
A specific value for $R^1$ is $(C_4-C_8)$alkyl.
A specific value for $R^1$ is $(C_6)$alkyl.
A specific value for $R^1$ is hexyl.
A specific value for $R^1$ is n-hex-1-yl.
A specific value for $R^1-(CH_2)_5CH_3$.

A specific value for $Z^{4a}$ is 5-10 membered heteroaryl, wherein any 5-10 membered heteroaryl or aryl of $Z^{4a}$ is optionally substituted with one or more groups selected from $(C_1-C_6)$alkyl, —OH, halogen and —O$(C_1-C_6)$alkyl.

A specific value for $Z^{4a}$ is a 5 membered heteroaryl or 6 membered heteroaryl, wherein any 5 membered heteroaryl or 6 membered heteroaryl of $Z^{4a}$ is optionally substituted with one or more groups selected from $(C_1-C_6)$alkyl, —OH, halogen and —O$(C_1-C_6)$alkyl.

A specific value for $Z^{4a}$ is a 5 membered heteroaryl or 6 membered heteroaryl.

A specific value for $Z^{4a}$ is imidazolyl, pyridinyl or thiazolyl, wherein any imidazolyl, pyridinyl or thiazolyl of $Z^{4a}$ is optionally substituted with one or more groups selected from $(C_1-C_6)$alkyl, —OH, halogen and —O$(C_1-C_6)$alkyl.

A specific value for $Z^{4a}$ is imidazolyl, pyridinyl or thiazolyl.

A specific value for $Z^{4a}$ is:

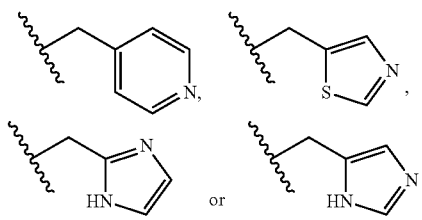

A compound selected from:

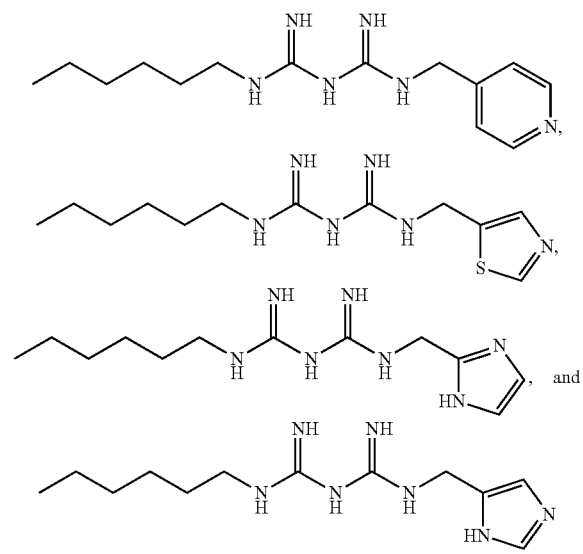

and salts thereof.

In one embodiment a salt is a pharmaceutically acceptable salt.

Processes for preparing compounds of formula I are provided as embodiments of the invention.

Provided herein are methods for treating or preventing the occurrence or recurrence of breast cancer (e.g., estrogen positive breast cancer) in a patient (e.g., a mammal such as a human) in need thereof, comprising administering to the patient in need thereof an effective amount of a compound that inhibits CYP3A4 epoxygenase activity.

In one embodiment the compound that inhibits CYP3A4 epoxygenase activity inhibits the synthesis of epoxyeicosatrienoic acids (EETs).

In one embodiment the epoxyeicosatrienoic acid is (±)-14,15-EET

The compounds of formula I (e.g., Ia, Ib) (or salts thereof) described herein are useful for preventing or treating cancer including breast cancer and in particular estrogen positive breast cancer. One property of the these compounds is their ability to inhibit CYP3A4 epoxygenase (such as inhibiting CYP3A4 epoxygenase activity which thereby inhibits the synthesis of epoxyeicosatrienoic acids (EETs)). Compounds of formula I (e.g., Ia, Ib) or pharmaceutically acceptable salts thereof in combination with one or more additional chemotherapeutic agents or hormonal agents such as a SERM are also useful for preventing or treating occurrence or recurrence of breast cancer (e.g., estrogen positive breast cancer) in a patient such as a mammal (e.g., a human).

In one embodiment the chemotherapeutic agent is a breast cancer chemotherapeutic agent.

In one embodiment the chemotherapeutic agents are independently selected from a selective estrogen receptor modifier, an aromatase inhibitor, a taxane, a epothilone, a halochondrin, a platin, a vinca alkaloid, a cyclophosphamide, an alkylating agent, a CDK4 inhibitor, a CDK6 inhibitor, a mTOR inhibitor and a HER2 targeted agent.

In one embodiment the chemotherapeutic agents are independently selected from tamoxifen, fulvestrant, raloxifene, anastrozole, letrozole, exemestane, paclitaxel, docetaxel, ixabepilone, eribulin, capecitabine, gemcitabine, vinorelbine, palbociclib, everolimus, trastuzumab, pertuzumab and lapatinib.

In one embodiment the hormonal agent is tamoxifen or an aromatase inhibitor.

In one embodiment the hormonal agent is tamoxifen and the patient is pre-menopausal or post-menopausal.

In one embodiment the hormonal agent is an aromatase inhibitor and the patient is post-menopausal.

Chemotherapeutic or hormonal agents that can be co-administered with compounds of formula I include but are not limited to those chemotherapeutic or hormonal agents that are more effective (e.g., more potent in inhibiting cancer cell growth) when co-administered with compounds of formula I or pharmaceutically acceptable salts thereof.

Compounds of formula I or pharmaceutically acceptable salts thereof may also useful in methods to treat diabetes (e.g., type II diabetes), metabolic syndrome or obesity in a patient.

It has been discovered that the in vitro activity of a compound of formula I derived from an MTT proliferation assay does not predict anti-breast tumor activity in a mouse xenograft model. Accordingly, one embodiment provides a method to identify compounds that are active in a mouse xenograft model and therefore are likely to predict anti-cancer activity in patients. The method comprises the step of determining whether addition of exogenous (±)-14,15-EET partially restores growth of the breast cancer cell line in the presence of a test compound. For example, exogenous (±)-14,15-EET partially restores growth of the MCF-7 but not the MDA-MB-231 line in the presence of HBB, thereby predicting activity in the xenograft model. Activity of HBB against clonogenicity also predicts activity in a xenograft model.

It has also been discovered that CYP3A4 is required for the growth of hepatocellular carcinoma [Drug Metab Pharmacokinet. 2011; 26(4):407-15]. Accordingly, one embodiment provides a method to treat hepatocellular carcinoma with biguanide compounds (compounds of formula I, Ib) listed herein.

Additionally, administration of a compound of formula I as a pharmaceutically acceptable acid or base salt may be appropriate. Examples of pharmaceutically acceptable salts include organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic acid addition salts may also be formed, which include a physiological acceptable anion, for example, chloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made. The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949. The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. In some embodiments, one or more of the compounds disclosed herein are co-administered with one or more other active therapeutic agents (e.g., antibacterial agents). Co-administration of a compound disclosed herein with one or more other active therapeutic agents generally refers to simultaneous or sequential administration of a compound disclosed herein and one or more other active therapeutic agents, such that therapeutically effective amounts of the compounds disclosed herein and one or more other active therapeutic agents are both present in the body of the patient.

In some embodiments, one or more of the compounds disclosed herein are co-administered with one or more active therapeutic agents (e.g., antibacterial agents) by combining the compounds disclosed herein with the other therapeutic agents in a unitary dosage form for simultaneous or sequential administration to a patient. Thus, this combination therapy may be administered as a simultaneous or sequential regimen. When administered sequentially, the combination may be administered in two or more administrations.

The invention will now be illustrated by the following non-limiting Examples.

Example 1

Preparation of Compounds 1-5.

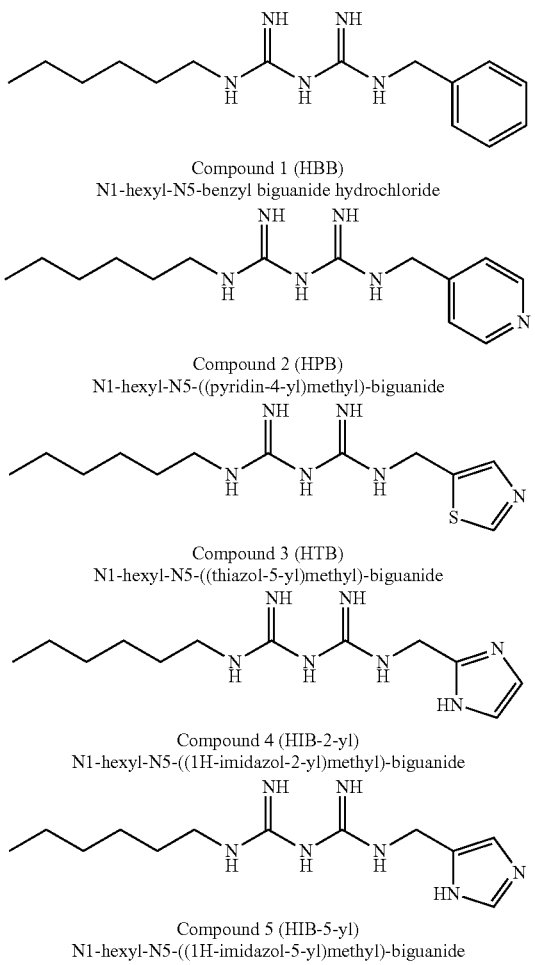

Compound 1 (HBB)
N1-hexyl-N5-benzyl biguanide hydrochloride

Compound 2 (HPB)
N1-hexyl-N5-((pyridin-4-yl)methyl)-biguanide

Compound 3 (HTB)
N1-hexyl-N5-((thiazol-5-yl)methyl)-biguanide

Compound 4 (HIB-2-yl)
N1-hexyl-N5-((1H-imidazol-2-yl)methyl)-biguanide

Compound 5 (HIB-5-yl)
N1-hexyl-N5-((1H-imidazol-5-yl)methyl)-biguanide

Preparation of Compound 1.

Compound 1 was prepared by refluxing sodium dicyanamide with n-hexylamine in a mixture of n-butanol and concentrated hydrochloric acid for 24 hours to obtain the intermediate 1-hexyl-3-cyanoguanidine. This intermediate was isolated by extraction using dichloromethane, concentrated to a sticky white residue, and used without further purification. Next, benzylamine was dissolved in n-butanol with concentrated hydrochloric acid; the product from the previous step was added before refluxing for 24 hours. The final product 1 (N1-hexyl-N5-benzyl biguanididine) was purified by flash column chromatography before subjecting the concentrated product to HCl-methanol to provide the desired salt hydrochloride salt (1A) as a fluffy white solid after concentration. Characterization by $^1$H NMR confirmed identity and purity.

1-hexyl-3-cyanoguanidine; $^{13}$C NMR (400 MHz, DMSO-$d_6$) δ161.1, 118.4, 40.6, 30.8, 28.8, 25.8, 22.0, 13.8.

N1-hexyl-N5-benzyl biguanide hydrochloride (1A); Compound 1A was determined to by >99% pure.

$^1$H NMR (40 MHz, DMSO-$d_6$) δ8.73 (br s, 1H), 7.34-7.28 (m, 5H), 6.93 (br s, 2H), 4.40 (br s, 2H), 3.16-3.09 (m, 2H), 1.47-1.24 (m, 8H), 0.85 (m, 3H).

N1-hexyl-N5-benzyl biguanide methysulfonate (1B); Compound 1B was prepared in a similar manner used to prepare compound 1A. Compound 1B was determined to by >99% pure.

Compounds 2 and 4 were prepared in a similar manner. The pyridin-4-yl moiety of compound 2 (HPB) was incorporated by use of pyridin-4-yl methanamine (aminomethypyridine). The imidazole of compound 4 [N1-hexyl-N5-((1H-imidazol-2-yl)methyl)-biguanide] was incorporated via use of imidazole methanamine. Compounds 3 and 5 can also be prepared using the procedures described for the preparation of compound 1.

HPB metformin analogue (compound 2) was prepared by refluxing sodium dicyanamide with n-hexylamine in a mixture of n-butanol and concentrated hydrochloric acid for 24 hours to obtain the intermediate 1-hexyl-3-cyanoguanidine. This intermediate was isolated by extraction using dichloromethane, concentrated to a sticky white residue, and used without further purification. Next, 4-(aminomethyl)pyridine was dissolved in n-butanol with concentrated hydrochloric acid; the product from the previous step was added before refluxing for 24 hours. The final product (N1-hexyl-N5-(pyridin-4-ylmethyl) biguanidine) was purified by flash column chromatography before subjecting the concentrated product to methanesulfonic acid to provide the desired salt as a sticky yellow solid after concentration. Characterization by $^1$H NMR confirmed identity and purity.

1-hexyl-3-cyanoguanidine $^{13}$C NMR (400 MHz, DMSO-$d_6$) δ161.1, 118.4, 40.6, 30.8, 28.8, 25.8, 22.0, 13.8.

N1-hexyl-N5-(pyridin-4-ylmethyl) biguanidine $^1$H NMR (40 MHz, DMSO-$d_6$) δ10.22 (br s, 1H), 8.90 (br s, 1H), 8.52-8.47 (m, 2H), 8.46 (br s, 2H), 8.23 (br s, 1H), 7.28 (d, 2H, J=5.64 Hz), 4.33 (m, 2H), 3.21 (m, 21-1), 1.51-1.46 (m, 2H), 1.26 (m, 6H), 0.87 (m, 3H).
Reference: Kim et al. patent. US 2012/0283299 A1
HBB-HCl—Inhibition of Breast Cancer Cell Proliferation Assay.

The $IC_{50}$ values for the MCF-7 (ER+) and MDA-MB-231 (triple negative) breast cancer lines is 20 uM as measured by MTT assay. HBB-HCl inhibits CYP3A4 epoxygenase with an $IC_{50}$ value of ~50 uM. The inhibitory activity of HBB-HCl on the MCF-7 line can be partially inhibited by the addition of (±)-14,15-epoxyeicosatrienoic acid [(±)-14,15-EET], suggesting that, HBB inhibits the growth of breast cancer cells by inhibition of epoxygenase activity. HBB-HCl also activates AMPK phosphorylation and inhibits STAT3 phosphorylation at >10 uM concentration, indicating that HBB-HCl is >100-fold more potent than metformin at modulating these signaling pathways.

Discussion

Cytochrome P450 (CYP) epoxygenases such as CYP2J2, CYP2C8/9, and CYP3A4 are linked to mammary tumor growth and metastasis, in part through biosynthesis of epoxyeicosatrienoic acid (EET)eicosanoids 1-4 (reviewed by Panigrahy et al. 5). Recently, EETs have been linked to cancer dormancy escape 4, which is important in the late recurrence of ER+ breast cancer.

Studies by the applicant have shown that cellintrinsic CYP3A4 is critical for tumor establishment of the estrogen receptor positive (ER+) breast cancer MCF-7 xenograft, but not the triple negative breast cancer MDA-MB-231 xenograft. These studies demonstrate that other CYP epoxygenases such as CYP2J2 and CYP2C8 cannot substitute for the angiogenic and proliferative function of CYP3A4 in the tumor epithelium (3). The finding that CYP3A4 is a breast cancer cellintrinsic (epithelial) epoxygenase has been noted in recent review articles 5-7, and a cancer promoting role for CYP3A4 was found in hepatoma (8). Data show that CYP3A4 snRNA-expressing MCF-7 cells exhibit reduced EET content and fail to form tumors (FIG. 1A); these cells fail to recruit intraepithelial host endothelial cells and only form small tumor nodules with necrotic centers (FIG. 1B,C). Instead of infiltrating tumor nodules to form microcapillaries, the endothelial cells ring the periphery of the nodule (FIG. 1C). CYP3A4 exhibits an oxygen Km of 22 uM for arachidonic acid (AA) epoxidation and therefore can function as an epoxygenase under conditions of tumor hypoxia and could play a role in recruitment of endothelial cells.

Applicants discovery of significant correlation between CYP3A4 and ERα expression by immunofluorescence (r=0.75; n=48 patients; P<0.0001) suggests that CYP3A4 inhibitors will be active in ER+ breast cancer. A class of biguanides which are inhibitors of CYP3A4 inhibitor could potentially be useful for breast cancer therapy. It was discovered that the biguanides metformin, buformin, and phenformin inhibit CYP3A4 epoxygenase. It was also discovered that (±)-14,15-EET rescues the MCF-7 line, but not the MDA-MB-231 line from these biguanides, suggesting that epoxygenase mechanisms are specific for ER+ breast cancer.

Figure 2B:
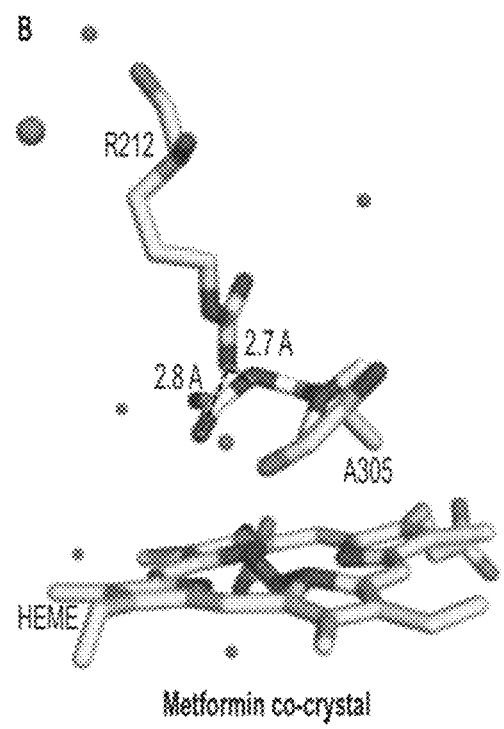
Figure 3A:
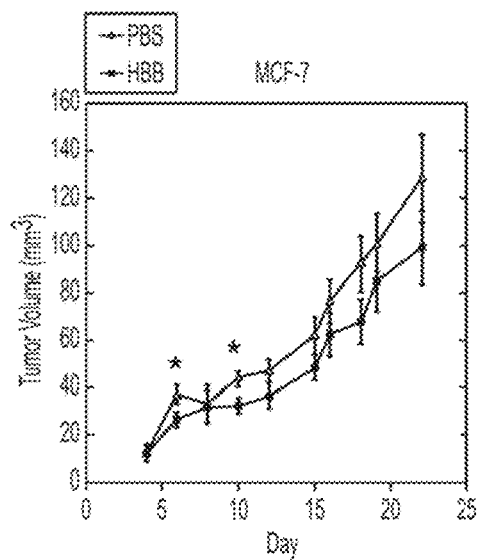
FIGS. 3A and 3B illustrate how HBB inhibits the ER+ MCF-7 but not the triple negative MDA-MB-231 xenograft.
Figure 3B:
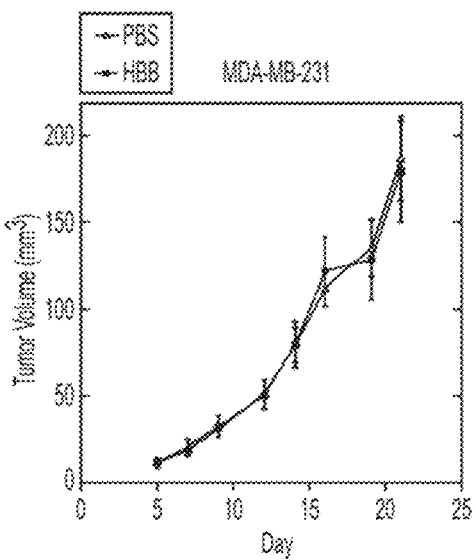
Figure 4:
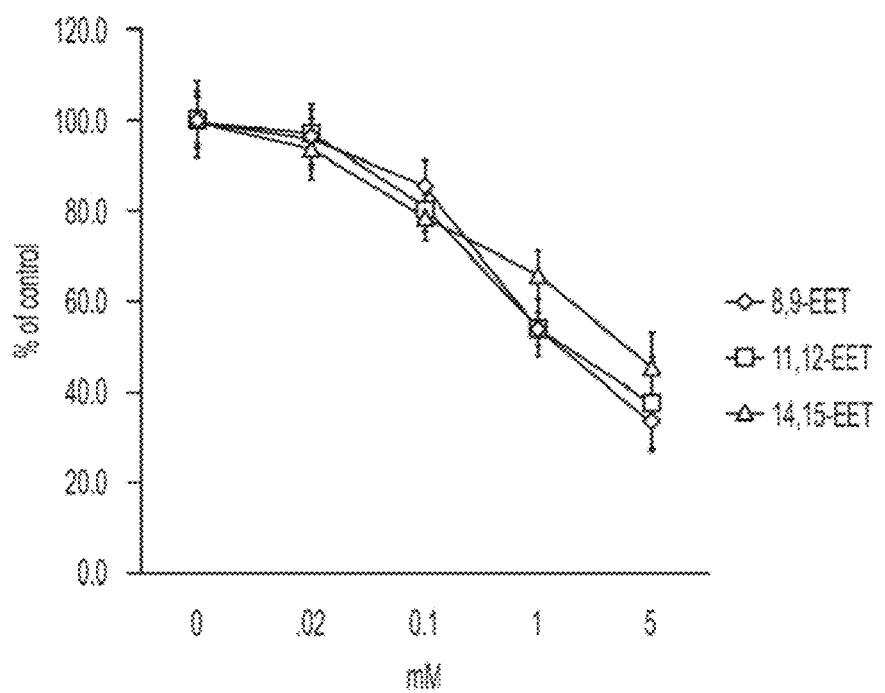
FIG. 4 illustrates that metformin inhibits AA metabolism to EET in breast cancer cells and CYP3A4 microsomes. All three of the measurable EET regioisomers exhibit reduced abundance with 0.10 mM metformin treatment of MCF-7 cells (6 h) (p<0.05 for each regioisomer for metformin concentrations ≥0.10 M).
Figure 5:
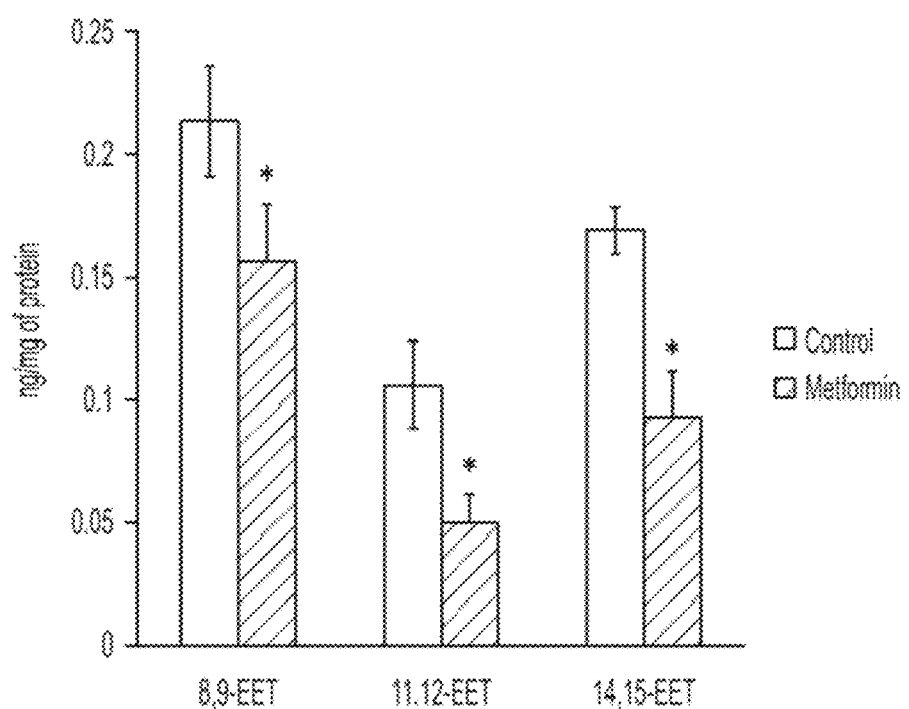
FIG. 5 illustrates the effect of metformin on EET production in MCF7. MCF7 cells were treated with 10 mM metformin for 6 hours and total EET was measured by LC-ESI-MS (n=3, *: statistical significant difference).
Figure 6:
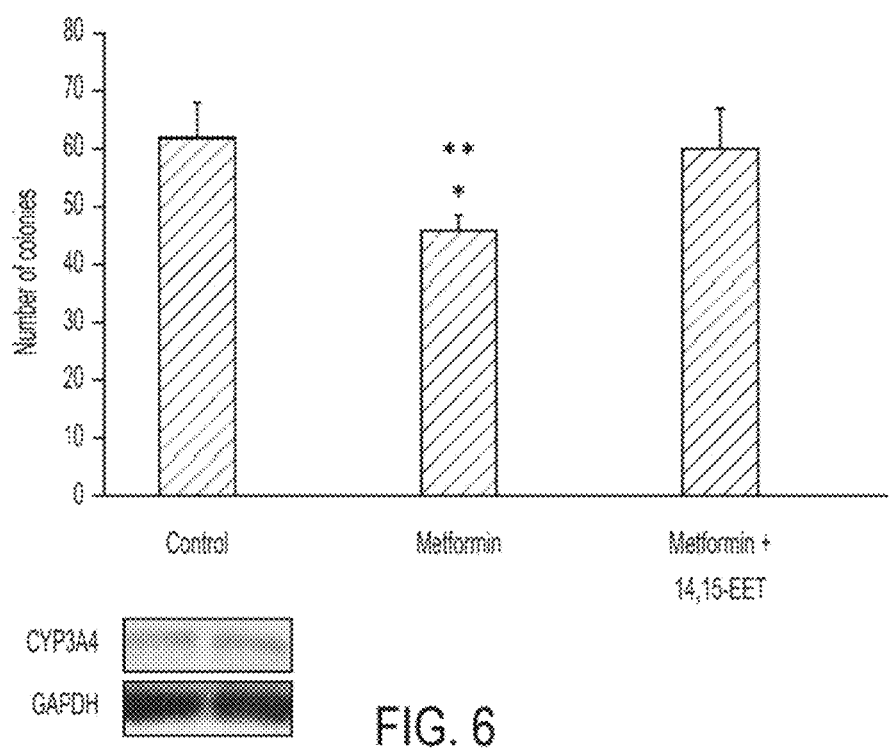
FIG. 6 illustrates the effect of metformin on clonogenicity of MCF7 cells. Cells were seeded in 6-well tissue culture plates in complete media. On the second day, compounds (14,15-EET 1 uM and metformin 1 mM) or vehicle were added. After 24 hour treatment, media containing testing compounds was removed and replaced with fresh media. On the 14th day, colonies were visualized with Geimsa staining and counted. Results represent mean±standard deviation (n=3, *, ** indicate statistical significant difference with other two groups, P<0.05). Metformin (1 mM) treatment for 48 hours does not change CYP3A4 protein level (right panel).
Figure 7:
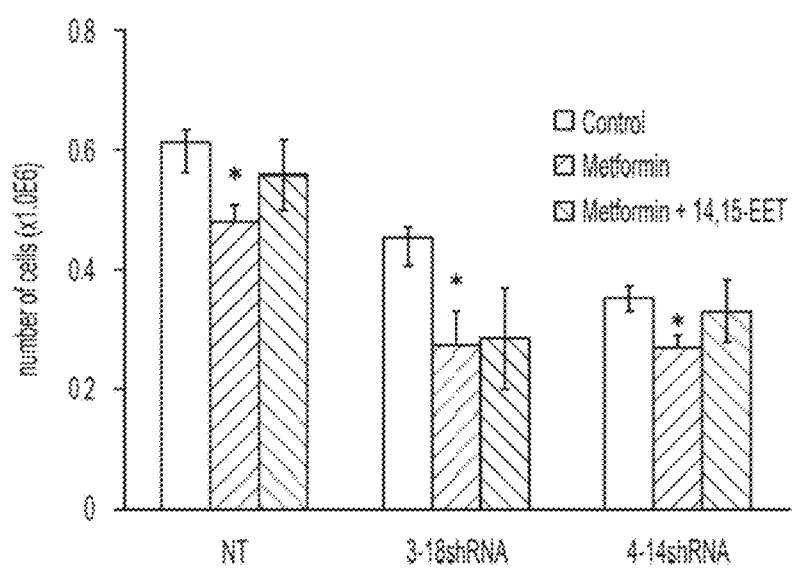
FIG. 7 illustrates the effect of metformin on proliferation of MCF7 CYP3A4 knockdown lines. Cells were seeded in 6-well tissue culture plate and grown to 50% confluence before testing compounds were added. After 24 hour treatment, cells were counted and percent inhibition was calculated. Results represent mean±standard deviation (n=3, * indicates statistical significant difference relative to control, P<0.05)
Figure 8:
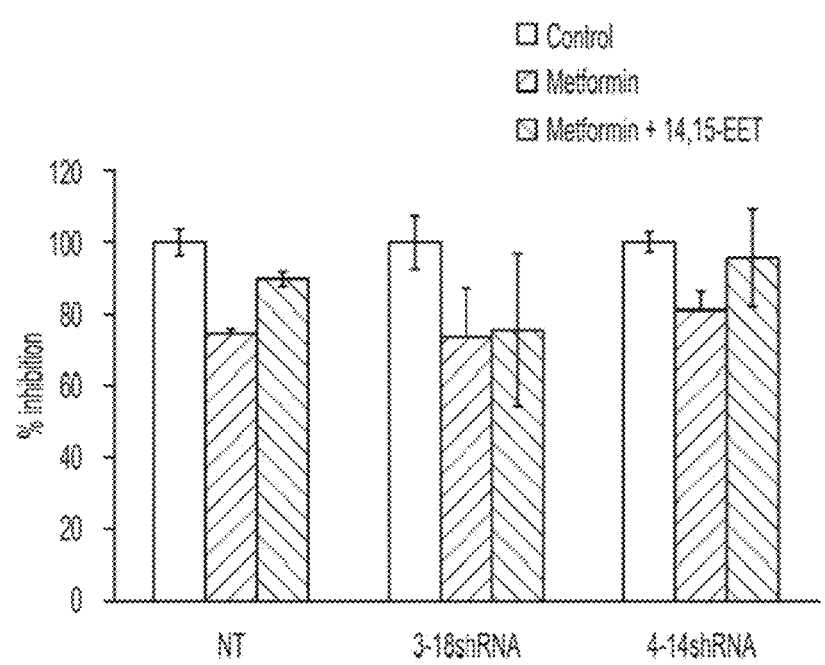
FIG. 8 illustrates the effect of metformin on proliferation of MCF7 CYP3A4 knockdown lines. Cells were seeded in 6-well tissue culture plate and grown to 50% confluence before testing compounds were added. After 24 hour treatment, cells were counted and percent inhibition was calculated. Results represent mean±standard deviation (n=3, * indicates statistical significant difference, P<0.05)
Figure 9A:
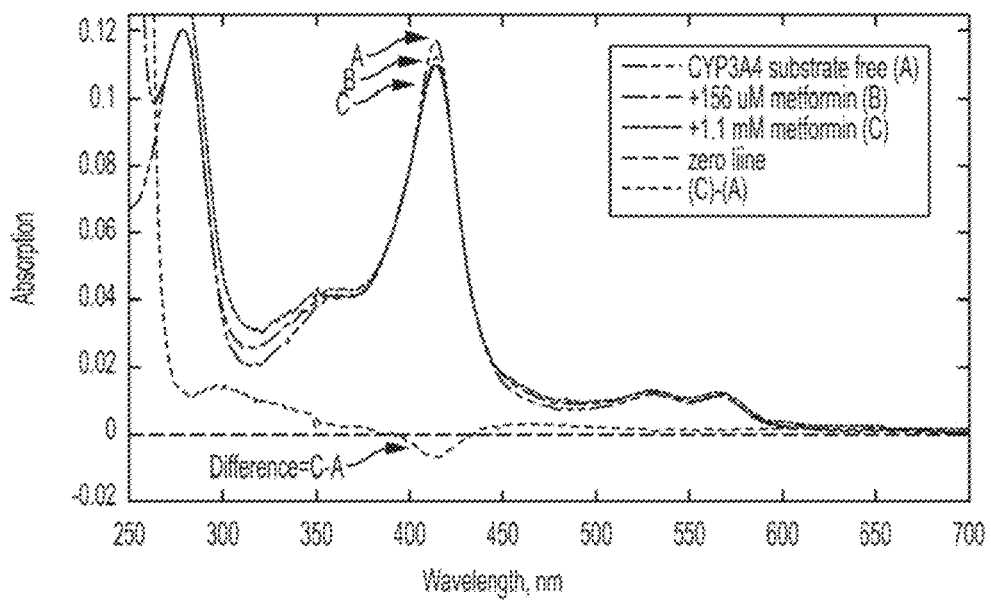
FIGS. 9A and 9B illustrate that metformin binds to functional CYP3A4 epoxygenase nanodiscs.
Figure 9B:
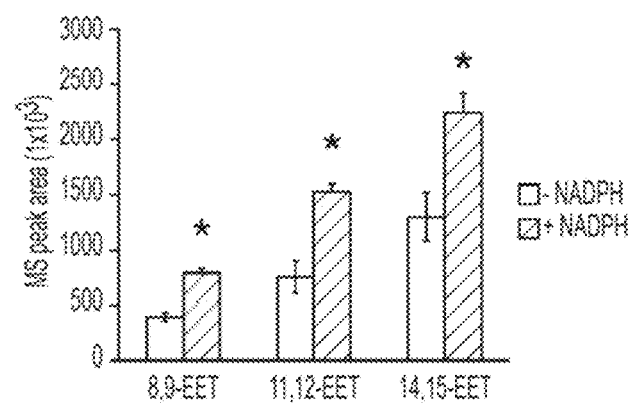
Figure 10:
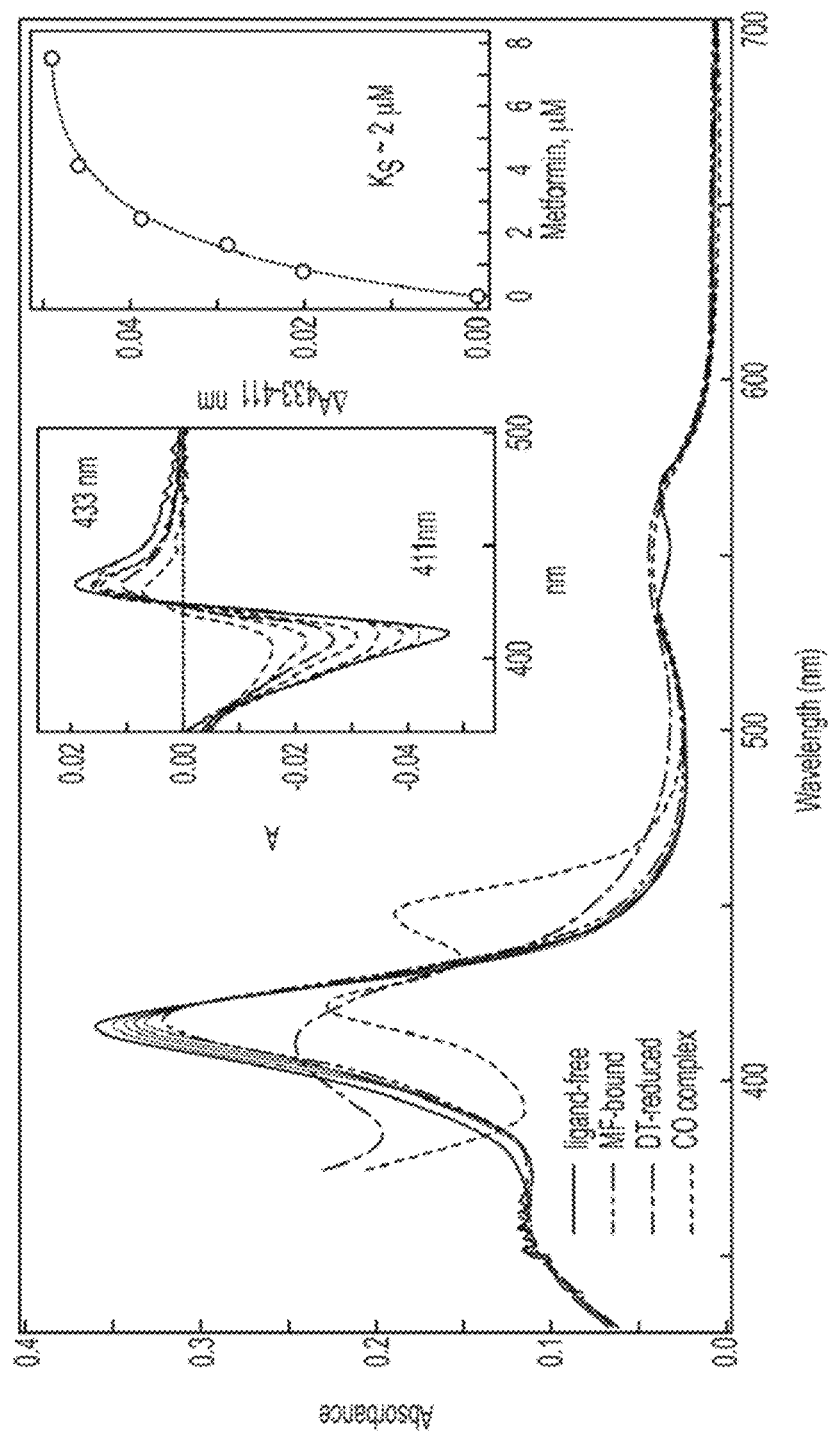
FIG. 10 illustrates that metformin binds to CYP3A4D3-24. Metformin binding to CYP3A4D3-24 is saturable and suppresses the Soret band with a weak type II spin shift. The difference spectrum indicates the spin shift (left inset). The $K_s$ spectral binding constant is ~2 uM (right inset).
Figure 11:
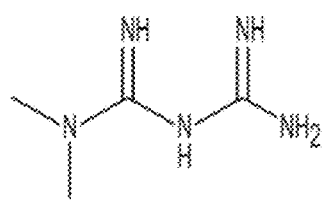
FIG. 11 illustrates HBB (N1-hexyl-N5-benzyl biguanide) compared with the metformin structure.
Figure 11:
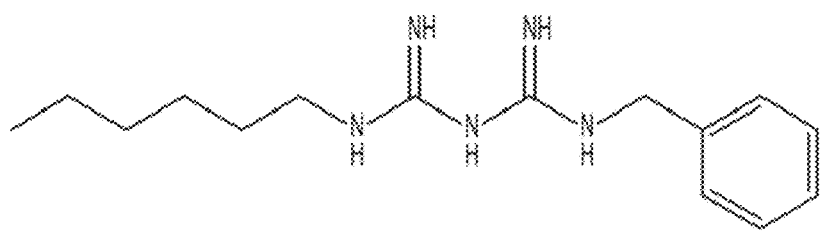
Figures 12A, 12B, 12C, 12D:
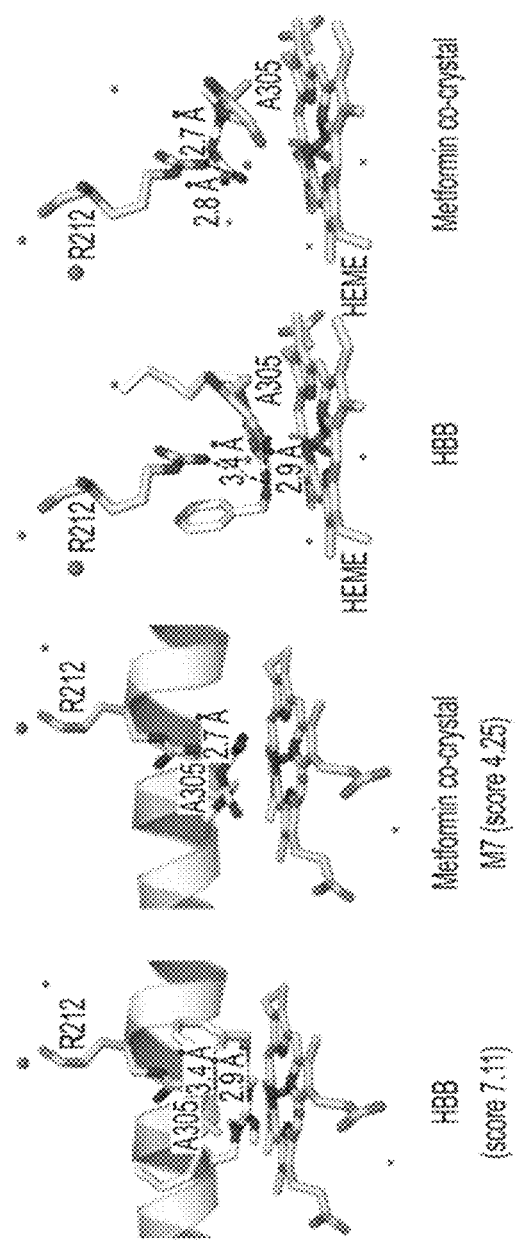
FIGS. 12A-12D illustrate the comparison of HBB Docking and the Metformin Co-crystal.
Figure 13:
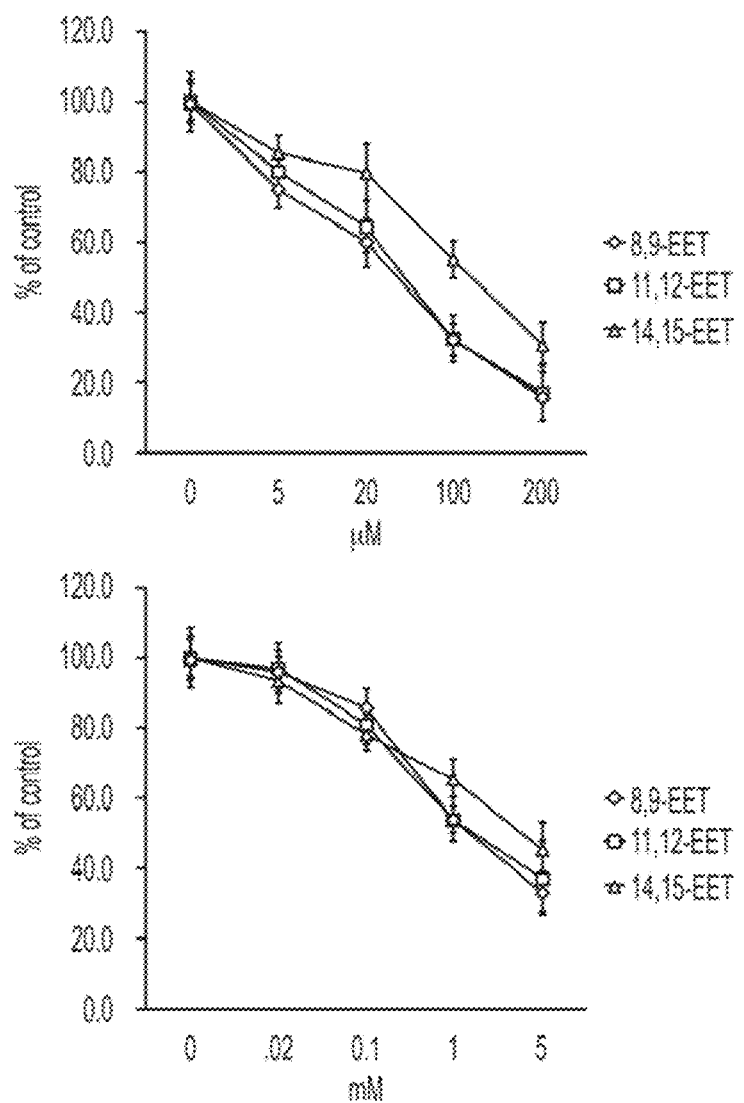
FIG. 13 illustrates that HBB (upper panel) is ~40-fold more potent than metformin (lower panel): CYP3A4 epoxygenase.
Figure 14:
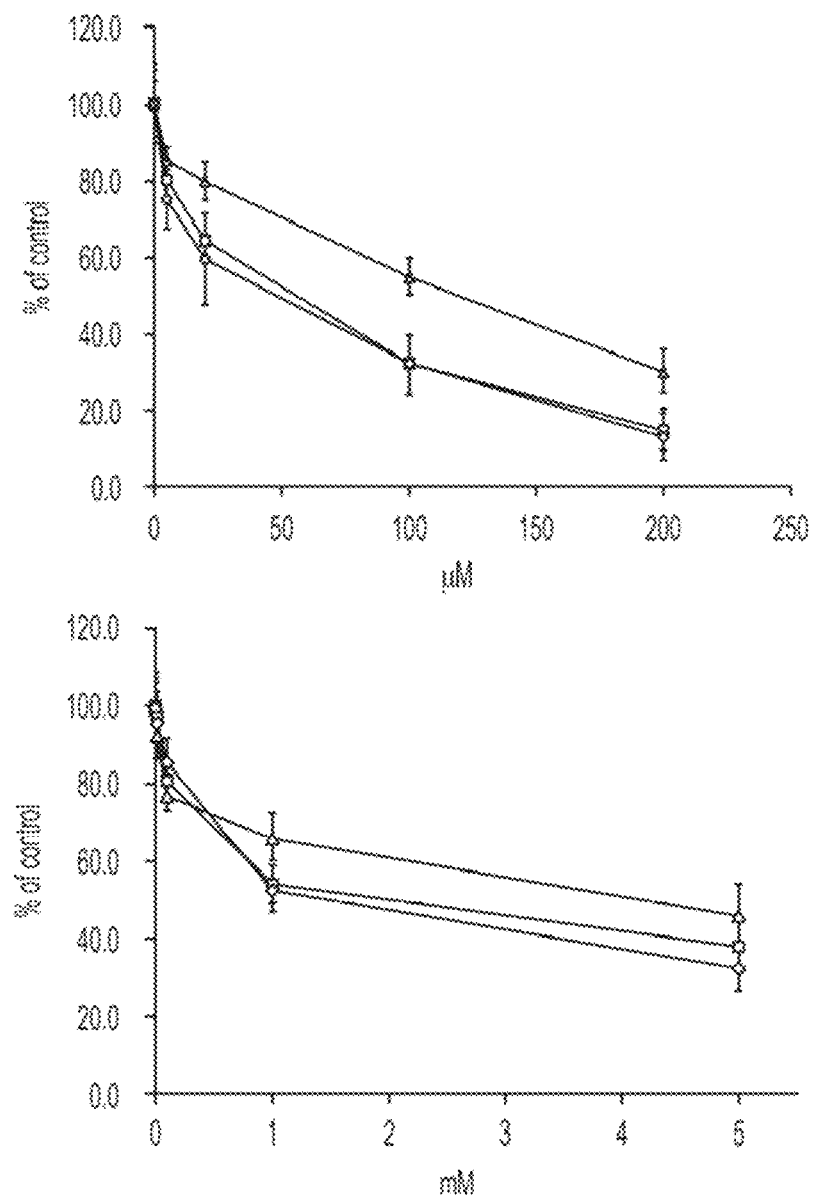
FIG. 14 illustrates HBB (upper panel) is ~50-fold more potent than metformin (lower panel): CYP3A4 epoxygenase CYP3A4 Supersomes were incubated with either HBB (upper panel) or metformin (lower panel) at the indicated compound concentrations at 37° C. for 30 minutes and the products were extracted by a $CH_2Cl_2$ extraction and analyzed by an ESI LC-MS/MS method. Measurements are reported as percentage of control reactions performed with vehicle but no compound. A $^{13}C$-EET recovery standard was used to control for recovery of EETs from extractions. EET regioisomer concentrations [(±) 8,9-EET (diamond), (±) 11,12-EET (square), (±) 14,15-EET (triangle)] are as plotted. EET measurements in these Supersome experiments are expressed as percentage of control reactions. Absolute EET measurements are determined by subtraction of regioisomer values in a baseline reaction lacking NADPH. Measurements were performed in triplicate and values are expressed as the mean±SD.
Figure 15A:
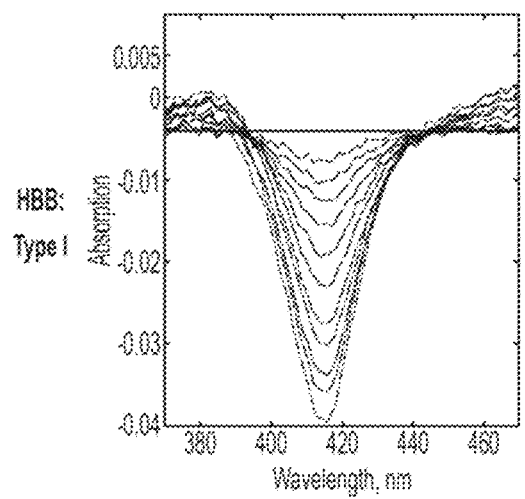
FIGS. 15A-15D illustrates HBB is ~4-fold more potent than metformin: CYP3A4 nanodisc spin shift.
Figure 15B:
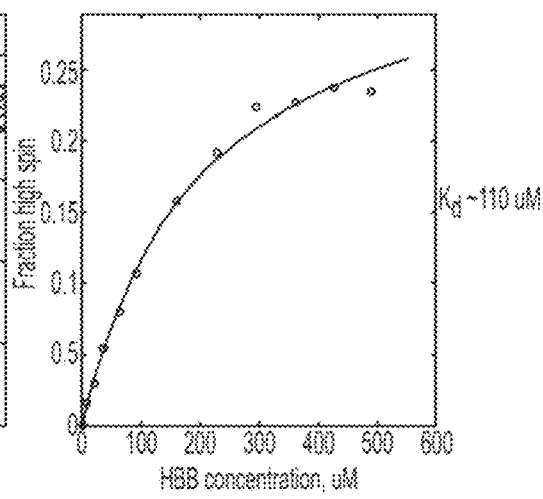
Figure 15C:
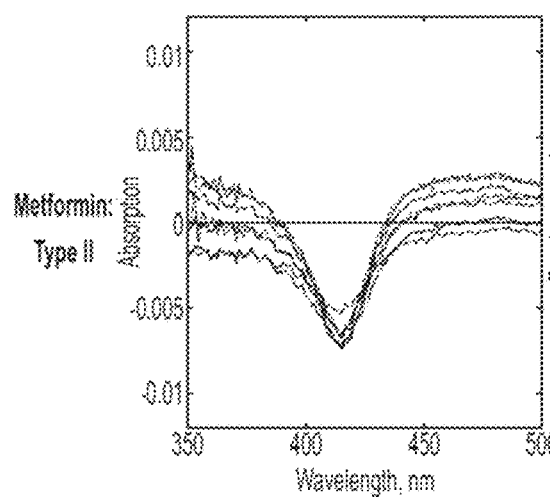
Figure 15D:
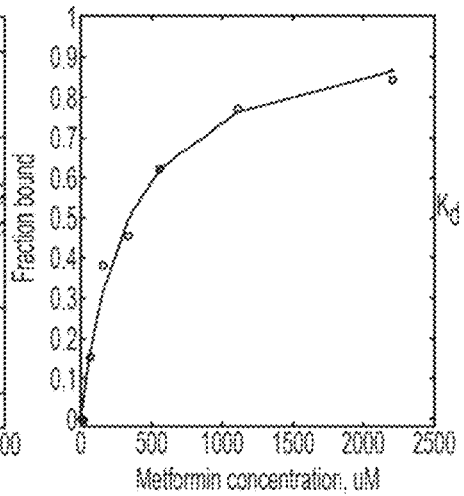
Figure 16:
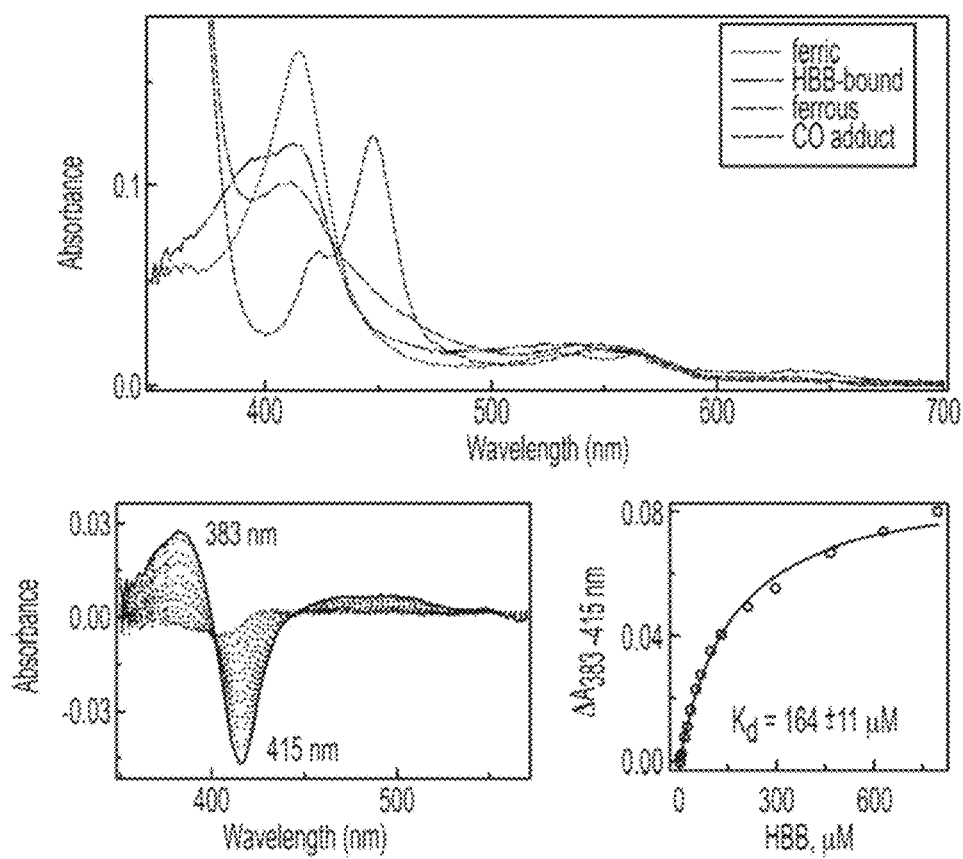
FIG. 16 illustrates HBB is ~12-fold more potent than metformin: delta 3-24 CYP3A4 spin shift.
Figure 17:
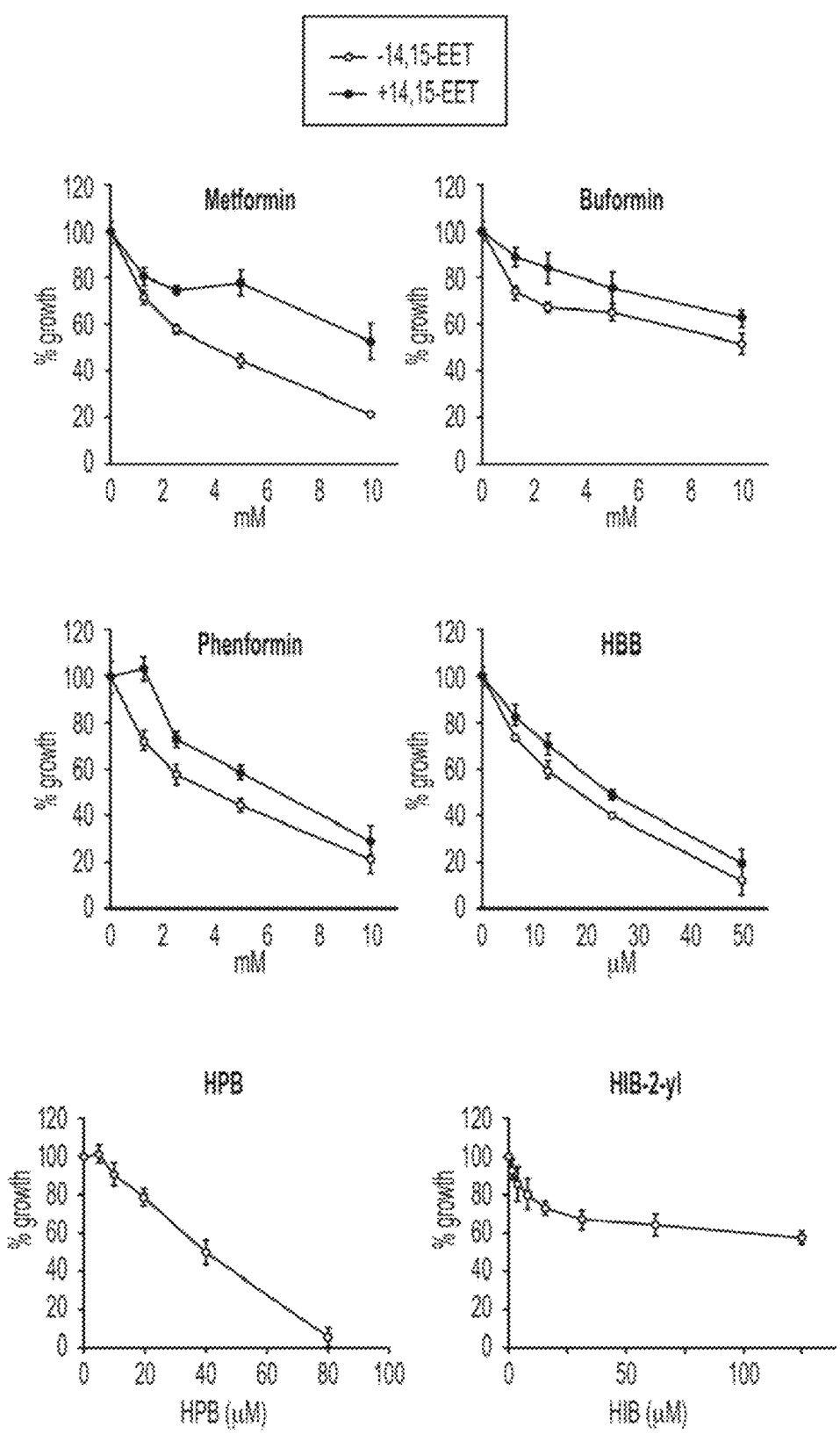
FIG. 17 illustrates HBB~250-fold More potent than metformin and EET restores growth inhibition caused by biguanides for the MCF-7 cell line. The top panel shows the partial rescue of the MCF-7 cell line by 14,15-EET (1 uM) in the presence of metformin, buformin, phenformin and HBB. The top panel also shows the relative potency of HBB ($IC_{50}$=20 uM), vs. metformin ($IC_{50}$>10 mM, buformin ($IC_{50}$>10 mM), and phenformin ($IC_{50}$=8 mM). The bottom panel shows the sensitivity of the MCF-7 cell line to HPB ($IC_{50}$=40 uM) and HIB 2-yl ($IC_{50}$>150 uM). The growth of the MCF-7 line was measured by MTT assay at 24 hours. Cells were plated in complete media in the presence of serum (10% FBS) and cultured at 37° C. with 5% $CO_2$ and treated with the biguanide or DMSO vehicle. Growth was measured at 24 hours by MTT assay. Results were converted to percent growth of control and represented as mean±SD (n=8).
Figure 18:
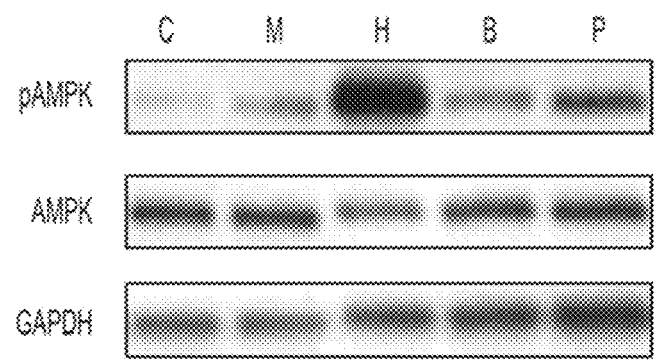
FIG. 18 illustrates HBB more potently activates AMPK. Effect of metformin and HBB on AMPK phosphorylation in MCF7 cells. MCF7 cells at 50% confluence were treated of vehicle (C), metformin (1 mM) (M), HBB (20 uM) (H), buformin (1 mM) (B) and phenformin (1 mM) (P) for 6 hour and harvested. Western blotting analysis was performed in triplicate.
Figure 19:
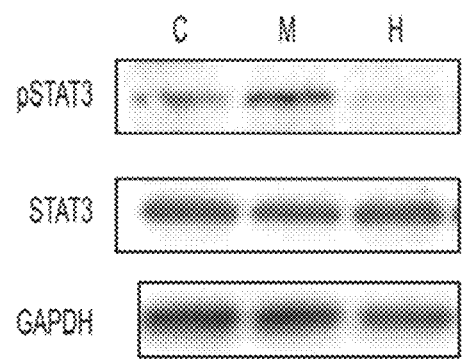
FIG. 19 illustrates the effect of metformin and HBB on STAT3 phosphorylation in MCF7 cells. MCF7 cells at 50% confluence were treated with vehicle, metformin (1 mM) and HBB (10 uM) for 1 hour and harvested. Western blotting analysis was performed (C=control, M=metform and H=HBB).
Figure 20:
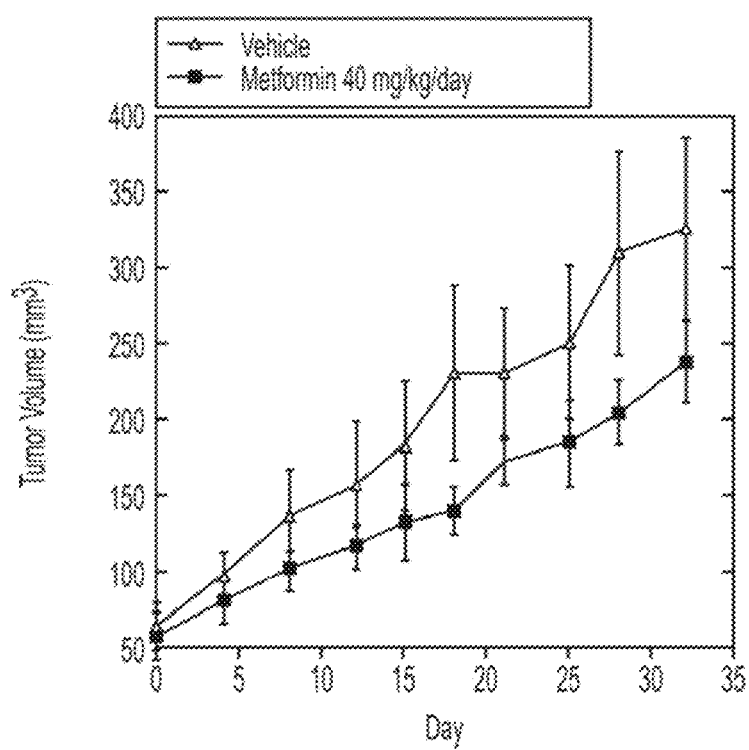
FIG. 20 illustrates that metformin inhibits the MCF-7 xenograft. Metformin 40 mg/kg/day was added to the drinking estradiol containing water or not (vehicle). Metformin (n) suppressed tumor growth vs. vehicle (r) (P<0.0001; error bars=SEM). MCF-7 cells were implanted in the mammary fat pad of 4-5 week mice and treatment was initiated when tumor size was ≥15 $mm^3$ by 2 sequential measurements with randomized assignment to the treatment arms.
Figure 21A:
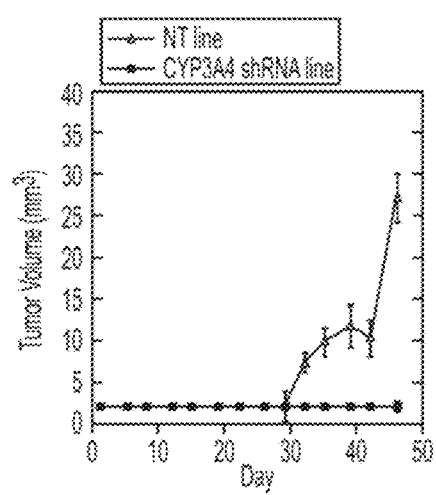
FIGS. 21A and 21B illustrate that CYP3A4 shRNA knock down inhibits the MCF-7 xenograft.
Figure 21B:
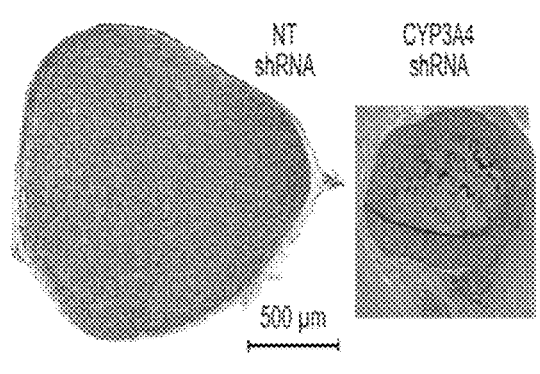
Figure 22A:
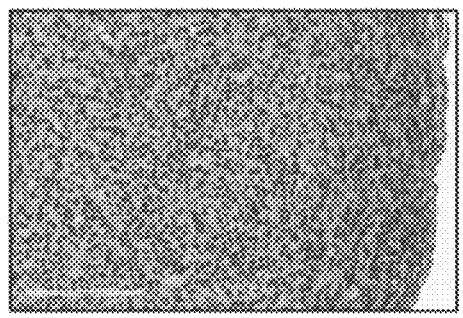
FIGS. 22A and 22B illustrates that CD31+ cells fail to migrate into CYP3A4 shRNA tumors. CD31 staining corresponds to endothelial cells.
Figure 22B:
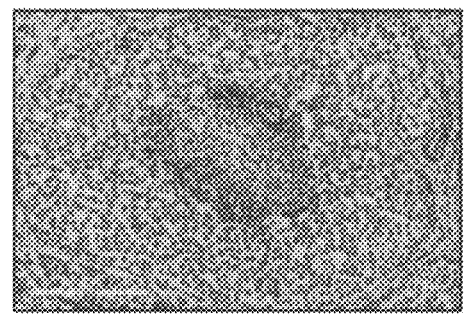
Figure 23A:
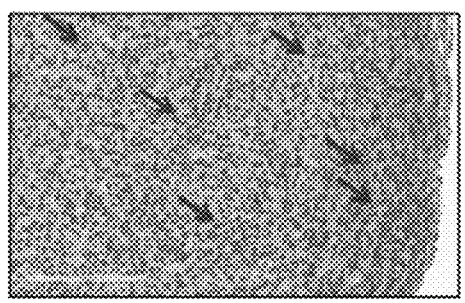
FIGS. 23A and 23B illustrate that CD31+ cells fail to migrate into CYP3A4 shRNA tumors.
Figure 23B:
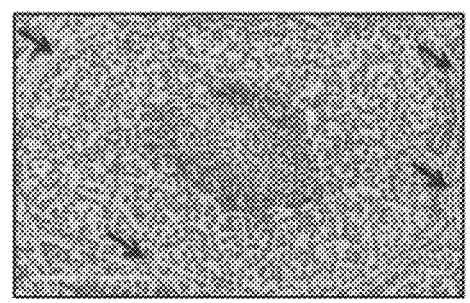
Figure 24:
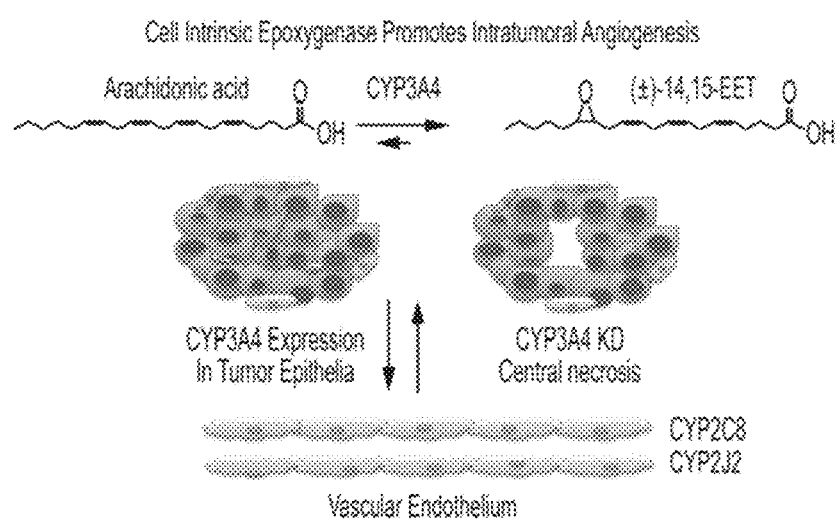
FIG. 24 illustrates intrinsic epoxygenase promotes intratumoral angiogenesis.
Figure 25:
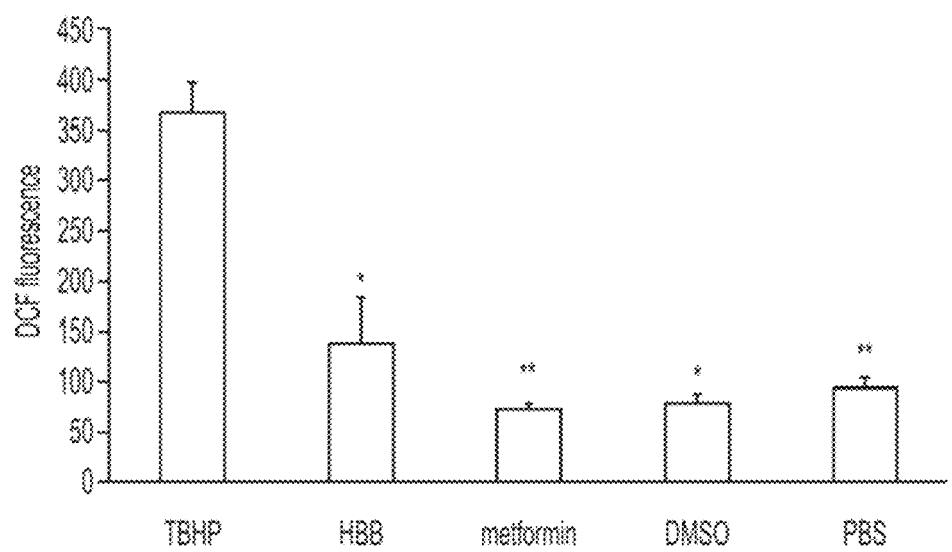
FIG. 25 illustrates the effect of HBB and metformin on ROS of MCF7 cells. MCF7 cells were seeded in 96-well plate and allowed to adhere overnight. Cells were incubated with DCFDA in dark at 37° C. for 45 minutes and washed with phenol red free medium. Testing compounds (TBHP: t-butyl hydrogen peroxide 50 uM, HBB 20 uM and metformin 5 mM) were add to cells and incubated for 2 hours before fluorescence was measured (Ex 485 nm/Em 535 nm). Results were expressed as mean±standard deviation (n=6, * and ** indicate statistical significant difference).
Figure 26:
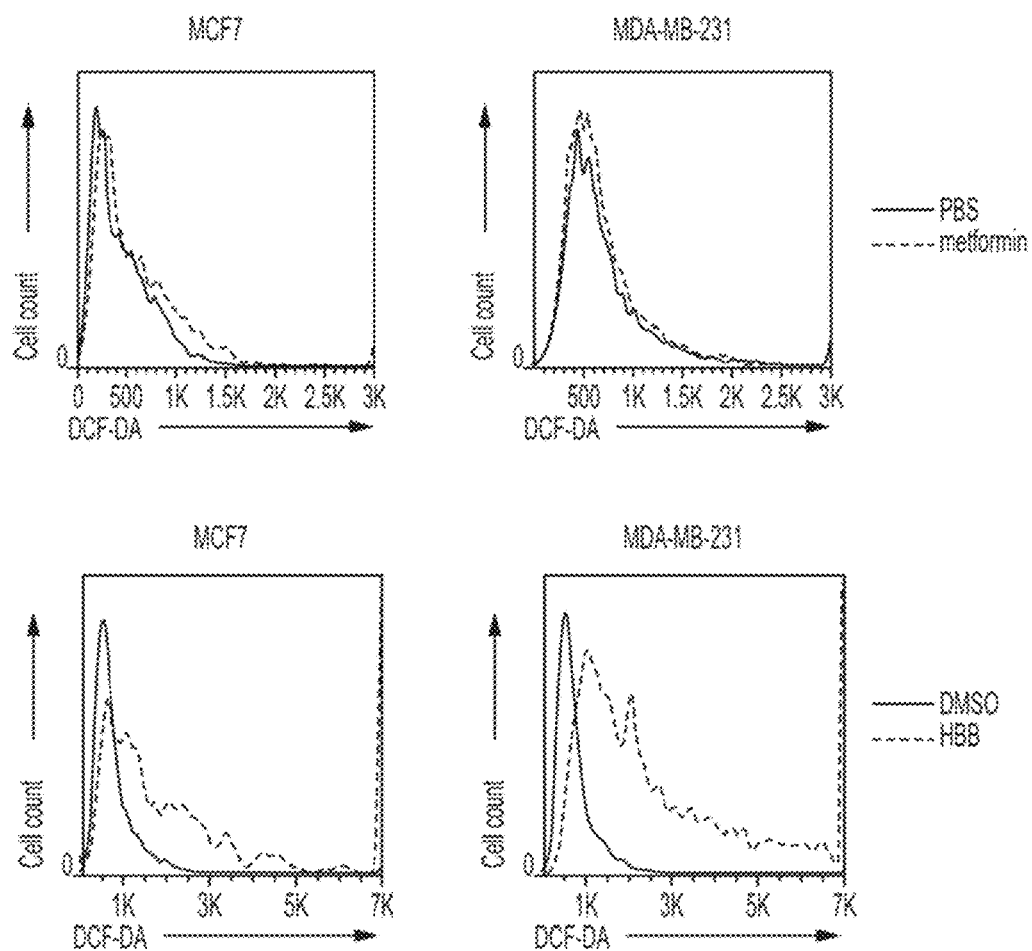
FIG. 26 illustrates the Induction of ROS by metformin in MCF7 and MDA-MB-231 cells. Cells were suspended in culture media containing 20 uM DCF-DA in dark at 37° C. for 30 minutes before treatment of PBS or 1.25 mM metformin. Flow cytometry analysis was performed after 2.5 hours. Induction of ROS by HBB in MCF7 and MDA-MB-231 cells. Cells were suspended in culture media containing 20 uM DCF-DA in dark at 37° C. for 30 minutes before treatment of DMSO or 100 uM HBB. Flow cytometry analysis was performed after 2.5 hours.
Figure 27:
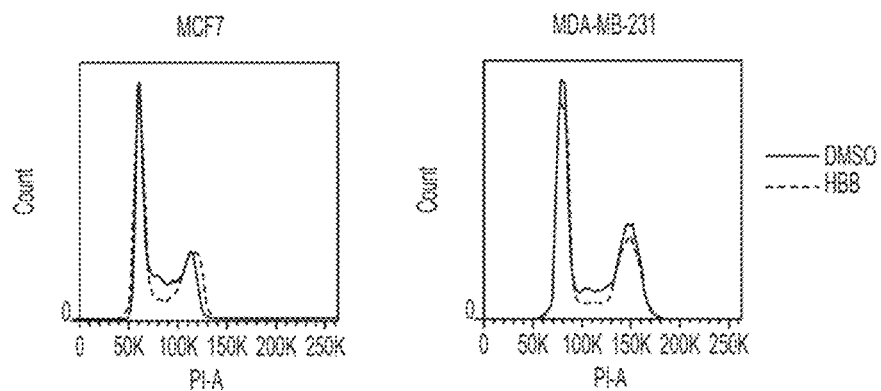
FIG. 27 illustrates the effect of HBB on MCF-7 and MDA-231 line.
Figure 28:
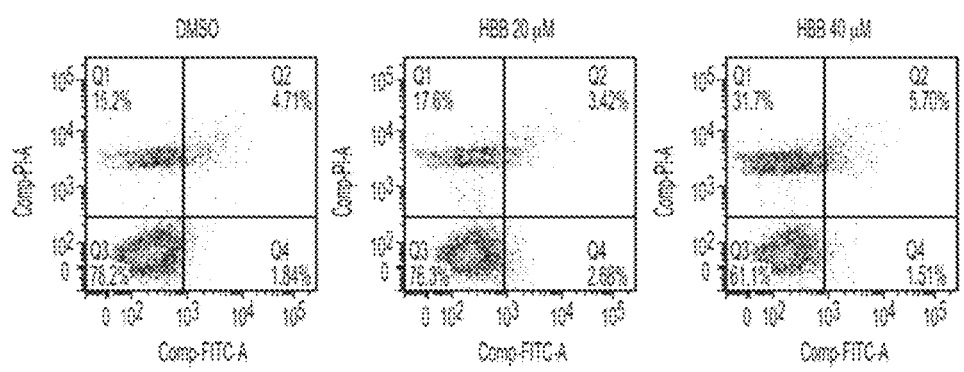
FIG. 28 illustrates the effect of HBB on MCF-7 line.
Figure 29:
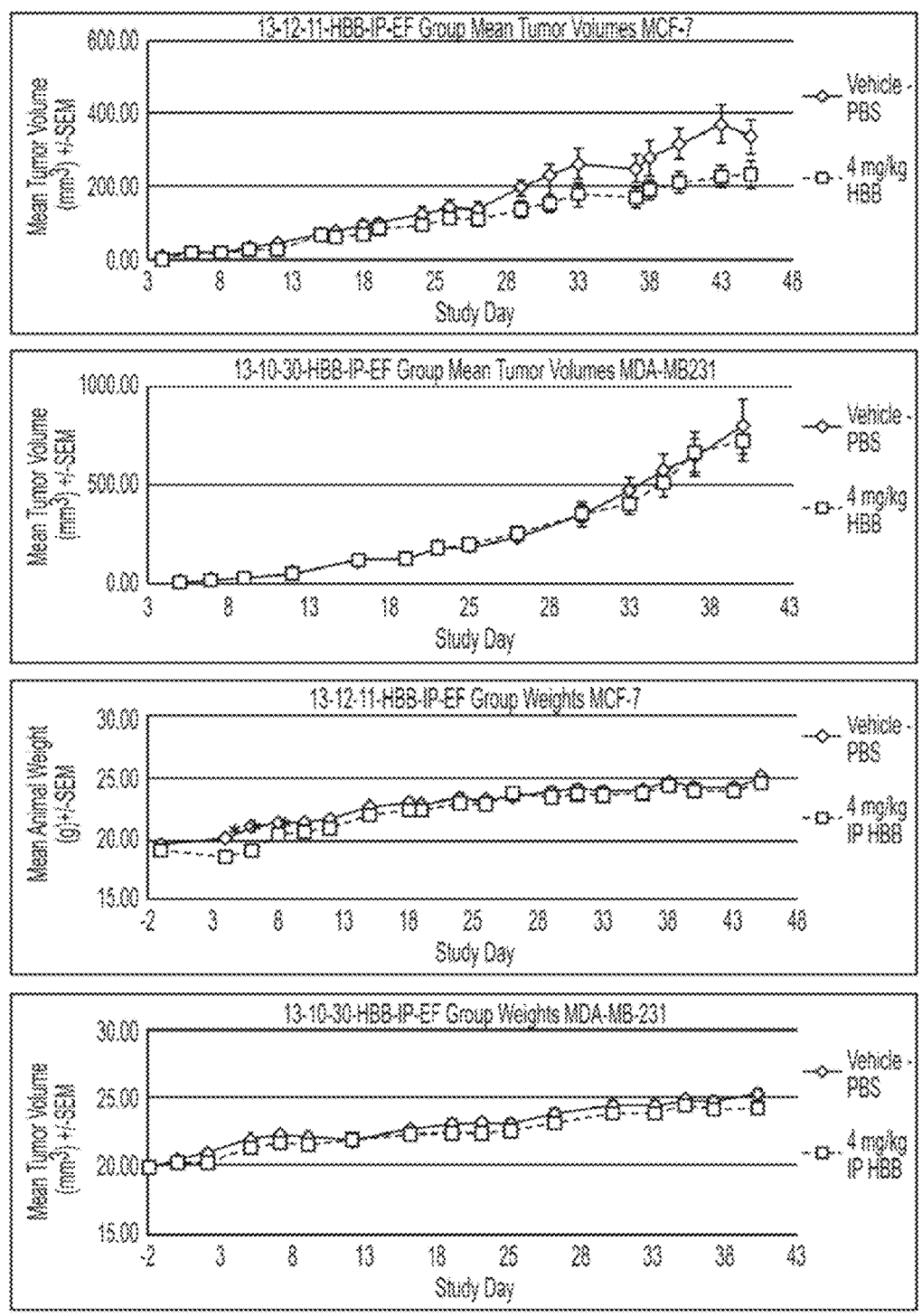
FIG. 29 illustrates HBB inhibits the ER+ MCF-7 but not the triple negative MDA-MB-231 xenograft. A. MCF-7 xenograft with 3×106 cells in the 2nd mammary fat pad on day 0. HBB (4 mg/kg ip daily) (red) or PBS (blue) treatment began on day 1. * indicates P<0.05 by unpaired t test with unequal variance. B. MDA-MB-231 xenograft with 1×10$^6$ cells in the 2nd mammary fat pad on day 0. HBB (4 mg/kg ip daily) (red) or PBS (blue) treatment began on day 1. N=20 mice per arm for each study; error bars are SEM.
Figure 30:
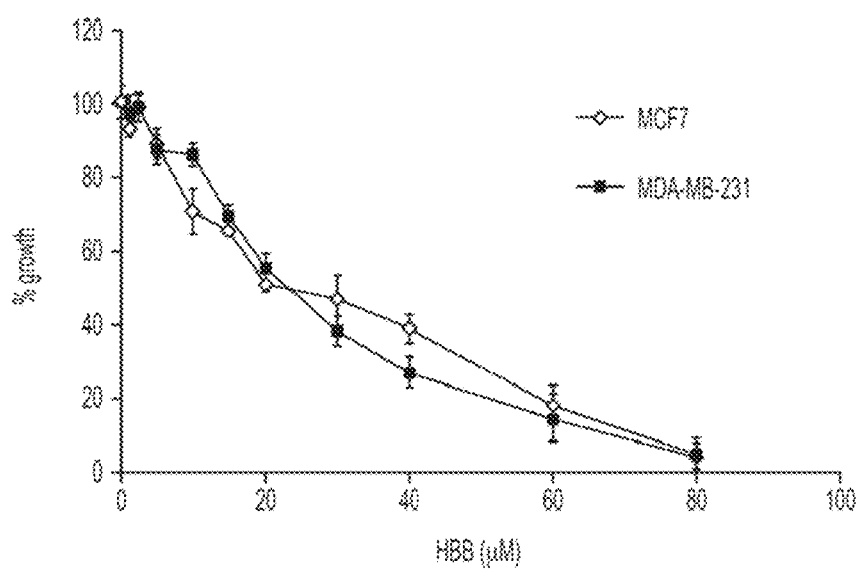
FIG. 30 illustrates HBB inhibits proliferation of MCF7 and MDA-MB-231 lines. Cells were plated in complete media in the presence of serum (10% FBS) and cultured at 37° C. with 5% $CO_2$ and treated with HBB or DMSO vehicle. Growth was measured at 24 hours by MTT assay. Results were converted to percent growth of control and represented as mean±S.E. (n=8). HBB exhibits $IC_{50}$ at 20 uM and 22.5 uM for MCF7 and MDA-MB-231, respectively.
Figure 31:
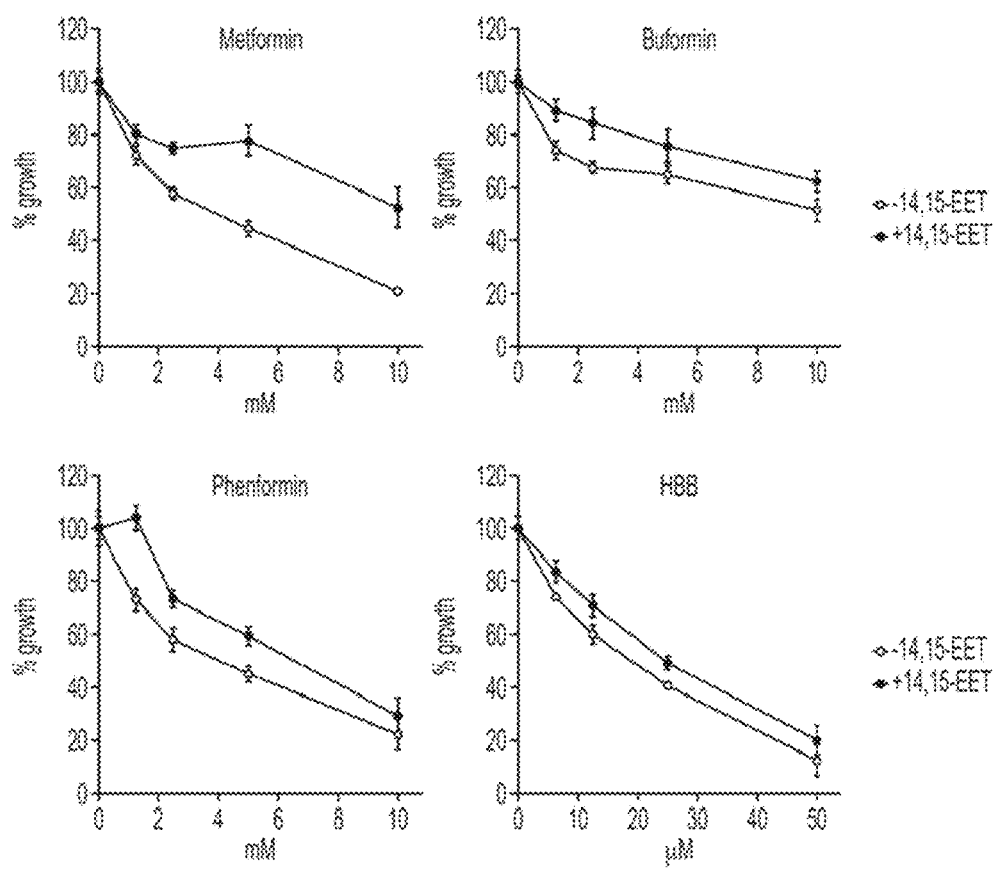
FIG. 31 illustrates that 14,15-EET partially protects MCF7 line from biguanide-mediated growth inhibition. Cells were plated in complete media in the presence of serum (10% FBS) and cultured at 37° C. with 5% $CO_2$ and treated with biguanides for 24 hours in the presence or absence of 1 uM 14,15-EET. Growth was then measured at 24 hour by MTT assay. Results were converted to percent growth of control and represented as mean±S.E. (n=8). 14,15-EET provided statistically significant 25%, 13%, 16% and 10% protection against metformin, buformin, phenformin and HBB, respectively, at $IC_{50}$ of each biguanide.
Figure 32:
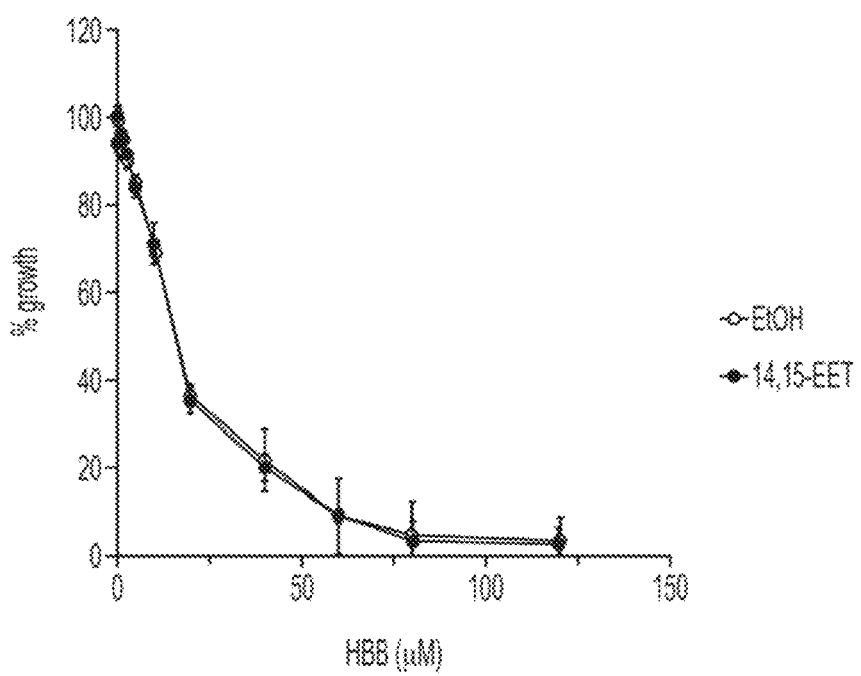
FIG. 32 illustrates that 14,15-EET provides no protection for MDA-MB-231 line against HBB-mediated growth inhibition. Cells were plated in complete media in the presence of serum (10% FBS) and cultured at 37° C. with 5% $CO_2$ and treated with HBB for 24 hours in the presence and absence of 1 uM 14,15-EET. Growth was then measured at 24 hours by MTT assay. Results were converted to percent growth of control and represented as mean±S.E. (n=8).
Figure 33:
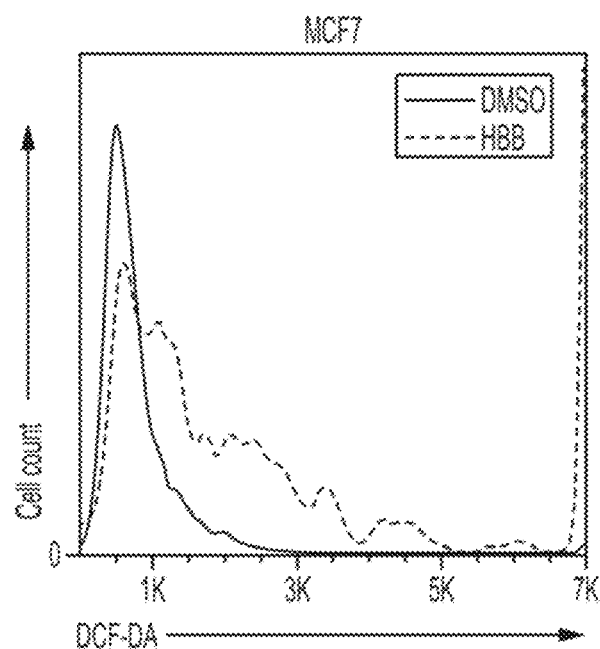
FIG. 33 illustrates that HBB induces reactive oxygen species (ROS) production in MCF7 and MDA-MB-231 lines. Cells in log phase growth in complete media were trypsinized and resuspended in complete media containing 20 uM DCFDA. After incubation at 37° C. for 30 minutes, cells were treated with 20 uM HBB or DMSO for 2.5 hours and analyzed by flow cytometer, monitoring fluorescence at 525 nm. Results are represented as histograms of cell count vs fluorescence intensity. Presence of HBB (red trace) induced significant ROS production in both lines relative to DMSO vehicle control (blue trace).
Figure 33:
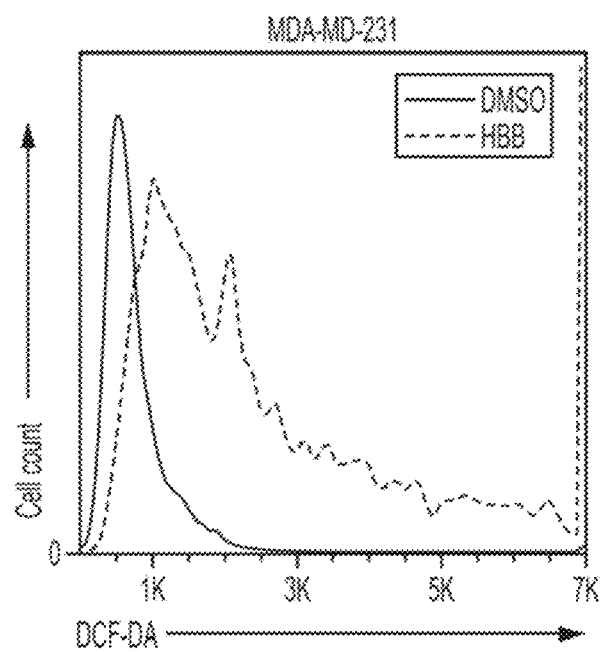
Figure 34:
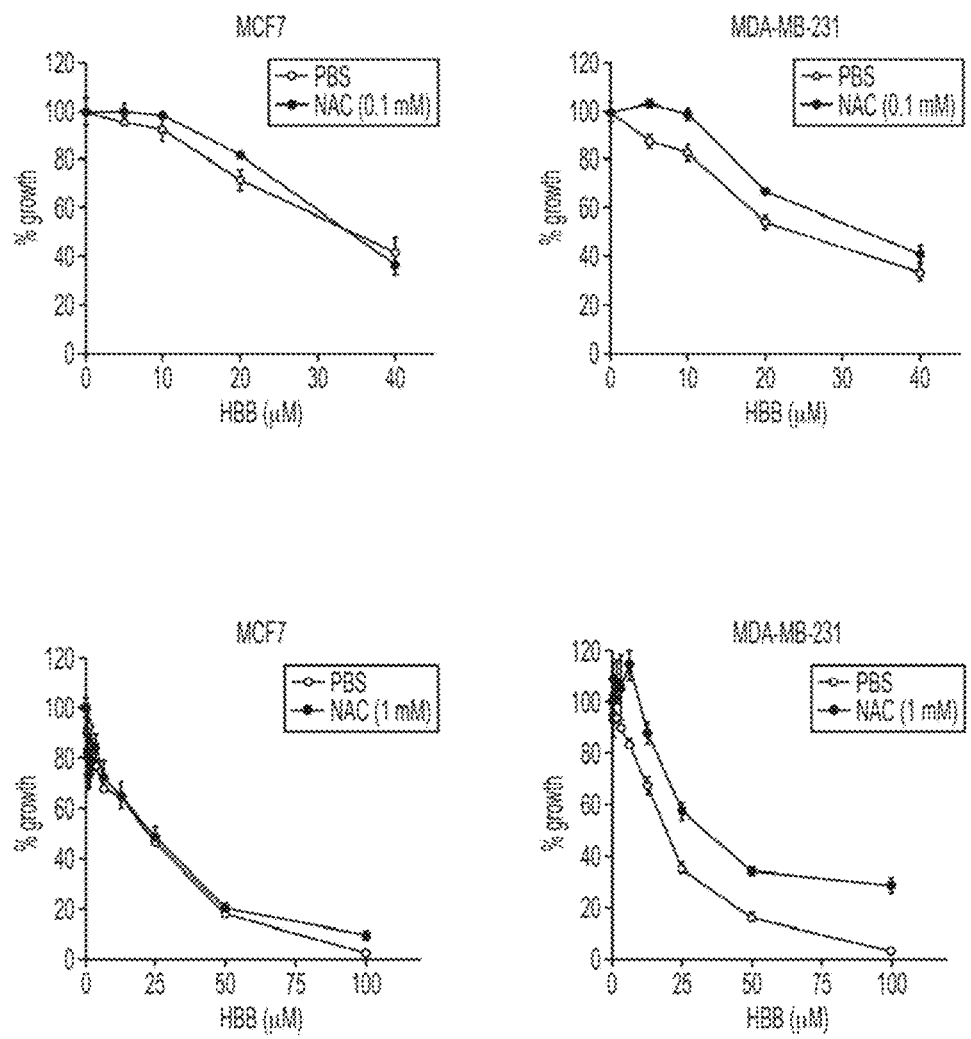
FIG. 34 illustrates that N-acetylcysteine (NAC) protects MDA-MB-231 but not MCF7 against HBB-mediated growth inhibition. Cells were plated in complete media in the presence of serum (10% FBS) and cultured at 37° C. with 5% $CO_2$ and treated with HBB in the presence of NAC or PBS control. Growth was then measured at 24 hours by MTT assay. Results were converted to percent growth of control and represented as mean±S.E. (n=8). The presence of 0.1 mM or 1 mM NAC failed to protect MCF7 line at $IC_{50}$ of HBB. For MDA-MB-231, 0.1 mM and 1 mM NAC protected MDA-MB-231 line by 10% and 30% at $IC_{50}$ of HBB.
Figure 35:
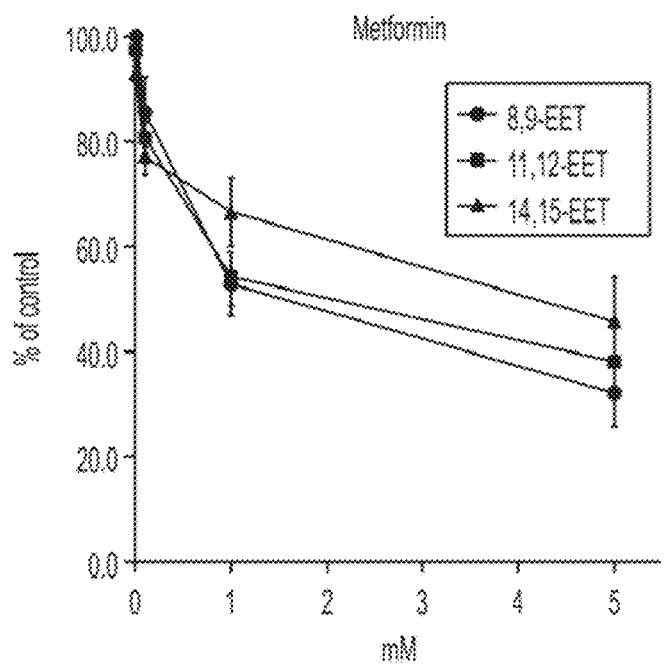
FIG. 35 illustrates that metformin and HBB inhibit CYP3A4-mediated EETs synthesis. In the presence or absence of metformin and HBB, CYP3A4 Supersome (BD Biosciences) were incubated with arachidonic acid (60 uM) and NADPH regenerating system (BD Biosciences) for 30 minutes at 37° C. After the reaction, EETs were then extracted with 1 mL dichloromethane and reconstituted in methanol and analyzed by LC-ESI-MS/MS. Percent of control was calculated and results are represented as mean±S.D. (n=3). Presence of metformin and HBB significantly reduced EETs production. HBB is a much more potent epoxygenase inhibitor comparing to metformin.
Figure 35:
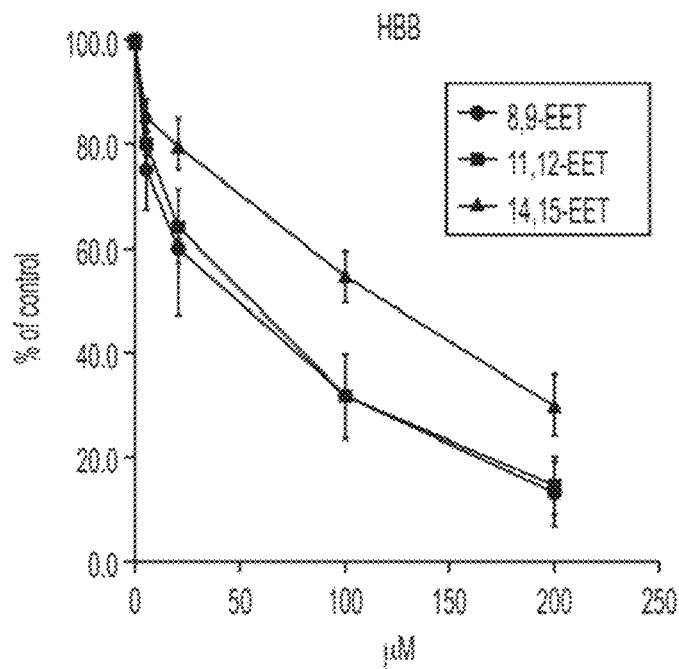
Figure 36:
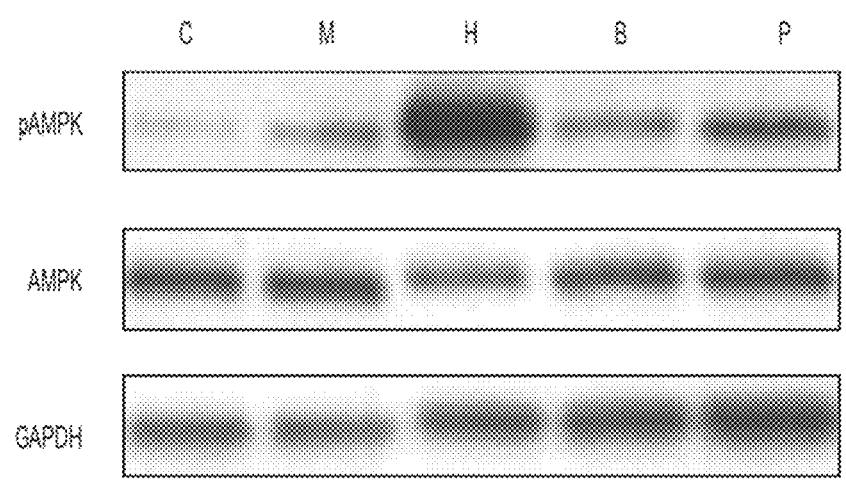
FIG. 36 illustrates that Biguanides activate AMPK in MCF7 line. Cells were plated in complete media in the presence of serum (10% FBS) and cultured at 37° C. with 5% $CO_2$ and treated with biguanides for 6 hours before harvesting. Total protein was extracted and analyzed by Western-blotting with GAPDH as an internal control. All four biguanides, metformin (1 mM, M), HBB (20 uM, H), buformin (1 mM, B) and phenformin (1 mM, P) increased phosphorylation of AMPK relative to control (C) with statistical significance (n=3, p<0.05).
Figure 37:
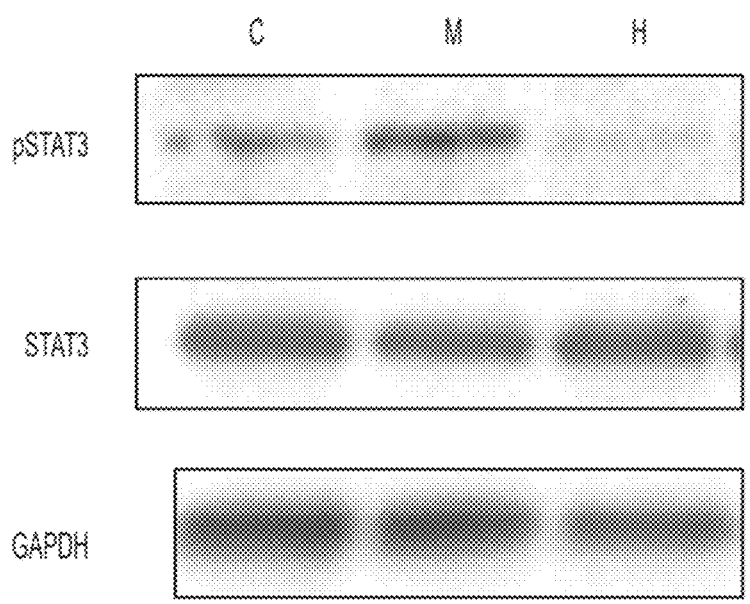
FIG. 37 illustrates that metformin and HBB inactivate STAT3 in MCF7 line. Cells were plated in complete media in the presence of serum (10% FBS) and cultured at 37° C. with 5% $CO_2$ and treated with metformin or HBB for 6 hours before harvesting. Total protein was extracted and analyzed by Western-blotting with GAPDH as an internal control. HBB (20 uM, H) decreased phosphorylation of STAT3 relative to control (C) with statistical significance (n=3, p<0.05) while metformin (10 uM, M) did not alter phosphorylation of STAT3 relative to control.
Figure 38:
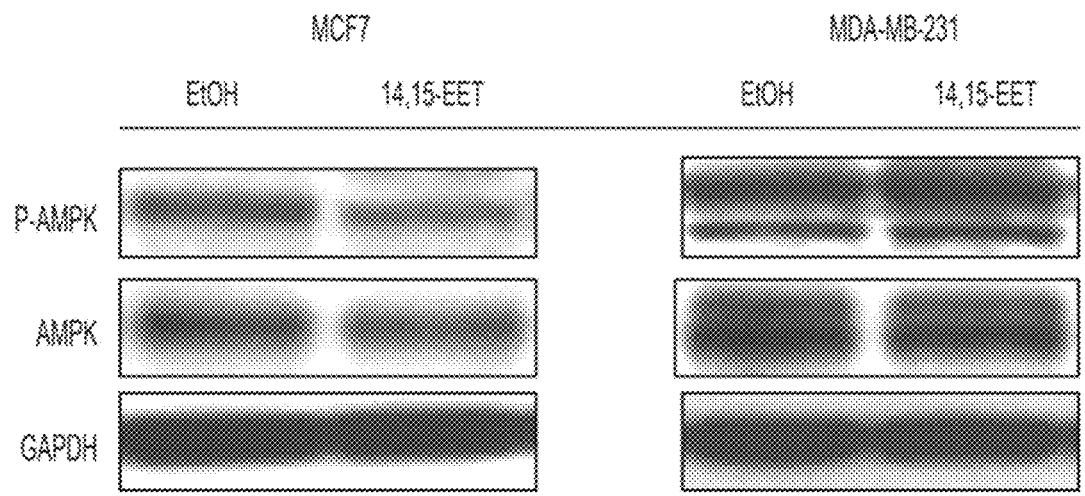
FIG. 38 illustrates that 14,15-EET inactivates AMPK in MCF7 line but not in MDA-MB-231 line. Cells were plated in complete media in the presence of serum (10% FBS) and cultured at 37° C. with 5% $CO_2$ and treated with 14,15-EET or EtOH control for 24 hours before harvesting. Total protein was extracted and analyzed by Western-blotting with GAPDH as an internal control. Presence of 1 uM 14,15-EET decreased phosphorylation of AMPK relative to EtOH with statistical significance (n=3, p<0.05) in MCF7 line. In MDA-MB-231 line, there was no statistical significant change of AMPK phosphorylation relative to control.
Figure 39:
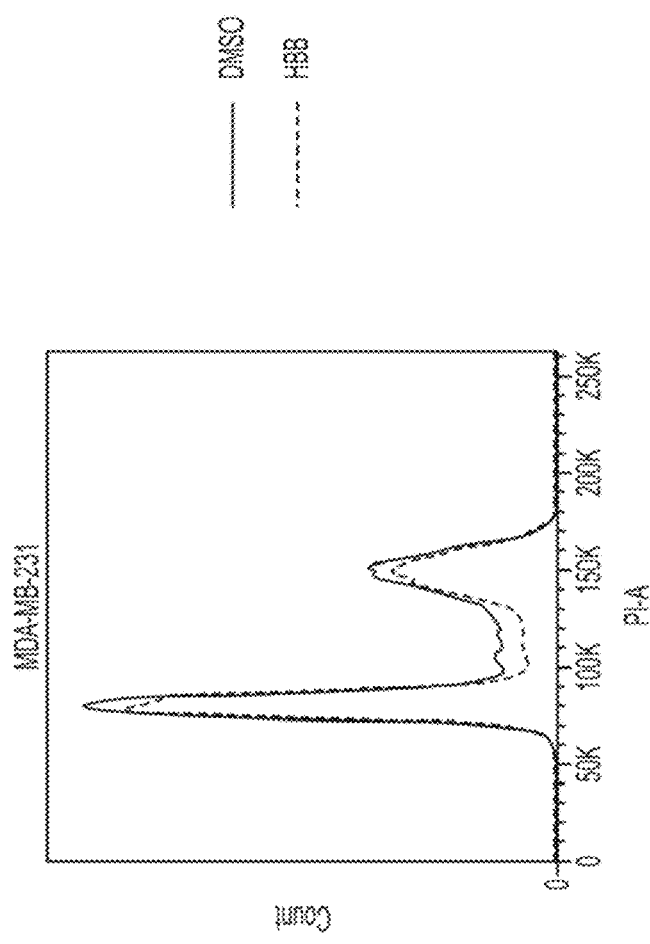
FIG. 39 illustrates that HBB induces $G_0/G_1$ and $G_2/M$ cell cycle arrest in MCF7 and MDA-MB-231 lines. Cells in log phase growth treated with HBB (20 uM) or DMSO for 6 hours were trypsinized and fixed in 70% ethanol at 4° C. overnight. The cells were washed with cold PBS and resuspended in Nicoletti buffer (50 μg/ml propidium iodide, 0.1% Triton X-100, 0.1% sodium citrate, pH 7.4, and 1 mg/ml RNase). The samples were then analyzed by flow cytometry (BD Biosciences), and data were analyzed using FlowJo software (Tree Star). Representative profile are shown.
Figure 39:
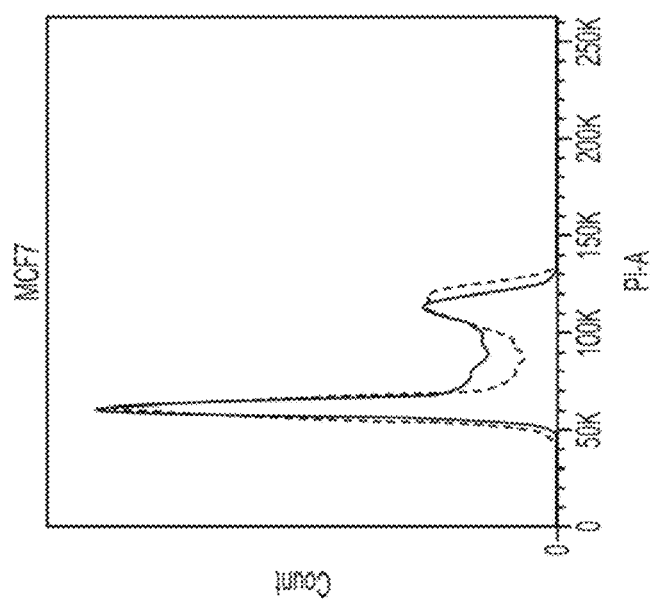
Figure 40:
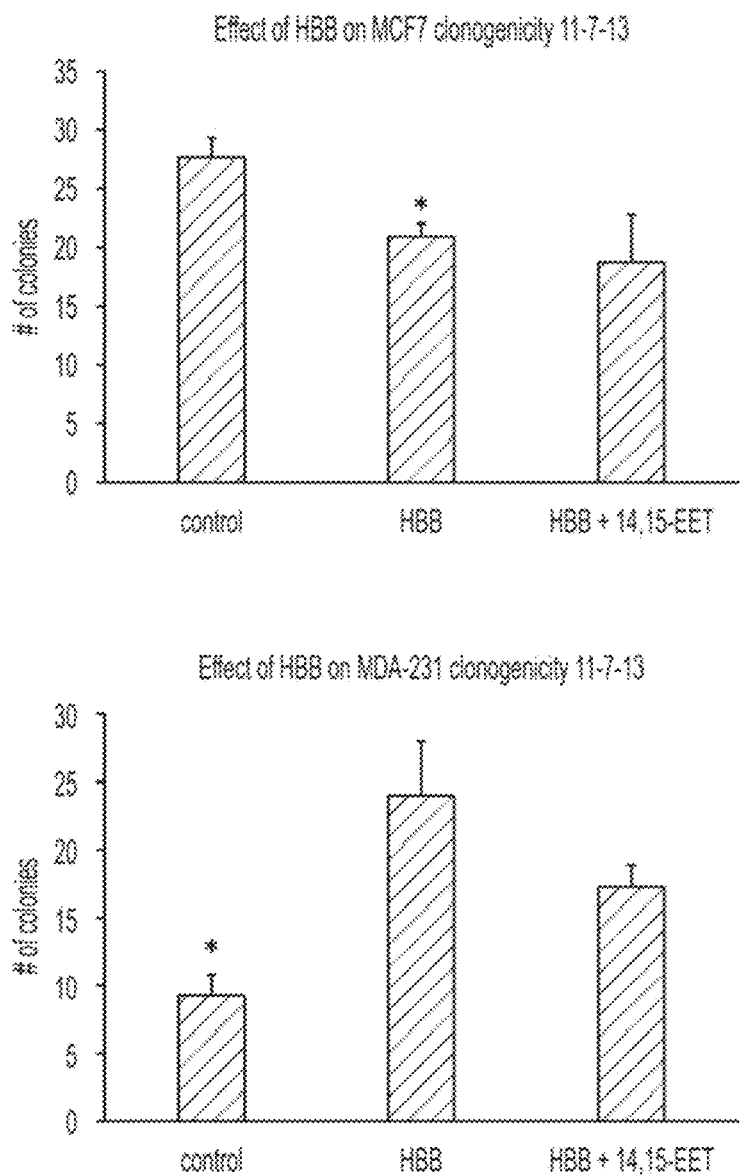
FIG. 40 illustrates the clonogenicity of MCF7 (upper panel) and MDA-MB-231 (lower panel) in the presence of HBB and 14,15-EET. To each well of 6-well tissue culture plate, about 100 cells were seeded in complete medium and incubated at 37° C. and 5% CO2 overnight. The cells were then treated with 10 uM HBB in the presence or absence of 1 uM 14,15-EET for 24 hours. Colonies were stained and counted 14 days later. Results are expressed as mean±standard deviation (n=4).
Figure 41:
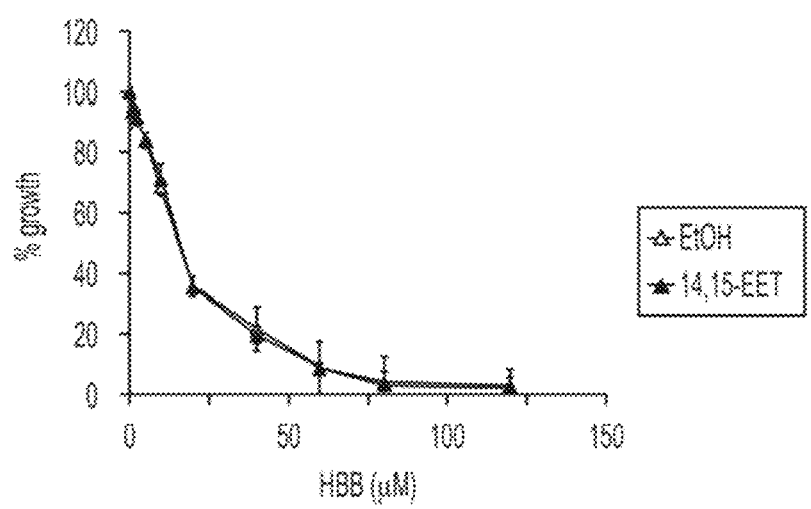
FIG. 41 illustrates the effect of 14,15-EET on HBB inhibition of MDA-MB-231 proliferation by MTT assay. Effect of HBB on the proliferation of MDA-MB-231 at 24 hours was assay by MTT in the presence and absence of 1 uM 14,15-EET. Results are expressed as mean±standard deviation (n=8).

Metformin was co-crystalized with CYP3A4 and the epoxygenase inhibitor, hexyl-benzyl-biguanide (HBB) (FIG. 2) was studied. Spin shift data indicate that HBB interacts much more closely with the CYP3A4 heme ring than metformin, increasing the likelihood of more potent epoxygenase inhibition. HBB exhibited a 50-fold more potent inhibition of CYP3A4 epoxygenase compared to metformin, with an IC50 of 110 uM vs. 5 mM. HBB inhibited proliferation of the MCF-7 lines in culture (~20 uM), but also inhibited the triple negative line MDA-MB-231 with a similar IC50. HBB was also ~50-fold more potent than metformin for inhibition of Stat3 phosphorylation and activation of AMPK phosphorylation. When HBB was tested in the ER+ MCF-7 xenograft model dosed at the maximum tolerated dose (MTD) of 4 mg/kg ip daily, there was a significant reduction in early engraftment/tumor growth compared to PBS control (P<0.05) (FIG. 3A) This result was consistent with lack of engraftment of the MCF-7 line in CYP3A4 shRNA clonal line 3-18 (FIG. 1). In contrast, the MDA-MB-231 xenograft was not inhibited (FIG. 3B), indicating that CYP3A4 epoxygenase inhibitors could be developed for ER+ breast cancer.

In summary, although metformin inhibits the MCF-7 xenograft (40 mg/kg/day, data not shown; P<0.001) and others have demonstrated inhibition of the MDA-MB-231 xenograft 12, the biguanides that were designed to more potently inhibit epoxygenase are selective for the ER+ breast cancer. This indicates that CYP3A4 is specifically required for ER+ breast cancer engraftment, and this process can be inhibited pharmacologically by epoxygenase inhibitors. Thus, a class of CYP3A4 target epoxygenase inhibitors was identified for treatment of ER+ breast cancer and suggests that how well the compound inhibits epoxidation of the endogenous arachidonic acid (AA) substrate is important.

Example 2. General Method for Developing Molecules (e.g., Biguanides) for ER+ HER2− Breast Cancer Therapeutics The following method was used to identify molecules as potential ER+ HER2− breast cancer therapeutics. This method is useful for screening molecules as potential ER+ HER2− breast cancer therapeutics. It is to be understood that embodiments of the invention include (a) all the steps described below, (b) any partial set of steps (e.g., steps 1 and 2, steps 2 and 3, steps 3 and 4, steps 2 and 4) and (c) any single step (e.g., step 1 or step 2 or step 3 or step 4). One embodiment provides a method comprising step 1. One embodiment provides a method comprising step 2. One embodiment provides a method comprising step 3. One embodiment provides a method comprising step 4.

Figure 49:
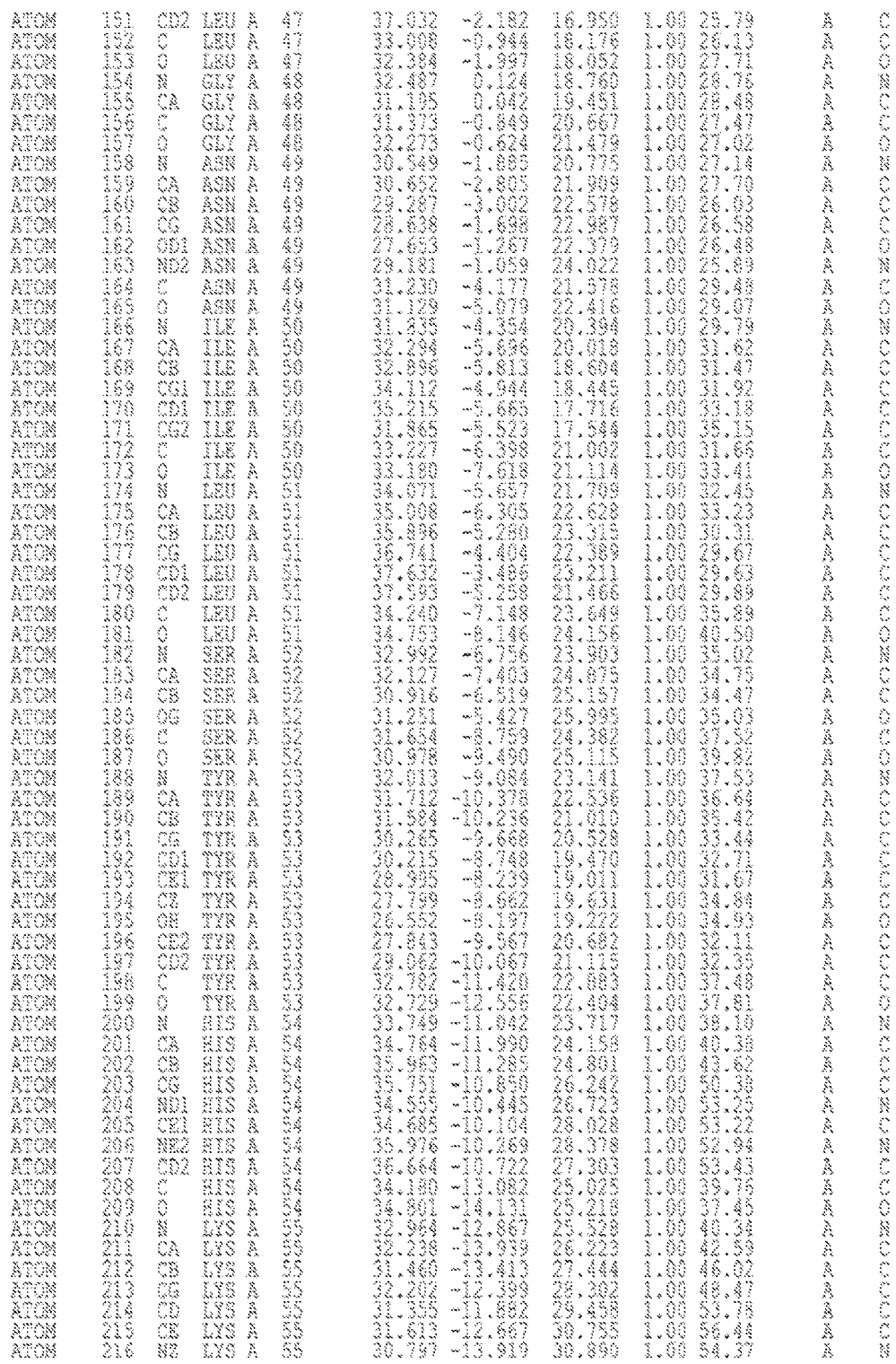
FIG. 49 displays coordinates for co-crystal of metformin HCl and CYP3A.
Figure 49:
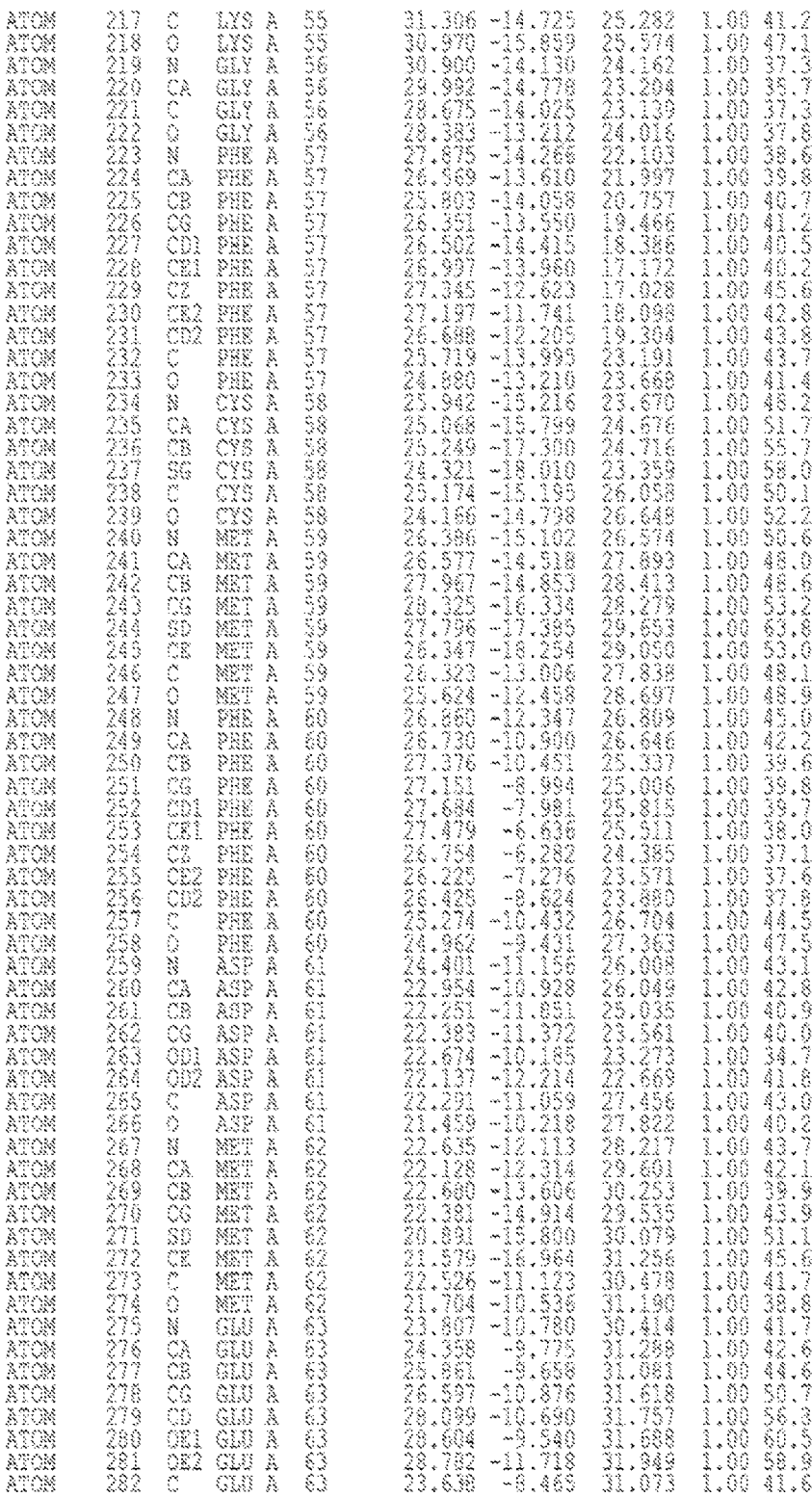
Figure 49:
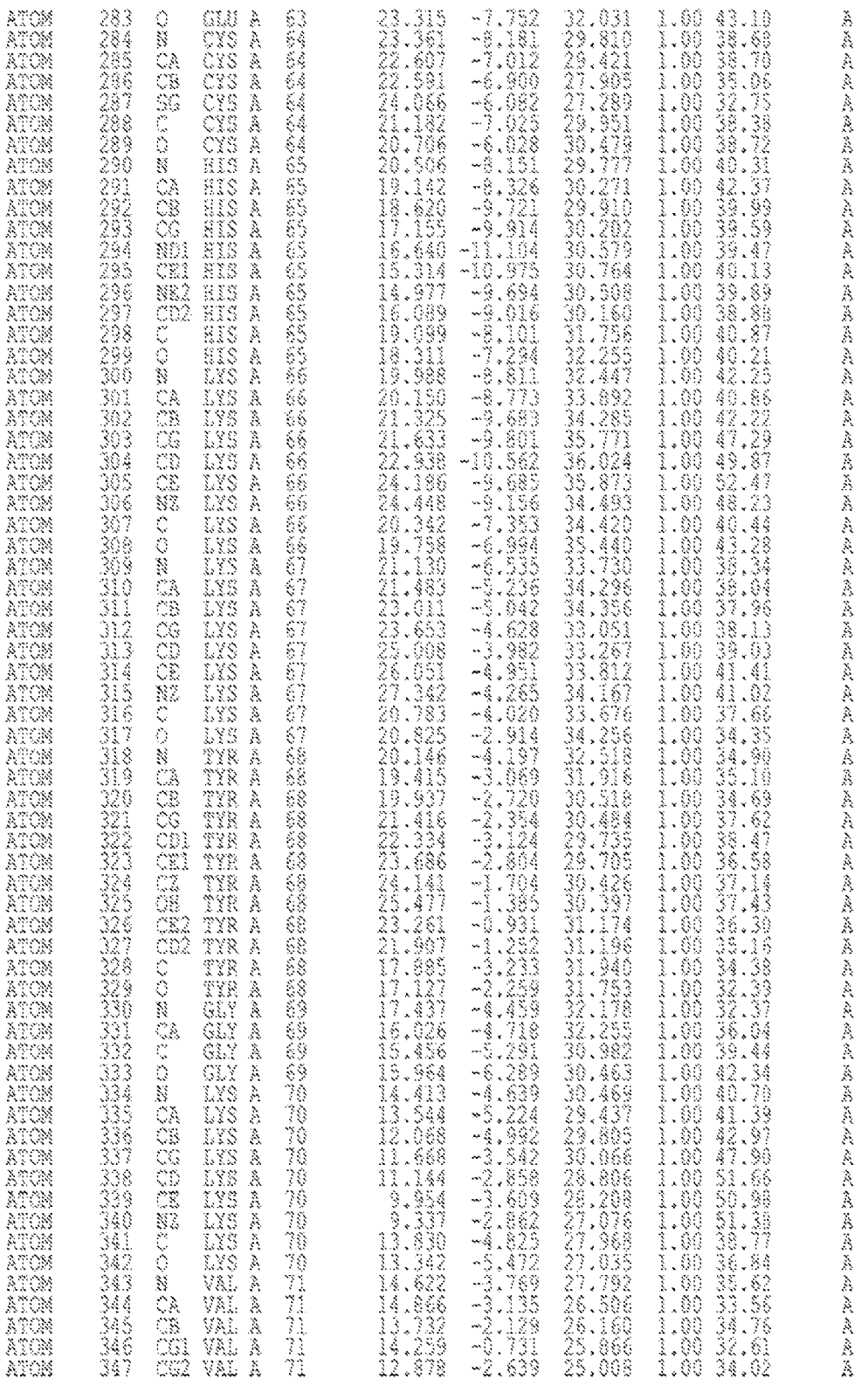
Figure 49:
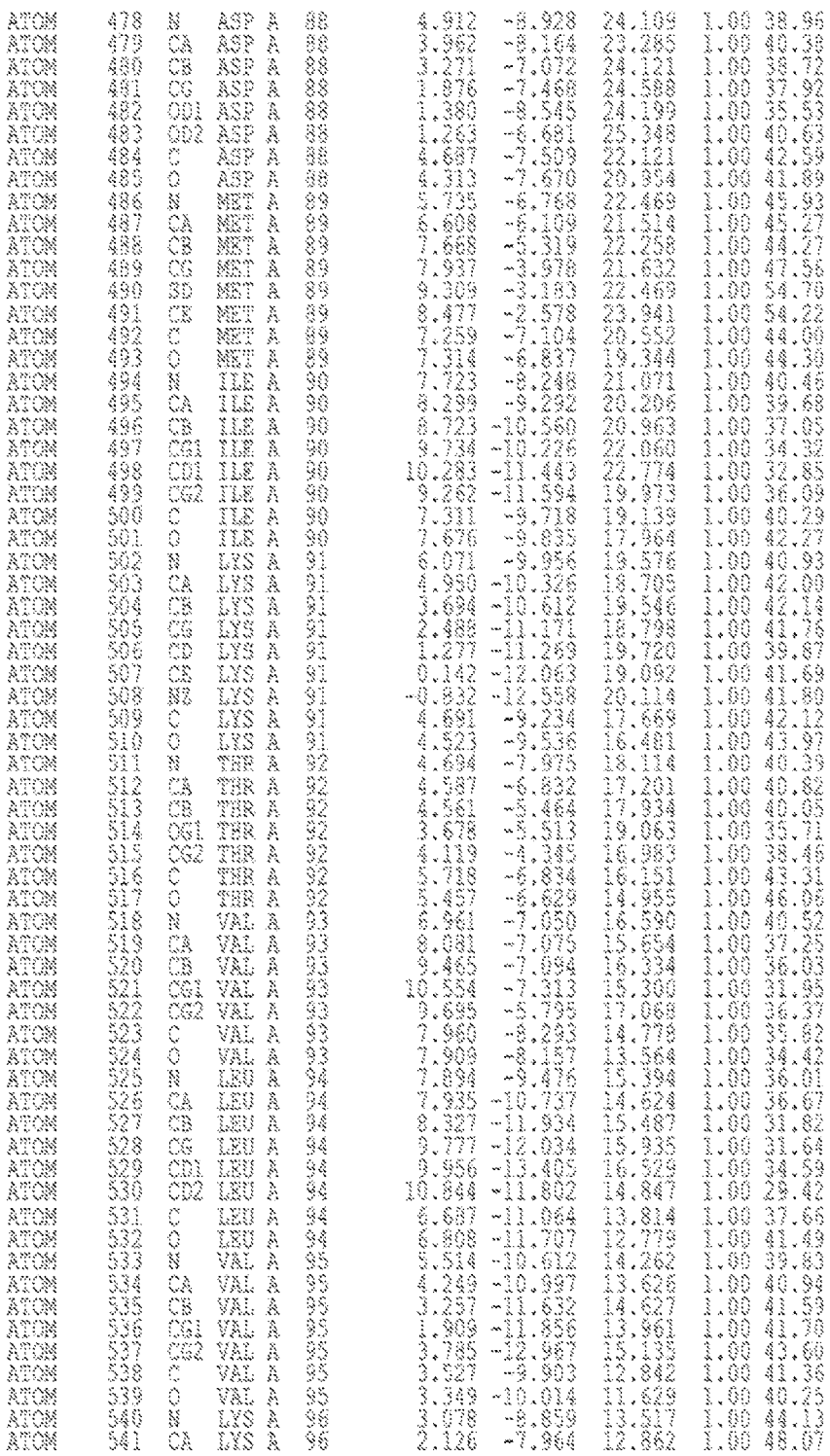
Figure 49:
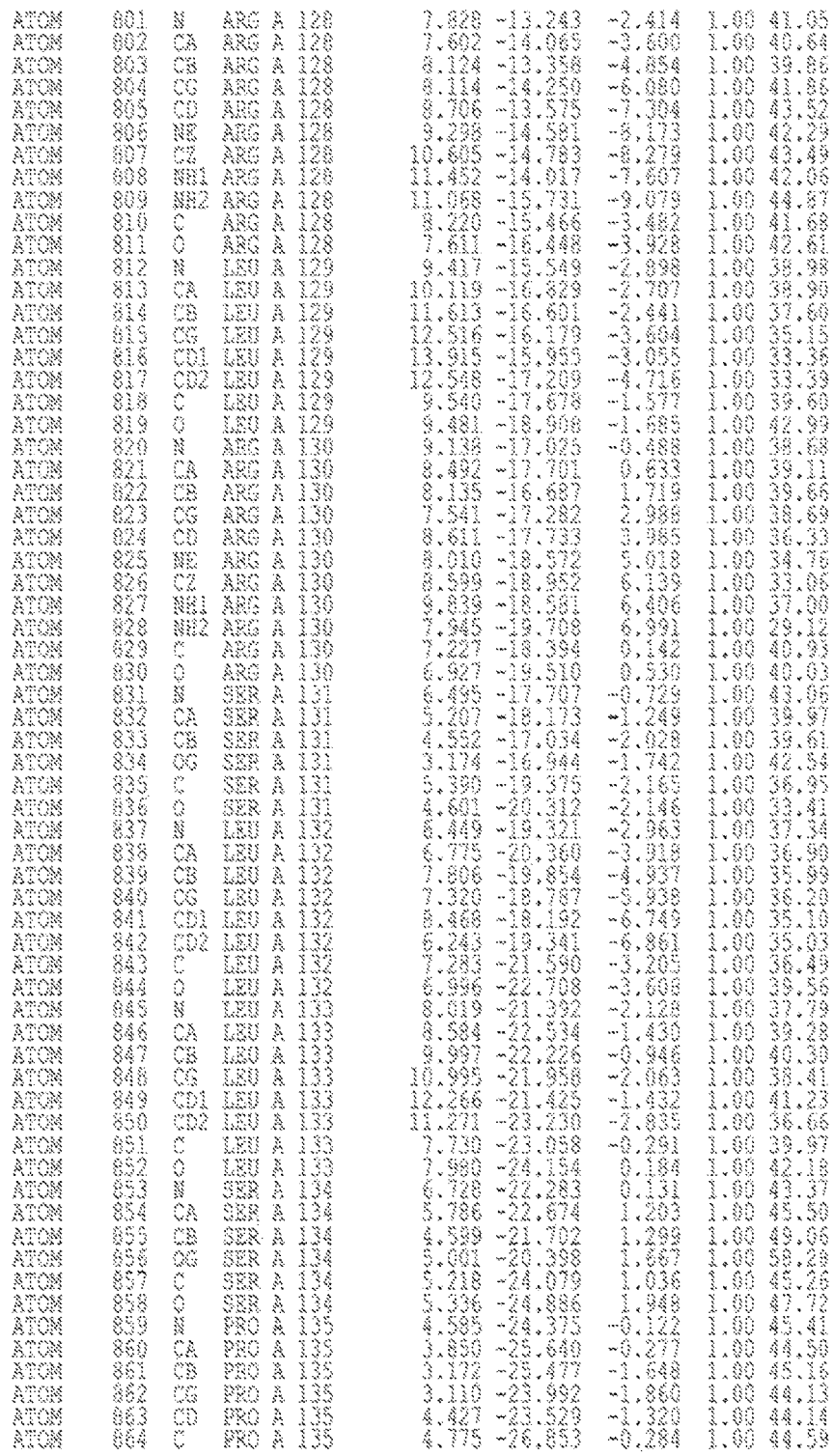
Figure 49:
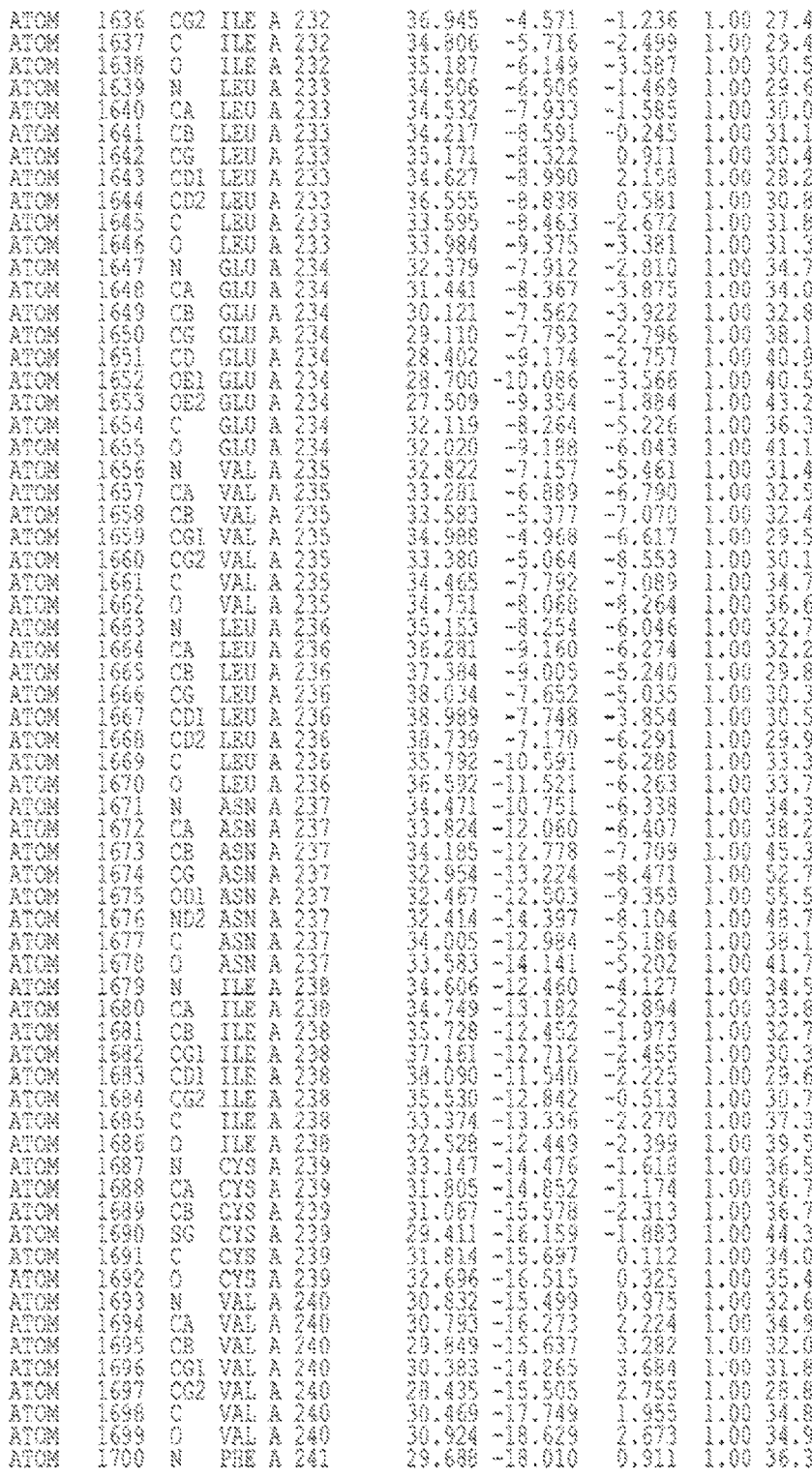
Figure 49:
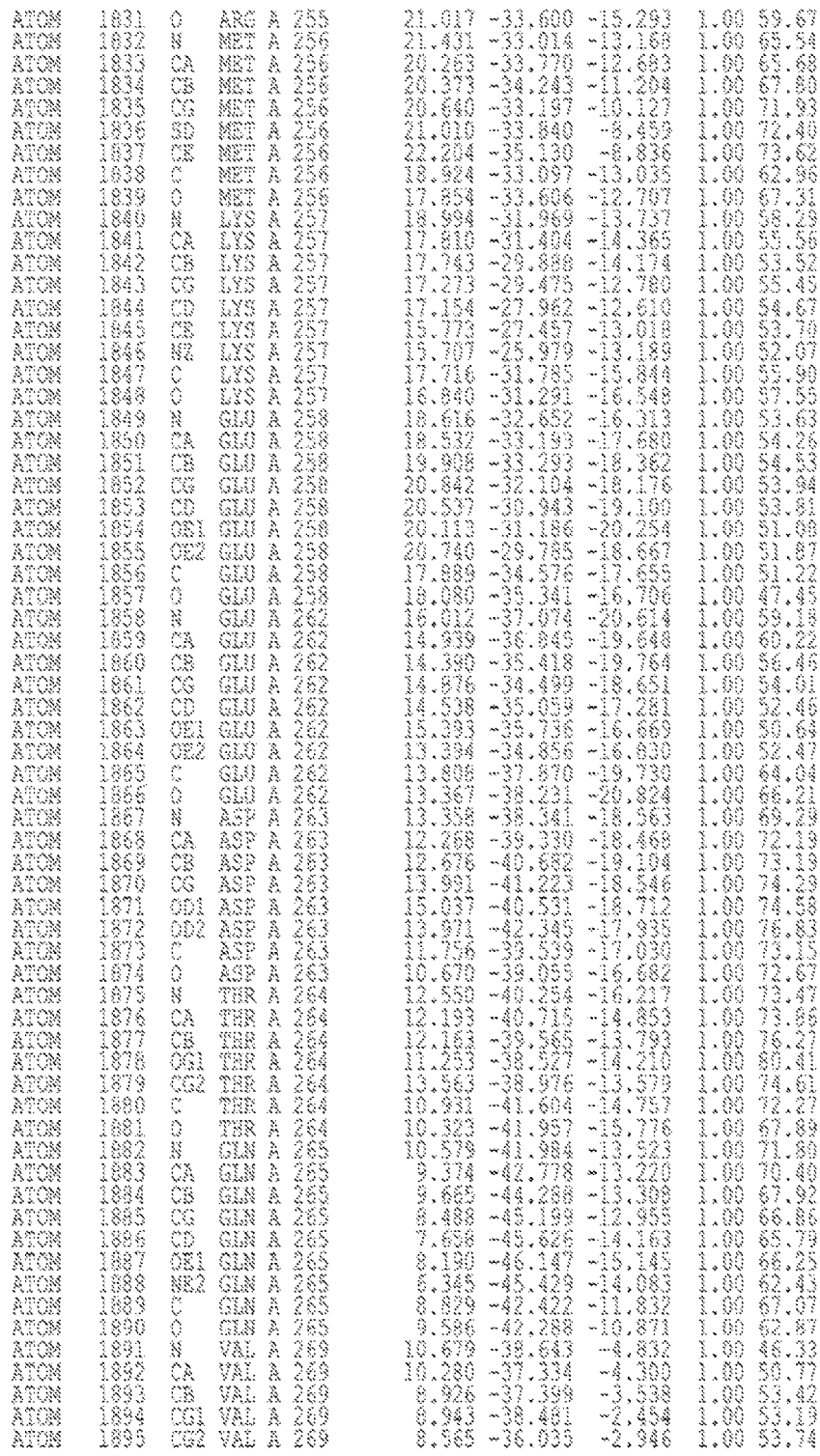
Figure 49:
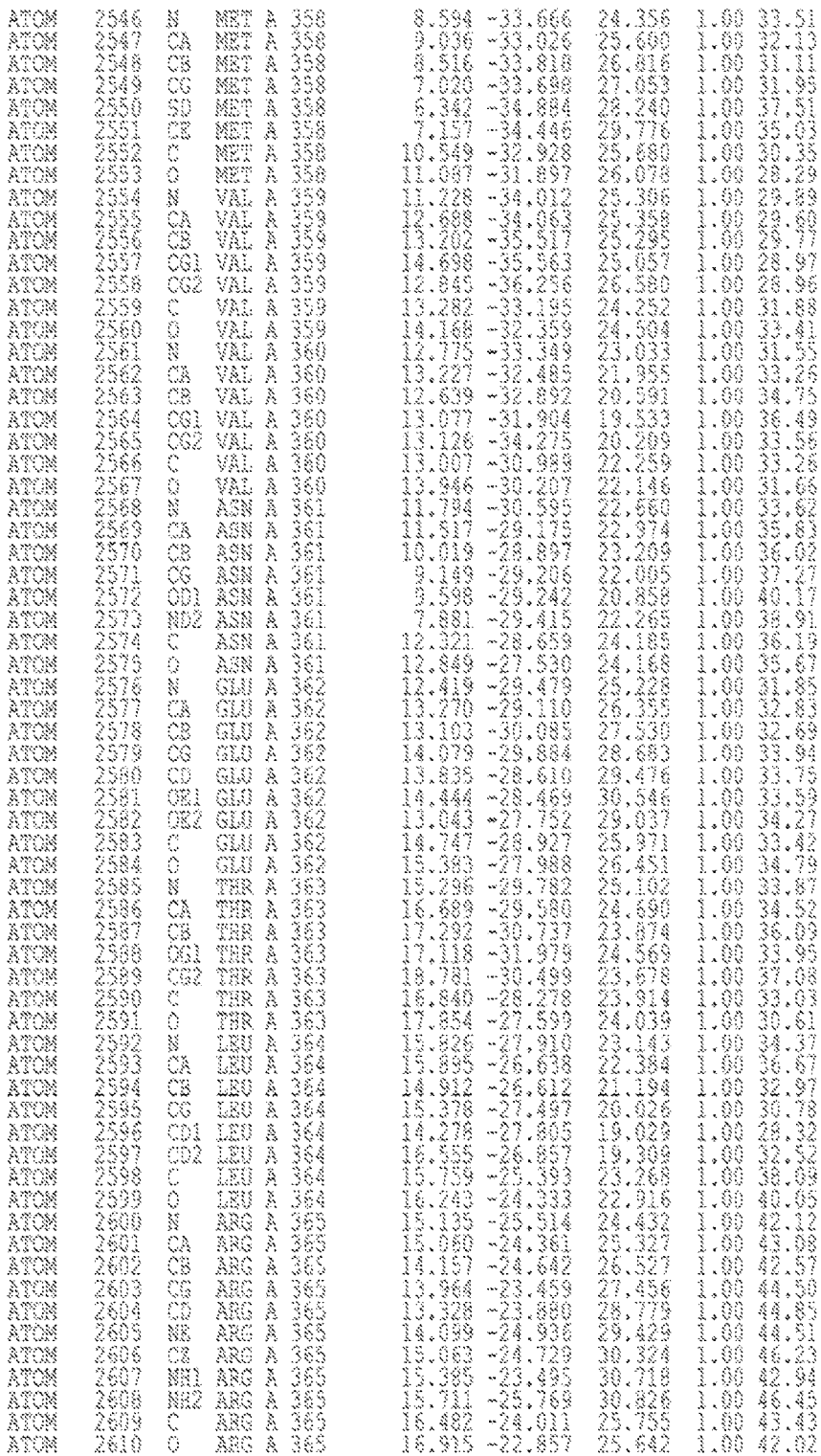

Step 1. Dock the candidate molecule (e.g., biguanide) in the CYP3A4 metformin co-crystal complex structure (FIG. 49). The docking of molecules was performed as described below.

Molecules were constructed using SYBYL-X 2.1 (Certara, L. P). Energy minimization of these compounds was performed using the Tripos forcefield with Gasteiger-Hückel charges for a maximum of 10000 iterations subject to a termination gradient of 0.001 kcal/(mol·Å).

Predicted bound configurations for these structures were obtained using Surflex-Dock (SYBYL-X 2.1, Certara, L. P), with our CYP3A4/metformin cocrystallized complex structure. The cocrystallized ligand metformin was used to guide the protocol generation process. Docked poses were ranked by total Surflex-Dock score expressed as $-\log(K_d)$. Threshold and bloat parameters were set to 0.5 and 0, respectively. Five additional starting conformations per molecule were used. The maximum number of conformations per compound fragment and the maximum number of poses per molecule were both set to twenty, and the maximum allowable number of rotatable bonds per structure was limited to 100. Post-dock minimizations were carried out on each ligand to optimize predicted configurations in the receptor site.

All calculations were carried out within the SYBYL-X 2.1 (Certara, L. P) environment on Minnesota Supercomputing Institute (MSI) Dell Precision T7400 workstations running under the CentOS 6.2 operating system. Visualizations were obtained using PyMOL, Version 1.5.0.4 (Schrödinger, LLC) in Mac OS X version 10.6.8.

Molecules were rank-ordered (e.g., dock score such as total Surflex-Dock score expressed as $-\log(K_d)$) and selected for step 2 (e.g., compounds with a dock score of about 7 or higher). Table 1 displays the ranked compounds.

Step 2. Prepare and test molecules identified from step 1 in the MCF-7 cell line by MTT assay performed for 24 or 48 hours. Molecules that exhibit an $IC_{50}$<30 uM for the MCF-7 cell line by MTT assay performed for 24 or 48 hours are selected.

Step 3. Test molecules identified from step 2 for oxygen consumption rates (OCR) and extracellular acidification rates (ECAR) using a Seahorse XF24 analyzer or similar machine. Optimal MCF-7 cell line density is 100,000 cells per well. Molecules that when tested at their $IC_{50}$ in the MTT assay result in reduction of OCR by 90 minutes for step 3 and ECAR by 120 minutes are selected for step 4. In one embodiment the molecules may also reduce HIF-1α by 10 to 30 minutes. This reduction can be confirmed by semi-quantitative or quantitative PCR for HK2, GLUT1, ENO1, PKM2, LDHA, and PDK1.

Step 4. Test molecules identified from step 3 for selective toxicity of MCF-7 cells vs. human dermal microvascular endothelial cells. The $IC_{50}$ should be 35 uM or higher, resulting in a ~2:1 ratio of $IC_{50}$ HDMEC vs. MCF-7 indicating selective sensitivity of cancer cells.

Step 5. Test molecules identified from step 4 for activity in a nude mouse xenograft model.

TABLE 1

Structures and Docking Scores of Molecules (e.g., biguanide compounds)

| Structures | Comp Rank | Structures |
|---|---|---|
| 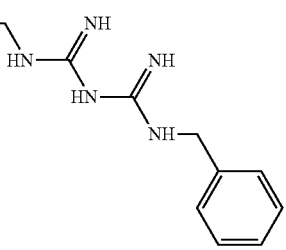 | 1 | 8.31 |
| 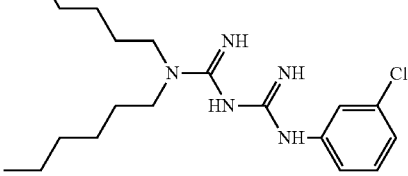 | 2 | 7.53 |
| 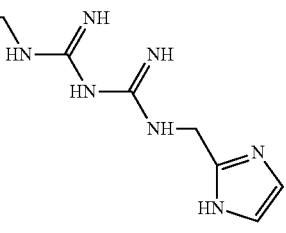 | 3 | 7.03 |
| 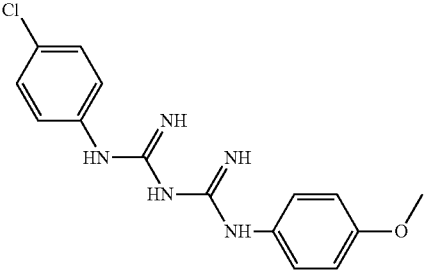 [SMILES: COc1ccc(NC(=N)NC(=N)Nc2ccc(Cl)cc2)cc1] | 3 | 7.03 |
| 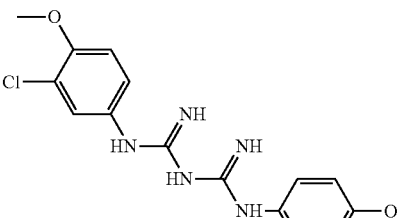 | 4 | 6.50 |

TABLE 1-continued
Structures and Docking Scores of Molecules (e.g., biguanide compounds)
| Structures | Comp Rank | Structures |
|---|---|---|
| 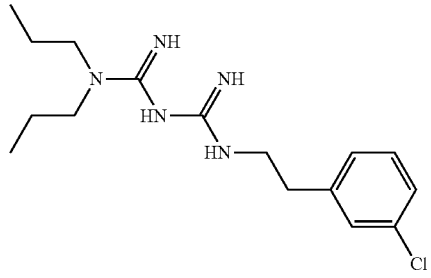 [SMILES: CCCN(CCC)C(=N)NC(=N)NCCc1cccc(Cl)c1] | 6 | 5.93 |
| 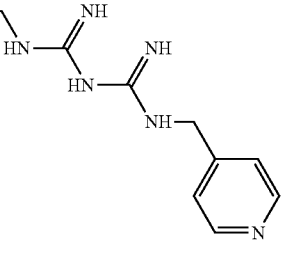 | 7 | 5.93 |
| 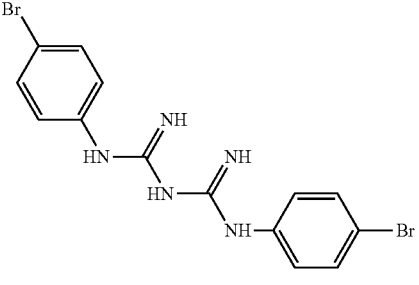 [SMILES: N=C(NC(=N)Nc1ccc(Br)cc1)Nc1ccc(Br)cc1] | 8 | 5.61 |
| 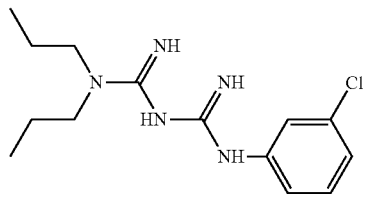 [SMILES: CCCN(CCC)C(=N)NC(=N)Nc1cccc(Cl)c1] | 8 | 5.61 |
| 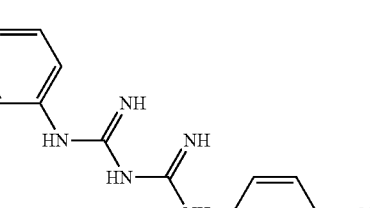 | 9 | 5.47 |
| 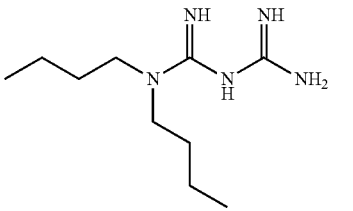 | 10 | 5.45 |
| 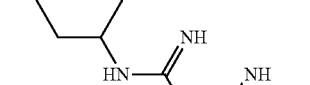 | 11 | 4.95 |
| 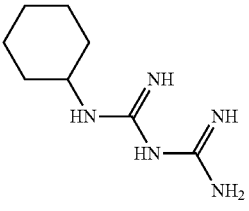 [SMILES: N=C(N)NC(=N)NC1CCCCC1] | 12 | 4.81 |
| 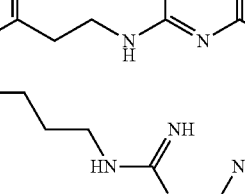 | 13 | 4.21 |
| 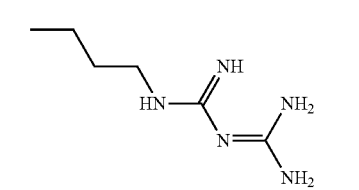 | 14 | 4.12 |
| 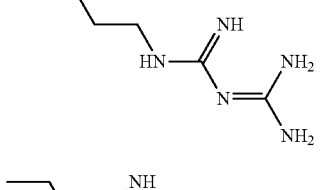 | 15 | 3.56 |
| 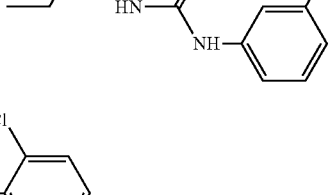 | 16 | 3.52 |

TABLE 1-continued

Structures and Docking Scores of Molecules (e.g., biguanide compounds)

| Structures | Comp Rank | Struct-ures |
|---|---|---|
| 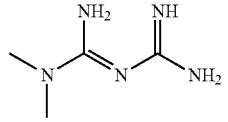 | 17 | 3.42 |
| 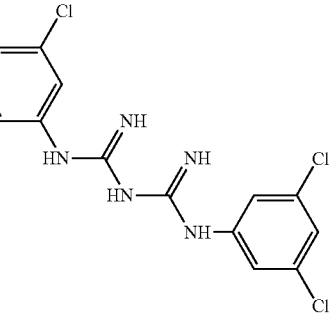 | 18 | 3.40 |
| 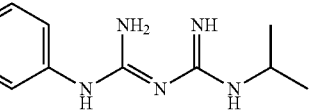 | 19 | 2.91 |

Figure 42:
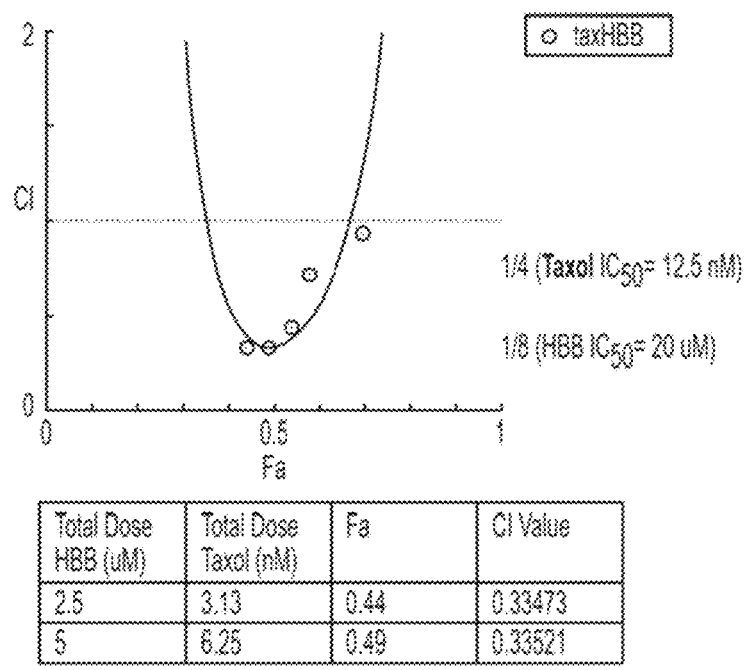
FIG. 42 is a combination index plot that shows the synergy between HBB and Taxol (MCF-7).

Example 3. Effect of HBB, Paclitaxel and Combination on MCF7 and MDA-MB-231 Cells and Chou-Talalay Analysis Cells were seeded into 96-well plates at 3,000 cells/well and grown over night. The cells were then treated with different doses of HBB, paclitaxel and combination of the two agents at a constant ratio (HBB vs paclitaxel=800:1). The treatments were conducted for each condition in quadruplicate. The cells were incubated for further 24 hours and an MTT assay was performed and dose-response curves and IC50 (the dose effective to achieve 50% cell killing) values for both agents were obtained. Combined dose-response curves were fitted to Chou-Talalay lines, and Chou-Talalay combination indices (CIs) were calculated for each fraction affected (Fa) using the equation CI=(D1/Dx1)+(D2/Dx2)+(D1)(D2)/[(Dx1)(Dx2)], where Dx1 and Dx2 are the HBB and paclitaxel doses, respectively, that are required for achieving a particular Fa, and D1 and D2 are the doses of the two agents (combined treatment) required for achieving the same Fa. For each Fa, CI values of 0.8 and 1.2 are cutoffs for synergy and antagonism, respectively (See FIG. 42).

Thus the use of compounds described herein (e.g., compounds of formula I or pharmaceutically acceptable salts thereof) may enhance the chemotherapy effect of certain chemotherapeutic agents in the treatment of breast cancer including ER+ and ER+ HER2− breast cancer. This is a major unmet need in the field of breast cancer and affects the use of chemotherapy in this histology, which includes about 60% of all breast cancer patients. Compounds described herein (e.g., compounds of formula I or pharmaceutically acceptable slats thereof) may also increase the effectiveness of hormonal therapy in the metastatic setting using mTOR inhibitors such as everolimus and cyclin dependent kinase inhibitors such as palbociclib. Everolimus and palbociclib increase the effectiveness of hormonal therapy for recurrent/metastatic disease but they don't increase the effectiveness of chemotherapy in ER+HER2− breast cancer. The major unmet need is to find a method to make chemotherapy more effective in ER+HER2− breast cancer, which can be relatively resistant to chemotherapy in part related to low proliferative rates as exemplified by the Ki67 labeling index. Typically, in neoadjuvant trials, ER+HER2− breast cancer treated with chemotherapy results in low pathological complete response rates (path CR) of ~20% of patients [Endocrine-Related Cancer (2005) 12, 383-392], compared to triple negative and HER2+ breast cancer, where the path CR rates range from 40 to 80% [Lancet Oncol. 2012 January; 13(1):25-32; J Clin Oncol. 2010 Mar. 1; 28(7):1145-53].

Example 4. Inhibition of Angiogenesis by HBB

Xenogaft tumors from the MCF-7 and MDA-MB-231 models were tested for inhibition of angiogenesis by HBB using CD31 staining.

Staining Protocol

The samples were cryosectioned at 6 um and fixed with chilled 100% acetone for 10 minutes. Samples were blocked with 3% donkey serum in PBS for 30 minutes at 37 C. The antibody used to stain CD-31 was from BD Pharmingen PE Rat anti Mouse CD31, catalog number 553373. It was used at a dilution of 1:50 in blocking buffer for 1 hour at 37 C.

The samples were then stained for 10 minutes with DAPI at a concentration of 1:2000, from Life Technologies, catalog number D1306.

Imaging Samples

Each sample was imaged in 4-5 areas. There were 3 samples per condition, PBS vs HBB. The data analyzed were found to be statistically significant with a p-value of less than 0.01.

Figure 43:
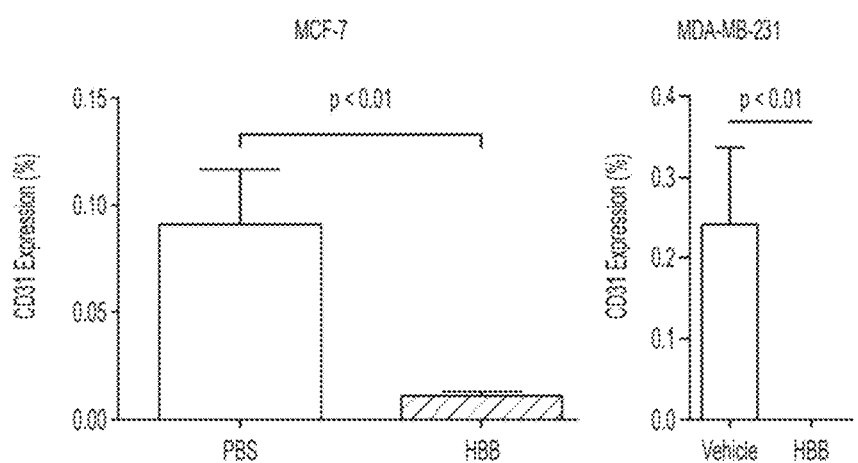
FIG. 43 shows the inhibition of angiogenesis by HBB through the reduction of CD31 expression.
Figure 44A:
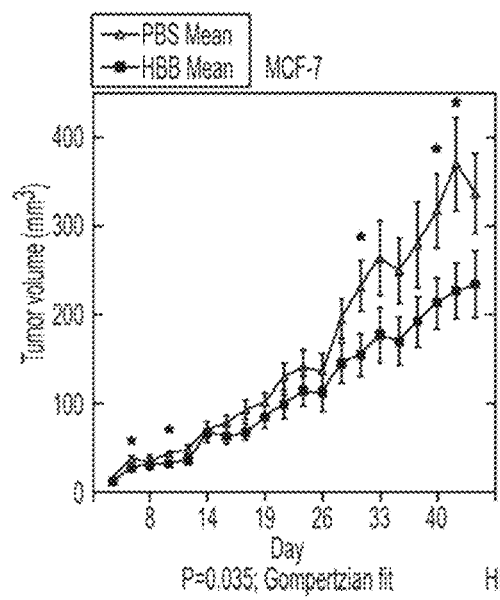
FIGS. 44A and 44B show that HBB inhibits the ER+ MCF-7 but not the triple negative MDA-MB-231 xenograft.
Figure 44B:
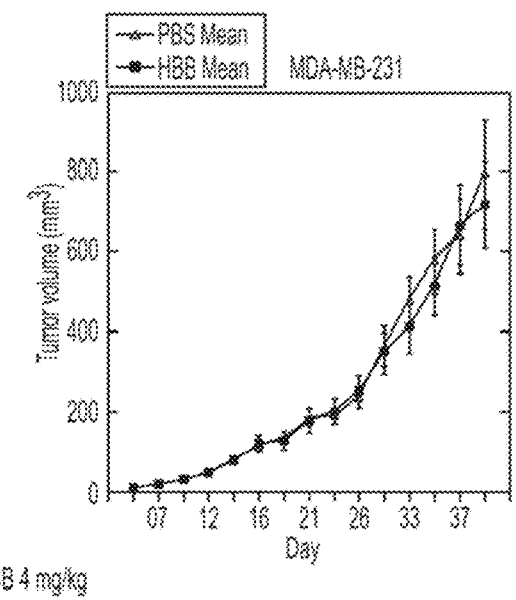

HBB inhibited angiogenesis in both models but tumor growth wasn't inhibited in the MDA-MB-231 model, only in the MCF-7 model (FIGS. 43, 44A and 44B). This result suggests that MCF-7 is more dependent on angiogenesis Inhibition of angiogenesis in both models is an indication that HBB was active in both models. Concentration of HBB 1 hour following ip administration was 0.527 uM as measured in the MCF-7 model. HBB was administered ip at 4 mg/kg/day in both models, which is the MTD for that dose, route and schedule.

Example 5. Co-Crystal of Metformin HCl and CYP3A4

Figure 45:
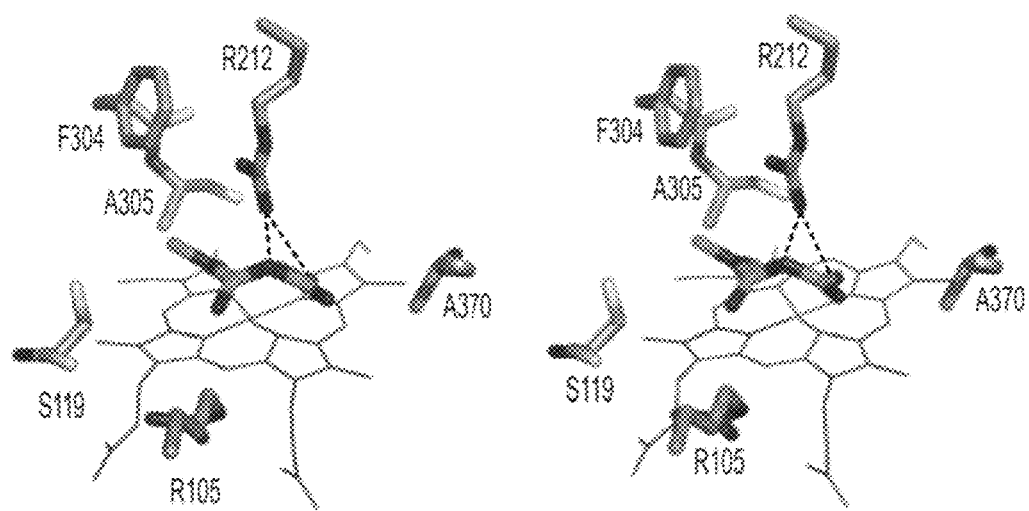
FIG. 45 shows the co-crystal of metformin HCl and CYP3A4.

Delta(3-22)CYP3A4 was co-crystallized with metformin at room temperature by a microbatch method under oil (FIG. 45). CYP3A4 (115 mg/ml) in 50 mM phosphate, pH 7.4, 20% glycerol and 100 mM NaCl was incubated for 20 min with a 40-fold excess of metformin. Prior to mixing with CYP3A4, pH of the aqueous metformin solution was adjusted to 7.0 with concentrated HCl. After removal of the precipitate by centrifugation, 0.4 microliters of the protein solution was mixed with 0.4 microliters of 12% PEG 3350 and 0.1 M sodium acetate pH 7.0, and the drop was covered with paraffin oil. Crystals were harvested 3 days later and cryoprotected with Paratone-N before freezing in liquid nitrogen. X-ray diffraction data were collected at −170 C at the Stanford Synchrotron Radiation Lightsource (SSRL) beamline 7-1.

C-terminal 4-histidine tagged wild type (WT) CYP3A4Δ 3-22 and the S119A mutant were produced, purified, and quantified as reported previously (Sevrioukova, I. F., and Poulos, T. L. (2010) Structure and mechanism of the complex between cytochrome P4503A4 and ritonavir. Proc. Natl. Acad. Sci. U.S.A. 107, 18422-18427).

| Data collection and refinement statistics for the CYP3A4-metformin structure | |
|---|---|
| Space group | I222 |
| Unit cell parameters | a = 77 Å, b = 101 Å, c = 128 Å, α = β = γ = 90° |
| Resolution range | 77.4-2.6 (2.72-2.60)[a] |
| Total reflections | 68,206 |
| Unique reflections | 15,443 |
| Redundancy | 4.4 (4.5) |
| Completeness | 98.2 (99.6) |
| Average I/σI | 10.5 (2.0) |
| $R_{merge}$ | 0.068 (0.559) |
| $R/R_{free}$[b] | 21.2/28.1 |
| r.m.s. deviations | |
| Bond lengths, Å | 0.010 |
| Bond angles, ° | 1.9 |

[a]Values in brackets are for the highest resolution shell.
[b]$R_{free}$ was calculated from a subset of 5% of the data that were excluded during refinement.

Example 6. Measuring Glycolysis and Oxidative Metabolism

Measuring glycolysis and oxidative metabolism. Cells were maintained in growth medium consisting of 10% FBS, at 37° C. with 5% $CO_2$ and seeded at 100,000 cells per well in XF24-well cell culture microplates (for primary cells HUVEC and HDMVEC, plates were pre-coated with 0.2% college before seeding). Concentrated stocks of HBB was prepared in DMSO. HBB was diluted to 10× working concentration in XF assay medium (a non-buffered medium including 2 mM of L-glutamine but no sodium bicarbonate (buffering agent), glucose, or sodium pyruvate).

Assays were performed in the XF Extracellular Flux Analyzer (Seahorse Bioscience that measures uptake and excretion of metabolic end products in real time. Oxygen consumption rate (OCR) and extracellular acidification rate (ECAR) were measured using an XF Assay Kit. OCR is reported in pmoles/minute and ECAR in mpH/minute.

Before analysis, the cells were switched from culture medium to XF assay medium. Following baseline measurements, 75 µl of HBB prepared in assay medium was injected into each well to reach final working concentrations. Following the addition of HBB, OCR and ECAR were measured at fixed time interval.

Figure 46:
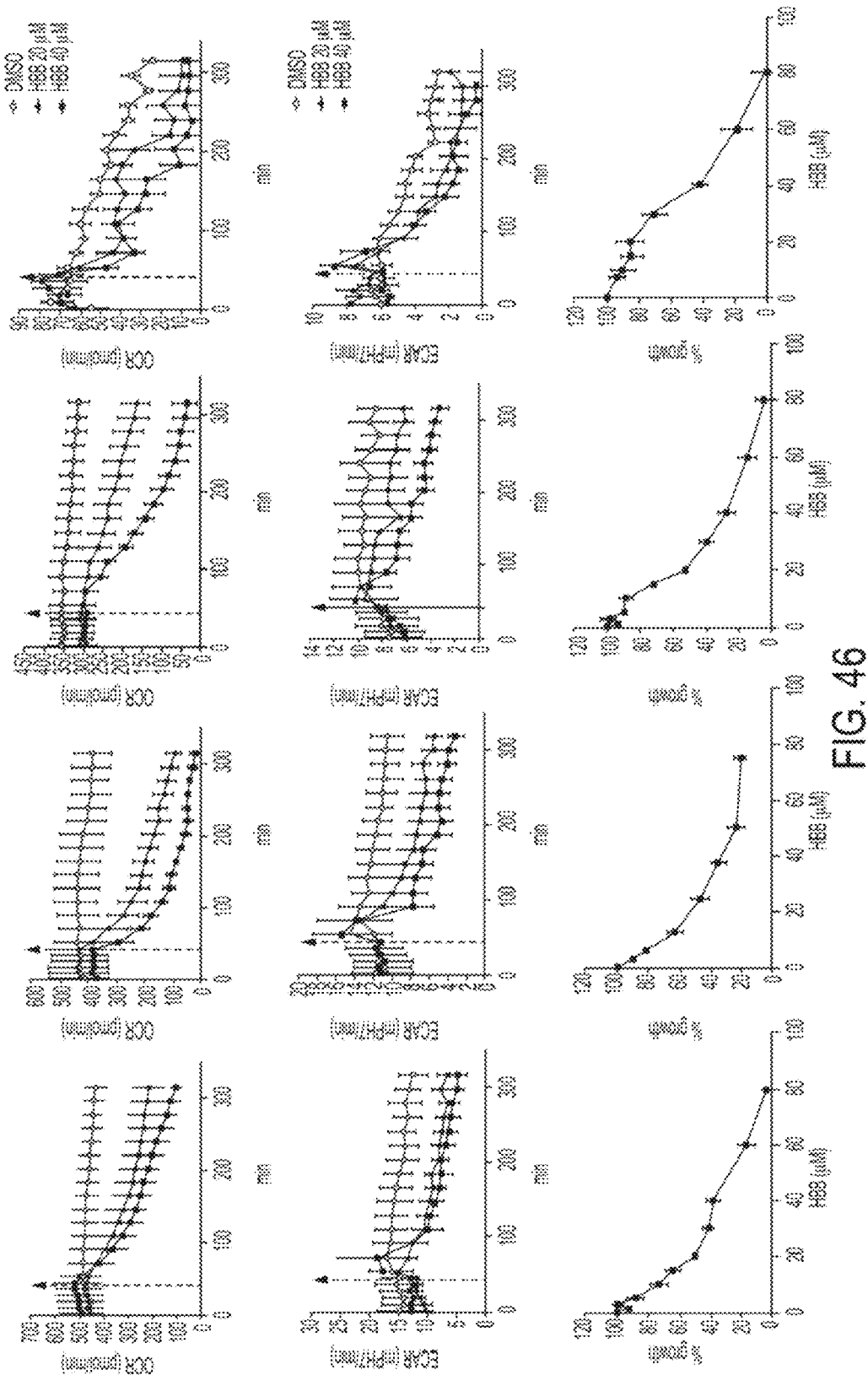
FIG. 46 shows that HBB inhibits oxygen consumption rate (OCR) and extracellular acidification rate (ECAR) in breast cancer cells and primary cells with varied potency. The top panel indicates the effect of HBB (20 uM—triangle or 40 uM—square or DMSO vehicle open circle) on OCR. The middle panel indicates the effect of HBB or DMSO vehicle on ECAR. The bottom panel is an MTT assay (24 hours growth) indicating the HBB growth inhibition curve for the indicated cell lines.

HBB inhibits oxygen consumption rate (OCR) and extracellular acidification rate (ECAR) in breast cancer cells and primary cells with varied potency (FIG. 46). Cells were maintained in growth medium consisting of 10% FBS, at 37° C. with 5% $CO_2$ and seeded at 100,000 cells per well in XF24-well cell culture microplates (for HUVEC, plates were pre-coated with 0.2% college before seeding). Before analysis, the cells were switched from culture medium to XF assay medium. Following baseline measurements, 75 µl of HBB prepared in assay medium was injected into each well to reach final working concentrations. Following the addition of HBB, OCR and ECAR were measured at fixed interval. OCR is reported as mean±standard deviation (n=5) in pmoles/minute and ECAR is reported as mean±standard deviation (n=5) in mpH/minute.

Figure 47:
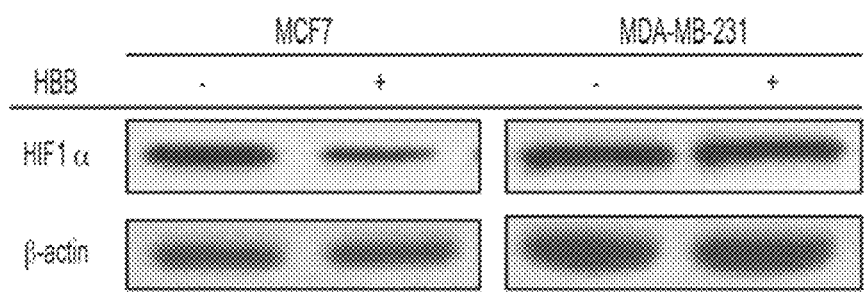
FIG. 47 shows that HBB treatment (20 uM) at 15 minutes inhibits HIF1 a in MCF7 but not MDA-MB-231 cells.

HBB inhibits proliferation of breast cancer cells and primary cells with varied potency (FIG. 47). Cells were plated in complete media in the presence of serum (10% FBS) and cultured at 37° C. with 5% $CO_2$ and treated with HBB or DMSO vehicle. Growth was measured at 24 hours by MTT assay. Results were converted to percent growth of control and represented as mean±standard deviation (n=7).

Figure 48:
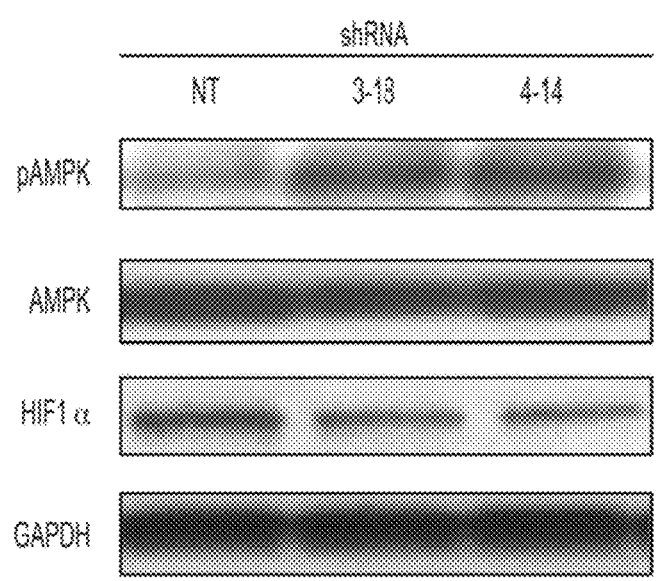
FIG. 48 shows CYP3A4 knock down activates AMPK and inactivates HIF1 a in MCF7 cells.

HBB treatment at 15 minute inhibits HIF1 a in MCF7 but not MDA-MB-231 cells (FIG. 48). Cells were maintained in complete media in the presence of serum (10% FBS) and cultured at 37° C. with 5% $CO_2$ at 70% confluence. The cells were treated with either DMSO or 20 uM HBB for 15 minutes and harvested. Total protein was extracted and analyzed by Western-blotting with b-actin as an internal control. HBB treated MCF7 cells exhibited lower HIF1 a level than the DMSO vehicle treated control with statistical significant difference (n=3, p=0.01). In MDA-MB-231 cells, HIF1 a levels were not different between the two conditions. The levels of HIF1 a normalized against actin internal control are 1.19±0.03 and 0.90±0.07 for DMSO and HBB treated MCF7 cells, respectively. The levels of HIF1 a normalized against actin internal control are 0.73±0.06 and 0.72±0.13 for DMSO and HBB treated MDA-MB-231 cells, respectively.

There are few, if any, previously described biguanide compounds that can induce energy crisis in cancer cells by simultaneously inhibiting oxidative phosphorylation, measured by oxygen consumption rates (OCR), and glycolysis, as measured by extracellular acidification rate (ECAR) [Toxicology and Applied Pharmacology 233 (2008) 203-210 Toxicology and Applied Pharmacology 233 (2008) 203-210]. Furthermore, HBB inhibits both OCR and ECAR specifically in ER+HER2− breast cancer cells at the $IC_{50}$ concentration of 20 uM. This property correlates with HBB sensitivity of the MCF-7 ER+HER2− breast cancer xenograft and lack of this property correlates with resistance of the triple negative MDA-MB-231 xenograft. Simultaneous OCR and ECAR inhibition also allows HBB to sensitize ER+HER− breast cancer to paclitaxel chemotherapy, which meets an unmet need in breast cancer oncology.

Example 7

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

REFERENCES

1. Jiang J G, Chen C L, Card J W, et al. Cytochrome P450 2J2 promotes the neoplastic phenotype of carcinoma cells and is up-regulated in human tumors. Cancer Res. 2005; 65(11):4707-4715.
2. Jiang J G, Ning Y G, Chen C, et al. Cytochrome p450 epoxygenase promotes human cancer metastasis. Cancer Res. 2007; 67(14):6665-6674.
3. Mitra R, Guo Z, Milani M, et al. CYP3A4 Mediates Growth of Estrogen Receptor-positive Breast Cancer Cells in Part by Inducing Nuclear Translocation of Phospho-Stat3 through Biosynthesis of ({+/−})-14,15-Epoxyeicosatrienoic Acid (EET). The Journal of Biological Chemistry. 2011; 286(20):17543-17559.
4. Panigrahy D, Edin M L, Lee C R, et al. Epoxyeicosanoids stimulate multiorgan metastasis and tumor dormancy escape in mice. The Journal of Clinical Investigation. 2012; 122(1):178-191.
5. Panigrahy D, Greene E R, Pozzi A, Wang D W, Zeldin D C. EET signaling in cancer. Cancer metastasis reviews. 2011.
6. Fleming I. The cytochrome P450 pathway in angiogenesis and endothelial cell biology. Cancer Metastasis Reviews. 2011.
7. Zhang G, Kodani S, Hammock B D. Stabilized epoxygenated fatty acids regulate inflammation, pain, angiogenesis and cancer. Progress in Lipid Research. 2013.
8. Oguro A, Sakamoto K, Funae Y, Imaoka S. Overexpression of CYP3A4, but not CYP2D6, promotes hypoxic response and cell growth of Hep3B cells. Drug Metabolism and Pharmacokinetics. 2011.
9. Choi Y H, Lee M G. Pharmacokinetic and pharmacodynamic interaction between nifedipine and metformin in rats: competitive inhibition for metabolism of nifedipine and metformin by each other via CYP isozymes. Xenobiotica; the fate of foreign compounds in biological systems. 2012; 42(5):483-495.
10. Peng C C, Pearson J T, Rock D A, Joswig-Jones C A, Jones J P. The effects of type II binding on metabolic stability and binding affinity in cytochrome P450 CYP3A4. Archives of Biochemistry and Biophysics. 2010; 497(1-2):68-81.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for treating breast cancer occurrence or recurrence in a human patient in need thereof, comprising:
   1) obtaining a biological sample comprising breast cancer cells from the patient;
   2) detecting whether N1-hexyl-N5-benzyl biguanide (HBB):

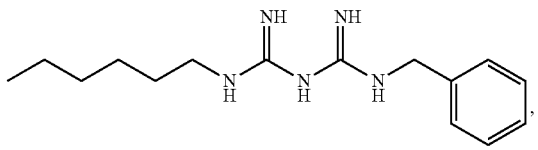 [SMILES: CCCCCCNC(=N)NC(=N)NCc1ccccc1]

or a pharmaceutically acceptable salt thereof, inhibits oxidative phosphorylation and glycolysis in the breast cancer cells by contacting the sample with HBB, or a pharmaceutically acceptable salt thereof, and measuring the oxygen consumption rate (OCR) and the extracellular acidification rate (ECAR) in the breast cancer cells;
   3) identifying the human patient as having a breast cancer that is treatable with HBB when inhibition of OCR and ECAR is detected, as compared to OCR and ECAR in the breast cancer cells contacted with a negative control compound; and
   4) administering to the human patient in need thereof a therapeutically effective amount of HBB, or a pharmaceutically acceptable salt thereof.

2. The method of claim 1, wherein the breast cancer is estrogen receptor positive (ER+), human epidermal growth factor receptor 2 (HER2) negative breast cancer.

3. The method of claim 1, further comprising administering paclitaxel to the patient.

* * * * *

UNITED STATES PATENT AND TRADEMARK OFFICE
CERTIFICATE OF CORRECTION

PATENT NO. : 10,272,055 B2
APPLICATION NO. : 14/641122
DATED : April 30, 2019
INVENTOR(S) : David A. Potter et al.

It is certified that error appears in the above-identified patent and that said Letters Patent is hereby corrected as shown below:

In the Specification

Column 1, Lines 11-15, Government Funding, please delete "This invention was made with government support under R01-CA113570 awarded by the National Cancer Institute. The government has certain rights in the invention." and insert -- This invention was made with government support under CA113570 awarded by the National Institutes of Health. The government has certain rights in the invention. -- therefor.

Signed and Sealed this
Fifth Day of November, 2019

Andrei Iancu
*Director of the United States Patent and Trademark Office*